US010646559B2

(12) United States Patent
Vipond et al.

(10) Patent No.: US 10,646,559 B2
(45) Date of Patent: May 12, 2020

(54) *COXIELLA BURNETII* ANTIGENS

(71) Applicant: SECRETARY OF STATE FOR HEALTH AND SOCIAL CARE, London (GB)

(72) Inventors: Julia Vipond, Salisbury (GB); Kevin Bewley, Salisbury (GB)

(73) Assignee: SECRETARY OF STATE FOR HEALTH AND SOCIAL CARE, London (GB)

( * ) Notice: Subject to any disclaimer, the term of this patent is extended or adjusted under 35 U.S.C. 154(b) by 0 days.

(21) Appl. No.: 15/761,012

(22) PCT Filed: Sep. 23, 2016

(86) PCT No.: PCT/GB2016/052979
§ 371 (c)(1),
(2) Date: Mar. 16, 2018

(87) PCT Pub. No.: WO2017/051196
PCT Pub. Date: Mar. 30, 2017

(65) Prior Publication Data
US 2018/0256696 A1 Sep. 13, 2018

(30) Foreign Application Priority Data
Sep. 25, 2015 (GB) .................... 1517019.4

(51) Int. Cl.
*A61K 39/02* (2006.01)
*C07K 14/29* (2006.01)
*A61K 45/06* (2006.01)
*C07K 14/195* (2006.01)
*C07K 16/12* (2006.01)
*G01N 33/569* (2006.01)
*A61K 39/00* (2006.01)

(52) U.S. Cl.
CPC .......... *A61K 39/0208* (2013.01); *A61K 45/06* (2013.01); *C07K 14/195* (2013.01); *C07K 14/29* (2013.01); *C07K 16/1203* (2013.01); *G01N 33/56911* (2013.01); *A61K 2039/575* (2013.01)

(58) Field of Classification Search
None
See application file for complete search history.

(56) References Cited

U.S. PATENT DOCUMENTS 6,790,450 B1 * 9/2004 Cowden ................ A61K 35/74
424/234.1

OTHER PUBLICATIONS

Flores-Ramirez G et al: "Identification of Coxiella burnetii surface-exposed and cell envelope associated proteins using a combined bioinformatics plus proteomics strategy", Proteomics, vol. 14, No. 16, Aug. 2014 (Aug. 2014), pp. 1868-1881, (Year: 2014).*
Deringer et al: "Immunoreactive Coxiella burnetii Nine Mile proteins separated by 2D electrophoresis and identified by tandem mass spectrometry", Microbiology, vol. 157, No. 2, Feb. 1, 2011 (Feb. 1, 2011), pp. 526-542, (Year: 2011).*
Flores-Ramirez et al. 2014 (Identification of Coxiella burnetii surface-exposed and cell envelope associated proteins using a combined bioinformatics plus proteomics strategy; Proteomics 14:1868-1881) (Year: 2014).*
Jiao et al. 2014 (Serological characterization of surface-exposed proteins of Coxiella burnetii; Microbiology 160:2718-2731 (Year: 2014).*
Vigil et al., Defining the humoral immune response to infectious agents using high-density protein microarrays, Future Microbiol., 5:241-251 (2010).
Chen et al., Identification of CD4+ T Cell Epitopes in C. burnetii Antigens Targeted by Antibody Responses, PLoS ONE, 6:e17712 (2011).
Flores-Ramirez et al., In silico prediction and identification of outer membrane proteins and lipoproteins from Coxiella burnetii by the mass spectrometry techniques, Clin. Microbiol. Infect., 15:196-197 (2009).
Flores-Ramirez et al., Identification of Coxiella burnetii surface-exposed and cell envelope associated proteins using a combined bioinformatics plus proteomics strategy, Proteomics, 14:1868-1881 (2014).
Martinez et al., Identification of OmpA, a Coxiella burnetii Protein Involved in Host Cell Invasion, by Multi-Phenotypic High-Content Screening, PLOS Pathogens, 10:e1004013 (2014).
Zhang et al., Identification and Cloning of Immunodominant Antigens of Coxiella burnetii, Infection and Immunity, 72:844-852 (2004).
Health Protection Report, Shingles Vaccine Coverage Report, England, Sep. 2014 to Feb. 2015, Public Health England, 9:1-19 XP002765045 (2015).
Deringer et al., Immunoreactive Coxiella burnetii Nine Mile proteins separated by 2D electrophoresis and identified by tandem mass sperctrometry, Microbiology, 157:526-542 (2011).
Bewley, The identification of immune-reactive proteins recognized in response to Coxiella burnetii infection, a Thesis, University of Portsmouth (2015).
Genbank Accession No. AAO89657.2, Peptidoglycan-associated lipoprotein [Coxiella burnetii RSA 493], (2005).
Seshadri et al., Complete genome sequence of the Q-fever pathogen Coxiella burnetii, Proceedings of the National Academy of Sciences, 100:5455-5460 (2003).
Tyczka et al., Immunization Experiments with Recombinant Coxiella burnetii Proteins in a Murine Infection Model, Annals New York Academy of Sciences, 1063:143-148 (2005).
Xiong et al., Mice immunized with bone marrow-derived dendritic cells stimulated with recombinant Coxiella burnetii Com1 and Mip demonstrate enhanced bacterial clearance in association with a Th1 immune response, Vaccine, 30:6809-6815 (2012).

(Continued)

*Primary Examiner* — Mary Maille Lyons
(74) *Attorney, Agent, or Firm* — Nevrivy Patent Law Group P.L.L.C.

(57) ABSTRACT

The present invention provides antigens, for use in the treatment or prevention of *C. burnetii* infection. Also provided are nucleic acids encoding such antigens, and antibodies raised against such antigens.

5 Claims, 13 Drawing Sheets

Specification includes a Sequence Listing.

(56) References Cited

OTHER PUBLICATIONS

Xiong et al., Exploratory Study on Th1 Epitope-Induced Protective Immunity against Coxiella bumetii Infection, PLOS ONE, 9:e87206 (2014).
Zhang et al., Mechanisms of vaccine-induced protective immunity against Coxiella burnetii infection in BALB/c Mice, The Journal of Immunology, 179:8372-8380 (2007).
Search Report from GB Appl. No. 1517019.4, dated Jul. 4, 2016.
International Search Report from International Appl. No. PCT/GB2016/052979, dated Jan. 2, 2017.
Zhang et al., Vaccines against coxiella infection, Expert Rev. Vaccines 3:577-584 (2004).
European Communication from Appl. No. 16 775 844.0-1116, dated Apr. 30, 2019.

* cited by examiner

COXIELLA BURNETII ANTIGENS

The present invention relates to antigens for the prevention, treatment or suppression of *Coxiella burnetii* infection. Also provided are methods for generating said antigens, methods for generating antibodies that bind to said antigens, and the use of said antibodies for the prevention, treatment, or suppression of *C. burnetii* infection.

Query (Q fever) is a bacterial infection affecting a variety of mammals, including humans. The causative agent of Q fever is the bacterium, *Coxiella burnetii*. *C. burnetii* has two phase variants: highly virulent phase I and avirulent phase II. Disease caused by *C. burnetii* can take several forms and has been described as clinically polymorphic.

Q fever is usually subclinical in livestock, although *C. burnetii* infection is associated with abortion in goats, cattle and sheep. Following initial abortions or infections with *C. burnetii*, animals no longer experience abortion, but typically remain sub-clinically infected, and females can carry *C. burnetii* indefinitely, exhibiting sporadic bacterial shedding in milk and at parturition.

Current evidence suggests that human infection by *C. burnetii* can occur after inhalation of as few as a single organism. This, coupled with the ability of *C. burnetii* to cause debilitating disease and the organism's extraordinarily high level of resistance to various means of inactivation have resulted in it being listed as a category B biological warfare and bioterrorism agent by the Centers for Disease Control (CDC).

In humans, presentation of *C. burnetii* infection ranges from asymptomatic, through acute disease, up to life-threatening chronic illness. In the majority of cases, acute disease presents as a self-limiting febrile illness with half of cases also suffering from severe headaches. In more severe cases of acute disease, atypical pneumonia is often reported. A proportion of those suffering from symptomatic acute Q fever will be admitted to hospital (2-4%). The largest reported human outbreak of Q fever occurred in the Netherlands between 2007 and 2010, and was associated with a much higher hospitalisation rate, closer to 20%. This outbreak gave rise to over 4,000 reported human cases and led to the culling of 50,000 pregnant goats on 88 farms in an attempt to interrupt disease transmission.

Progression to chronic disease develops in approximately 5% of those infected, and the vast majority of these cases present as a bacterial culture negative endocarditis, often in patients with predisposing heart-damage or immunosuppression. Without effective treatment, Q fever endocarditis is generally fatal, however earlier diagnosis of cases coupled with more effective treatment strategies has brought the death rate down to below 5% in some cases.

In addition to acute and chronic disease in humans, two other clinical manifestations of Q fever are of note due to their less than satisfactory outcomes with current treatment strategies.

These are Q fever during pregnancy and post-Q fever fatigue syndrome (QFS). Infection with *C. burnetii* during pregnancy leads to premature delivery in almost half of those affected and spontaneous abortion in over a quarter. There are indications that in those infected during the first trimester and treated with suboptimal drug regimes, the abortion rate is 100%. This is compounded by the fact that the frontline bactericidal drugs for treatment (doxycycline and hydroxychloroquine) are contraindicated for use during pregnancy. A bacteriostatic regimen (co-trimoxazole) has therefore been proposed for use until delivery. Without satisfactory treatment during and after pregnancy there is also a high probability for infection to lead to chronic Q fever in the mother (70% was reported in a group of pregnant women in France). QFS was first reported in 1996, but an association between Q fever and chronic fatigue had been observed as early as 1982. Between 10% and 15% of those who have acute Q fever will develop a chronic fatigue syndrome that typically lasts between five and ten years, and in some cases even longer.

The current Q fever vaccine licensed for human use (in Australia only, named "Q-VAX") is a formalin-killed whole-cell vaccine (WCV) produced by cultivating virulent *C. burnetii* in live embryonated chicken eggs. Yolk sacs are removed and homogenised, and the preparation is inactivated with formaldehyde. This method of production is labour-intensive, poorly defined and difficult to reproduce, and is high-risk (requiring high biological containment). Moreover, the removal of fats and egg proteins is not 100% effective, leading to contamination of the final product with host cell components.

The current Q fever vaccine is also associated with severe local reactions in those with pre-existing immunity. The severity is such that pre-screening of potential vaccination candidates for skin reactions (to a small quantity of vaccine) and blood antibody levels must be performed prior to vaccination. Such screening is time-consuming and expensive. Moreover, despite pre-screening efforts, severe reactions against this vaccine are still reported in some individuals. Q-VAX is therefore deemed unsuitable for general vaccination strategies, and its use is limited to individuals in defined occupational risk groups, such as abattoir workers.

Alternative vaccines based on more highly purified whole-cell preparations such as chloroform:methanol residues (CMR) of the formalin-inactivated whole-cell material have been developed and shown to have similar levels of protection in some animal models with potentially fewer side-effects. However, the production of CMR vaccines suffers the same production issues as the current Q fever vaccine. Also, although vaccination with CMR appeared to protect against disease upon challenge, it did not protect against splenomegaly, hepatomegaly, or lesions in the liver. Indeed, animals vaccinated with CMR showed significant splenomegaly and hepatomegaly when either challenged with live *C. burnetii* or injected with killed WCV vaccine. This indicates that inadequate immunity against *C. burnetii* may lead to enhanced disease rather than partial protection. In addition, the production of CMR is hampered by the same limitations as WCV, particularly the requirement to produce large quantities of virulent *C. burnetii* at high containment during their manufacture. Vaccines based on the phase II, avirulent form of the organism (due to a 30 kb genomic deletion leading to a surface lipopolysaccharide lacking in 0-antigen) were briefly investigated but found to be non-protective. Attempts to produce a vaccine based on a small number of recombinantly expressed immunodominant *C. burnetii* proteins also failed to induce protection in a mouse model.

Accordingly, there exists an urgent need for further vaccines against *C. burnetii* infection. In particular, there exists a need for vaccines with an improved safety profile. An improved safety profile would increase the number of individuals that may enjoy the benefits of vaccination against *C. burnetii* infection, and would reduce the risk of patients suffering from adverse reactions, and would reduce or avoid the requirement for pre-screening. There also exists a need for vaccines against *C. burnetii*, whose production does not require the culturing of organisms at high levels of biological containment. Advantageously, such vaccines would be less expensive to produce than existing vaccines; more simple to produce than existing vaccines; less dangerous to produce than existing vaccines; and would avoid the current challenges in providing acceptable batch-to-batch variation.

It is an object of the invention to provide further antigens for use in preventing, treating or and/or suppressing *C. burnetii* infection. It is also an object of the invention to provide immunogenic compositions that are effective in raising an immune response against *C. burnetii*, and which avoid the above-mentioned limitations with existing vaccines against *C. burnetii*.

The inventors have identified a number of *C. burnetii* protein antigens which are involved in immunity and infection. The protein antigens of the invention avoid one or more of the above-mentioned limitations associated with existing vaccines against *C. burnetii* infection. The protein antigens of the present invention are capable of eliciting an immune response against *C. burnetii*, and are thus suitable for use in vaccines against *C. burnetii* infection. The provision of specific protein antigens that stimulate the immune system avoids the requirement to administer poorly defined complex mixtures of microbial antigens (as is the case for WCV and CMR vaccines), and so the chances of adverse reactions to the vaccines of the invention are significantly reduced. Moreover, the protein antigens of the invention can be produced recombinantly, without the requirement for high-level containment, and at lower cost than the current vaccines.

The inventors have identified 71 immune-reactive proteins from *C. burnetii*. Despite previous efforts to identify immune-reactive proteins from *C. burnetii*, the inventors believe that none of these 71 immune-reactive proteins have been previously identified as such.

Thus, in one aspect, the invention provides a protein antigen selected from: (1) a CBU_0091 antigen; (2) a CBU_1648 antigen; (3) a CBU_1652 antigen; (4) a CBU_0510 antigen; (5) a CBU_2009 antigen; (6) a CBU_1579 antigen; (7) a CBU_1193 antigen; (8) a CBU_1400 antigen; (9) a CBU_1401 antigen; (10) a CBU_0962 antigen; (11) a CBU_0094 antigen; (12) a CBU_0338 antigen; (13) a CBU_1352 antigen; (14) a CBU_0532 antigen; (15) a CBU_0758 antigen; (16) a CBU_0631 antigen; (17) a CBU_0075 antigen; (18) a CBU_1136 antigen; (19) a CBU_1708 antigen; (20) a CBU_1337 antigen; (21) a CBU_0232 antigen; (22) a CBU_0852 antigen; (23) a CBU_0326 antigen; (24) a CBU_0897 antigen; (25) a CBU_1384 antigen; (26) a CBU_1475 antigen; (27) a CBU_0517 antigen; (28) a CBU_0270 antigen; (29) a CBU_0629 antigen; (30) a CBU_0974 antigen; (31) a CBU_1088 antigen; (32) a CBU_1116 antigen; (33) a CBU_1296 antigen; (34) a CBU_1397 antigen; (35) a CBU_1720 antigen; (36) a CBU_0638 antigen; (37) a CBU_0640 antigen; (38) a CBU_0073 antigen; (39) a CBU_1275 antigen; (40) a CBU_0297 antigen; (41) a CBU_0916 antigen; (42) a CBU_1183 antigen; (43) a CBU_ 235 antigen; (44) a CBU_2086 antigen; (45) a CBU_0043 antigen; (46) a CBU_0296 antigen; (47) a CBU_0531 antigen; (48) a CBU_0796 antigen; (49) a CBU_1830 antigen; (50) a CBU_0234 antigen; (51) a CBU_0445 antigen; (52) a CBU_0808 antigen; (53) a CBU_0851 antigen; (54) a CBU_1325 antigen; (55) a CBU_1383 antigen; (56) a CBU_1473 antigen; (57) a CBU_ 594 antigen; (58) a CBU_1841 antigen; (59) a CBU_1970 antigen; (60) a CBU_2087 antigen; (61) a CBU_0502 antigen; (62) a CBU_0288 antigen; (63) a CBU_0928 antigen; (64) a CBU_0738 antigen; (65) a CBU_2012 antigen; (66) a CBU_2092 antigen; (67) a CBU_0155 antigen; (68) a CBU_0943 antigen; (69) a CBU_1916 antigen; (70) a CBU_0114 antigen; and (71) a CBU_0656 antigen.

In one embodiment, the invention provides a protein antigen selected from: (1) a CBU_0091 antigen; (2) a CBU_1648 antigen; (3) a CBU_1652 antigen; (4) a CBU_0510 antigen; (5) a CBU_2009 antigen; (6) a CBU_1579 antigen; (7) a CBU_1193 antigen; (8) a CBU_1400 antigen; (9) a CBU_1401 antigen; (10) a CBU_0962 antigen; (11) a CBU_0094 antigen; (12) a CBU_0338 antigen; (13) a CBU_1352 antigen; (14) a CBU_0532 antigen; (15) a CBU_0758 antigen; (16) a CBU_0631 antigen; (17) a CBU_0075 antigen; (18) a CBU_1136 antigen; and (19) a CBU_1708 antigen. These antigens are highly suitable for eliciting a humoral immune response to *C. burnetii* in a patient. CBU_0091 and CBU_1648 antigens have also been demonstrated herein to elicit a cell-mediated immune response. The inventors have identified CBU_0532 and CBU_0758 as candidates for eliciting a cell-mediated immune response.

In one embodiment, the invention provides a protein antigen selected from: (1) a CBU_0091 antigen; (2) a CBU_1648 antigen; (3) a CBU_1652 antigen; (4) a CBU_0510 antigen; and (5) a and CBU_2009 antigen. These antigens are particularly suitable for eliciting a humoral immune response to *C. burnetii* in a patient. CBU_0091 and CBU_1648 antigens have also been demonstrated herein to elicit a cell-mediated immune response.

In one embodiment, the invention provides a protein antigen selected from: (1) a CBU_0091 antigen; (2) a CBU_1648 antigen; (3) a CBU_0510 antigen; and (4) a CBU_2009 antigen; and optionally (5) a CBU_1652 antigen. These antigens are particularly suitable for eliciting a humoral immune response to *C. burnetii* in a patient. CBU_0091 and CBU_1648 antigens have also been demonstrated herein to elicit a cell-mediated immune response.

In one embodiment, the invention provides a protein antigen selected from: (1) a CBU_0091 antigen; (2) a CBU_1648 antigen; (3) a CBU_0532 antigen; (4) a CBU_0758 antigen; (5) a CBU_1652 antigen; (6) a CBU_0510 antigen; and (7) a CBU_2009 antigen. These antigens are particularly suitable for eliciting a humoral immune response to *C. burnetii* in a patient. CBU_0091 and CBU_1648 antigens have also been demonstrated herein to elicit a cell-mediated immune response. The inventors have identified CBU_0532 and CBU_0758 as candidates for eliciting a cell-mediated immune response.

In one embodiment, the invention provides a protein antigen selected from: (1) a CBU_0091 antigen; (2) a CBU_1648 antigen; (3) a CBU_0532 antigen; (4) a CBU_0758 antigen; (5) a CBU_0510 antigen; and (6) a CBU_2009 antigen; and optionally (7) a CBU_1652. These antigens are particularly suitable for eliciting a humoral immune response to *C. burnetii* in a patient. CBU_0091 and CBU_1648 antigens have also been demonstrated herein to elicit a cell-mediated immune response. The inventors have identified CBU_0532 and CBU_0758 as candidates for eliciting a cell-mediated immune response.

In one embodiment, the invention provides a protein antigen selected from: (1) a CBU_0091 antigen; and (2) a CBU_1648 antigen. These antigens are particularly suitable for eliciting a humoral immune response and also a cell-mediated immune response to *C. burnetii* in a patient.

In one embodiment, the invention provides a protein antigen selected from: (1) a CBU_0091 antigen; (2) a CBU_1648 antigen; (3) a CBU_0532 antigen; and (4) a CBU_0758 antigen.

In one embodiment, the invention provides a protein antigen selected from: (1) a CBU_0091 antigen; (2) a CBU_1648 antigen; and (3) a CBU_0532 antigen.

In one embodiment, the invention provides a protein antigen selected from: (1) a CBU_0091 antigen; (2) a CBU_1648 antigen; and (3) a CBU_0758 antigen.

In one embodiment, the invention provides a protein antigen selected from: (1) a CBU_1337 antigen; (2) a CBU_0232 antigen; (3) a CBU_0852 antigen; (4) a CBU_0326 antigen; (5) a CBU_0897 antigen; (6) a CBU_1384 antigen; (7) a CBU_1475 antigen; (8) a CBU_0517 antigen; (9) a CBU_0270 antigen; (10) a CBU_0629 antigen; (11) a CBU_0974 antigen; (12) a CBU_1088 antigen; (13) a CBU_1116 antigen; (14) a CBU_1296 antigen; (15) a CBU_1397 antigen; (16) a CBU_1720 antigen; (17) a CBU_0638 antigen; (18) a CBU_0640 antigen; (19) a CBU_0073 antigen; (20) a CBU_1275 antigen; (21) a CBU_0297 antigen; (22) a CBU_0916 antigen; (23) a CBU_1183 antigen; (24) a CBU_1235 antigen; (25) a CBU_2086 antigen; (26) a CBU_0043 antigen; (27) a CBU_0296 antigen; (28) a CBU_0531 antigen; (29) a CBU_0796 antigen; (30) a CBU_1830 antigen; (31) a CBU_0234 antigen; (32) a CBU_0445 antigen; (33) a CBU_0808 antigen; (34) a CBU_0851 antigen; (35) a CBU_1325 antigen; (36) a CBU_1383 antigen; (37) a CBU_1473 antigen; (38) a CBU_1594 antigen; (39) a CBU_1841 antigen; (40) a CBU_1970 antigen; (41) a CBU_2087 antigen; (42) a CBU_0502 antigen; (43) a CBU_0288 antigen; (44) a CBU_0928 antigen; (45) a CBU_0738 antigen; (46) a CBU_2012 antigen; (47) a CBU_2092 antigen; (48) a CBU_0155 antigen; (49) a CBU_0943 antigen; (50) a CBU_1916 antigen; (51) a CBU_0114 antigen; and (52) a CBU_0656 antigen. These antigens are highly suitable for eliciting a cell-mediated immune response to C. burnetii in a patient. Highly advantageously, CBU_0091 and CBU_1648 antigens were demonstrated herein to be capable of eliciting a cell-mediated immune response (in addition to being capable of eliciting a humoral immune response, as demonstrated herein). CBU_0532 and CBU_0758 have also been identified as candidates for eliciting a cell-mediated immune response (in addition to being capable of eliciting a humoral immune response, as demonstrated herein).

Typically, the CBU_0091 antigen comprises an amino acid sequence having 70% or more identity to SEQ ID NO: 62; the CBU_1648 antigen comprises an amino acid sequence having 70% or more identity to SEQ ID NO: 28; the CBU_1652 antigen comprises an amino acid sequence having 70% or more identity to SEQ ID NO: 29; the CBU_0510 antigen comprises an amino acid sequence having 70% or more identity to SEQ ID NO: 69; the CBU_2009 antigen comprises an amino acid sequence having 70% or more identity to SEQ ID NO: 71; the CBU_1579 antigen comprises an amino acid sequence having 70% or more identity to SEQ ID NO: 7; the CBU_1193 antigen comprises an amino acid sequence having 70% or more identity to SEQ ID NO: 15; the CBU_1400 antigen comprises an amino acid sequence having 70% or more identity to SEQ ID NO: 18; the CBU_1401 antigen comprises an amino acid sequence having 70% or more identity to SEQ ID NO: 19; the CBU_0962 antigen comprises an amino acid sequence having 70% or more identity to SEQ ID NO: 23; the CBU_0094 antigen comprises an amino acid sequence having 70% or more identity to SEQ ID NO: 25; the CBU_0338 antigen comprises an amino acid sequence having 70% or more identity to SEQ ID NO: 26; the CBU_1352 antigen comprises an amino acid sequence having 70% or more identity to SEQ ID NO: 27; the CBU_0532 antigen comprises an amino acid sequence having 70% or more identity to SEQ ID NO: 35; the CBU_0758 antigen comprises an amino acid sequence having 70% or more identity to SEQ ID NO: 36; the CBU_0631 antigen comprises an amino acid sequence having 70% or more identity to SEQ ID NO: 41; the CBU_0075 antigen comprises an amino acid sequence having 70% or more identity to SEQ ID NO: 54; the CBU_1136 antigen comprises an amino acid sequence having 70% or more identity to SEQ ID NO: 64; the CBU_1708 antigen comprises an amino acid sequence having 70% or more identity to SEQ ID NO: 66; the CBU_1337 antigen comprises an amino acid sequence having 70% or more identity to SEQ ID NO: 1; the CBU_0232 antigen comprises an amino acid sequence having 70% or more identity to SEQ ID NO: 2; the CBU_0852 antigen comprises an amino acid sequence having 70% or more identity to SEQ ID NO: 3; the CBU_0326 antigen comprises an amino acid sequence having 70% or more identity to SEQ ID NO: 4; the CBU_0897 antigen comprises an amino acid sequence having 70% or more identity to SEQ ID NO: 5; the CBU_1384 antigen comprises an amino acid sequence having 70% or more identity to SEQ ID NO: 6; the CBU_1475 antigen comprises an amino acid sequence having 70% or more identity to SEQ ID NO: 8; the CBU_0517 antigen comprises an amino acid sequence having 70% or more identity to SEQ ID NO: 9; the CBU_0270 antigen comprises an amino acid sequence having 70% or more identity to SEQ ID NO: 10; the CBU_0629 antigen comprises an amino acid sequence having 70% or more identity to SEQ ID NO: 11; the CBU_0974 antigen comprises an amino acid sequence having 70% or more identity to SEQ ID NO: 12; the CBU_1088 antigen comprises an amino acid sequence having 70% or more identity to SEQ ID NO: 13; the CBU_1116 antigen comprises an amino acid sequence having 70% or more identity to SEQ ID NO: 14; the CBU_1296 antigen comprises an amino acid sequence having 70% or more identity to SEQ ID NO: 16; the CBU_1397 antigen comprises an amino acid sequence having 70% or more identity to SEQ ID NO: 17; the CBU_1720 antigen comprises an amino acid sequence having 70% or more identity to SEQ ID NO: 20; the CBU_0638 antigen comprises an amino acid sequence having 70% or more identity to SEQ ID NO: 21; the CBU_0640 antigen comprises an amino acid sequence having 70% or more identity to SEQ ID NO: 22; the CBU_0073 antigen comprises an amino acid sequence having 70% or more identity to SEQ ID NO: 24; the CBU_1275 antigen comprises an amino acid sequence having 70% or more identity to SEQ ID NO: 30; the CBU_0297 antigen comprises an amino acid sequence having 70% or more identity to SEQ ID NO: 31; the CBU_0916 antigen comprises an amino acid sequence having 70% or more identity to SEQ ID NO: 32; the CBU_1183 antigen comprises an amino acid sequence having 70% or more identity to SEQ ID NO: 33; the CBU_1235 antigen comprises an amino acid sequence having 70% or more identity to SEQ ID NO: 34; the CBU_2086 antigen comprises an amino acid sequence having 70% or more identity to SEQ ID NO: 37; the CBU_0043 antigen comprises an amino acid sequence having 70% or more identity to SEQ ID NO: 38; the CBU_0296 antigen comprises an amino acid sequence having 70% or more identity to SEQ ID NO: 39; the CBU_0531 antigen comprises an amino acid sequence having 70% or more identity to SEQ ID NO: 40; the CBU_0796 antigen comprises an amino acid sequence having 70% or more identity to SEQ ID NO: 42; the CBU_1830 antigen comprises an amino acid sequence having 70% or more identity to SEQ ID NO: 43; the CBU_0234 antigen comprises an amino acid sequence having 70% or more identity to SEQ ID NO: 44; the CBU_0445 antigen comprises an amino acid sequence having 70% or more identity to SEQ ID NO: 45; the CBU_0808 antigen comprises an amino acid sequence having 70% or more identity to SEQ ID NO: 46; the CBU_0851 antigen comprises an amino acid sequence having 70% or more identity to SEQ ID NO: 47; the CBU_1325 antigen comprises an amino acid sequence having 70% or more identity to SEQ ID NO: 48; the CBU_1383 antigen comprises an amino acid sequence having 70% or more identity to SEQ ID NO: 49; the CBU_1473 antigen comprises an amino acid sequence having 70% or more identity to SEQ ID NO: 50; the CBU_1594 antigen comprises an amino acid sequence having 70% or more identity to SEQ ID NO: 51; the CBU_1841 antigen comprises an amino acid sequence having 70% or more identity to SEQ ID NO: 52; the CBU_1970 antigen comprises an amino acid sequence having 70% or more identity to SEQ ID NO: 53; the CBU_2087 antigen comprises an amino acid sequence having 70% or more identity to SEQ ID NO: 55; the CBU_0502 antigen comprises an amino acid sequence having 70% or more identity to SEQ ID NO: 56; the CBU_0288 antigen comprises an amino acid sequence having 70% or more identity to SEQ ID NO: 57; the CBU_0928 antigen comprises an amino acid sequence having 70% or more identity to SEQ ID NO: 58; the CBU_0738 antigen comprises an amino acid sequence having 70% or more identity to SEQ ID NO: 59; the CBU_2012 antigen comprises an amino acid sequence having 70% or more identity to SEQ ID NO: 60; the CBU_2092 antigen comprises an amino acid sequence having 70% or more identity to SEQ ID NO: 61; the CBU_0155 antigen comprises an amino acid sequence having 70% or more identity to SEQ ID NO: 63; the CBU_0943 antigen comprises an amino acid sequence having 70% or more identity to SEQ ID NO: 65; the CBU_1916 antigen comprises an amino acid sequence having 70% or more identity to SEQ ID NO: 67; the CBU_0114 antigen comprises an amino acid sequence having 70% or more identity to SEQ ID NO: 68; and/or the CBU_0656 antigen comprises an amino acid sequence having 70% or more identity to SEQ ID NO: 70.

Typically, the CBU_0091 antigen comprises 7 or more consecutive amino acids of SEQ ID NO: 62; the CBU_1648 antigen comprises 7 or more consecutive amino acids of SEQ ID NO: 28; the CBU_1652 antigen comprises 7 or more consecutive amino acids of SEQ ID NO: 29; the CBU_0510 antigen comprises 7 or more consecutive amino acids of SEQ ID NO: 69; the CBU_2009 antigen comprises 7 or more consecutive amino acids of SEQ ID NO: 71; the CBU_1579 antigen comprises 7 or more consecutive amino acids of SEQ ID NO: 7; the CBU_1193 antigen comprises 7 or more consecutive amino acids of SEQ ID NO: 15; the CBU_1400 antigen comprises 7 or more consecutive amino acids of SEQ ID NO: 18; the CBU_1401 antigen comprises 7 or more consecutive amino acids of SEQ ID NO: 19; the CBU_0962 antigen comprises 7 or more consecutive amino acids of SEQ ID NO: 23; the CBU_0094 antigen comprises 7 or more consecutive amino acids of SEQ ID NO: 25; the CBU_0338 antigen comprises 7 or more consecutive amino acids of SEQ ID NO: 26; the CBU_1352 antigen comprises 7 or more consecutive amino acids of SEQ ID NO: 27; the CBU_0532 antigen comprises 7 or more consecutive amino acids of SEQ ID NO: 35; the CBU_0758 antigen comprises 7 or more consecutive amino acids of SEQ ID NO: 36; the CBU_0631 antigen comprises 7 or more consecutive amino acids of SEQ ID NO: 41; the CBU_0075 antigen comprises 7 or more consecutive amino acids of SEQ ID NO: 54; the CBU_1136 antigen comprises 7 or more consecutive amino acids of SEQ ID NO: 64; the CBU_1708 antigen comprises 7 or more consecutive amino acids of SEQ ID NO: 66; the CBU_1337 antigen comprises 7 or more consecutive amino acids of SEQ ID NO: 1; the CBU_0232 antigen comprises 7 or more consecutive amino acids of SEQ ID NO: 2; the CBU_0852 antigen comprises 7 or more consecutive amino acids of SEQ ID NO: 3; the CBU_0326 antigen comprises 7 or more consecutive amino acids of SEQ ID NO: 4; the CBU_0897 antigen comprises 7 or more consecutive amino acids of SEQ ID NO: 5; the CBU_1384 antigen comprises 7 or more consecutive amino acids of SEQ ID NO: 6; the CBU_1475 antigen comprises 7 or more consecutive amino acids of SEQ ID NO: 8; the CBU_0517 antigen comprises 7 or more consecutive amino acids of SEQ ID NO: 9; the CBU_0270 antigen comprises 7 or more consecutive amino acids of SEQ ID NO: 10; the CBU_0629 antigen comprises 7 or more consecutive amino acids of SEQ ID NO: 11; the CBU_0974 antigen comprises 7 or more consecutive amino acids of SEQ ID NO: 12; the CBU_1088 antigen comprises 7 or more consecutive amino acids of SEQ ID NO: 13; the CBU_1116 antigen comprises 7 or more consecutive amino acids of SEQ ID NO: 14; the CBU_1296 antigen comprises 7 or more consecutive amino acids of SEQ ID NO: 16; the CBU_1397 antigen comprises 7 or more consecutive amino acids of SEQ ID NO: 17; the CBU_1720 antigen comprises 7 or more consecutive amino acids of SEQ ID NO: 20; the CBU_0638 antigen comprises 7 or more consecutive amino acids of SEQ ID NO: 21; the CBU_0640 antigen comprises 7 or more consecutive amino acids of SEQ ID NO: 22; the CBU_0073 antigen comprises 7 or more consecutive amino acids of SEQ ID NO: 24; the CBU_1275 antigen comprises 7 or more consecutive amino acids of SEQ ID NO: 30; the CBU_0297 antigen comprises 7 or more consecutive amino acids of SEQ ID NO: 31; the CBU_0916 antigen comprises 7 or more consecutive amino acids of SEQ ID NO: 32; the CBU_1183 antigen comprises 7 or more consecutive amino acids of SEQ ID NO: 33; the CBU_1235 antigen comprises 7 or more consecutive amino acids of SEQ ID NO: 34; the CBU_2086 antigen comprises 7 or more consecutive amino acids of SEQ ID NO: 37; the CBU_0043 antigen comprises 7 or more consecutive amino acids of SEQ ID NO: 38; the CBU_0296 antigen comprises 7 or more consecutive amino acids of SEQ ID NO: 39; the CBU_0531 antigen comprises 7 or more consecutive amino acids of SEQ ID NO: 40; the CBU_0796 antigen comprises 7 or more consecutive amino acids of SEQ ID NO: 42; the CBU_1830 antigen comprises 7 or more consecutive amino acids of SEQ ID NO: 43; the CBU_0234 antigen comprises 7 or more consecutive amino acids of SEQ ID NO: 44; the CBU_0445 antigen comprises 7 or more consecutive amino acids of SEQ ID NO: 45; the CBU_0808 antigen comprises 7 or more consecutive amino acids of SEQ ID NO: 46; the CBU_0851 antigen comprises 7 or more consecutive amino acids of SEQ ID NO: 47; the CBU_1325 antigen comprises 7 or more consecutive amino acids of SEQ ID NO: 48; the CBU_1383 antigen comprises 7 or more consecutive amino acids of SEQ ID NO: 49; the CBU_1473 antigen comprises 7 or more consecutive amino acids of SEQ ID NO: 50; the CBU_1594 antigen comprises 7 or more consecutive amino acids of SEQ ID NO: 51; the CBU_1841 antigen comprises 7 or more consecutive amino acids of SEQ ID NO: 52; the CBU_1970 antigen comprises 7 or more consecutive amino acids of SEQ ID NO: 53; the CBU_2087 antigen comprises 7 or more consecutive amino acids of SEQ ID NO: 55; the CBU_0502 antigen comprises 7 or more consecutive amino acids of SEQ ID NO: 56; the CBU_0288 antigen comprises 7 or more consecutive amino acids of SEQ ID NO: 57; the CBU_0928 antigen comprises 7 or more consecutive amino acids of SEQ ID NO: 58; the CBU_0738 antigen comprises 7 or more consecutive amino acids of SEQ ID NO: 59; the CBU_2012 antigen comprises 7 or more consecutive amino acids of SEQ ID NO: 60; the CBU_2092 antigen comprises 7 or more consecutive amino acids of SEQ ID NO: 61; the CBU_0155 antigen comprises 7 or more consecutive amino acids of SEQ ID NO: 63; the CBU_0943 antigen comprises 7 or more consecutive amino acids of SEQ ID NO: 65; the CBU_1916 antigen comprises 7 or more consecutive amino acids of SEQ ID NO: 67; the CBU_0114 antigen comprises 7 or more consecutive amino acids of SEQ ID NO: 68; and/or the CBU_0656 antigen comprises 7 or more consecutive amino acids of SEQ ID NO: 70.

The protein antigens of the invention are referred to by their "CBU" Locus Tag, and are described below:

1. CBU_1337 Antigens

The original "CBU_1337" sequence is annotated as "DNA polymerase III alpha subunit", and is involved in DNA metabolism—replication, recombination and repair. For reference purposes, the amino acid sequence of the full length CBU_1337 sequence is provided in SEQ ID NO: 1 herein.

Preferred CBU_1337 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 1; and/or (b) comprising a fragment of at least "n" consecutive amino acids of SEQ ID NO: 1, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 1 comprise an epitope of SEQ ID NO: 1. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 1. Preferred fragments of SEQ ID NO: 1 comprise an epitope of SEQ ID NO: 1.

2. CBU_0232 Antigens

The original "CBU_0232" sequence is annotated as "DNA-directed RNA polymerase beta' chain" and is involved in transcription. For reference purposes, the amino acid sequence of the full length CBU_0232 sequence is provided in SEQ ID NO: 2 herein.

Preferred CBU_0232 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 2; and/or (b) comprising a fragment of at least "n" consecutive amino acids of SEQ ID NO: 2, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 2 comprise an epitope of SEQ ID NO: 2. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 2. Preferred fragments of SEQ ID NO: 2 comprise an epitope of SEQ ID NO: 2.

3. CBU_0852 Antigens

The original "CBU_0852" sequence is annotated as "Polyribonucleotide nucleotidyltransferase/Polynucleotide adenylyltransferase" and is involved in transcription. For reference purposes, the amino acid sequence of the full length CBU_0852 sequence is provided in SEQ ID NO: 3 herein.

Preferred CBU_0852 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 3; and/or (b) comprising a fragment of at least "n" consecutive amino acids of SEQ ID NO: 3, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 3 comprise an epitope of SEQ ID NO: 3. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 3. Preferred fragments of SEQ ID NO: 3 comprise an epitope of SEQ ID NO: 3.

4. CBU_0326 Antigens

The original "CBU_0326" sequence is annotated as "Phosphoribosylamine-glycine ligase" and is involved in nucleotide and nucleoside biosynthesis and metabolism. For reference purposes, the amino acid sequence of the full length CBU_0326 sequence is provided in SEQ ID NO: 4 herein.

Preferred CBU_0326 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 4; and/or (b) comprising a fragment of at least "n" consecutive amino acids of SEQ ID NO: 4, wherein "n" is 7 or more (e.g. 8, 9, 10, 11, 12, 13, 14, 15, 61, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 4 comprise an epitope of SEQ ID NO: 4. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 4. Preferred fragments of SEQ ID NO: 4 comprise an epitope of SEQ ID NO: 4.

5. CBU_0897 Antigens

The original "CBU_0897" sequence is annotated as "Amidophosphoribosyltransferase" and is involved in nucleotide and nucleoside biosynthesis and metabolism. For reference purposes, the amino acid sequence of the full length CBU_0897 sequence is provided in SEQ ID NO: 5 herein.

Preferred CBU_0897 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 5; and/or (b) comprising a fragment of at least "n" consecutive amino acids of SEQ ID NO: 5, wherein "n" is 7 or more (e.g. 8, 9, 10, 11, 12, 13, 14, 15, 61, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 5 comprise an epitope of SEQ ID NO: 5. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more)

from the C-terminus of SEQ ID NO: 5. Preferred fragments of SEQ ID NO: 5 comprise an epitope of SEQ ID NO: 5.

6. CBU_1384 Antigens

The original "CBU_1384" sequence is annotated as "Uridylate kinase" and is involved in nucleotide and nucleoside biosynthesis and metabolism. For reference purposes, the amino acid sequence of the full length CBU_1384 sequence is provided in SEQ ID NO: 6 herein.

Preferred CBU_1384 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 6; and/or (b) comprising a fragment of at least "n" consecutive amino acids of SEQ ID NO: 6, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 6 comprise an epitope of SEQ ID NO: 6. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 6. Preferred fragments of SEQ ID NO: 6 comprise an epitope of SEQ ID NO: 6.

7. CBU_1579 Antigens

The original "CBU_1579" sequence is annotated as "Trp repressor binding protein" and is involved in regulatory function. For reference purposes, the amino acid sequence of the full length CBU_1579 sequence is provided in SEQ ID NO: 7 herein.

Preferred CBU_1579 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 7; and/or (b) comprising a fragment of at least "n" consecutive amino acids of SEQ ID NO: 7, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 7 comprise an epitope of SEQ ID NO: 7. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 7. Preferred fragments of SEQ ID NO: 7 comprise an epitope of SEQ ID NO: 7.

8. CBU_1475 Antigens

The original "CBU_1475" sequence is annotated as "Aspartyl/glutamyl-tRNA(Asn/Gln) amidotransferase subunit B" and is involved in translation (protein biosynthesis). For reference purposes, the amino acid sequence of the full length CBU_1475 sequence is provided in SEQ ID NO: 8 herein.

Preferred CBU_1475 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 8; and/or (b) comprising a fragment of at least "n" consecutive amino acids of SEQ ID NO: 8, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 8 comprise an epitope of SEQ ID NO: 8. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 8. Preferred fragments of SEQ ID NO: 8 comprise an epitope of SEQ ID NO: 8.

9. CBU_0517 Antigens

The original "CBU_0517" sequence is annotated as "Aspartate aminotransferase/Succinyldiaminopimelate aminotransferase" and is involved in amino acid biosynthesis and metabolism. For reference purposes, the amino acid sequence of the full length CBU_0517 sequence is provided in SEQ ID NO: 9 herein.

Preferred CBU_0517 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 9; and/or (b) comprising a fragment of at least "n" consecutive amino acids of SEQ ID NO: 9, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 9 comprise an epitope of SEQ ID NO: 9. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 9. Preferred fragments of SEQ ID NO: 9 comprise an epitope of SEQ ID NO: 9.

10. CBU_0270 Antigens

The original "CBU_0270" sequence is annotated as "Short-chain alcohol dehydrogenase" and is involved in energy metabolism—electron transport. For reference purposes, the amino acid sequence of the full length CBU_0270 sequence is provided in SEQ ID NO: 10 herein.

Preferred CBU_0270 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 10; and/or (b) comprising a fragment of at least "n" consecutive amino acids of SEQ ID NO: 10, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 10 comprise an epitope of SEQ ID NO: 10. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 10. Preferred fragments of SEQ ID NO: 10 comprise an epitope of SEQ ID NO: 10.

11. CBU_0629 Antigens

The original "CBU_0629" sequence is annotated as "Proline dehydrogenase/Delta-1-pyrroline-5-carboxylate dehydrogenase" and is involved in energy metabolism—electron transport. For reference purposes, the amino acid sequence of the full length CBU_0629 sequence is provided in SEQ ID NO: 1 herein.

Preferred CBU_0629 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 11; and/or (b) comprising a fragment of at least "n" consecutive amino acids of SEQ ID NO: 11, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 11 comprise an epitope of SEQ ID NO: 11. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 11. Preferred fragments of SEQ ID NO: 11 comprise an epitope of SEQ ID NO: 11.

12. CBU_0974 Antigens

The original "CBU_0974" sequence is annotated as "Acetyl-CoA acetyltransferase" and is involved in energy metabolism—electron transport. For reference purposes, the amino acid sequence of the full length CBU_0974 sequence is provided in SEQ ID NO: 12 herein.

Preferred CBU_0974 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 12; and/or (b) comprising a fragment of at least "n" consecutive amino acids of SEQ ID NO: 12, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 12 comprise an epitope of SEQ ID NO: 12. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 12. Preferred fragments of SEQ ID NO: 12 comprise an epitope of SEQ ID NO: 12.

13. CBU_1088 Antigens

The original "CBU_1088" sequence is annotated as "Bifunctional NAD(P)H-hydrate repair enzyme Nnr" and is involved in energy metabolism—electron transport. For reference purposes, the amino acid sequence of the full length CBU_1088 sequence is provided in SEQ ID NO: 13 herein.

Preferred CBU_1088 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 13; and/or (b) comprising a fragment of at least "n" consecutive amino acids of SEQ ID NO: 13, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 13 comprise an epitope of SEQ ID NO: 13. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 13. Preferred fragments of SEQ ID NO: 13 comprise an epitope of SEQ ID NO: 13.

14. CBU_1116 Antigens

The original "CBU_1116" sequence is annotated as "Alanine dehydrogenase" and is involved in energy metabolism—electron transport. For reference purposes, the amino acid sequence of the full length CBU_1116 sequence is provided in SEQ ID NO: 14 herein.

Preferred CBU_1116 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 14; and/or (b) comprising a fragment of at least "n" consecutive amino acids of SEQ ID NO: 14, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 14 comprise an epitope of SEQ ID NO: 14. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 14. Preferred fragments of SEQ ID NO: 14 comprise an epitope of SEQ ID NO: 14.

15. CBU_1193 Antigens

The original "CBU_1193" sequence is annotated as "Thioredoxin reductase" and is involved in energy metabolism—electron transport. For reference purposes, the amino acid sequence of the full length CBU_1193 sequence is provided in SEQ ID NO: 15 herein.

Preferred CBU_1193 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 15; and/or (b) comprising a fragment of at least "n" consecutive amino acids of SEQ ID NO: 15, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 15 comprise an epitope of SEQ ID NO: 15. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 15. Preferred fragments of SEQ ID NO: 15 comprise an epitope of SEQ ID NO: 15.

16. CBU_1296 Antigens

The original "CBU_1296" sequence is annotated as "ATP-NAD kinase" and is involved in energy metabolism—electron transport. For reference purposes, the amino acid sequence of the full length CBU_1296 sequence is provided in SEQ ID NO: 16 herein.

Preferred CBU_1296 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 16; and/or (b) comprising a fragment of at least "n" consecutive amino acids of SEQ ID NO: 16, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 16 comprise an epitope of SEQ ID NO: 16. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 16. Preferred fragments of SEQ ID NO: 16 comprise an epitope of SEQ ID NO: 16.

17. CBU_1397 Antigens

The original "CBU_1397" sequence is annotated as and is involved in energy metabolism—electron transport "Succinyl-CoA synthetase beta chain". For reference purposes, the amino acid sequence of the full length CBU_1397 sequence is provided in SEQ ID NO: 17 herein.

Preferred CBU_1397 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 17; and/or (b) comprising a fragment of at least "n" consecutive amino acids of SEQ ID NO: 17, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 17 comprise an epitope of SEQ ID NO: 17. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 17. Preferred fragments of SEQ ID NO: 17 comprise an epitope of SEQ ID NO: 17.

18. CBU_1400 Antigens

The original "CBU_1400" sequence is annotated as and is involved in energy metabolism—electron transport "Succinate dehydrogenase iron-sulfur protein". For reference purposes, the amino acid sequence of the full length CBU_1400 sequence is provided in SEQ ID NO: 18 herein.

Preferred CBU_1400 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 18; and/or (b) comprising a fragment of at least "n" consecutive amino acids of SEQ ID NO: 18, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 18 comprise an epitope of SEQ ID NO: 18. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 18. Preferred fragments of SEQ ID NO: 18 comprise an epitope of SEQ ID NO: 18.

19. CBU_1401 Antigens

The original "CBU_1401" sequence is annotated as and is involved in energy metabolism—electron transport "Succinate dehydrogenase flavoprotein subunit". For reference purposes, the amino acid sequence of the full length CBU_1401 sequence is provided in SEQ ID NO: 19 herein.

Preferred CBU_1401 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 19; and/or (b) comprising a fragment of at least "n" consecutive amino acids of SEQ ID NO: 19, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 19 comprise an epitope of SEQ ID NO: 19. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 19. Preferred fragments of SEQ ID NO: 19 comprise an epitope of SEQ ID NO: 19.

20. CBU_1720 Antigens

The original "CBU_1720" sequence is annotated as "Aconitate hydratase" and is involved in energy metabolism—electron transport. For reference purposes, the amino acid sequence of the full length CBU_1720 sequence is provided in SEQ ID NO: 20 herein.

Preferred CBU_1720 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 20; and/or (b) comprising a fragment of at least "n" consecutive amino acids of SEQ ID NO: 20, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 20 comprise an epitope of SEQ ID NO: 20. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 20. Preferred fragments of SEQ ID NO: 20 comprise an epitope of SEQ ID NO: 20.

21. CBU_0638 Antigens

The original "CBU_0638" sequence is annotated as "Dihydrolipoamide acetyltransferase component of pyruvate dehydrogenase complex" and is involved in intermediary metabolism and other metabolic pathways. For reference purposes, the amino acid sequence of the full length CBU_0638 sequence is provided in SEQ ID NO: 21 herein.

Preferred CBU_0638 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 21; and/or (b) comprising a fragment of at least "n" consecutive amino acids of SEQ ID NO: 21, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 21 comprise an epitope of SEQ ID NO: 21. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 21. Preferred fragments of SEQ ID NO: 21 comprise an epitope of SEQ ID NO: 21.

22. CBU_0640 Antigens

The original "CBU_0640" sequence is annotated as "Pyruvate dehydrogenase E1 component alpha subunit" and is involved in intermediary metabolism and other metabolic pathways. For reference purposes, the amino acid sequence of the full length CBU_0640 sequence is provided in SEQ ID NO: 22 herein.

Preferred CBU_0640 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 22; and/or (b) comprising a fragment of at least "n" consecutive amino acids of SEQ ID NO: 22, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 22 comprise an epitope of SEQ ID NO: 22. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 22. Preferred fragments of SEQ ID NO: 22 comprise an epitope of SEQ ID NO: 22.

23. CBU_0962 Antigens

The original "CBU_0962" sequence is annotated as "Short chain dehydrogenase" and is involved in intermediary metabolism and other metabolic pathways. For reference purposes, the amino acid sequence of the full length CBU_0962 sequence is provided in SEQ ID NO: 23 herein.

Preferred CBU_0962 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 23; and/or (b) comprising a fragment of at least "n" consecutive amino acids of SEQ ID NO: 23, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 23 comprise an epitope of SEQ ID NO: 23. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 23. Preferred fragments of SEQ ID NO: 23 comprise an epitope of SEQ ID NO: 23.

24. CBU_0073 Antigens

The original "CBU_0073" sequence is annotated as "Xaa-Pro aminopeptidase" and is involved in posttranslational modification, degradation, protein turnover, chaperones. For reference purposes, the amino acid sequence of the full length CBU_0073 sequence is provided in SEQ ID NO: 24 herein.

Preferred CBU_0073 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 24; and/or (b) comprising a fragment of at least "n" consecutive amino acids of SEQ ID NO: 24, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 24 comprise an epitope of SEQ ID NO: 24. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 24. Preferred fragments of SEQ ID NO: 24 comprise an epitope of SEQ ID NO: 24.

25. CBU_0094 Antigens

The original "CBU_0094" sequence is annotated as "ClpB protein" and is involved in posttranslational modification, degradation, protein turnover, chaperones. For reference purposes, the amino acid sequence of the full length CBU_0094 sequence is provided in SEQ ID NO: 25 herein.

Preferred CBU_0094 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 25; and/or (b) comprising a fragment of at least "n" consecutive amino acids of SEQ ID NO: 25, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 25 comprise an epitope of SEQ ID NO: 25. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 25. Preferred fragments of SEQ ID NO: 25 comprise an epitope of SEQ ID NO: 25.

26. CBU_0338 Antigens

The original "CBU_0338" sequence is annotated as "Membrane alanine aminopeptidase" and is involved in posttranslational modification, degradation, protein turnover, chaperones. For reference purposes, the amino acid sequence of the full length CBU_0338 sequence is provided in SEQ ID NO: 26 herein.

Preferred CBU_0338 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 26; and/or (b) comprising a fragment of at least "n" consecutive amino acids of SEQ ID NO: 26, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 26 comprise an epitope of SEQ ID NO: 26. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 26. Preferred fragments of SEQ ID NO: 26 comprise an epitope of SEQ ID NO: 26.

27. CBU_1352 Antigens

The original "CBU_1352" sequence is annotated as "Cell division protein ftsH" and is involved in cell division, chromosome partitioning. For reference purposes, the amino acid sequence of the full length CBU_1352 sequence is provided in SEQ ID NO: 27 herein.

Preferred CBU_1352 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 27; and/or (b) comprising a fragment of at least "n" consecutive amino acids of SEQ ID NO: 27, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 27 comprise an epitope of SEQ ID NO: 27. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 27. Preferred fragments of SEQ ID NO: 27 comprise an epitope of SEQ ID NO: 27.

28. CBU_1648 Antigens

The original "CBU_1648" sequence is annotated as "DotA protein" and is involved in protein and peptide secretion and trafficking. For reference purposes, the amino acid sequence of the full length CBU_1648 sequence is provided in SEQ ID NO: 28 herein.

Preferred CBU_1648 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 28; and/or (b) comprising a fragment of at least "n" consecutive amino acids of SEQ ID NO: 28, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 28 comprise an epitope of SEQ ID NO: 28. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 28. Preferred fragments of SEQ ID NO: 28 comprise an epitope of SEQ ID NO: 28.

29. CBU_1652 Antigens

The original "CBU_1652" sequence is annotated as "lcmX protein" and is involved in protein and peptide secretion and trafficking. For reference purposes, the amino acid sequence of the full length CBU_1652 sequence is provided in SEQ ID NO: 29 herein.

Preferred CBU_1652 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 29; and/or (b) comprising a fragment of at least "n" consecutive amino acids of SEQ ID NO: 29, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 29 comprise an epitope of SEQ ID NO: 29. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 29. Preferred fragments of SEQ ID NO: 29 comprise an epitope of SEQ ID NO: 29.

30. CBU_1275 Antigens

The original "CBU_1275" sequence is annotated as "Starvation sensing protein rspA" and is involved in aptation to atypical conditions—response to starvation. For reference purposes, the amino acid sequence of the full length CBU_1275 sequence is provided in SEQ ID NO: 30 herein.

Preferred CBU_1275 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 30; and/or (b) comprising a fragment of at least "n" consecutive amino acids of SEQ ID NO: 30, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 30 comprise an epitope of SEQ ID NO: 30. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 30. Preferred fragments of SEQ ID NO: 30 comprise an epitope of SEQ ID NO: 30.

31. CBU_0297 Antigens

The original "CBU_0297" sequence is annotated as "Exodeoxyribonuclease III" and is involved in DNA metabolism—Replication, recombination and repair. For reference purposes, the amino acid sequence of the full length CBU_0297 sequence is provided in SEQ ID NO: 31 herein.

Preferred CBU_0297 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 31; and/or (b) comprising a fragment of at least "n" consecutive amino acids of SEQ ID NO: 31, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 31 comprise an epitope of SEQ ID NO: 31. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 31. Preferred fragments of SEQ ID NO: 31 comprise an epitope of SEQ ID NO: 31.

32. CBU_0916 Antigens

The original "CBU_0916" sequence is annotated as "Endonuclease/Exonuclease/phosphatase family protein" and is involved in DNA metabolism—Replication, recombination and repair. For reference purposes, the amino acid sequence of the full length CBU_0916 sequence is provided in SEQ ID NO: 32 herein.

Preferred CBU_0916 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 32; and/or (b) comprising a fragment of at least "n" consecutive amino acids of SEQ ID NO: 32, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 32 comprise an epitope of SEQ ID NO: 32. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 32. Preferred fragments of SEQ ID NO: 32 comprise an epitope of SEQ ID NO: 32.

33. CBU_1183 Antigens

The original "CBU_1183" sequence is annotated as "Glycine-rich RNA-binding protein" and is involved in DNA metabolism—Replication, recombination and repair. For reference purposes, the amino acid sequence of the full length CBU_1183 sequence is provided in SEQ ID NO: 33 herein.

Preferred CBU_1183 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 33; and/or (b) comprising a fragment of at least "n" consecutive amino acids of SEQ ID NO: 33, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 33 comprise an epitope of SEQ ID NO: 33. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 33. Preferred fragments of SEQ ID NO: 33 comprise an epitope of SEQ ID NO: 33.

34. CBU_1235 Antigens

The original "CBU_1235" sequence is annotated as "Oligoribonuclease" and is involved in DNA metabolism—Replication, recombination and repair. For reference purposes, the amino acid sequence of the full length CBU_1235 sequence is provided in SEQ ID NO: 34 herein.

Preferred CBU_1235 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 34; and/or (b) comprising a fragment of at least "n" consecutive amino acids of SEQ ID NO: 34, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 34 comprise an epitope of SEQ ID NO: 34. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 34. Preferred fragments of SEQ ID NO: 34 comprise an epitope of SEQ ID NO: 34.

35. CBU_0532 Antigens

The original "CBU_0532" sequence is annotated as "COME operon protein 1" and is involved in DNA—medicated transformation (competence). For reference purposes, the amino acid sequence of the full length CBU_0532 sequence is provided in SEQ ID NO: 35 herein.

Preferred CBU_0532 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 35; and/or (b) comprising a fragment of at least "n" consecutive amino acids of SEQ ID NO: 35, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 35 comprise an epitope of SEQ ID NO: 35. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 35. Preferred fragments of SEQ ID NO: 35 comprise an epitope of SEQ ID NO: 35.

36. CBU_0758 Antigens

The original "CBU_0758" sequence is annotated as "Lipoprotein, ComL family" and is involved in DNA—medicated transformation (competence). For reference purposes, the amino acid sequence of the full length CBU_0758 sequence is provided in SEQ ID NO: 36 herein.

Preferred CBU_0758 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 36; and/or (b) comprising a fragment of at least "n" consecutive amino acids of SEQ ID NO: 36, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 36 comprise an epitope of SEQ ID NO: 36. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 36. Preferred fragments of SEQ ID NO: 36 comprise an epitope of SEQ ID NO: 36.

37. CBU_2086 Antigens

The original "CBU_2086" sequence is annotated as "Transcription termination factor rho" and is involved in transcription. For reference purposes, the amino acid sequence of the full length CBU_2086 sequence is provided in SEQ ID NO: 37 herein.

Preferred CBU_2086 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 37; and/or (b) comprising a fragment of at least "n" consecutive amino acids of SEQ ID NO: 37, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 37 comprise an epitope of SEQ ID NO: 37. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 37. Preferred fragments of SEQ ID NO: 37 comprise an epitope of SEQ ID NO: 37.

38. CBU_0043 Antigens

The original "CBU_0043" sequence is annotated as "Xanthosine triphosphate pyrophosphatase" and is involved in nucleotide and nucleoside biosynthesis and metabolism. For reference purposes, the amino acid sequence of the full length CBU_0043 sequence is provided in SEQ ID NO: 38 herein.

Preferred CBU_0043 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 38; and/or (b) comprising a fragment of at least "n" consecutive amino acids of SEQ ID NO: 38, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 38 comprise an epitope of SEQ ID NO: 38. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 38. Preferred fragments of SEQ ID NO: 38 comprise an epitope of SEQ ID NO: 38.

39. CBU_0296 Antigens

The original "CBU_0296" sequence is annotated as "Orotate phosphoribosyltransferase" and is involved in nucleotide and nucleoside biosynthesis and metabolism. For reference purposes, the amino acid sequence of the full length CBU_0296 sequence is provided in SEQ ID NO: 39 herein.

Preferred CBU_0296 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 39; and/or (b) comprising a fragment of at least "n" consecutive amino acids of SEQ ID NO: 39, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 39 comprise an epitope of SEQ ID NO: 39. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 39. Preferred fragments of SEQ ID NO: 39 comprise an epitope of SEQ ID NO: 39.

40. CBU_0531 Antigens

The original "CBU_0531" sequence is annotated as "Orotidine 5'-phosphate decarboxylase" and is involved in nucleotide and nucleoside biosynthesis and metabolism. For reference purposes, the amino acid sequence of the full length CBU_0531 sequence is provided in SEQ ID NO: 40 herein.

Preferred CBU_0531 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 40; and/or (b) comprising a fragment of at least "n" consecutive amino acids of SEQ ID NO: 40, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 40 comprise an epitope of SEQ ID NO: 40. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 40. Preferred fragments of SEQ ID NO: 40 comprise an epitope of SEQ ID NO: 40.

41. CBU_0631 Antigens

The original "CBU_0631" sequence is annotated as "Phosphoribosylformylglycinamidine synthase" and is involved in nucleotide and nucleoside biosynthesis and metabolism. For reference purposes, the amino acid sequence of the full length CBU_0631 sequence is provided in SEQ ID NO: 41 herein.

Preferred CBU_0631 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 41; and/or (b) comprising a fragment of at least "n" consecutive amino acids of SEQ ID NO: 41, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 41 comprise an epitope of SEQ ID NO: 41. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 41. Preferred fragments of SEQ ID NO: 41 comprise an epitope of SEQ ID NO: 41.

42. CBU_0796 Antigens

The original "CBU_0796" sequence is annotated as "Adenosine 5'-monophosphoramidase/Guanosine 5'-monophosphoramidase" and is involved in nucleotide and nucleoside biosynthesis and metabolism. For reference purposes, the amino acid sequence of the full length CBU_0796 sequence is provided in SEQ ID NO: 42 herein.

Preferred CBU_0796 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 42; and/or (b) comprising a fragment of at least "n" consecutive amino acids of SEQ ID NO: 2, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 42 comprise an epitope of SEQ ID NO: 42. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 42. Preferred fragments of SEQ ID NO: 42 comprise an epitope of SEQ ID NO: 42.

43. CBU_1830 Antigens

The original "CBU_1830" sequence is annotated as "Ribose-phosphate pyrophosphokinase" and is involved in nucleotide and nucleoside biosynthesis and metabolism. For reference purposes, the amino acid sequence of the full length CBU_1830 sequence is provided in SEQ ID NO: 43 herein.

Preferred CBU_1830 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 43; and/or (b) comprising a fragment of at least "n" consecutive amino acids of SEQ ID NO: 43, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 43 comprise an epitope of SEQ ID NO: 43. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 43. Preferred fragments of SEQ ID NO: 43 comprise an epitope of SEQ ID NO: 43.

44. CBU_0234 Antigens

The original "CBU_0234" sequence is annotated as "SSU ribosomal protein S7P" and is involved in translation—protein biosynthesis. For reference purposes, the amino acid sequence of the full length CBU_0234 sequence is provided in SEQ ID NO: 44 herein.

Preferred CBU_0234 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 44; and/or (b) comprising a fragment of at least "n" consecutive amino acids of SEQ ID NO: 44, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 44 comprise an epitope of SEQ ID NO: 44. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 44. Preferred fragments of SEQ ID NO: 44 comprise an epitope of SEQ ID NO: 44.

45. CBU_0445 Antigens

The original "CBU_0445" sequence is annotated as "SSU ribosomal protein S16P" and is involved in translation—protein biosynthesis. For reference purposes, the amino acid sequence of the full length CBU_0445 sequence is provided in SEQ ID NO: 45 herein.

Preferred CBU_0445 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 45; and/or (b) comprising a fragment of at least "n" consecutive amino acids of SEQ ID NO: 45, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 45 comprise an epitope of SEQ ID NO: 45. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 45. Preferred fragments of SEQ ID NO: 45 comprise an epitope of SEQ ID NO: 45.

46. CBU_0808 Antigens

The original "CBU_0808" sequence is annotated as "Valyl-tRNA synthetase" and is involved in translation—protein biosynthesis. For reference purposes, the amino acid sequence of the full length CBU_0808 sequence is provided in SEQ ID NO: 46 herein.

Preferred CBU_0808 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 46; and/or (b) comprising a fragment of at least "n" consecutive amino acids of SEQ ID NO: 46, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 46 comprise an epitope of SEQ ID NO: 46. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 46. Preferred fragments of SEQ ID NO: 46 comprise an epitope of SEQ ID NO: 46.

47. CBU_0851 Antigens

The original "CBU_0851" sequence is annotated as "SSU ribosomal protein S15P" and is involved in translation—protein biosynthesis. For reference purposes, the amino acid sequence of the full length CBU_0851 sequence is provided in SEQ ID NO: 47 herein. Preferred CBU_0851 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 47; and/or (b) comprising a fragment of at least "n" consecutive amino acids of SEQ ID NO: 47, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 47 comprise an epitope of SEQ ID NO: 47. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 47. Preferred fragments of SEQ ID NO: 47 comprise an epitope of SEQ ID NO: 47.

48. CBU_1325 Antigens

The original "CBU_1325" sequence is annotated as "Bacterial Protein Translation Initiation Factor 3 (IF-3)" and is involved in translation—protein biosynthesis. For reference purposes, the amino acid sequence of the full length CBU_1325 sequence is provided in SEQ ID NO: 48 herein.

Preferred CBU_1325 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 48; and/or (b) comprising a fragment of at least "n" consecutive amino acids of SEQ ID NO: 48, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 48 comprise an epitope of SEQ ID NO: 48. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 48. Preferred fragments of SEQ ID NO: 48 comprise an epitope of SEQ ID NO: 48.

49. CBU_1383 Antigens

The original "CBU_1383" sequence is annotated as "Ribosome Recycling Factor (RRF)" and is involved in translation—protein biosynthesis. For reference purposes, the amino acid sequence of the full length CBU_1383 sequence is provided in SEQ ID NO: 49 herein.

Preferred CBU_1383 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 49; and/or (b) comprising a fragment of at least "n" consecutive amino acids of SEQ ID NO: 49, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 49 comprise an epitope of SEQ ID NO: 49. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 49. Preferred fragments of SEQ ID NO: 49 comprise an epitope of SEQ ID NO: 49.

50. CBU_1473 Antigens

The original "CBU_1473" sequence is annotated as "Aspartyl/glutamyl-tRNA(Asn/Gln) amidotransferase subunit C" and is involved in translation—protein biosynthesis. For reference purposes, the amino acid sequence of the full length CBU_1473 sequence is provided in SEQ ID NO: 50 herein.

Preferred CBU_1473 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 50; and/or (b) comprising a fragment of at least "n" consecutive amino acids of SEQ ID NO: 50, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 50 comprise an epitope of SEQ ID NO: 50. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 50. Preferred fragments of SEQ ID NO: 50 comprise an epitope of SEQ ID NO: 50.

51. CBU_1594 Antigens

The original "CBU_1594" sequence is annotated as "GatB/Yqey domain protein" and is involved in translation—protein biosynthesis. For reference purposes, the amino acid sequence of the full length CBU_1594 sequence is provided in SEQ ID NO: 51 herein.

Preferred CBU_1594 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 51; and/or (b) comprising a fragment of at least "n" consecutive amino acids of SEQ ID NO: 51, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 51 comprise an epitope of SEQ ID NO: 51. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 51. Preferred fragments of SEQ ID NO: 51 comprise an epitope of SEQ ID NO: 51.

52. CBU_1841 Antigens

The original "CBU_1841" sequence is annotated as "Peptidyl-tRNA hydrolase" and is involved in translation—protein biosynthesis. For reference purposes, the amino acid sequence of the full length CBU_1841 sequence is provided in SEQ ID NO: 52 herein.

Preferred CBU_1841 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 52; and/or (b) comprising a fragment of at least "n" consecutive amino acids of SEQ ID NO: 52, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 52 comprise an epitope of SEQ ID NO: 52. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 52. Preferred fragments of SEQ ID NO: 52 comprise an epitope of SEQ ID NO: 52.

53. CBU_1970 Antigens

The original "CBU_1970" sequence is annotated as "Diaminopimelate epimerase" and is involved in amino acid biosynthesis and metabolism. For reference purposes, the amino acid sequence of the full length CBU_1970 sequence is provided in SEQ ID NO: 53 herein.

Preferred CBU_1970 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 53; and/or (b) comprising a fragment of at least "n" consecutive amino acids of SEQ ID NO: 53, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 53 comprise an epitope of SEQ ID NO: 53. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 53. Preferred fragments of SEQ ID NO: 53 comprise an epitope of SEQ ID NO: 53.

54. CBU_0075 Antigens

The original "CBU_0075" sequence is annotated as "2-polyprenyl-6-methoxyphenol hydroxylase" and is involved in energy metabolism—electron transport. For reference purposes, the amino acid sequence of the full length CBU_0075 sequence is provided in SEQ ID NO: 54 herein.

Preferred CBU_0075 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 54; and/or (b) comprising a fragment of at least "n" consecutive amino acids of SEQ ID NO: 54, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 54 comprise an epitope of SEQ ID NO: 54. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 54. Preferred fragments of SEQ ID NO: 54 comprise an epitope of SEQ ID NO: 54.

55. CBU_2087 Antigens

The original "CBU_2087" sequence is annotated as "Thioredoxin" and is involved in energy metabolism—electron transport. For reference purposes, the amino acid sequence of the full length CBU_2087 sequence is provided in SEQ ID NO: 55 herein.

Preferred CBU_2087 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 55; and/or (b) comprising a fragment of at least "n" consecutive amino acids of SEQ ID NO: 55, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 55 comprise an epitope of SEQ ID NO: 55. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 55. Preferred fragments of SEQ ID NO: 55 comprise an epitope of SEQ ID NO: 55.

56. CBU_0502 Antigens

The original "CBU_0502" sequence is annotated as "DNase, TatD family" and is involved in intermediary metabolism and other metabolic pathways. For reference purposes, the amino acid sequence of the full length CBU_0502 sequence is provided in SEQ ID NO: 56 herein.

Preferred CBU_0502 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 6; and/or (b) comprising a fragment of at least "n" consecutive amino acids of SEQ ID NO: 56, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 56 comprise an epitope of SEQ ID NO: 56. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 56. Preferred fragments of SEQ ID NO: 56 comprise an epitope of SEQ ID NO: 56.

57. CBU_0288 Antigens

The original "CBU_0288" sequence is annotated as and is involved in intermediary metabolism and other metabolic pathways "Phosphopantetheine adenylyltransferase". For reference purposes, the amino acid sequence of the full length CBU_0288 sequence is provided in SEQ ID NO: 57 herein.

Preferred CBU_0288 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 57; and/or (b) comprising a fragment of at least "n" consecutive amino acids of SEQ ID NO: 57, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 57 comprise an epitope of SEQ ID NO: 57. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 57. Preferred fragments of SEQ ID NO: 57 comprise an epitope of SEQ ID NO: 57.

58. CBU_0928 Antigens

The original "CBU_0928" sequence is annotated as "Pyridoxamine 5'-phosphate oxidase" and is involved in intermediary metabolism and other metabolic pathways. For reference purposes, the amino acid sequence of the full length CBU_0928 sequence is provided in SEQ ID NO: 58 herein.

Preferred CBU_0928 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 58; and/or (b) comprising a fragment of at least "n" consecutive amino acids of SEQ ID NO: 58, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 58 comprise an epitope of SEQ ID NO: 58. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 58. Preferred fragments of SEQ ID NO: 58 comprise an epitope of SEQ ID NO: 58.

59. CBU_0738 Antigens

The original "CBU_0738" sequence is annotated as "ATP-dependent endopeptidase clp proteolytic subunit clpP" and is involved in posttranslational modification, degradation, protein turnover, chaperones. For reference purposes, the amino acid sequence of the full length CBU_0738 sequence is provided in SEQ ID NO: 59 herein.

Preferred CBU_0738 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 59; and/or (b) comprising a fragment of at least "n" consecutive amino acids of SEQ ID NO: 59, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 59 comprise an epitope of SEQ ID NO: 59. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 59. Preferred fragments of SEQ ID NO: 59 comprise an epitope of SEQ ID NO: 59.

60. CBU_2012 Antigens

The original "CBU_2012" sequence is annotated as "ATP-dependent endopeptidase hsl ATP-binding subunit hslU" and is involved in posttranslational modification, degradation, protein turnover, chaperones. For reference purposes, the amino acid sequence of the full length CBU_2012 sequence is provided in SEQ ID NO: 60 herein.

Preferred CBU_2012 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 60; and/or (b) comprising a fragment of at least "n" consecutive amino acids of SEQ ID NO: 60, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 60 comprise an epitope of SEQ ID NO: 60. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 60. Preferred fragments of SEQ ID NO: 60 comprise an epitope of SEQ ID NO: 60.

61. CBU_2092 Antigens

The original "CBU_2092" sequence is annotated as "Phosphoenolpyruvate carboxykinase [ATP]" and is involved in lipopolysaccharide biosynthesis and metabolism. For reference purposes, the amino acid sequence of the full length CBU_2092 sequence is provided in SEQ ID NO: 61 herein.

Preferred CBU_2092 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 61; and/or (b) comprising a fragment of at least "n" consecutive amino acids of SEQ ID NO: 61, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 61 comprise an epitope of SEQ ID NO: 61. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 61. Preferred fragments of SEQ ID NO: 61 comprise an epitope of SEQ ID NO: 61.

62. CBU_0091 Antigens

The original "CBU_0091" sequence is annotated as "Peptidoglycan-associated lipoprotein OmpA-like" and is involved in protein and peptide secretion and trafficking. For reference purposes, the amino acid sequence of the full length CBU_0091 sequence is provided in SEQ ID NO: 62 herein.

Preferred CBU_0091 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 62; and/or (b) comprising a fragment of at least "n" consecutive amino acids of SEQ ID NO: 62, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 62 comprise an epitope of SEQ ID NO: 62. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 62. Preferred fragments of SEQ ID NO: 62 comprise an epitope of SEQ ID NO: 62.

63. CBU_0155 Antigens

The original "CBU_0155" sequence is annotated as "Type 4 pili biogenesis protein pilB (nucleotide-binding protein)" and is involved in protein and peptide secretion and trafficking. For reference purposes, the amino acid sequence of the full length CBU_0155 sequence is provided in SEQ ID NO: 63 herein.

Preferred CBU_0155 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 63; and/or (b) comprising a fragment of at least "n" consecutive amino acids of SEQ ID NO: 63, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 63 comprise an epitope of SEQ ID NO: 63. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 63. Preferred fragments of SEQ ID NO: 63 comprise an epitope of SEQ ID NO: 63.

64. CBU_1136 Antigens

The original "CBU_1136" sequence is annotated as "Enhanced entry protein enhC, tetratricopeptide repeat family" and is involved in pathogenicity and pathogenesis. For reference purposes, the amino acid sequence of the full length CBU_1136 sequence is provided in SEQ ID NO: 64 herein.

Preferred CBU_1136 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 64; and/or (b) comprising a fragment of at least "n" consecutive amino acids of SEQ ID NO: 64, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 64 comprise an epitope of SEQ ID NO: 64. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 64. Preferred fragments of SEQ ID NO: 64 comprise an epitope of SEQ ID NO: 64.

65. CBU_0943 Antigens

The original "CBU_0943" sequence is annotated as "Rhodanese-related sulfurtransferases" and is involved in detoxication and resistance. For reference purposes, the amino acid sequence of the full length CBU_0943 sequence is provided in SEQ ID NO: 65 herein.

Preferred CBU_0943 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 65; and/or (b) comprising a fragment of at least "n" consecutive amino acids of SEQ ID NO: 65, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 65 comprise an epitope of SEQ ID NO: 65. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 65. Preferred fragments of SEQ ID NO: 65 comprise an epitope of SEQ ID NO: 65.

66. CBU_1708 Antigens

The original "CBU_1708" sequence is annotated as "Superoxide dismutase" and is involved in detoxication and resistance. For reference purposes, the amino acid sequence of the full length CBU_1708 sequence is provided in SEQ ID NO: 66 herein.

Preferred CBU_1708 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 66; and/or (b) comprising a fragment of at least "n" consecutive amino acids of SEQ ID NO: 66, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 66 comprise an epitope of SEQ ID NO: 66. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 66. Preferred fragments of SEQ ID NO: 66 comprise an epitope of SEQ ID NO: 66.

67. CBU_1916 Antigens

The original "CBU_1916" sequence is annotated as "Universal stress protein A" and is involved in adaptation to atypical condition—response to starvation. For reference purposes, the amino acid sequence of the full length CBU_1916 sequence is provided in SEQ ID NO: 67 herein.

Preferred CBU_1916 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 67; and/or (b) comprising a fragment of at least "n" consecutive amino acids of SEQ ID NO: 67, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 67 comprise an epitope of SEQ ID NO: 67. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 67. Preferred fragments of SEQ ID NO: 67 comprise an epitope of SEQ ID NO: 67.

68. CBU_0114 Antigens

The original "CBU_0114" sequence is annotated as "Protein yajQ". For reference purposes, the amino acid sequence of the full length CBU_0114 sequence is provided in SEQ ID NO: 68 herein.

Preferred CBU_0114 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 68; and/or (b) comprising a fragment of at least "n" consecutive amino acids of SEQ ID NO: 68, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 68 comprise an epitope of SEQ ID NO: 68. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 68. Preferred fragments of SEQ ID NO: 68 comprise an epitope of SEQ ID NO: 68.

69. CBU_0510 Antigens

The original "CBU_0510" sequence is annotated as "Hypothetical protein". For reference purposes, the amino acid sequence of the full length CBU_0510 sequence is provided in SEQ ID NO: 69 herein.

Preferred CBU_0510 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 69; and/or (b) comprising a fragment of at least "n" consecutive amino acids of SEQ ID NO: 69, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 69 comprise an epitope of SEQ ID NO: 69. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 69. Preferred fragments of SEQ ID NO: 69 comprise an epitope of SEQ ID NO: 69.

70. CBU_0656 Antigens

The original "CBU_0656" sequence is annotated as "Hypothetical transcriptional regulatory protein". For reference purposes, the amino acid sequence of the full length CBU_0656 sequence is provided in SEQ ID NO: 70 herein.

Preferred CBU_0656 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 70; and/or (b) comprising a fragment of at least "n" consecutive amino acids of SEQ ID NO: 70, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 70 comprise an epitope of SEQ ID NO: 70. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 70. Preferred fragments of SEQ ID NO: 70 comprise an epitope of SEQ ID NO: 70.

71. CBU_2009 Antigens

The original "CBU_2009" sequence is annotated as "Hypothetical protein". For reference purposes, the amino acid sequence of the full length CBU_2009 sequence is provided in SEQ ID NO: 71 herein.

Preferred CBU_2009 polypeptides for use with the invention comprise an amino acid sequence (a) having 70% or more identity (e.g. 70%, 75%, 80%, 85%, 90%, 91%, 92%, 93%, 94%, 95%, 96%, 97%, 98%, 99%, 99.5%, 99.9% or more) to SEQ ID NO: 71; and/or (b) comprising a fragment of at least "n" consecutive amino acids of SEQ ID NO: 71, wherein "n" is 7 or more (e.g. 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250 or more). Preferred variants of SEQ ID NO: 71 comprise an epitope of SEQ ID NO: 71. Other preferred fragments lack one or more amino acids (e.g. 1, 2, 3, 4, 5, 6, 7, 8, 9, 10, 11, 12, 13, 14, 15, 20, 25, 30 or more) from the N-terminus and/or one or more amino acids (e.g. 1, 2, 3, 4, 5, 6, 7, 8, 9, 10, 11, 12, 13, 14, 15, 20, 25, 30 or more) from the C-terminus of SEQ ID NO: 71. Preferred fragments of SEQ ID NO: 71 comprise an epitope of SEQ ID NO: 71.

Protein antigens of the invention typically induce protective antibodies or stimulate an amnestic cytotoxic T-cell response against *C. burnetii*. In other words, protein antigens of the invention are typically protective antigens.

In one embodiment of the invention, the protein antigen is involved in DNA metabolism—replication, recombination and repair. Thus, in one embodiment, the protein antigen is selected from: a CBU_1337 antigen, a CBU_0297 antigen, a CBU_0916 antigen, a CBU_1183 antigen, and a CBU_1235 antigen.

In one embodiment of the invention, the protein antigen is involved in DNA—mediated transformation (competence). Thus, in one embodiment, the protein antigen is selected from: a CBU_0532 antigen and a CBU_0758 antigen.

In one embodiment of the invention, the protein antigen is involved in transcription. Thus, in one embodiment, the protein antigen is selected from: a CBU_0232 antigen, a CBU_0852 antigen, and a CBU_2086 antigen.

In one embodiment of the invention, the protein antigen is involved in nucleotide and nucleoside biosynthesis and metabolism. Thus, in one embodiment, the protein antigen is selected from: a CBU_0326 antigen, a CBU_0897 antigen, a CBU_1384 antigen, a CBU_0043 antigen, a CBU_0296 antigen, a CBU_0531 antigen, a CBU_0631 antigen, a CBU_0796 antigen, and a CBU_1830 antigen.

In one embodiment of the invention, the protein antigen is involved in regulatory function. Thus, in one embodiment, the protein antigen is a CBU_1579 antigen.

In one embodiment of the invention, the protein antigen is involved in translation—protein biosynthesis. Thus, in one embodiment, the protein antigen is selected from: a CBU_1475 antigen, a CBU_0234 antigen, a CBU_0445 antigen, a CBU_0808 antigen, a CBU_0851 antigen, a CBU_1325 antigen, a CBU_1383 antigen, a CBU_1473 antigen, a CBU_1594 antigen, and a CBU_1841 antigen.

In one embodiment of the invention, the protein antigen is involved in Amino acid biosynthesis and metabolism. Thus, in one embodiment, the protein antigen is selected from: a CBU_0517 antigen, and a CBU_1970 antigen.

In one embodiment of the invention, the protein antigen is involved in energy metabolism—electron transport. Thus, in one embodiment, the protein antigen is selected from: a CBU_0270 antigen, a CBU_0629 antigen, a CBU_0974 antigen, a CBU_1088 antigen, a CBU_1116 antigen, a CBU_1193 antigen, a CBU_1296 antigen, a CBU_1397 antigen, a CBU_1400 antigen, a CBU_1401 antigen, a CBU_1720 antigen, a CBU_0075 antigen, and a CBU_2087 antigen.

In one embodiment of the invention, the protein antigen is involved in Intermediary metabolism and other metabolic pathways. Thus, in one embodiment, the protein antigen is selected from: a CBU_0638 antigen, a CBU_0640 antigen, a CBU_0962 antigen, a CBU_0502 antigen, a CBU_0288 antigen, and a CBU_0928 antigen.

In one embodiment of the invention, the protein antigen is involved in posttranslational modification, degradation, protein turnover, chaperones. Thus, in one embodiment, the protein antigen is selected from: a CBU_0073 antigen, a CBU_0094 antigen, a CBU_0338 antigen, a CBU_0738 antigen, and a CBU_2012 antigen.

In one embodiment of the invention, the protein antigen is involved in cell division, chromosome partitioning. Thus, in one embodiment, the protein antigen is a CBU_1352 antigen.

In one embodiment of the invention, the protein antigen is involved in Protein and peptide secretion and trafficking. Thus, in one embodiment, the protein antigen is selected from: a CBU_1648 antigen, a CBU_1652 antigen, a CBU_0091 antigen, and a CBU_0155 antigen.

In one embodiment of the invention, the protein antigen is involved in adaptation to atypical conditions—response to starvation. Thus, in one embodiment, the protein antigen is selected from: a CBU_1275 antigen, and a CBU_1916 antigen.

In one embodiment of the invention, the protein antigen is involved in lipopolysaccharide biosynthesis and metabolism. Thus, in one embodiment, the protein antigen is a CBU_2092 antigen.

In one embodiment of the invention, the protein antigen is involved in pathogenicity and pathogenesis. Thus, in one embodiment, the protein antigen is a CBU_1136 antigen.

In one embodiment of the invention, the protein antigen is involved in detoxication and Resistance. Thus, in one embodiment, the protein antigen is selected from: CBU_0943 antigen, and a CBU_1708 antigen.

In one embodiment of the invention, the protein antigen is selected from: a CBU_0114 antigen, a CBU_0510 antigen, a CBU_0656 antigen, and a CBU_2009 antigen.

Proteins of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Proteins of the invention can be prepared by various means (e.g. recombinant expression, purification from cell culture, chemical synthesis, etc.). Protein antigens of the invention are typically recombinant.

Polypeptides used with the invention are preferably provided in purified or substantially purified form i.e. substantially free from other polypeptides (e.g. free from naturally-occurring polypeptides), particularly from other *C. burnetii* or host cell polypeptides, and are generally at least about 50% pure (by weight), and usually at least about 90% pure, e.g. about 95% pure. In other words, typically, less than about 50%, and more preferably less than about 10%, e.g. 5% of a composition of the invention comprises other expressed proteins. Thus the antigens in the compositions of the invention are separated from the whole organism with which the molecule is expressed.

Protein antigens of the invention may be expressed as a fusion protein, Fusion proteins of the invention may comprise 1, 2, 3, 4, 5 or more protein antigens of the invention.

In one embodiment, at least two of the protein antigens of the invention are in the form of a hybrid protein.

In one embodiment, a protein antigen of the invention comprises a sequence -P-A- or -A-P-, wherein: —P— is a protein antigen sequence as described above (i.e. a CBU antigen), and -A- is not a sequence as defined above. Examples of -A- include, purification tag(s), signal peptide(s), chaperonin(s), discussed below.

To facilitate removal of the -A- moiety during purification, a unique protease site may be inserted between the -A- moiety and the protein antigen per se. Such protease sites may include those for thrombin, factor Xa, enterokinase, PreScission™, Sumo™. Alternatively, removal of the -A- moiety may be achieved via inclusion of an intein sequence between the signal peptide and the protein antigen per se. Inteins are self-cleaving proteins and in response to a stimulus (e.g. lowered pH) are capable of self-splicing at the junction between the intein and the protein antigen construct thus eliminating the need for the addition of specific proteases. Examples of inteins include domains derived from *Mycobacterium tuberculosis* (RecA), and *Pyrococcus horikoshii* (RadA).

In one embodiment, protein antigens of the invention comprise a fusion protein partner to facilitate soluble expression. Fusion protein partners may be attached at the N- or C-terminus of the protein antigen but are usually placed at the N-terminal end. Examples of fusion partners are: NusA, thyrodoxin, maltose-binding protein, small ubiquitin-like molecules (Sumo-tag).

To facilitate purification, protein antigens of the invention may include one or more purification tags to enable specific chromatography steps (e.g. metal ion chelating, affinity chromatography) to be included in the purification processes. Such purification tags may, for example, include: repeat histidine residues (e.g. 6-10 histidine residues), maltose binding protein, glutathione S-transferase; and strepavidin. These tags may be attached at the N- and/or C-terminus of the protein antigens of the invention. To facilitate removal of such tags during purification, protease sites and/or inteins (examples above) may be inserted between the protein antigen and the purification tag(s).

Thus, a typical protein antigen of the invention (starting from the N-terminus) may comprise:

- a first purification tag
- a fusion protein partner (to facilitate expression)
- a first (preferably specific) protease sequence or intein sequence
- the protein antigen sequence
- an optional second (preferably specific) protease sequence or intein sequence
- an optional second purification tag The first and second purification tags may be the same or different. Similarly, the first and second protease/intein sequence may be the same or different. The first and second options are preferably different to enable selective and controllable cleavage/purification.

In one embodiment spacers are introduced to distance the purification tag from the protein antigen—this can help to increase binding efficiency to affinity purification column media. The spacer may be placed (immediately) after the purification tag or between the fusion protein partner and the protein antigen per se. Typical spacer sequences may consist of between 10-40 amino acid residues to give either a linear or alpha-helical structure.

Accordingly, in one embodiment, a protein antigen of the invention may comprise (starting from the N-terminus):

- a first purification tag
- an optional first spacer sequence
- a fusion protein partner (to facilitate expression)
- an optional second spacer sequence
- a (preferably specific) protease sequence or intein sequence
- the protein antigen sequence
- an optional second (preferably specific) protease sequence or intein sequence
- an optional third spacer sequence
- an optional second purification tag In one embodiment, protein antigens of the invention comprise a signal peptide to target them for secretion into the periplasm of the host cell. A signal peptide may be attached at the N- or C-terminus of the protein antigen but is usually placed at the N-terminal end. Examples of fusion partners are: PelB and ompT.

In one embodiment, protein antigens of the invention comprise a chaperonin protein to help enhance folding, presentation and immunogenicity of the protein antigen(s) per se. A chaperonin may be attached at the N- or C-terminus of the protein antigen but is usually placed at the N-terminal end. Examples of chaperonins are: GroEL and GroES.

In one embodiment, one or more protein antigens of the invention are used as carrier protein(s), typically for use in a conjugate vaccine. In one embodiment, protein antigen(s) of the invention are conjugated to one or more saccharide antigen(s). In one embodiment, protein antigen(s) of the invention are conjugated to one or more lipid antigen(s). In one embodiment, one or more protein antigen(s) of the invention are conjugated to one or more lipopolysaccharide antigen(s). Typically, conjugation of one or more protein antigen (s) of the invention to a polysaccharide, lipid or lipopolysaccharide provides an increased immune response, compared with the immune response elicited by un-conjugated polysaccharide, lipid or lipopolysaccharide. In one embodiment, the polysaccharide, lipid or lipopolysaccharide is from *C. burnetii*. Non-limiting methods of conjugating protein(s) to polysaccharide, lipid or lipopolysaccharide are known in the art; for example, via the use of heterobifunctional crosslinking agents or homobifunctional crosslinking agents.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In one homology comparison, the identity exists over a region of the sequences that is at least 10 or 20 or 30 or 40 or 50 amino acid residues in length. In another homology comparison, the identity exists over a region of the sequences that is at least 60 or 70 or 80 or 90 or 100 amino acid residues in length.

Where the invention concerns an "epitope", this epitope may be a B-cell epitope and/or a T-cell epitope, Such epitopes can be identified empirically [e.g. using PEPSCAN or similar methods), or they can be predicted {e.g. using the Jameson-Wolf antigenic index, matrix-based approaches, MAPITOPE, TEPITOPE, neural networks, OptiMer & EpiMer, ADEPT, Tsites, hydrophilicity, antigenic index or other methods known in the art. Epitopes are the parts of an immunogen that are recognised by and bind to the antigen binding sites of antibodies or T-cell receptors, and they may also be referred to as "antigenic determinants".

In one aspect, the invention provides an immunogenic composition comprising one or more protein antigens of the invention.

In one embodiment of the invention, the immunogenic composition comprises a single type of protein antigen of the invention. In one embodiment, immunogenic composition comprises two or more different types of protein antigen of the invention (e.g. 2, 3, 4, 5, 6, 7, 8, 9, 10 or more different protein antigens).

In one embodiment, said one or more protein antigens of the invention are selected from: (1) a CBU_0091 antigen; (2) a CBU_1648 antigen; (3) a CBU_1652 antigen; (4) a CBU_0510 antigen; (5) a CBU_2009 antigen; (6) a CBU_1579 antigen; (7) a CBU_1193 antigen; (8) a CBU_1400 antigen; (9) a CBU_1401 antigen; (10) a CBU_0962 antigen; (11) a CBU_0094 antigen; (12) a CBU_0338 antigen; (13) a CBU_1352 antigen; (14) a CBU_0532 antigen; (15) a CBU_0758 antigen; (16) a CBU_0631 antigen; (17) a CBU_0075 antigen; (18) a CBU_1136 antigen; and (19) a CBU_1708 antigen.

In one embodiment, said one or more protein antigens of the invention are selected from: (1) a CBU_0091 antigen; (2) a CBU_1648; (3) a CBU_1652 antigen; (4) a CBU_0510 antigen; and (5) a CBU_2009 antigen.

The immunogenic composition of the invention is typically a vaccine, preferably a subunit vaccine.

In one embodiment, the immunogenic composition comprises a pharmaceutically acceptable carrier or excipient. For the preparation of immunogenic compositions of the invention, the active immunogenic ingredients (whether these be protein antigen(s) of the present invention and/or corresponding antibodies of the invention that bind thereto) may be mixed with carriers or excipients, which are pharmaceutically acceptable and compatible with the active ingredient. Suitable carriers and excipients include, for example, water, saline, dextrose, glycerol, ethanol, or the like and combinations thereof. In addition, if desired, the immunogenic composition may contain minor amounts of auxiliary substances such as wetting or emulsifying agents, pH buffering agents, and/or adjuvants which enhance the effectiveness of the immunogenic composition.

In one embodiment, the immunogenic composition comprises an adjuvant. A non-limiting example of an adjuvant with the scope of the invention is aluminium hydroxide. Other non-limiting examples of adjuvants include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

In one embodiment, immunogenic compositions of the invention comprise a chaperonin protein. In one embodiment, chaperonin is in the form of a fusion protein. In one embodiment, chaperonin is not in the form of a fusion protein.

In one embodiment of the invention, preventing, treating or suppressing C. burnetii infection comprises administration of one or more additional therapeutic agent(s). In one embodiment, the immunogenic composition comprises one or more additional therapeutic agent(s). Such additional therapeutic agent(s) include, for example, bacteriostatic agent(s), such as co-trimoxazole, and/or bactericidal agent(s), such as doxycycline and/or hydroxychloroquine.

Typically, the immunogenic compositions of the invention are prepared as injectables, either as liquid solutions or suspensions. Solid forms suitable for solution in, or suspension in, liquid prior to injection may also be prepared. The preparation may also be emulsified, or the peptide encapsulated in liposomes or microcapsules. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of about 0.5% to 10%, including for instance, about 1%-2%.

Protein antigens of the invention may be formulated for human or animal use in a number of ways. For example, formulation may include treatment with an agent to introduce intra-molecular cross-links. One example of such an agent is formaldehyde, which may be incubated, for example, with protein antigen of the invention for between 1-24 hours. Alternatively, longer incubation times of, for example, up to 2, 4, 6, 8 or 10 days may be employed. Following treatment with such an agent, protein antigens of the invention may be combined with a suitable adjuvant, which may differ depending on whether the protein antigen is intended for human or animal use.

An immunogenic composition of the invention vaccine may contain one or more protein antigen(s) of the present invention. Thus, in one embodiment, formulation of an immunogenic composition of the invention comprises the following steps:
  providing one or more protein antigen(s) in suitable buffer system;
  optionally treating said one or more protein antigen(s) of the invention with a toxoiding component such as formaldehyde;
  optionally transferring the one or more protein antigen(s) to a new buffer system;
  combining the one or more protein antigen(s) with one or more suitable adjuvants and optionally other excipients.

In one embodiment, the immunogenic composition is for use in raising an immune response in a patient.

In a preferred embodiment, the immune response is a protective immune response. A protective immune response confers immunological cellular memory upon the subject, with the effect that a secondary exposure to the same or a similar antigen is characterised by e.g. (a) shorter lag phase than after initial exposure to the antigen; (b) production of antibody which continues for a longer period than after initial exposure to the antigen; (c) a change in the type and quality of antibody produced in comparison to initial exposure to the antigen; (d) a shift in class response, with IgG antibodies appearing in higher concentrations and with greater persistence than IgM, than after initial exposure to the antigen; (e) increased average affinity (binding constant) of the antibodies for the antigen compared with initial exposure to the antigen; and/or (f) characteristics known in the art to characterize a secondary immune response.

In one embodiment, the immunogenic composition of the invention is for use in preventing, treating or suppressing C. burnetii infection in a patient. In one embodiment, the invention provides use of the immunogenic composition of the invention in preventing, treating or suppressing C. burnetii infection in a patient. In one embodiment, the invention provides a method of preventing, treating or suppressing C. burnetii infection in a patient, said method comprising administering to the patient the immunogenic composition of the invention.

The patient is typically a mammal. In one embodiment, the mammal is a human. In one embodiment, the mammal is non-human. Typical non-human patients include ungulates (typically cow, sheep or goat). Use of the invention with domesticated live stock is highly advantageous because it provides reduced abortion frequency (providing economic benefits, and reduced animal suffering), and decreased risk of secondary transmission of C. burnetii infection to humans.

Thus, the present invention provides an effective means for preventing, treating or suppressing C. burnetii infection (or a symptom thereof).

In one embodiment, immunogenic compositions of the invention are used prophylactically to prevent the onset of C. burnetii infection in a patient. In such embodiments, the patient is typically at increased risk of becoming infected with C. burnetii, e.g. a worker in an abattoir, resident in the close vicinity of an abattoir, laboratory workers, or military personnel. In one embodiment, the patient is pregnant. In one embodiment, the patient is likely to become pregnant. In one embodiment, the patient is immune-suppressed. In one embodiment, the patient has heart damage. Due to the reduced side effects associated with the protein antigens of the invention, immunogenic compositions of the invention may be used for widespread vaccination strategies. Immunogenic compositions for use in prophylaxis are administered at a prophylactically effective amount, i.e. they contain protein antigen(s) in any amount that, when administered alone or in combination to a patient, triggers an immune response against C. burnetii, and so inhibits or delays the onset or recurrence of at least one of the clinical symptoms of C. burnetii infection. In one embodiment, the prophylactically effective amount prevents the onset or reoccurrence of the C. burnetii infection. "Inhibiting" the onset means either lessening the likelihood of the infection's onset, or preventing the onset entirely.

In one embodiment, immunogenic compositions of the invention are used to treat or suppress C. burnetii infection in a patient. In such cases, the patient is infected with C. burnetii, or has a symptom of C. burnetii infection (e.g. symptoms from high fevers (up to 40-41° C.), severe headache, general malaise, myalgia, chills and/or sweats, nonproductive cough, nausea, vomiting, diarrhoea, abdominal pain and chest pain). In one embodiment, treating or suppressing C. burnetii infection comprises administering a composition of the invention to the patient within 5 days of infection with C. burnetii. In one embodiment, the composition is administered to the patient within 2 days of infection, preferably within 1 day of infection with C. burnetii, more preferably within 12 hours of infection with *C. burnetii*, most preferably within 6 hours of infection with *C. burnetii*. Said "infection with *C. burnetii*" includes exposure to a sample suspected of containing, or known to contain *C. burnetii*.

In one embodiment, treating or suppressing *C. burnetii* infection comprises administering a composition of the invention to the patient within 5 days of displaying symptoms of *C. burnetii* infection. In one embodiment, the composition is administered to the patient within 2 days of displaying symptoms of *C. burnetii* infection, preferably within 1 day of displaying symptoms of *C. burnetii* infection, more preferably within 12 hours of displaying symptoms of *C. burnetii* infection, most preferably within 6 hours of displaying symptoms of *C. burnetii* infection.

In one embodiment, treating or suppressing *C. burnetii* infection comprises administering a composition of the invention to the patient 5 days or more after infection with *C. burnetii*. In one embodiment, the composition is administered to the patient between 5-10 days after infection with *C. burnetii*. In one embodiment, the composition is administered to the patient between 5-10 days after infection with *C. burnetii* e.g. 5-9, 5-8 or 5-7 days after infection with *C. burnetii*. Said "infection with *C. burnetii*" includes exposure to a sample suspected of containing, or known to contain *C. burnetii*.

In one embodiment, treating or suppressing *C. burnetii* infection comprises administering a composition of the invention to the patient 5 days or more after displaying symptoms of *C. burnetii* infection. In one embodiment, the composition is administered to the patient between 5-10 days after displaying symptoms of *C. burnetii* infection. In one embodiment, the composition is administered to the patient between 5-10 days after displaying symptoms of *C. burnetii* infection e.g. 5-9, 5-8 or 5-7 days after displaying symptoms of *C. burnetii* infection.

In one embodiment, treating or suppressing *C. burnetii* infection in a patient comprises administering to the patient one or more protein antigens of the invention. In one embodiment, treating or suppressing *C. burnetii* infection in a patient comprises administering to the patient one or more antibodies of the invention. Typically, treating or suppressing *C. burnetii* infection in a patient comprises administering to the patient one or more antibodies of the invention.

Administration of immunogenic compositions of the invention is generally by conventional routes e.g. intravenous, intramuscular, subcutaneous, intraperitoneal, or mucosal routes. The administration may be by parenteral injection, for example, a subcutaneous or intramuscular injection. In one embodiment, administration is intravenous. In one embodiment, administration is intraperitoneal. In one embodiment, administration is intramuscular.

The immunogenic compositions are administered in a manner compatible with the dosage formulation, and in such amount as will be effective for treatment, prevention and/or suppression of *C. burnetii* infection. The quantity to be administered, which is generally in the range of 5 micrograms to 250 micrograms of antigen per dose, depends on the subject to be treated, capacity of the patient's immune system to synthesize antibodies, and the degree of protection desired. Precise amounts of active ingredient required to be administered may depend on the judgment of the practitioner and may be particular to each patient.

The immunogenic compositions of the invention may be given in a single dose schedule, or optionally in a multiple dose schedule. A multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In one embodiment, the one or more additional therapeutic agent(s) is administered prior to administration of one or more protein antigen(s) of the invention. In one embodiment, the one or more additional therapeutic agent(s) is administered after administration of one or more protein antigen(s) of the invention. In one embodiment, the one or more additional therapeutic agent(s) is administered concurrently with one or more protein antigen(s) of the invention.

In addition, the immunogenic compositions of the invention may be administered in conjunction with other immunoregulatory agents, for example, immunoglobulins, antibiotics, interleukins (e.g., IL-2, IL-12), and/or cytokines.

The invention provides nucleic acid encoding one or more of the protein antigens of the invention. The nucleic is typically an isolated nucleic acid.

Nucleic acids encoding protein antigens of the invention may be generated by PCR from *C. burnetii* genomic DNA. Amplification products may be sequenced by standard methods to ensure integrity. In a preferred embodiment, nucleic acids of the invention are codon optimised for expression in a host cell. Methods of optimising nucleic acids for expression in a host cell are known in the art. The host cell is preferably *E. coli*.

In one embodiment, the invention provides a vector comprising a promoter operatively linked to nucleic acid as defined above. In one embodiment, the vector is a pET vector. Other suitable vectors are readily identifiable.

The invention also provides a cell capable of protein expression comprising a vector as described above. Preferably, the cell capable of protein expression is not *C. burnetii*. In one embodiment, the cell is *E. coli*. In one embodiment, the cell is a human cell. In one embodiment, the human cell is a HEK293T cell.

The present invention also provides a method for expressing one or more of the aforementioned protein antigens of the invention, said method comprising:

1) providing a nucleic acid sequence that encodes one or more of said protein antigens in a host cell, wherein said nucleic acid sequence is operably linked to a promoter; and 2) expressing said nucleic acid sequence in the host cell.

The invention also provides a *C. burnetii* protein antigen obtainable from a host cell of the invention.

The invention also provides a composition comprising (i) one or more nucleic acid(s) of the invention, or one or more nucleic acid(s) complementary thereto. Optionally, said composition further comprises a pharmaceutically acceptable carrier or excipient. In one embodiment, said composition is for use in nucleic acid immunisation.

Antibodies of the present invention interact with epitopes of *C. burnetii* protein antigen(s) of the invention. An antibody that binds to a protein antigen of the invention is one capable of binding that antigen with sufficient affinity such that the antibody is useful as a therapeutic agent. An antibody that binds to a protein antigen of the invention is one that binds to said protein antigen with an affinity ($K_a$) of at least $10^4$ M. In one embodiment, the antibody is a neutralising antibody. Neutralising activity of a substance may be measured by its ability to reduce or prevent the infection of mammalian cells grown in culture. Infection of cultured mammalian cells is associated with the presence of large vacuoles containing many *C. burnetii*.

Thus, the invention provides an antibody that binds to a protein antigen of the invention.

Antibodies of the invention are typically protective antibodies.

The invention provides antibody of the invention for use in the prevention, treatment or suppression of *C. burnetii* infection in a patient.

The invention also provides a corresponding method prevention, treatment or suppression of *C. burnetii* infection in a patient, comprising administering to said patient antibody of the invention.

A therapeutically effective amount refers to the amount of the antibody, which when administered alone or in combination to a patient for treating, suppressing or preventing *C. burnetii* infection, or at least one of the clinical symptoms of *C. burnetii* infection, is sufficient to affect such treatment of the infection, or symptom. The therapeutically effective amount can vary depending, for example, on the antibody, the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects.

In one embodiment, the method of treating *C. burnetii* infection comprises administering antibody of the invention systemically (e.g. once or twice per day, or once or twice or 3- or 4-times per every 3-4 days; for a short period of typically 1-2 weeks) followed by a more prolonged period of administration (e.g. once or twice or 3- or 4- or 5- or 6-times per day, or once or twice or 3- or 4- or 5- or 6-times per every 3-4 days, or once or twice or 3- or 4- or 5- or 6-times per week) of antibody. Administration routes include subcutaneous, intramuscular, intraperitoneal, and intravenous. The administration route is preferably intravenous, intramuscular or intraperitoneal.

When administered systemically, the antibodies are formulated accordingly (e.g. such formulations are typically provided as isotoxic aqueous formulations and do not require means for protection against stomach acid or stomach enzymes such as trypsin and/or chymotrypsin).

In one embodiment, preventing, treating or suppressing *C. burnetii* infection comprises administering antibody of the invention to the patient prior to infection with *C. burnetii* infection, and before presentation of symptoms of *C. burnetii* infection. In one embodiment, the composition is administered to the patient within 1 day of infection with *C. burnetii*. In one embodiment, the composition is administered to the patient within 2 days of infection with *C. burnetii*. In one embodiment, the composition is administered to the patient within 3 days of infection with *C. burnetii*. In one embodiment, the composition is administered to the patient within 4 days of infection with *C. burnetii*. In one embodiment, the composition is administered to the patient within 5 days of infection with *C. burnetii*. In one embodiment, the composition is administered to the patient within 6 days of infection with *C. burnetii*. In one embodiment, the composition is administered to the patient within 7 days of infection with *C. burnetii*.

In use, the present invention employs a composition, comprising antibody of the present invention in a form suitable administration. The purified intact antibodies, or their fragments, are formulated for such delivery. For example, antibody, or its fragment, at a concentration between 5-50 or 15-50 or 25-50 g/litre may be formulated in buffer. Examples of suitable buffer components include physiological salts such as sodium citrate and/or citric acid. Preferred buffers contain 100-200 or 125-175 or approximately 150 (e.g. 153) mM physiological salts such as sodium chloride.

In preparing compositions of the invention, the antibodies and/or fragments thereof can be dissolved in a vehicle, and sterilised, for example by filtration through a sterile filter using aseptic techniques, before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

The dosage ranges for administration of the antibodies of the present invention are those to produce the desired therapeutic effect. It will be appreciated that the dosage range required depends on the precise nature of the antibody or composition, the nature of the formulation, the age of the patient, the nature, extent or severity of the patient's condition, contraindications, if any, and the judgement of the attending physician. Variations in these dosage levels can be adjusted using standard empirical routines for optimisation.

In one embodiment, typical daily dosages are in the range of 5-20 mg (e.g. 8-15 mg or approximately 10 mg) per kg of body weight. The unit dosage can vary from less than 100 mg, but typically will be in the region of 250-500 mg per dose, which may be administered daily (e.g. 1×, 2×, 3× or 4× per day) or less frequently (e.g. on alternative days, or say once per week).

An "antibody" is used in the broadest sense and specifically covers polyclonal antibodies and antibody fragments so long as they exhibit the desired biological activity. In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a C. burnetii protein antigen of the invention, e.g., a molecule in which one or more immunoglobulin chains is not full length, but which binds to a C. burnetii protein antigen of the invention. Examples of binding portions encompassed within the term antibody include (i) a Fab fragment, a monovalent fragment consisting of the VLC, VHC, CL and CHI domains; (ii) a F(ab')$_2$ fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341: 544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-ATi-Alβ; and Huston et al. (1988) Proc. Natl. Acad. ScL USA 85:5879-5883). Such single chain antibodies are also encompassed within the term antibody. These are obtained using conventional techniques known to those with skill in the art, and the portions are screened for utility in the same manner as are intact antibodies.

The invention provides one or more of the aforementioned protein antigens of the invention, for use in the generation of antibodies that bind to said one or more protein antigens in a host animal.

The protein antigens of the invention may be used as immunogens separately or in combination, either concurrently or sequentially, in order to produce antibodies specific for individual C. burnetii antigens or combinations. For example, two or more protein antigens of the invention may be mixed together and used as a single immunogen. Alternatively a C. burnetii protein antigen of the invention may be used separately as a first immunogen on a first host, and another C. burnetii protein antigen of the invention may be used separately on a second host. The antibodies produced by separate immunisation may be combined to yield an antibody composition directed against C. burnetii antigens. Non-limiting examples of suitable adjuvants for animal/veterinary use include Freund's (complete and incomplete forms), alum (aluminium phosphate or aluminium hydroxide), saponin and its purified component Quil A.

A related aspect of the invention provides one or more antibodies that bind to one or more aforementioned protein of the invention, for use in the prevention, treatment or suppression of C. burnetii infection in a patient. Thus, the invention provides compositions comprising one or more antibodies of the invention.

In one embodiment, said antibodies have been generated by immunisation of a host with one or more of the aforementioned protein antigens of the present invention. The host is typically a non-human animal such as goat, sheep or horse).

The present invention includes a method of producing antibodies against C. burnetii protein antigens of the invention, for use in compositions of the invention. Said method generally involves (i) administering a protein antigen of the invention to a host animal, (ii) allowing sufficient time for the generation of antibodies in the host animal, and (iii) obtaining the antibodies from the host animal. Preferred host animals for the production of antibodies include sheep, goat or horse.

The invention also provides a method of producing an antibody, said method comprising the following steps:
 (i) administering to a host animal protein antigen of the invention;
 (ii) allowing sufficient time for the generation of antibodies in the host animal; and
 (iii) obtaining the antibodies from the host animal.

Said host animal is typically a mammal, preferably a sheep, goat or horse.

The invention also provides a method for producing an antibody, said method comprising the following steps:
 (a) contacting a B cell with an effective amount of at least one protein antigen of the invention;
 (b) fusing the B cell of step (a) with a myeloma cell to obtain a hybridoma cell; and
 (c) isolating the antibody produced by the cultivated hybridoma cell.

The invention also provides an in vitro method for isolating antibodies that bind to C. burnetii protein antigen of the invention, said method comprising
 a) immobilising on a surface (for example on a matrix within a column) one or more C. burnetii protein antigen(s) according to any of the invention;
 b) contacting the immobilised protein(s) with a solution containing antibodies that bind to the C. burnetii protein antigen(s);
 c) allowing said antibodies to bind to said C. burnetii protein antigen(s), thereby forming a bound complex of antibody and protein antigen(s);
 d) washing away any unbound antibody or protein; and
 e) eluting the bound antibodies from the surface, thereby providing affinity-purified antibodies.

The invention also provides an antibody obtainable by a method described herein.

The antibody may be obtained from the serum. Thus, the procedures generate antisera containing antibodies capable of binding C. burnetii antigens. In a further embodiment, the antibodies are isolated and/or purified. Thus, another aspect of the present invention involves purifying the antibodies from antiserum.

The method of producing antibodies allows all modes of immunisation (i.e. to generate the antibodies of the invention), including subcutaneous, intramuscular, intraperitoneal, and intravenous. The invention also contemplates a wide variety of immunisation schedules. In one embodiment, an animal is administered protein antigen on day zero and subsequently receives protein antigen at intervals thereafter. It will be appreciated that the interval range and dosage range required depends on the route of administration, the nature of the formulation, and the judgement of the attending person. Variations in these dosage levels can be adjusted using standard empirical routines for optimisation. Similarly, it is not intended that the present invention be limited to any particular schedule for collecting antibody. The preferred collection time is someday after day 56. Levels of the specific antibody i.e. that which binds to the immunogen, preferably represents at least 3 g per litre of serum.

The antibodies of the invention may be modified as necessary after collection from the host animal, so that, in certain instances, they are less immunogenic in the patient to whom they are administered. For example, if the patient is a human, the antibodies may be despeciated by methods well known in the art. One example as to how an antibody can be made less immunogenic is to prepare the $F(ab)_2$ fragment. The antibodies of the invention may be used to produce such antibody fragments for which various techniques have been developed. For example, the fragments may be derived by proteolytic digestion of intact antibodies. Other techniques for their production will be apparent to the skilled practitioner.

The invention provides an in vitro method for confirming the presence or absence of C. burnetii in a patient sample (i.e. diagnosis of C. burnetii infection). The presence of a C. burnetii is confirmed by detecting the binding of an antibody of the invention to a C. burnetii antigen present in said sample, and wherein failure to detect the binding of said to a C. burnetii antigen in said sample confirms the absence of C. burnetii. Suitable methods for detecting antibody binding are well-known e.g direct or indirect detection methods, involving detection of a fluorescent or chromogenic signal.

In one embodiment, upon confirmation of C. burnetii in the patient sample, said patient is administered agent for treatment of suppression of C. burnetii infection. Said agent is typically selected from: (a) composition of the invention; (b) antibody of the invention; (c) bacteriostatic agent, such as co-trimoxazole; and/or (d) bactericidal agent, such as doxycycline and/or hydroxychloroquine and/or ciprofloxacin.

In one embodiment, protein antigens of the invention are for use as ligands for use in affinity chromatography procedures. In such procedures, protein antigens of the invention may be covalently immobilised onto a matrix, such as Sepharose, e.g. using cyanogen bromide-activated Sepharose. Such affinity columns may then be used to purify antibody from antisera or partially purified solutions of immunoglobulins by passing them through the column and then eluting the bound IgG fraction (e.g. by low pH). Almost all of the antibody in the eluted fraction will be directed against the protein antigens of the invention, with non-specific antibodies such as IgG and other proteins having been removed. These affinity purified IgG fractions have applications both as immunotherapeutics and as a reagents in diagnostics. For immunotherapeutics, affinity purified antibodies enable a lower dose to be administered making adverse side effects less likely. For diagnostics, affinity purified agents often give improved specificity and fewer false positive results.

BRIEF DESCRIPTION OF DRAWINGS

There now follows a brief description of the Figures, which illustrate aspects and/or embodiments of the present invention.

EXAMPLES

In Vivo Experiments

Figure 1:
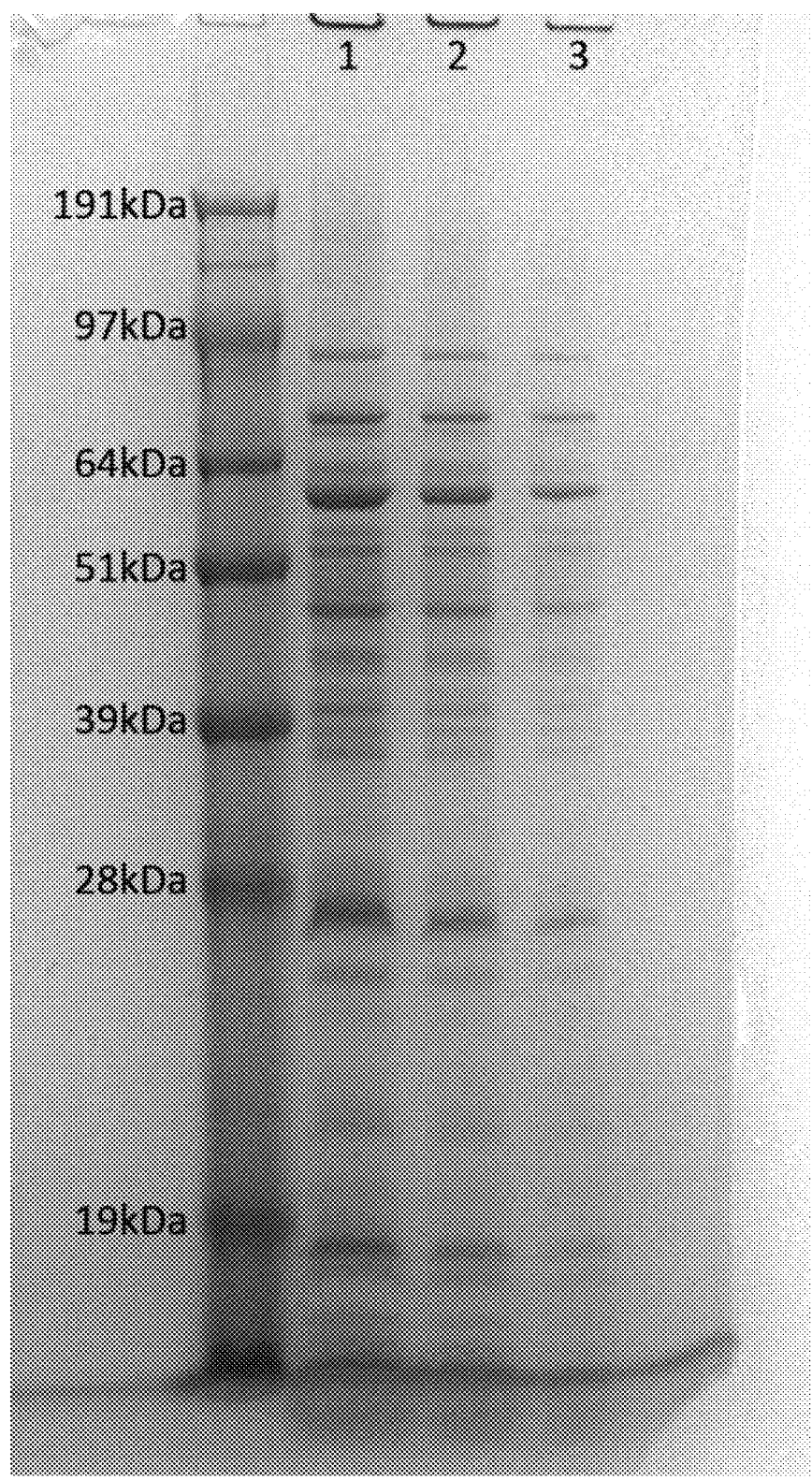
FIG. 1—One-dimensional SDS-PAGE image of extracted C. burnetii protein run on a 12 Bis-Tris gel in MOPS-SDS running buffer at 200 V for 50 m. The three lanes are 10 µl, 5 µl, and 2.5 µl of protein boiled in Laemmli buffer to ensure good band clarity. The figure shows that the extracted protein contained a wide range of proteins of different masses present in distinct species with little evidence of degradation (bands were sharply delineated with little smearing).

To generate representative immune-reactive sera, the inventors modelled the symptoms seen in acute Q fever disease in humans in small laboratory animal species. The key features of human disease are that the major mode of infection is by the inhalation of contaminated aerosols; that the organism needs to be in the wild-type virulent phase I form and; the disease is characterised by a fever that may reach a plateau of 40° C. before returning to normal. Further, relatively common disease features include pneumonia and hepatitis.

While the mouse model for Q fever has been reported more frequently than guinea pig model, the mouse model lacks several critical features of human infection. In view of the lack of fever, fewer overt signs of disease and the lower susceptibility to infection in the mouse model, the inventors identified guinea pig, infected via an inhaled aerosol, as the preferred model for this study.

Aerosol Infection of Guinea Pigs and Two Strains of Mouse

An aerosol infection experiment (Collison nebulizer) was performed to assess the signs of clinical infection in guinea pig and two strains of mouse that the literature had suggested may show some signs of infection. This experiment was also performed to generate convalescent anti-sera and antibodies for subsequent use later in this study, to identify *C. burnetii* proteins that are immune-reactive.

Two *C. burnetii* stocks, one spleen homogenate from an infected guinea pig and one egg yolk sack grown stock, were assessed for clinical signs of virulence after intraperitoneal infection with $1.5 \times 10^7$ copies/ml. Both stocks proved virulent in this experiment but the egg-yolk sack-grown stock to a substantially greater degree. Animals were therefore challenged with egg yolk sack grown *Coxiella burnetii*, Nile Mile strain, designated batch EP2 GP1 EP1. Seven Dunkin-Hartley guinea pigs and two strains of mice (7×BALB/c and 7×NJ), all male, were used in this experiment. Each animal was implanted with a subcutaneous identification and temperature monitoring chip (Animalcare identichip with Bio-Thermo # XID050). The animals' weight, temperature, and general health were recorded twice daily for two days prior to aerosol challenge and four times each day post-challenge. Any animals with a bodyweight loss of greater than 20% or with severe disease symptoms were euthanized in accordance with Home Office project license 30/2423.

The inventors designed, developed and implemented a real-time quantitative PCR assay to detect and enumerate *C. burnetii* in tissue, blood and culture samples. The PCR assay amplifies and detects the *C. burnetii* isocitrate-dehydrogenase (icd) gene.

TABLE 1 qPCR titres of the bacterial culture material in the Collison nebuliser (generator 1 - $C_{nebuliser}$) samples taken prior to challenge of each group as well as the impinger samples ($C_{impinger}$) and the derived $C_{aero}$ concentrations in copies/ml (derived from $C_{impinger}$ × 20 ml (the sample volume)/l/min (sample flow) × 10 min(sampling time)/1000).

| Sample | Copies/ml $C_{nebuliser}$ | Copies/ml $C_{impinger}$ | Copies/ml $C_{aero}$ |
|---|---|---|---|
| Guinea Pig - Group 1 | $1.10 \times 10^7$ | $1.30 \times 10^4$ | $4.54 \times 10^0$ |
| Mouse (BALB/c) - Group 2 | $1.10 \times 10^7$ | $3.20 \times 10^4$ | $1.68 \times 10^1$ |
| Mouse (A/J) - Group 3 | $6.30 \times 10^6$ | $1.10 \times 10^4$ | $5.02 \times 10^0$ |

TABLE 2

Volume of infectious aerosol inspired by the animals in each group and the calculated inhaled dose (copies) of *C. burnetii* calculated from $C_{aero}$ × Inspired volume. The inhaled dose is an estimate of the number of organisms to which each animal was exposed.

| Animal Group (mean weight) | Inspired volume (ml) | Inhaled Dose (copies) |
|---|---|---|
| Guinea Pig (356.8 g) - Group 1 | 1,724 | $7.8 \times 10^3$ |
| Mouse (BALB/c) (20.7 g) - Group 2 | 204.1 | $3.4 \times 10^3$ |
| Mouse (A/J) (21.0 g) - Group 3 | 206.3 | $1.0 \times 10^3$ |

To estimate the dose of organism inhaled by each animal (Table 2) the $C_{aero}$ was multiplied by the inspired volume. Due to their smaller size, the mice received less inoculum but overall a dose of 1,000-7,800 organisms (copies) was predicted by the literature to be sufficient to infect laboratory animals. This was supported by the clinical data obtained by the inventors (data not shown).

At the end of the study, (days 15 and 21 post-exposure respectively) two blood samples of 2 ml volume were taken under terminal anaesthesia by cardiac puncture from guinea pigs and placed into EDTA and SST blood tubes. Any remaining blood was placed into a Heparin tube. For mice, the blood samples were taken as for guinea pig but were divided equally between paediatric EDTA and SST blood tubes.

In addition, the following organs were harvested for qPCR analysis; spleen, kidney, liver, heart, lung and testicle. For the qPCR, approximately ⅓ of the total organ mass was removed from each organ. DNA was extracted and assessed by qPCR (data not shown).

Results—In Vivo Experiments

All guinea pigs in this study demonstrated overt signs of disease as evidenced by a lower rate of bodyweight gain and concurrent increase in body temperature. Therefore, the inoculum was virulent by the aerosol route at the dose used. Neither mouse strain demonstrated a measurable febrile response.

No significant bacterial blood load of *C. burnetii* was found in any of the study animals. This is consistent with natural infections in humans with *C. burnetii* where bacteraemia is transient and confined to the febrile portion of disease. The bacterial load in the tissues of guinea pigs was undetectable in all but the lungs at day 21 post-infection. In contrast, both strains of mice had detectable *C. burnetii* in all tissues tested at day 21. This indicates that in guinea pig the infection is being cleared, consistent with an acute infection; whereas in mice the infection may be of a more chronic nature.

The egg-yolk sack grown *C. burnetii* is clearly infectious in both guinea pig and mouse by the aerosol route. Clinical measurements were more pronounced in guinea pig than in mice. Disease after aerosol infection of guinea pigs appears to have more features consistent with human acute Q fever than mouse.

Terminal blood was harvested from all animals and the anti-sera harvested and stored.

Protein Isolation

Proteomic comparisons between virulent phase I and avirulent phase II organisms have identified that, in addition to a truncated LPS, phase II organisms have a restricted proteome. Comparisons have also found differences in the proteomes of the two morphological forms, the large- (LCV) and small-cell variants (SCV). Therefore, the inventors performed immune-reactive protein isolation using phase I organisms that are present in a mixture of the two morphological forms.

Immune reactive proteins are specific proteins, present in the pathogen, that have been recognised by the host during infection. This is evidenced by the presence of antibodies in the sera that bind to those proteins.

The inventors also repost isolation of the proteins that are immunoreactive with the antibody (IgG fraction) present in the serum from the aerosol infected guinea pigs. These proteins are isolated to permit downstream mass spectrometric identification.

Growth of *C. burnetii*

The inventors grew a stock of *C. burnetii*, free of host proteins, in axenic media. This stock was produced from a low passage stock of phase I material and contained a mixture of the two morphological forms (SCV and LCV) to maximise the probability that a comprehensive representation of the organism's proteins are present in the preparation.

Optimisation of Inoculation Concentration

To axenically culture *C. burnetii*, acidified citrate cysteine media (ACCM-2) was prepared as described in the literature. Bacterial inoculum stock was *C. burnetii*, Nine Mile strain (EP2, GP1 EP1)—30% (w/v) egg yolk sack in PBS homogenate. DNA was extracted from this material and its average titre estimated by three separate determinations in qPCR as described above. This titre was $2.9 \times 10^7$ copies/ml. As this material was the first chick egg passage after a guinea pig passage, and was demonstrated by the inventors to be pathogenic in animals, it was concluded that it was in the virulent phase I form of the organism.

Into the wells of six-well cell-culture plates (ThermoScientific/Nunc #140675) 2 ml of ACCM-2 media was pipetted. The wells were then inoculated with *C. burnetii* such that there were five concentrations of organisms, from $1.0 \times 10^2$ copies/ml to $1.0 \times 10^6$ copies/ml in $10^1$ increments. The plates were sealed into a 2.5 l gas-tight box with a microaerophilic atmosphere generating pack (Biomerieux GENbox microaer #96125) and the box placed in an incubator set at 37° C. At intervals throughout the ten day experiment, the box was opened, samples taken for DNA extraction/qPCR analysis, a fresh gas pack added, and the box re-sealed and returned to the incubator.

The qPCR analysis data was plotted graphically to determine which seeding concentration yielded the best growth of the organism. Optimal growth was determined to be that which, given the smallest inoculum concentration, gave the greatest increase over the ten day incubation. Seeding concentration is an important consideration due to the proportion of egg yolk sac-associated protein contaminating the final material.

The growth curves for different *C. burnetii* seeding concentrations show that for inoculation concentrations in the range $1 \times 10^2$ to $1 \times 10^4$ copies/ml, growth was exponential (results not shown). For the two highest titres ($1 \times 10^5$ and $1 \times 10^6$ copies/ml), growth was initially exponential until day five post-inoculation, where the titre reaches a plateau and begins to fall. The optimal inoculation concentration was determined to be $1 \times 10^4$ copies/ml because the endpoint titre at day ten post-inoculation is almost as high as the peak titre observed for higher inoculation concentrations but without the associated fall in titre at the end.

Larger Scale Growth

Ten 250 ml plastic sterile conical flasks were filled with 100 ml each of ACCM-2 media. Each flask was inoculated with *C. burnetii* (Nine Mile strain described above) such that the estimated titre in each flask was $1 \times 10^4$ copies/ml. This consisted of 35 μl of yolk sac homogenate per 100 ml flask. Each flask was sealed into an O-ring sealed, screw-capped BioJar containing a microaerophilic atmosphere generating pack. The BioJars were then incubated for nine days in a shaking incubator set at 37° C. and 75 rpm.

Prior to harvest, a sample of the pooled cultured organisms was taken for DNA extraction/qPCR titration and other quality assessment measures. To harvest the bacteria the cultures were combined and centrifuged at 12,000×g for 30 min to pellet the cells. The pellets were re-suspended in a small amount of the spent ACCM-2 media, combined and re-pelleted. All media was aspirated from the pellets and they were stored at −80° C. until lysis and protein extraction. The estimated titre of the culture at harvest was $1.1 \times 10^9$ copies/ml (using icd real-time qPCR).

Quality Assessments

Electron Microscopy

To assess the quality of the cultured *C. burnetii* prior to cell lysis and protein extraction, agarose-embedding followed by transmission electron microscopy (TEM) of a sample of the material was undertaken. The electron micrographs of the ACCM-2 grown *C. burnetii* (data not shown) show that the material (larger scale growth) consists almost exclusively of bacterial material with little to no contaminating matter. The micrographs show a mixture of morphological forms, the smaller electron-dense particles are likely to be the SCV and the larger more diffuse particles with visible structural detail (electron dense chromatin in the core and a double-walled plasma membrane) the LCV.

Immunofluorescent Microscopy

Quality assessment of the cultured C. burnetii was also performed using immunofluorescent microscopy. The immunofluorescent microscopy image of the ACCM-2 grown C. burnetii (data not shown) shows that the material consists almost exclusively of bacterial material (stained as bright green coccobacilli) with little to no contaminating matter. The Evans blue counterstain has stained very little material and this material is likely to be the dried proteinaceous residue from the ACCM-2 media (bacterial cells were not washed before drying onto the slides as it was found that without some quantity of salt and protein in the buffer, Coxiellae did not adhere to the glass).

Extraction of Proteins from ACCM-2 Grown C. Burnetii

The ACCM-2 grown C. burnetii pelleted organisms from the larger scale growth were weighed and found to contain approximately 165 mg (wet-pellet), this was re-suspended in PBS and divided equally between four 2 ml microcentrifuge tubes to yield approximately 41 mg/tube. This material was re-pelleted at 16,000×g and the PBS discarded.

The pellets were re-suspended in 1.0 ml each of Bug Buster master mix (containing Benzonase Nuclease and rLysozyme; Novagen #71456-3) containing 1× protease inhibitor cocktail (Roche cOmplete ULTRA, EDTA-free #05892953001) to lyse the bacterial cells, solubilise proteins and break down the nucleic acids. The lysis was allowed to continue for 2 h at room temperature before clarification by centrifugation at 16,000×g for 20 min. The soluble protein fraction was then filtered through a 0.1 μm PVDF syringe filter (Millipore # SLVV033RS) to remove any residual infectious particles.

Soluble C. burnetii protein was stored at −80° C. in small aliquots until required.

One Dimensional Protein Separation and Detection

One Dimensional Protein Separation

To produce a denatured, reduced protein preparation suitable for one-dimensional (1D) PAGE, 50 μl of soluble protein was mixed with 50 μl of 2× concentrated Laemmli sample buffer (Sigma 53401-10VL). This mixture was heated in a heating block at 95° C. for 10 min.

The denatured, reduced proteins were loaded directly into an 1 mm thick, 8 cm square 12 Bis-Tris Protein Gel (Life Technologies NuPage® Novex® NP0343BOX) submerged in MOPS SDS running buffer (Life Technologies NuPage® Novex® NP0001) at the anode and MOPS SDS running buffer containing antioxidant (Life Technologies NuPage® NP0005) at the cathode. The Bis-Tris gel system is a modification of the original SDS-PAGE that runs at a neutral pH rather than the basic pH of the original method. Into the first lane was loaded a pre-stained protein standard marker (Life Technologies SeeBlue® Plus2 LC5925). The gel was then electrophoresed at 200 V for 50 min.

Coomassie Staining of Gels

For general protein visualisation, where sensitivity to protein bands or spots containing more than 10 ng was sufficient, or where downstream mass spectrometry analysis was desired, Coomassie staining was used. After electrophoresis, gels were removed from their plastic cassettes and subjected to three, 5 min washes with deionised water on a rocking platform. The gels were then covered with 20 ml of Coomassie G-250 stain (Life Technologies SimplyBlue™ SafeStain LC6060) and rocked on the platform for 1 h at room temperature. The stain was discarded and the gel de-stained using deionised water for two, 1 h washes.

Gel images were captured using a PC running the BioRad QuantityOne software package attached to a self-contained dark-room gel-documentation system containing a digital camera (BioRad XR System #170-8170).

Silver Staining of Gels

For greater sensitivity staining of protein gels (spot or band abundance as low as 0.25 ng), silver staining was used. A mass spectrometry compatible protocol, included in the reagent kit, was used (Pierce® silver stain kit; ThermoScientific #24612). After electrophoresis, gels were removed from their plastic cassettes and subjected to two, 5 min washes with deionised water on a rocking platform. The gels were then fixed with two, 15 min washes in 30% (v/v) ethanol: 10% (v/v) acetic acid. Gels were washed with two; 5 min washes in 10% (v/v) ethanol followed by two, 5 min washes in deionised water.

Gels were sensitised for 1 min in sensitiser working solution and washed for two, 1 min washes in deionised water. The gel was stained for 5 min in stain working solution followed by two, 20 s washes in deionised water. The stain was developed in developer working solution until the bands had a good intensity (less than 3 min) and the developing stopped by two, 10 min washes in 5% (v/v) acetic acid.

Western Blotting

To produce membranes with bound C. burnetii proteins, a Western Blot was performed. This was achieved using an iBlot® semi-dry blotting system (Life Technologies IB1001UK) using a PVDF mini transfer stack (Life Technologies iBlot® 164010-02). The pre-run PAGE gel was removed from the cassette, trimmed and floated off into deionised water. The iBlot anode stack was inserted into the iBlot device. The gel was carefully laid onto the PVDF membrane without introducing air-bubbles. An iBlot filter paper, wetted with deionised water, was carefully laid on top of the gel and the de-bubbling roller used to remove any residual air bubbles. The cathode stack was then place on the stack and the lid of the iBlot (fitted with a cathode sponge) closed. The transfer itself was performed by running programme preset P3 (20 V for 7 min). After transfer, the membranes were used either immediately for antibody probing or stored.

For storage, the membranes were air-dried and placed into 50 ml screw-capped Falcon tubes and kept at −20° C. Before use, frozen membranes were warmed to room temperature and re-wetted with methanol for 10 s, thoroughly rinsed with deionised water and used as freshly-transferred membranes.

Antibody Probing of Transferred Proteins

Blocking of unoccupied protein binding sites on the membranes was achieved by incubating them in polypropylene tubes on a roller containing 30 ml of 5% (w/v) non-fat milk (Milk; Sigma M7049-1BTL) diluted in PBS containing 0.05% (v/v) Tween-20 buffer (PBS-T; Thermo Scientific™ Pierce™ 20×PBS Tween™ 20 PI-28352) (5% Milk/PBS-T) at room temperature for 1-2 h, or overnight at 8° C.

After blocking, the membranes were incubated with 5 ml of primary antibody diluted (generally at 1:1000) in 5% Milk/PBS-T for 1 h at room temperature on a roller. Membranes were washed three times for 5 min in PBS-T (without milk).

Membranes were probed with secondary antibody diluted 1:3000 in 5% Milk/PBS-T for 1 h at room temperature. The conjugate used was dependent upon the detection method used downstream (see below). For ECL detection, anti-guinea pig IgG (whole molecule)-peroxidase produced in goat (Sigma A7289) was used and for BCIP/NBT detection and anti-guinea pig IgG (whole molecule)-alkaline phosphatase produced in goat (Sigma A5062) was used. After incubation, membranes were washed three times for 5 min in PBS-T.

Horseradish peroxidase-conjugated secondary antibody was detected using enhanced chemiluminescence (Amersham ECL Prime Western Blotting Detection Reagent RPN 2232); reagents A and B were mixed 50:50 v/v, applied to the membranes and incubated in the dark at room temperature for 5 min. The ECL mixture was aspirated from the membranes and the membranes blotted dry. Visualisation and imaging was performed using a gel documentation system (BioRad XRS System #170-8071).

Alkaline phosphatase-conjugated secondary antibodies were detected using 5-bromo-4-chloro-3-indolyl-phosphate (BCIP) and nitro blue tetrazolium (NBT) (Western Blue® substrate; Promega S3841). Approximately 5 ml were applied to the membranes and the reaction allowed to proceed at room temperature until protein spots/bands were clearly visible and the background had just began to take up stain. The reaction was stopped by washing the substrate away with deionised water. Visualisation and imaging was performed using a gel documentation system (BioRad XR System #170-8170).

Confirmation of Antibody Activity in Convalescent Sera

To confirm the reactivity of the antibodies present in the convalescent guinea pig sera from the aerosol-exposure experiment with the *C. burnetii* proteins, a 1D PAGE was performed with the *C. burnetii* proteins described above and the proteins blotted onto a membrane as described above. The membrane was cut into strips and the sera from each guinea pig used to probe a single strip.

Results—One Dimensional Protein Separation

Basic Assessment of Protein Extraction

The initial assessment of the *C. burnetii* protein extraction process was performed by running three lanes of the reduced, denatured protein; 10 µl, 5 µl, 2.5 µl. The gel image (FIG. 1) shows a range of many well-defined bands from approximately 100 kDa down to smaller than 19 kDa. This is an indication that the BugBuster extraction process is successfully extracting a mixture of proteins from the organism.

Confirmation of Antibody Activity in Convalescent Sera

Figure 2:
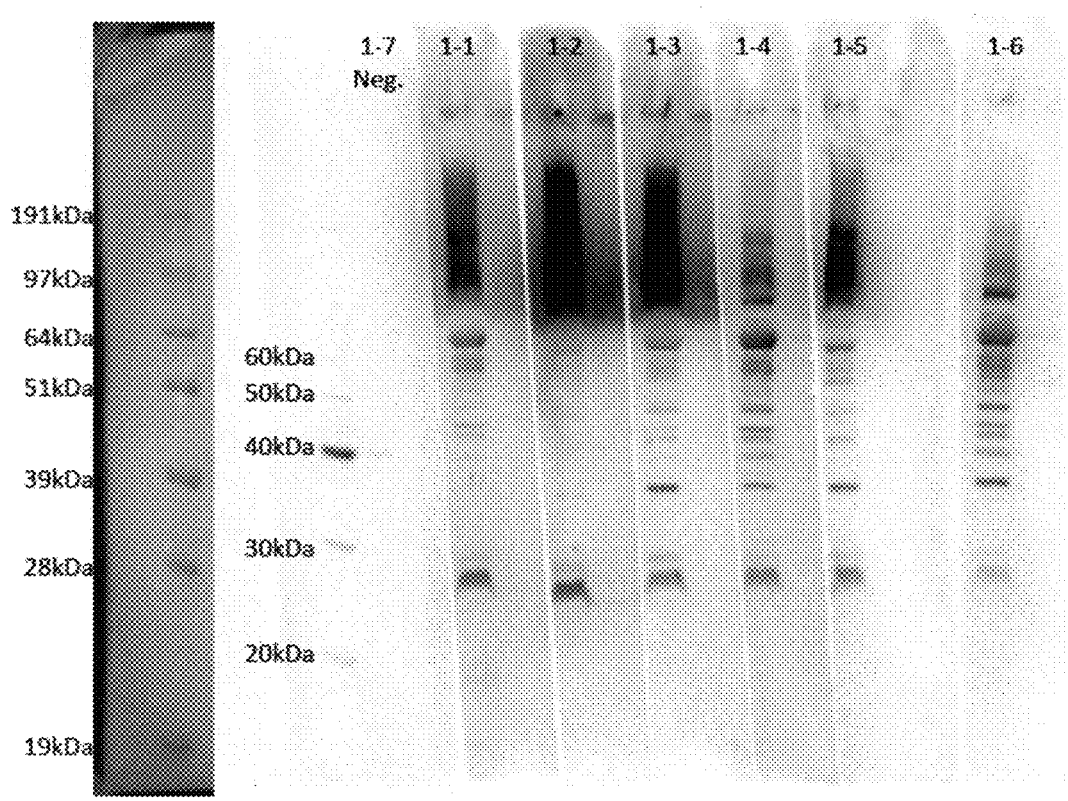
FIG. 2—Western blot of C. burnetii proteins (on the membrane) probed with the aerosol-exposed guinea pig sera (containing immune-reactive antibodies), that binding detected with anti-guinea pig IgG conjugate, and visualised with ECL prime substrate. Lane 1 is the transferred SeeBlue Plus2 Molecular Weight standard and lane 2 contains the MagicMark XP Standard. Figure shows that the sera from all of the exposed guinea pigs reacted to some degree with the proteins present in the C. burnetii extract whereas the unexposed guinea pig (A1-7) did not react. The image also suggests that individuals A1-4 and A1-6 reacted with a more proteins over a wider mass range than the other exposed animals.

The Western blots of *C. burnetii* proteins (on the membranes) probed with guinea pig sera (IgG fraction only detected by the conjugate) from the aerosol-exposure experiment show that the negative animal (4427 V1-7) had no response to the proteins present in the protein preparation (FIG. 2). The faint band seen at ~40 kDa is likely to be bleed-through from the MW marker in the adjacent lane. Guinea pigs A1-1 to A1-6 all showed good responses to a wide range of proteins present in the preparation. The quality of the response in animals 1-4 and 1-6 is subjectively better in that the bands detected are sharper and more well-defined with more bands detected in the 19-60 kDa range; these two animals were autopsied at day 15 post-exposure whereas the others were autopsied at day 21 post-exposure.

The one-dimensional protein separations and Western blots showed that the extracted proteins contained a satisfactory range of protein species and that the guinea pig sera from the aerosol-infection experiments reacted strongly with a restricted subset of the protein bands. This demonstrated that the antisera could be used to select only those proteins recognised by the guinea pig immune-system during infection, organism clearance and recovery.

Two-Dimensional Protein Separation and Immune-Reactive Protein Isolation

Prior to two-dimensional (2D) PAGE, protein samples require relatively accurate quantification as well as a more thorough clean-up procedure to ensure no substances (ionic detergents or salts) that will interfere with the isoelectric focusing (IEF) process are present.

Protein Quantitation

The *C. burnetii* protein prepared above was quantitated using the 2-D Quant Kit (GE Healthcare 80-6483-56) by the following procedure. A standard curve was prepared in 1.5 ml microcentrifuge tubes from the 2 mg/ml bovine sera albumin (BSA) supplied with the kit; 0, 10, 20, 30, 40, 50 µg. Two microcentrifuge tubes were also set up with 10 µl each of the *C. burnetii* protein. To all tubes, 500 µl of precipitant (containing trichloroacetic acid) was added, the tubes vortex-mixed and incubated at room temperature for 3 min. To all tubes, 500 µl of co-precipitant (containing deoxycholic acid) was added, the tubes vortex-mixed and the proteins pelleted by centrifugation at 10,000×g for 5 min.

The supernatants were decanted to waste and the tubes re-centrifuged at 10,000×g for a brief pulse. Any residual supernatant was removed with a micropipette. To all tubes, 100 µl of copper solution and 400 µl of deionised water were added and the tubes vortex-mixed to dissolve the precipitated protein. To all tubes, 1 ml of working colour reagent (100 parts of colour reagent A mixed with 1 part colour reagent B) was added and mixed by inversion, the tubes were then incubated for 15 min at room temperature.

The absorbance of all samples and the standard curve were read in triplicate on a NanoDrop spectrophotometer (ND-2000) using 10 mm disposable plastic cuvettes at wavelength 480 nm using deionised water as a reference. The standard curve data were subjected to linear regression analysis in MiniTab v16, the regression equation re-arranged and used to calculate the quantity of protein in the extracted *C. burnetii* protein preparation.

Protein Purification

Prior to first-dimension separation of proteins according to charge by isoelectric focussing, the proteins from the *C. burnetii* lysis material prepared above were subjected to a precipitation-based purification to remove contaminants such as salt that could give the material a high conductivity or charged detergents that could interfere with the separation. This purification was performed using the 2-D Clean-Up Kit (GE Healthcare 80-6484-51). For 7 cm pI=3-11 NL IEF separations 17 µl (41 µg) and pI=3-5.6 NL and pI=7-11 NL separations 25 µl (60 µg) per strip were used.

The required number of µg of lysed *C. burnetii* material was pipetted into 1.5 ml microcentrifuge tubes. To each tube, 300 µl precipitant was added and the tubes vortex-mixed, the samples were then incubated on ice (4° C.) for 30 min. To each tube, 300 µl of co-precipitant was added and the contents vortex-mixed. The tubes were centrifuged at 12,000×g at 4° C. for 10 min. The supernatant was removed and discarded, the tubes were then pulse centrifuged at the same speed and temperature as above. Residual supernatant was removed and discarded using a fine micropipette. Onto the pellets, 40 µl of co-precipitant was carefully layered so as to not disturb the pellet. The tubes were then incubated on ice for 5 min. The tubes were centrifuged at 12,000×g at 4° C. for 10 min and the supernatant discarded using a micropipette.

Onto each pellet was pipetted 25 µl of deionised water and the tubes vortex-mixed for 30-60 s to disperse the pellet. Pre-chilled wash buffer (−20° C.) was added to each tube, 1 ml per tube containing 5 µl of wash additive and vortex-mixed. The tubes were then incubated in a freezer at −20° C. for 1 h with vortex-mixing every 15 min. Protein was pelleted by centrifuging the tubes at 16,000×g at 4° C. for 10 min and the supernatant discarded. The pellets were allowed to air-dry for 5 min in a rack with the lids open at room temperature. Pellets were re-suspended in 125 µl of IPG strip rehydration solution (GE Healthcare 17-6003-19) by repeated pipetting. The re-suspended, purified proteins were then stored at −80° C. until just prior to IEF strip rehydration.

Isoelectric Focusing of *C. burnetii* Proteins

For first dimension separation of proteins according to their charge or isoelectric point (pi), isoelectric focusing (IEF) was performed. An Ettan IPGPhor II instrument using 7 cm Immobiline DryStrip gels which consist of a pre-formed pH gradient immobilized into a polyacrylamide gel on a stiff plastic backing was used. To the thawed purified proteins suspended in rehydration solution, the immobilised pH gradient (IPG) buffer containing carrier ampholytes (GE Healthcare pI 3-11NL 17-6004-40, pI 7-11NL 17-6004-39, pI 3-5.6NL 17-6002-02) with the appropriate pI interval to the strip being run, was added to a final concentration of 1 (v/v). Into the IPG strip holder of the IPGPhor, 125 µl of the protein preparation was pipetted. The protective backing was removed from the IPGstrip (GE Healthcare pI 3-11NL 17-6003-73, pI 7-11NL 17-6003-68, pI 3-5.6NL 17-6003-53), and the strip placed, gel side down, onto the protein solution. The strip was then overlaid with cover fluid (GE Healthcare 17-1335-01) and the lid placed on top. The rehydration was left overnight in the IPGPhor at room temperature.

After rehydration, the IPG strips were removed from the strip holders and thoroughly washed with deionised water. The strip holders were washed and dried to remove all traces of cover fluid. Two filter paper electrode bridges were cut and placed into the strip holders and either both soaked with deionised water for acidic pI range (pI 3-3.5NL) or the anode with deionised water and the cathode with rehydration solution for basic pI ranges (pI 3-11NL and pI 7-11NL). The rehydrated IPG strip was carefully placed, gel side down, such that the electrode bridges made contact with each end of the gel, the strip holder filled with cover fluid and the lid placed on top. The lid of the IPGPhor was closed and the IEF programme, appropriate to the strip, run. The parameters used are presented below (Table 3). After IEF, the strips were washed with deionised water and either used immediately for second dimension separation or stored in petri dishes sealed with Parafilm® M (Sigma-Aldrich P7793) at −20° C.

TABLE 3

For first dimension separation of *C. burnetii* proteins by isoelectric point the IPG Strip running conditions here were used for focussing the 7 cm Immobiline DryStrips on the Ettan IPGPhor II Isoelectric focussing instrument. Temperature was held at 20° C. and current was capped at 50 µA/strip.

| pI Interval | Step voltage mode | Voltage (V) | Time (h:min) |
|---|---|---|---|
| 3.0-11.0 NL | 1. Step and Hold | 300 | 1:00 |
|  | 2. Gradient | 1,000 | 0:30 |
|  | 3. Gradient | 5,000 | 1:20 |
|  | 4. Step and Hold | 5,000 | 0:25 |
| 3.0-5.6 NL | 1. Step and Hold | 300 | 1:00 |
|  | 2. Gradient | 1,000 | 0:30 |
|  | 3. Gradient | 5,000 | 1:30 |
|  | 4. Step and Hold | 5,000 | 0:36 |

TABLE 3-continued

For first dimension separation of *C. burnetii* proteins by isoelectric point the IPG Strip running conditions here were used for focussing the 7 cm Immobiline DryStrips on the Ettan IPGPhor II Isoelectric focussing instrument. Temperature was held at 20° C. and current was capped at 50 µA/strip.

| pI Interval | Step voltage mode | Voltage (V) | Time (h:min) |
|---|---|---|---|
| 7.0-11.0 NL | 1. Step and Hold | 300 | 1:00 |
|  | 2. Gradient | 1,000 | 1:00 |
|  | 3. Gradient | 5,000 | 1:30 |
|  | 4. Step and Hold | 5,000 | 0:55 |

Second Dimension Protein Separation

For second dimension separation of the pI-separated proteins according to their size, polyacrylamide gel electrophoresis (PAGE) was performed. Lithium dodecyl sulphate buffer (4× NuPAGE® LDS sample buffer; Life Technologies NP0008) was diluted to 1× with deionised water. The proteins in the IPG strips were reduced in immunoassay reagent troughs in 1×LDS sample buffer containing 1:10 sample reducing agent (NuPAGE® sample reducing agent 10×; Life Technologies NP0009) at room temperature for 15 min with gentle rocking. The reducing buffer was decanted off and replaced with alkylating buffer consisting of 1×LDS sample buffer containing 125 mM iodoacetamide (Sigma 11149) at room temperature for 15 min with gentle rocking. The alkylating buffer was decanted off and discarded.

The plastic backing strip of the IPG strip was trimmed to 7 cm and the strip carefully inserted into the IPG well of the PAGE gel (NuPAGE® Novex® 4-12% Bis-Tris ZOOM® protein gel, 1 mm thick; Life Technologies NP0330BOX). Approximately 400 µl of molten 0.5% (w/v) agarose (VWR Electran® 438795A) in MOPS-SDS running buffer (NuPAGE® MOPS SDS running buffer; Life Technologies NP0001) were pipetted into the well containing the IPG strip and allowed to set.

The gel was loaded into the electrophoresis unit with MOPS SDS running buffer at the anode and MOPS SDS running buffer containing antioxidant (Life Technologies NuPage® NP0005) at the cathode. Into the molecular weight lane, a pre-stained protein standard marker (Life Technologies SeeBlue® Plus2 LC5925) was loaded. The gel was then electrophoresed at 200 V for 45 min.

Gels were stained and visualised using either Coomassie or silver protocols as described above. Western blots and antibody probing of membranes were performed as described above.

Isolation of Immune-Reactive Protein Spots

Parallel 2D PAGE gels were prepared of the *C. burnetii* proteins for three pI ranges; 3-11, 3-5.6, and 7-11. One gel from each pair was used to produce a Western Blot, probed with guinea pig sera from the aerosol-exposure experiment group one, subject four (4427 1-4), and detected with Western Blue® (NCIP/NBT) substrate as described above. The other gel was stained with Coomassie (as above); despite the use of a mass spectrometric-compatible protocol, silver staining was avoided because it is less compatible with down-stream mass spectrometry analysis than Coomassie.

The stained Western blot membrane was placed on a lightbox and the Coomassie-stained protein gel placed in a petri dish on top of this. The protein gel was moved until the two gels were aligned using the molecular weight markers and the larger spot-features as a guide. Protein spots that visibly corresponded to spots on the Western blot membrane were carefully excised using sterile, trimmed, 1 ml micropipette tips or, for larger regions of interest, with a disposable scalpel. In some cases it could not be ascertained which protein spot corresponded to an individual spot on the Western blot membrane, in those cases no spot was collected.

The spots and regions that were cut were collected into labelled 500 µl microcentrifuge tubes and stored at −80° C. prior to further processing.

Figure 3:
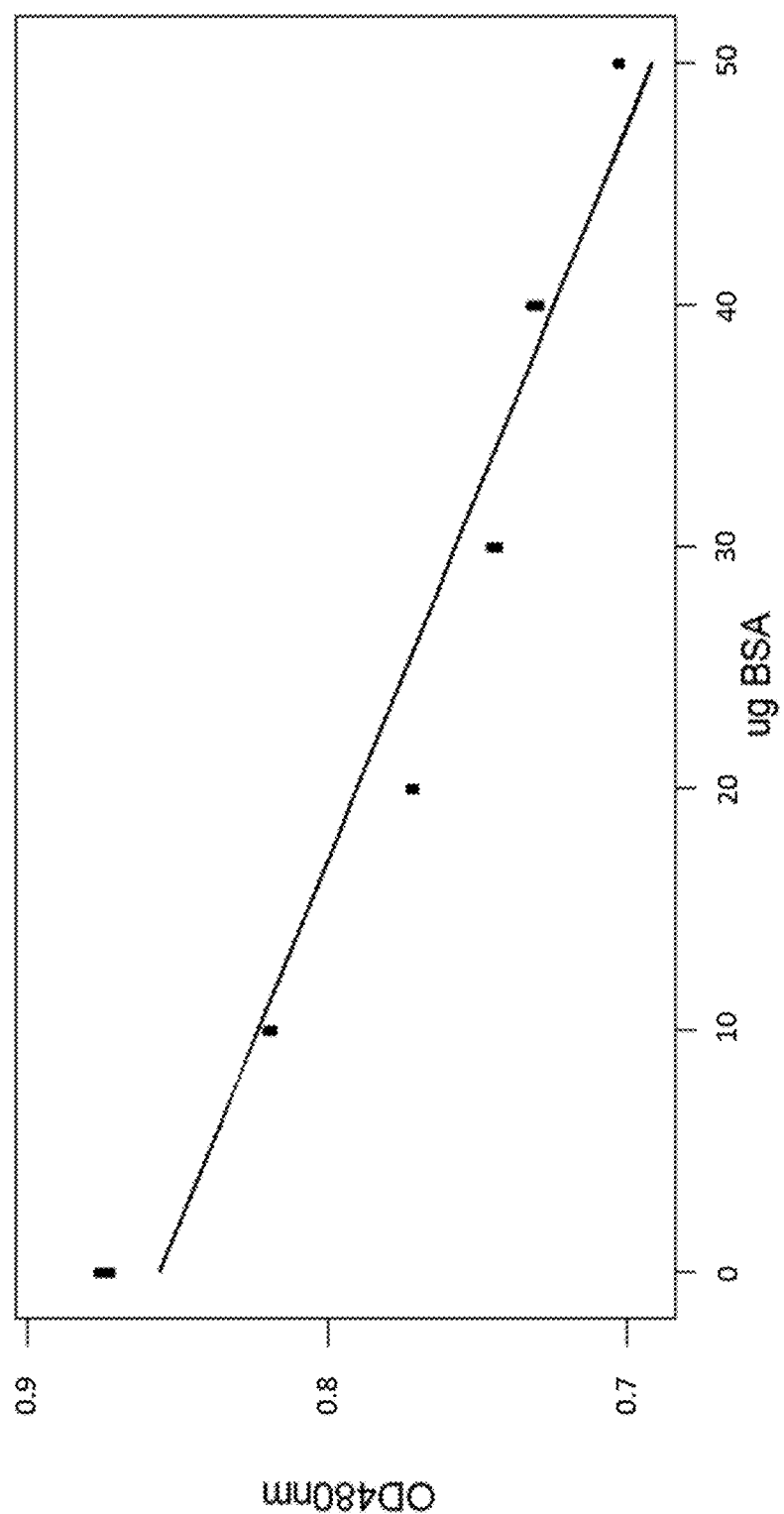
FIG. 3—Linear Regression of protein quantitation standards and the resulting line equation used to calculate the protein quantities present in the C. burnetii extract. Line equation OD480 nm=0.856-0.003 µg BSA; S=0.013; $R^2$=94.8%; R2 (adj)=94.5%; P<0.001. The derived line equation was used to determine the loading quantities of proteins for the first-dimension (isoelectric focussing) of the 2D SDS-PAGE process to reduce the risk of under or overloading the gels.
Figure 4:
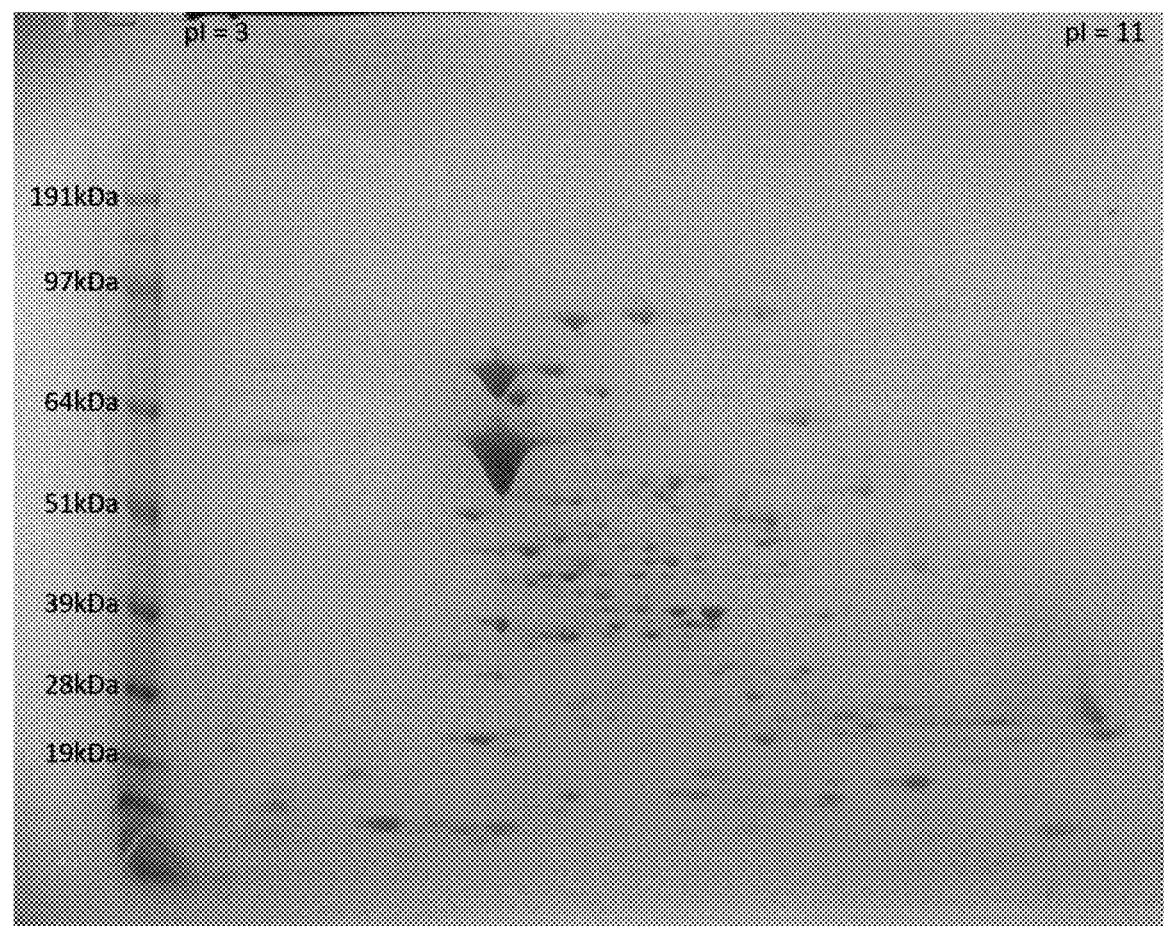
FIG. 4—Coomassie-stained 2D PAGE separation of C. burnetii proteins across the wide pI range 3.0-11.0 (non-linear). Isoelectric point ranges from pI=3 at the left side of the image to pI=11 at the right side of the image.
Figure 5:
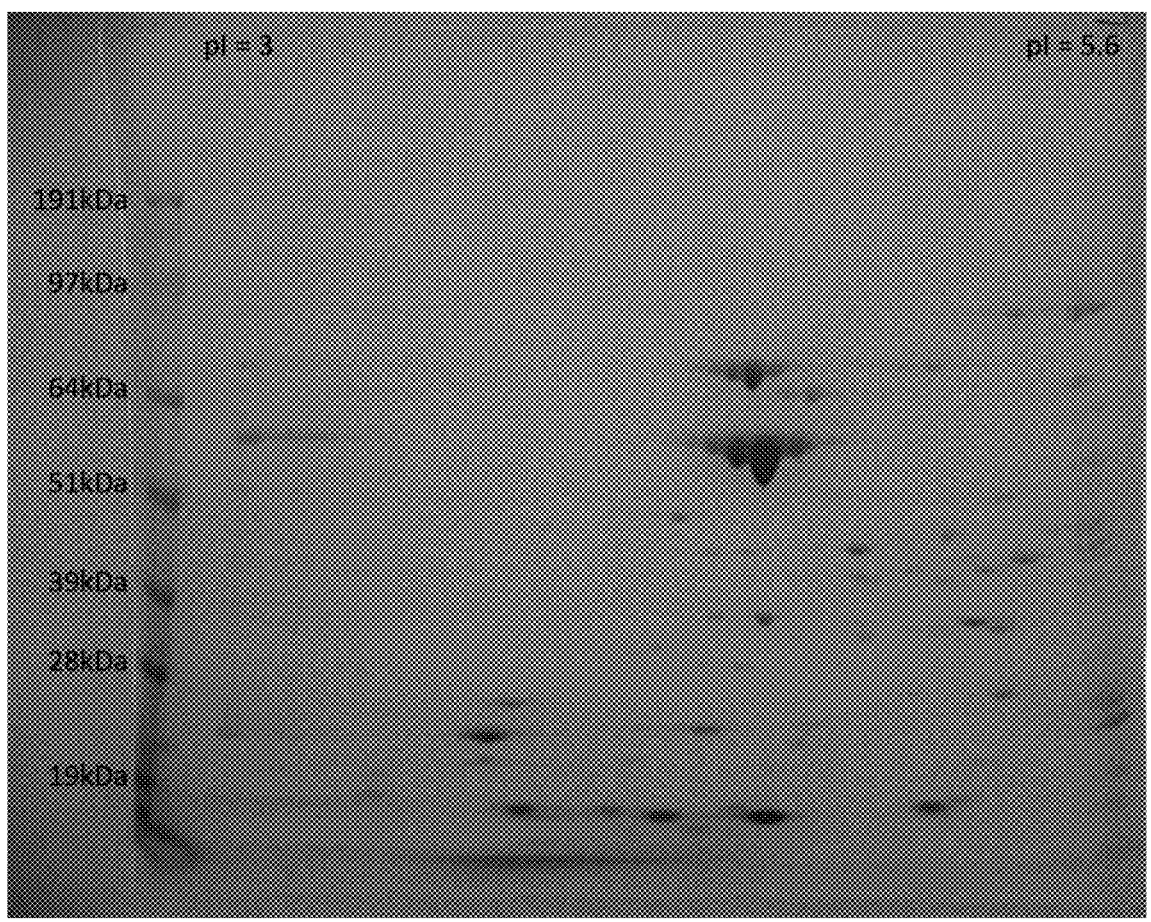
FIG. 5—Coomassie-stained 2D PAGE separation of C. burnetii proteins across the narrower (acidic) pI range 3.0-5.6 (non-linear). Isoelectric point ranges from pI=3 at the left side of the image to pI=5.6 at the right side of the image.
Figure 6:
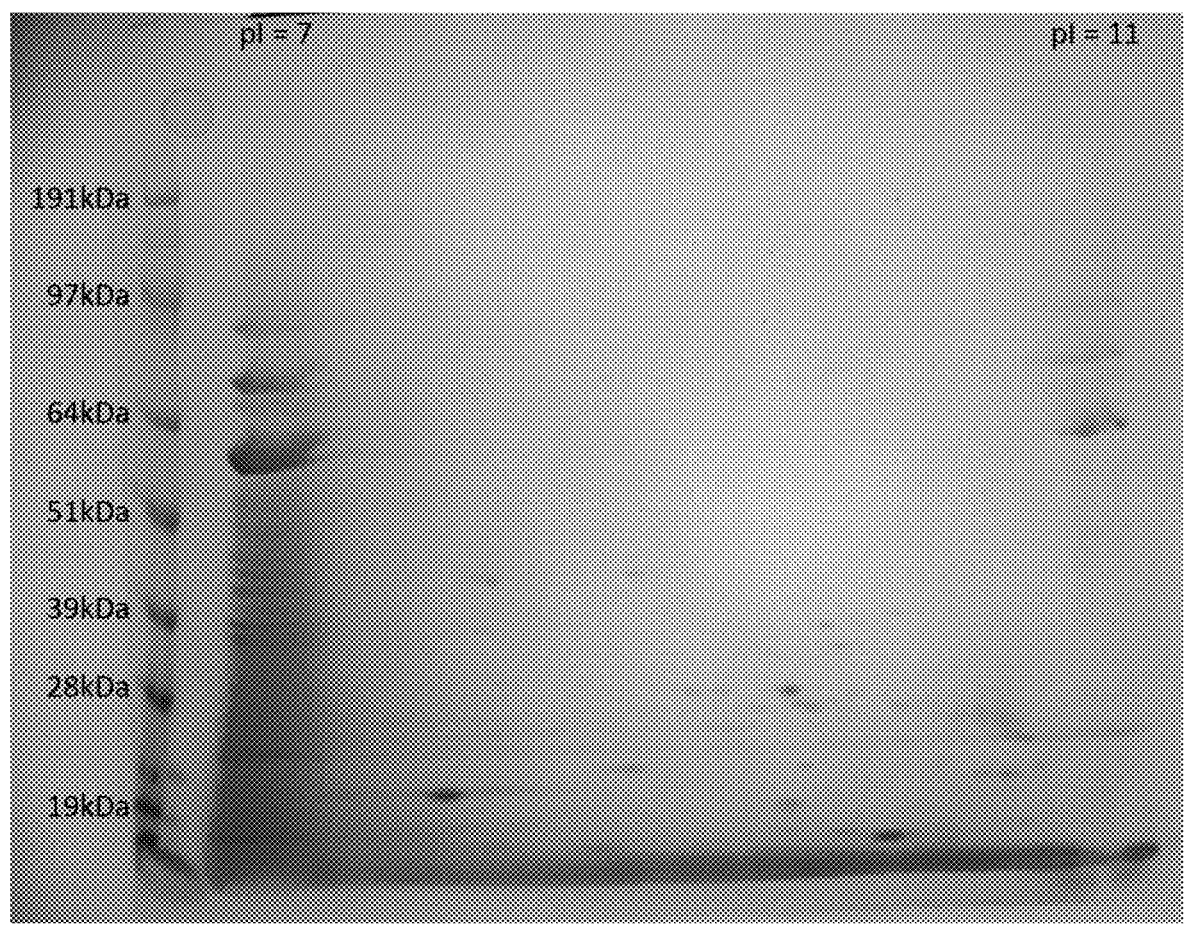
FIG. 6—Coomassie-stained 2D PAGE separation of C. burnetii proteins across the narrower (basic) pI range 7.0-11.0 (non-linear). Isoelectric point ranges from pI=7 at the left side of the image to pI=11 at the right side of the image.

Results—Two-Dimensional Protein Separation and Immune-Reactive Protein Isolation Protein Quantitation The standard curve generated during the protein assay (FIG. 3) yielded the line equation:

$$OD480\ nm = 0.856 - 0.003 \times \mu g\ BSA$$

To calculate the quantity of protein present in the *C. burnetii* protein preparation this was re-arranged to the form:

$$\mu g\ BSA = \frac{OD\ 480\ nm - 0.856}{0.003}$$

The two samples of the *C. burnetii* extract gave protein quantities of 21 and 26 µg in the 10 µl tested. For the purposes of the 2D PAGE the mean value of 2.4 µg/µl was used.

Two-Dimensional Protein Separation

Protein separations in two-dimensions over the three pI ranges chosen showed a satisfactory range of spots in terms of both molecular weight and pI (FIGS. 4-7). There appears to be a slight bias towards the number of spots in the low pI (3-5.6) range compared to the higher (7-11) range.

Immune-Probing of 2D PAGE Western Blots and Protein Spot Excision

Figure 7:
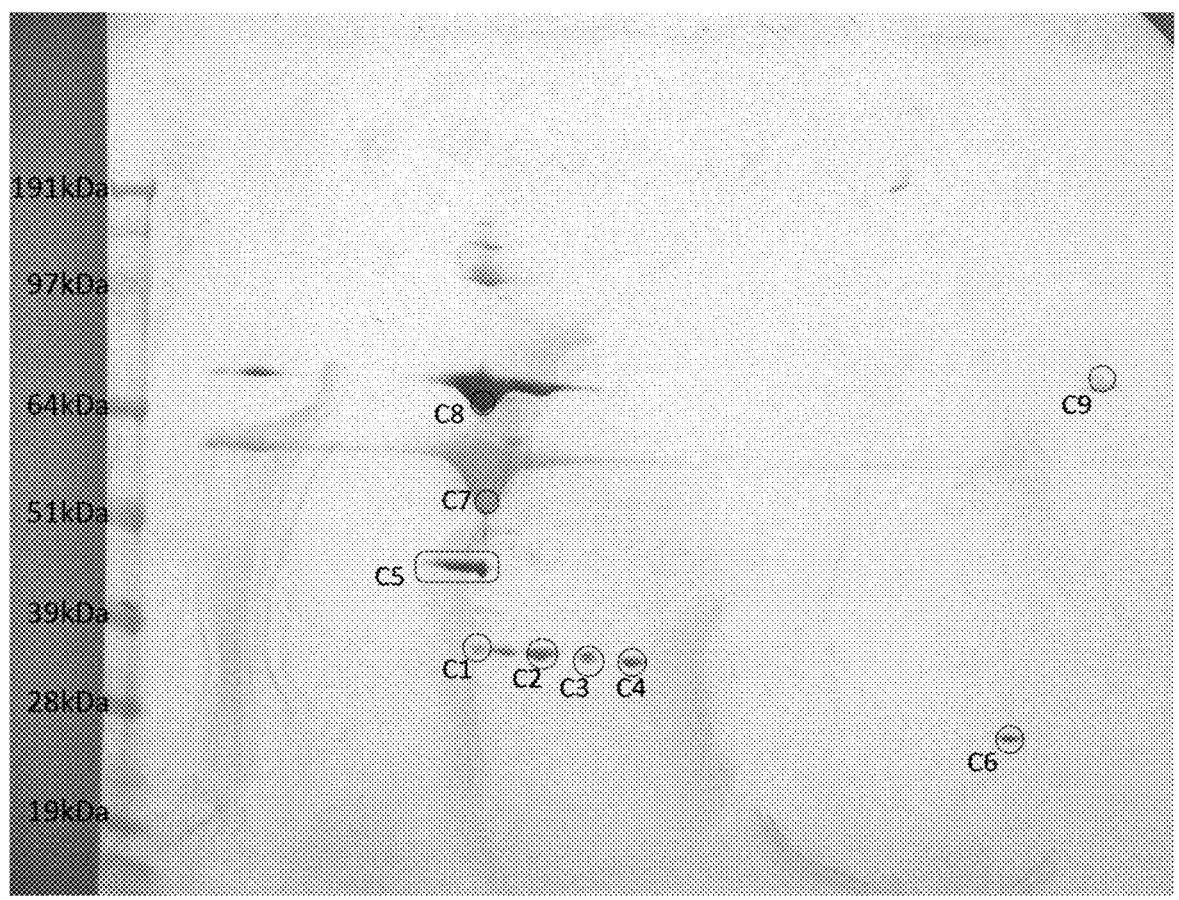
FIG. 7—Western Blue® (BCIP/NBT)-stained antibody-probed Western blot of C. burnetii proteins detected in wide pI range 3-11 (non-linear). Immunoreactive proteins probed with antibody (IgG) present in guinea pig sera (A1-4), the bound antibody was detected with anti-Guinea Pig IgG/alkaline phosphatase conjugate. The areas marked C1-C9 indicate the locations from where spots of the corresponding protein gel were excised for protein identification.
Figure 8:
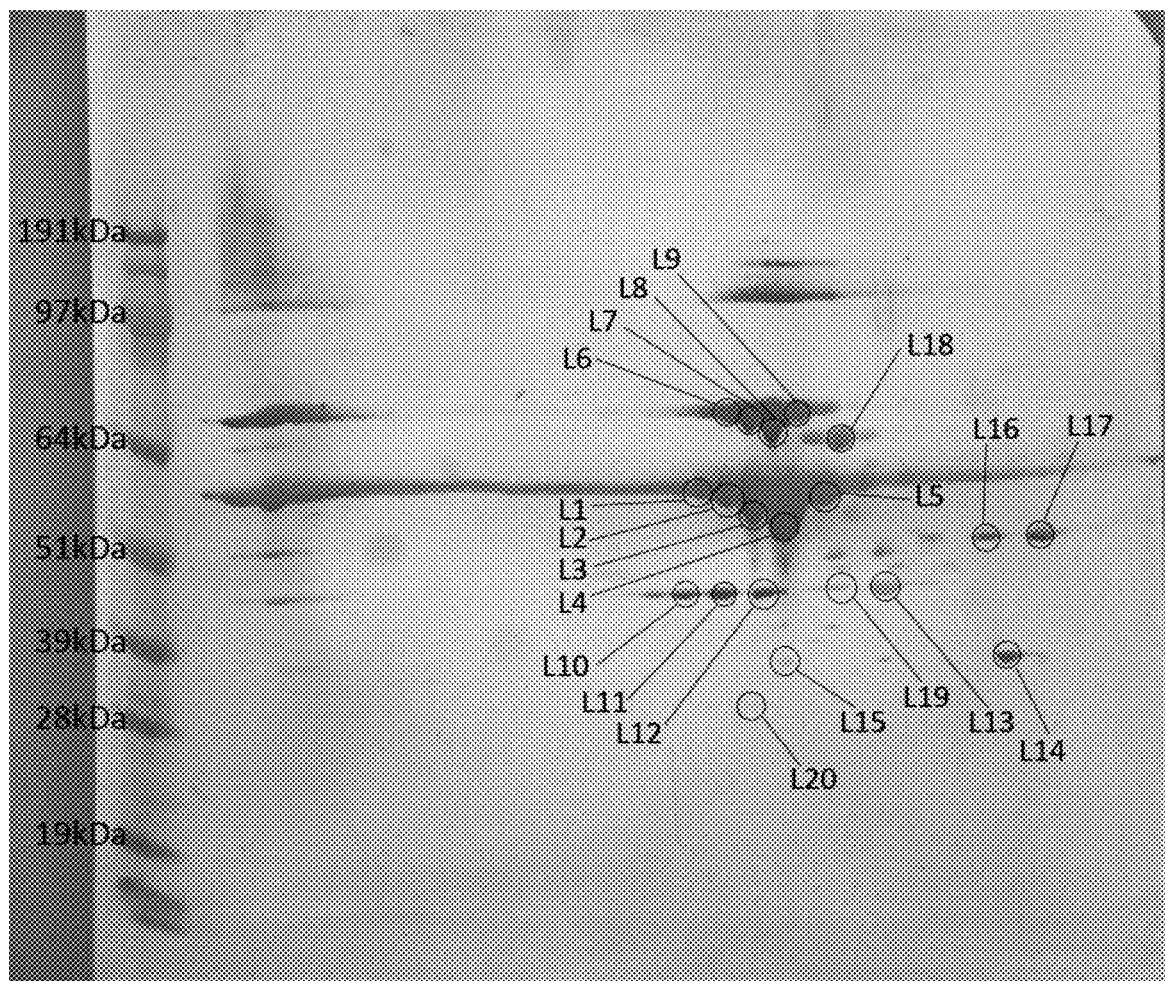
FIG. 8—Western Blue® (BCIP/NBT)-stained antibody-probed Western blot of C. burnetii proteins detected in lower, narrow pI range 3-5.6 (non-linear). Immunoreactive proteins probed with antibody (IgG) present in guinea pig sera (A1-4), the bound antibody was detected with anti-Guinea Pig IgG/alkaline phosphatase conjugate. The areas marked L1-L20 indicate the location from where spots of the corresponding protein gel were excised for protein identification.
Figure 9:
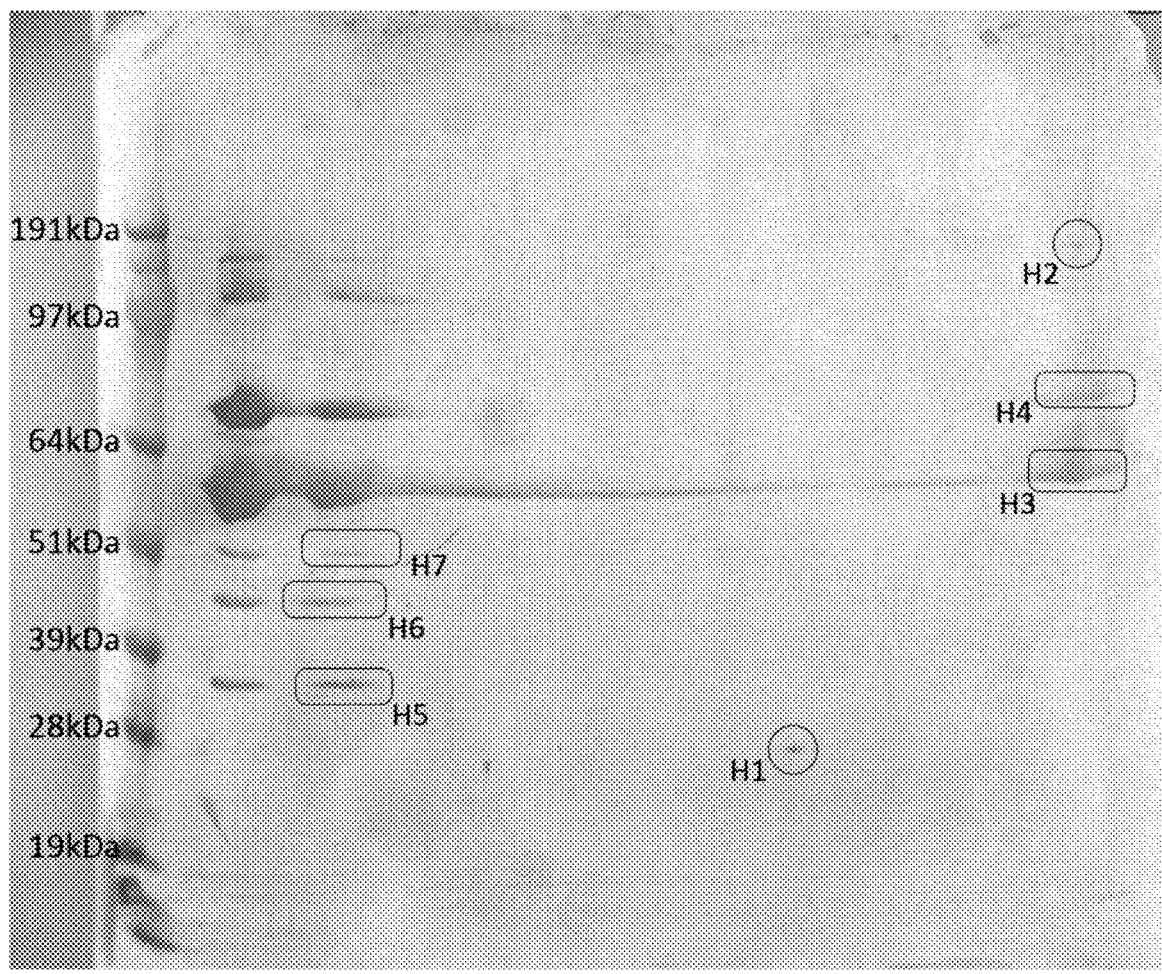
FIG. 9—Western Blue® (BCIP/NBT)-stained antibody-probed Western blot of C. burnetii proteins detected in higher, narrow pI range 7-11 (non-linear). Immunoreactive proteins probed with antibody (IgG) present in guinea pig sera (A1-4), the bound antibody was detected with anti-Guinea Pig IgG/alkaline phosphatase conjugate. The areas marked H1-H7 indicate the location from where spots of the corresponding protein gel were excised for protein identification.
Figure 10:
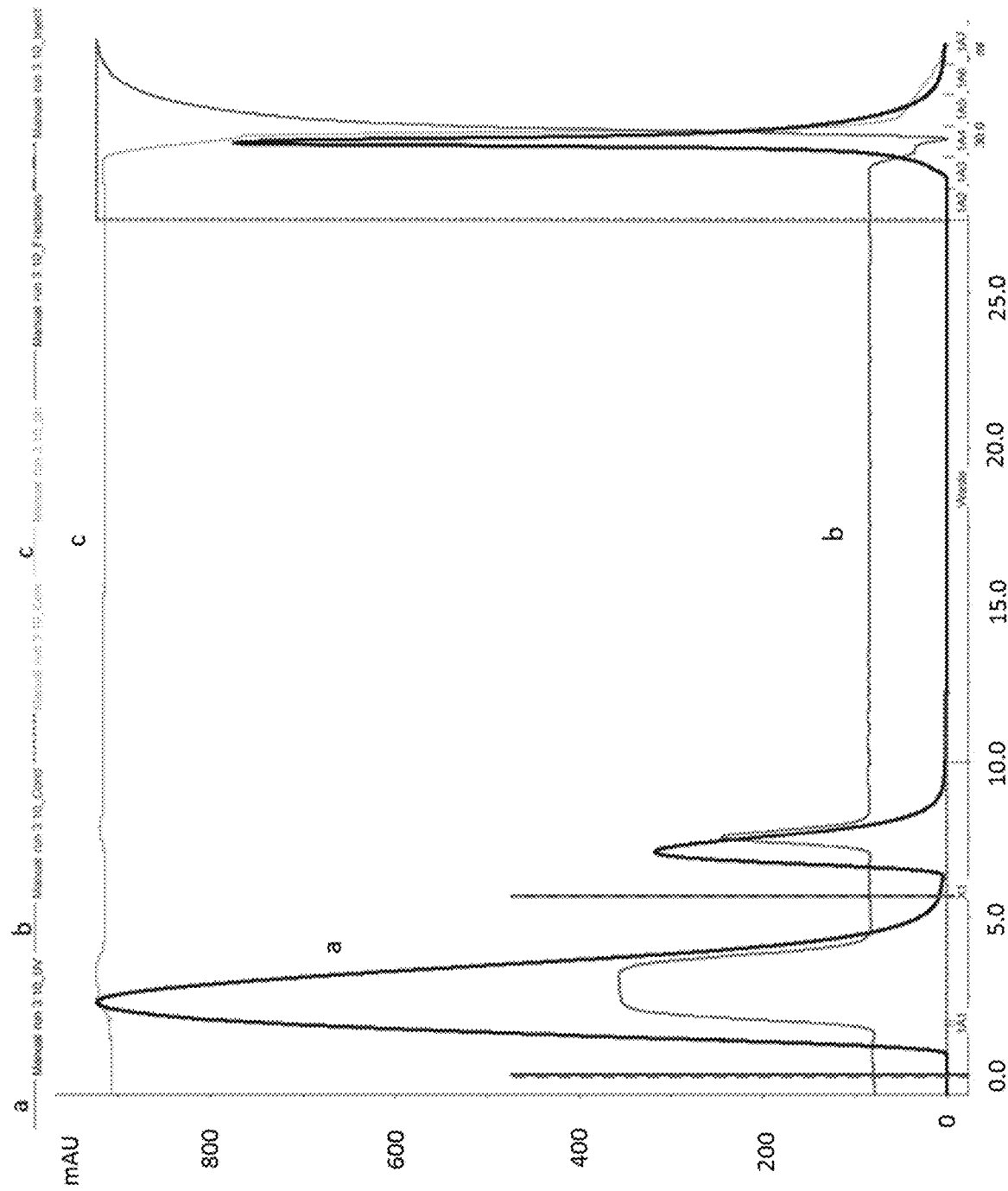
FIG. 10—Output trace of the AKTA FPLC instrument during affinity purification of the guinea pig antisera. The blue trace shows protein concentration (arbitrary units) measured by UV, the two sample injection points are indicated by the pink vertical bars, the switch of the instrument from binding buffer to elution buffer is indicated by the change in conductivity shortly after 25 ml (green trace) and the eluted protein fraction identities are in red text from this point.
Figure 11:
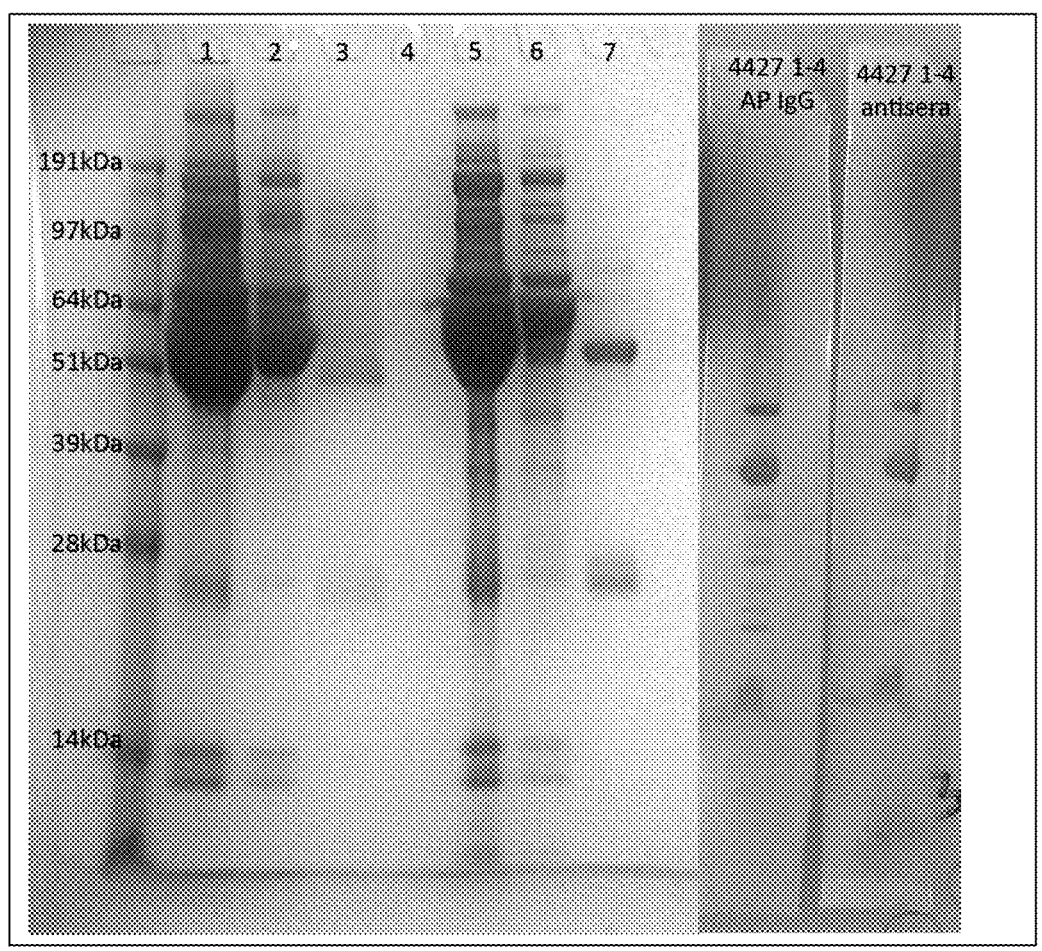
FIG. 11—Left-hand pane—1D PAGE analysis of affinity purified guinea pig IgG. Lanes 1-3 non-reduced protein. Lanes 5-7 reduced protein. Lanes 1 and 5 are antisera, lanes 2 and 6 are purification column wash through, lanes 3 and 7 are the eluted, dialysed and concentrated IgG. In lane 7 the heavy (~50 kDa) and light (~23 kDa) chains of IgG can be clearly seen, in lane 3 the ~150 kDa single band of the un-reduced IgG is not easily visualised, this is likely due to lane-to-lane bleed of the reducing agents partly reducing the IgG. Right-hand pane—Antibody-probed Western Blots of *C. burnetii* protein detected with Western Blue® substrate showing no difference in activity between the un-treated antisera and the affinity-purified antibody.
Figure 12:
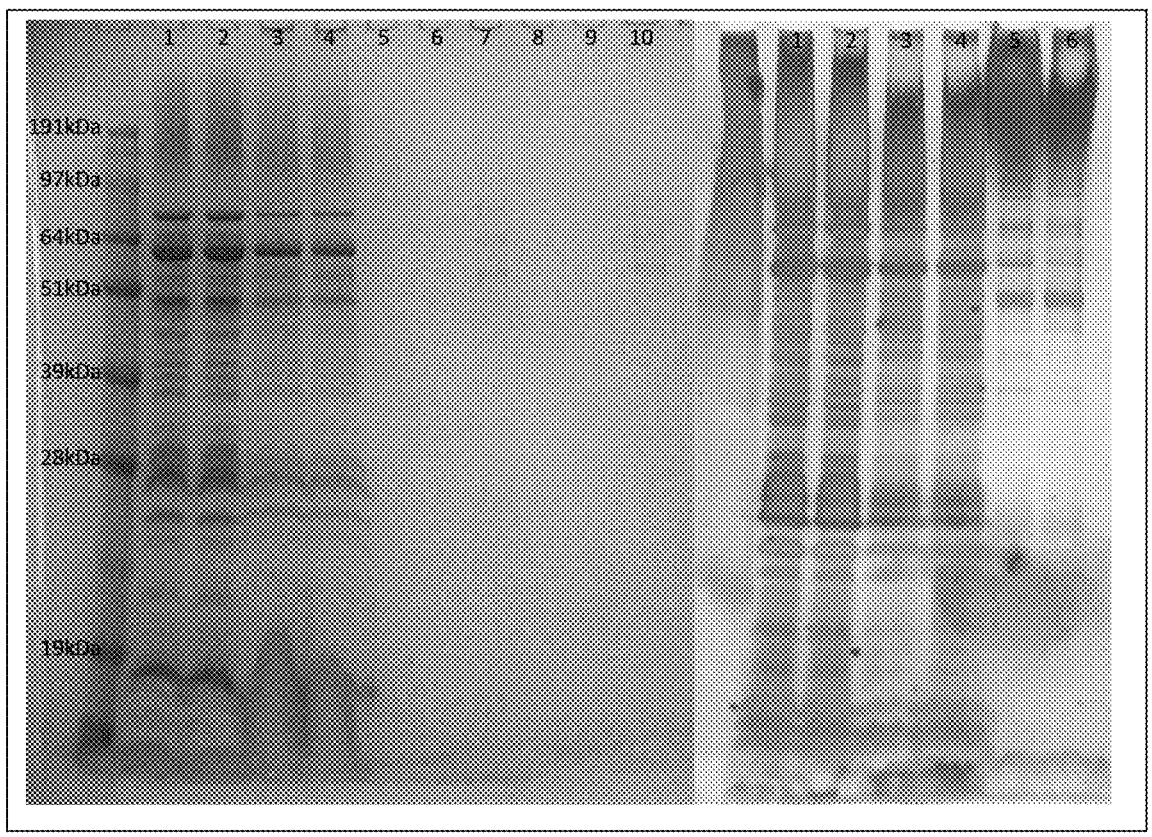
FIG. 12—The left-hand pane is the Coomassie-stained 1D PAGE of the immunoprecipitation (IP) experiment protein samples. Lanes 1 and 2 are the Native *C. burnetii* protein material pre- and post-IP. Lanes 3 and 4 are the Denatured material pre- and post-IP. Lane 7 is the post-IP (Convalescent guinea pig IgG-captured) eluted native proteins. Lane 10 is the post-IP eluted denatured proteins. The right-hand panel is the residual protein remaining in the gel after Western blotting the same material with the exception that lanes 5 and 6 are the eluted native and denatured protein materials. The greater sensitivity of the silver staining procedure shows that a good range of protein species were eluted from the IP experiment.
Figure 13:
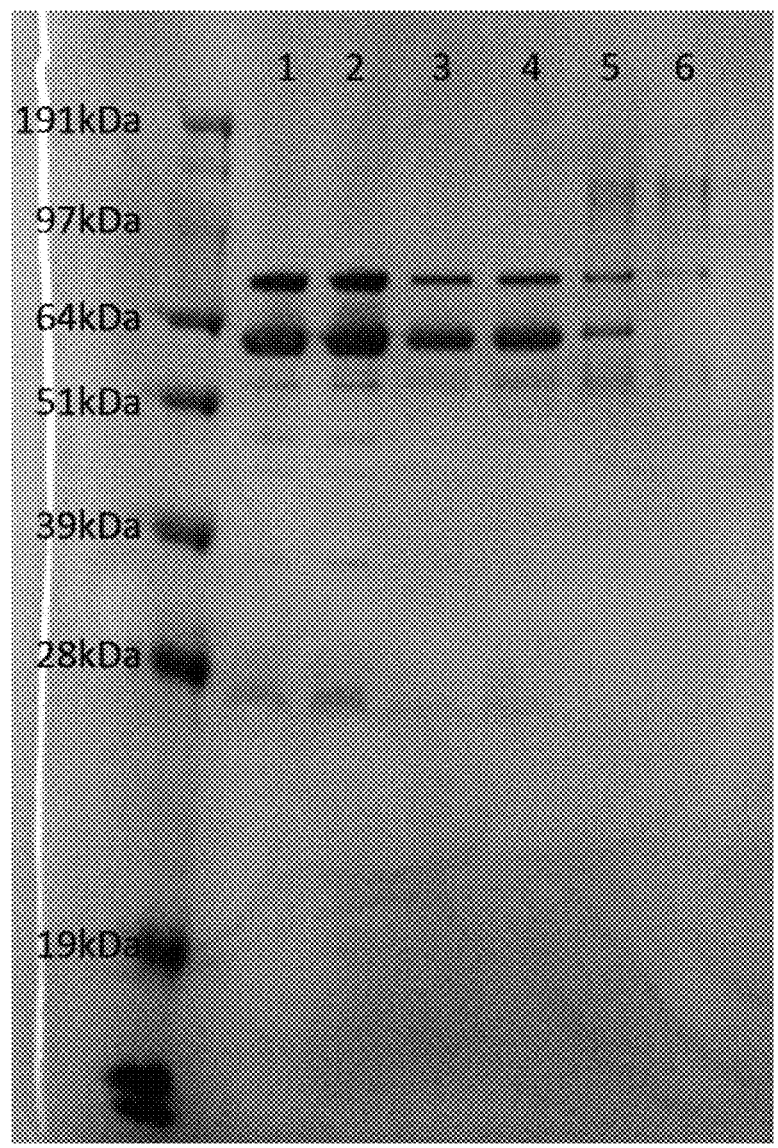
FIG. 13—Western-blot of the immunoprecipitation (IP) experiment protein samples probed with guinea pig convalescent sera (4427 1-4). Lanes 1 and 2 are the Native *C. burnetii* protein material pre- and post-IP. Lanes 3 and 4 are the Denatured material pre- and post-IP. Lane 5 is the post-IP (Convalescent guinea pig IgG-captured) eluted native proteins. Lane 6 is the post-IP eluted denatured proteins.

Western blot membranes that were probed with guinea pig sera (4427 A1-4) were used to identify spots or regions on the Coomassie stained 2D PAGE gels that contained immune-reactive proteins. The locations and assigned identities of the cut proteins are indicated on the images of the blots below (FIGS. 7-9).

Overall, the two-dimensional protein separations further supported the observations from the one-dimensional work by yielding a wide range of protein species in terms of both size and charge (pI). The Western blot analysis of the 2D-separated proteins again demonstrated that only a subset of the proteins present reacted with the sera from the guinea pigs. Sections of the 2D PAGE gels corresponding to reactive areas on the immunoblots were excised and stored for further analysis.

Immunoprecipitation of Immune-Reactive Proteins

A single spot picked from a 2D PAGE gel may well contain numerous protein species and there is no convenient method for identifying which of the identities corresponds to the immune-reactive protein species detected on the sera-probed Western blot. Accordingly, the inventors carried out immunoprecipitation (IP) to produce a second dataset of protein identities generated by using the guinea pig sera to 'capture' the immune-reactive proteins. The captured proteins were then eluted, and identified by tandem mass spectrometry discussed below. The inventors were the first to use IP for the detection of immune-reactive proteins in *C. burnetii*.

Antibody Affinity Purification

Immunoprecipitation (IP) requires an affinity purified class G immunoglobulin (IgG) antibody to use as the capture antibody. This was prepared from 500 µl guinea pig sera as follows.

A 1 ml recombinant Protein A (1 ml) column (HiTrap™ rProtein A FF GE Healthcare #17-5079-02) was fitted to an AKTA fast protein liquid chromatography (FPLC) instrument. The flow rate of the instrument was set to 1 ml/min. The column was flushed to remove any residual storage buffer with 5 ml of binding buffer (Appendix 1). The column was regenerated with 5 ml of Elution Buffer (Appendix 1) and finally equilibrated with 10 ml of binding buffer.

The guinea pig antisera (4427 1-4) was made up to 5 ml with binding buffer and filtered through a 0.45 µm syringe filter. This was then injected into a 5 ml loading loop on the FPLC instrument. Due to the precious nature of the antisera, the syringe was washed with binding buffer and the contents injected onto the column. The column was then washed with 15 ml of binding buffer.

Finally, the bound IgG was eluted by washing 5 ml of elution buffer through the column. Fractions (7×1 ml) were collected into tubes each containing 200 µl of 1 M Tris-HCl, pH 9.0 to rapidly neutralise the low pH of the elution buffer and minimise damage to the purified antibodies.

Dialysis and Concentration of Affinity Purified Antibody

To buffer-exchange the antibodies into a buffer compatible with IP, the pooled fractions (four and five) containing the eluted, affinity-purified IgG (approximately 2.5 ml) were dialysed against phosphate buffered saline (PBS) in a Slide-A-Lyzer dialysis cassette (Thermo #66380-10,000 MWCO). Three dialyses were performed, two stirred 500 ml volumes at room temp for 2 h each, followed by a third overnight at 8° C.

The dialysed antibody was concentrated using a centrifugal concentrator (VivaSpin500 Sartorious # VS0121; 30K MWCO) by first washing the storage buffer off the column with 500 µl PBS for 10 min at 15,000×g. The purified antibody was loaded onto the column 500 µl at a time and concentrated for 10 min at 15,000×g until all of the antibody had been loaded and concentrated, and the final volume was approximately 50 µl. The concentrated antibody was quantitated by measuring the absorbance at 280 nm (NanoDrop ND-2000 spectrophotometer) using PBS as a blank.

Purity and Activity Check of Affinity Purified Antibody

Non-reducing and reducing 1D PAGE was performed on the neat guinea pig sera, the column wash through, and the eluted, dialysed and concentrated IgG. To reduce the samples they were heated to 95° C. for 10 min in the presence of 50 mM dithiothreitol (DTT; Life Technologies P2325).

In addition, to assess there was no activity loss during processing of the IgG, two Western blot strips of *C. burnetii* protein were probed as described above, one with the pre-treated guinea pig sera (4427 1-4) and the other with the purified, concentrated IgG.

Preparation of Proteins for Immunoprecipitation

For capture of the proteins recognised by the antibodies by their conformation, the native epitopes, 0.5 mg of *C. burnetii* protein was buffer-exchanged into the IP lysis/wash buffer supplied with the Pierce™ Crosslink Magnetic IP (Thermo #8805) kit. The buffer-exchange was carried out by performing three, 1 ml concentrations into IP lysis/wash buffer in a 5 kDa MWCO centrifugal concentrator (Sartorius Vivaspin 2; VS0211) at 20° C. and 4,000×g.

The majority of proteins isolated so far using the 2D PAGE spot picking method, were all denatured and reduced and consisted of predominantly linear epitopes. To produce a denatured protein preparation, 0.5 mg of *C. burnetii* protein was made to 1% (v/v) sodium dodecyl sulphate with 10% (v/v) stock solution (Life Technologies 24730-020) and 10 mM dithiothreitol (DTT; Life Technologies P2325) and heated to 95° C. for 15 min. This mixture was then alkylated by the addition of iodoacetamide (IAA; Sigma 11149) to a final concentration of 50 mM and incubated in the dark at room temperature for 45 min. To remove the substances that would interfere with the IP reaction, the denatured, reduced, and alkylated proteins were buffer-exchanged into IP lysis/wash buffer as described above for the native proteins.

Immunoprecipitation of *C. burnetii* Immune-Reactive Proteins

Immunoprecipitation was performed using a Pierce™ Crosslink Magnetic IP (Thermo #8805) kit. For each immunoprecipitation experiment, antibody was bound to protein A/G magnetic beads by pipetting 50 μL of the magnetic beads into a 2.0 ml microcentrifuge tube. The tubes were placed in a magnetic stand and the storage buffer discarded. The beads were twice washed for 1 min in 500 μl of modified coupling buffer (MCB—consisting of 100 μl of 20× coupling buffer and 100 μl mL of IP lysis/wash buffer made up to 2 ml with deionised water) on a rotating platform followed by magnetic collection and discarding of the supernatant. The affinity-purified guinea pig IgG was diluted to a final volume of 200 μl of MCB containing 20 μg of antibody. To bind antibody to the beads, the diluted antibody solution was added to the beads and the tubes incubated on a rocking platform for 30 min at room temperature—vortexing every 10 min during incubation. The beads were collected with a magnetic stand and the supernatant discarded.

The beads were washed with 100 μl of MCB, vortexed, magnetically collected and the supernatant discarded. This was repeated with a 300 μl volume of MCB twice more to remove any unbound antibody.

Antibody was cross-linked to the magnetic beads using disuccinimidyl suberate (DSS). The DSS was diluted to 0.25 mM in dimethylformamide (DMF). The cross-linking buffer consisted of 100 μl coupling buffer containing 20 μM DSS. The cross-linking buffer was added to the beads, vortexed and incubated for 30 min at room temperature on a rocking platform. The beads were collected in a magnetic stand and the cross-linking solution discarded. To remove any non-crosslinked antibody and stop the cross-linking reaction, 100 μl volumes of elution buffer were added to the beads and mixed for 5 min at room temperature before magnetically collection and discarding the supernatant. This was performed twice. The beads were finally given two, 200 μl washes in 8° C. IP lysis/wash buffer.

The native or denatured protein preparations (see "preparation of proteins for immunoprecipitation") were added to tubes containing cross-linked magnetic beads and incubated for 1 h at room temperature followed by overnight incubation at 8° C. on a rotating mixer. The beads were collected and the unbound proteins removed and retained. The beads were washed twice with 500 μl of IP lysis/wash buffer and once with 500 μl of deionised water. Bound proteins were eluted by adding 100 μL of elution buffer to each tube followed by incubate for 5 min at room temperature on a rotating platform. The beads were magnetically collected, the supernatant containing the eluted proteins removed, and the pH neutralised with 10 μl of neutralisation buffer. The elution step was repeated twice and the supernatants pooled.

The eluted proteins were immediately purified and concentrated by precipitation using a 2-D Clean-Up Kit (GE Healthcare 80-6484-51) described above. The precipitated protein was denatured and reduced by re-suspended in 1× Laemmli buffer, heating to 95° C. for 10 min and subjecting to 1D PAGE as described above. Western blots were also performed and the blots probed with guinea pig antisera.

The eluted protein lanes from the Coomassie-stained gel were cut into 7× sections (each approximately 1 cm×0.5 cm) and stored at −20° C. for mass spectrometric analysis.

Results—Immunoprecipitation of Immune-Reactive Proteins

Antibody Affinity Purification

The output of the FPLC instrument is shown below (FIG. 10). It can be seen that fractions four and five contain the bulk of the eluted IgG. The concentrated antibody preparation produced yielded a mean quantity of 2.9 μg/μl (A280 nm=3.945).

The purity and activity assessment (FIG. 11) show that the majority of the non-antibody serum proteins were washed from the column in the flow-through (lanes 2 and 6) and the affinity purified antibody contained almost pure IgG (heavy and light IgG chains in the reduced gel image). In addition, the antibody-probed Western blots show the activity of the purified IgG to be indiscernible from the untreated antisera from which it was derived.

Immunoprecipitation

The protein results of the immunoprecipitation (IP) experiment (FIG. 12) do not show any obvious loss of protein in the post-IP lanes. However, the eluted proteins from both the native and denatured protein samples contain a good range of sizes of protein species. Some of these proteins are present at low abundance, evidenced by the fact that they are only visible on the more sensitive silver-stained gels.

Immunoprobing the Western-blot membrane with the IgG present in guinea pig sera (4427 A1-4) shows reactions with proteins present in all lanes (FIG. 13). This is further confirmation that the IP experiment did not remove all of the immune-reactive proteins from the post-IP samples. Reactions with the eluted protein lanes demonstrate that the proteins that were immunoprecipitated were immune-reactive species. Many of the protein species bands from the highly-sensitive silver-stained gel were not detected on the immunoblot; this is likely due to the low abundance of these proteins rather than their lack of immunogenicity. However, it is possible that some of the native proteins, due to their denatured and reduced state here, would not be recognised by their corresponding antibody.

Protein Identification

The inventors sought to identify the proteins contained in the 2D-PAGE spots that corresponded to reactive areas on the immunoblots, and identify the proteins contained in the gel slices of immunoreactive proteins captured by the convalescent guinea pig IgG by immunoprecipitation. The inventors also employed in silico predictive tools to obtain more information about the newly-identified identified proteins.

In Gel Tryptic Digestion of Proteins

Excised gel spots or regions from Coomassie-stained polyacrylamide gels were de-stained and the proteins contained in the gel, reduced and alkylated. These proteins were then digested or cleaved into peptides with trypsin followed by passive elution using the procedure described below based on a published protocol.

Destaining buffer, consisting of 25 mM ammonium bicarbonate (Fisher Scientific #10207183) in 50% (v/v) aqueous acetonitrile (Fisher Scientific #10080000) and digestion buffer, consisting of 25 mM aqueous ammonium bicarbonate were prepared in advance of the procedure and stored at 8° C. Trypsin enzyme (Trypsin Gold, Mass spectrometry grade; Promega V5280) was re-suspended in 50 mM acetic acid to produce a 1 μg/μl stock. This stock was divided into 10 μl aliquots and stored at −80° C. For each digestion, a fresh vial of trypsin was thawed. To minimise missed-cleavage artefacts during analysis of the mass spectrometric data downstream, freeze-thawed enzyme was never used for this work.

Each gel piece was incubated with 500 μl of destaining buffer for 30 min at 37° C. in a shaking incubator set at 300 rpm. The destaining solution was carefully aspirated from around the gel piece and discarded. This step was repeated until all of the blue colouring from the gel had been removed. The gel pieces were then dehydrated by incubating twice with 500 μl of acetonitrile for 10 min, after the second incubation the acetonitrile was removed and the gel pieces allowed to air-dry (caps open) at room temperature for 10 min.

The proteins were reduced by adding 50 μl of 10 mM dithiothreitol (DTT; Life Technologies P2325) diluted in 25 mM ammonium bicarbonate to each gel piece and heating to 60° C. for 30 min. After incubation, the excess solution was discarded. To alkylate the proteins, the gel pieces were suspended in 50 μl of 55 mM of iodoacetamine (Sigma 11149) diluted in 25 mM ammonium bicarbonate and incubated at room temperature in the dark for 45 min. The alkylation buffer was removed and the gel pieces subjected to three, 5 min washes with 500 μl digestion buffer. The gel pieces were then dehydrated by incubating twice with 500 μl of acetonitrile for 10 min, after the second incubation the acetonitrile was removed and the gel pieces allowed to air-dry (caps open) at room temperature for 10 min.

Trypsin was thawed and diluted in 25 mM ammonium bicarbonate to a working concentration of 10 ng/μl. To each gel piece, 75 μl of working trypsin solution was added and the tubes incubated overnight at 37° C. at 300 rpm in a shaking incubator.

Peptides were extracted by centrifuging the gel pieces at 10,000×g for 5 min and aspirating off and storing the digested peptide/trypsin solution in individual tubes. The tubes were then incubated at 37° C. for 1 h with 100 μl of 0.1% (v/v) aqueous trifluoroacetic acid (Fisher Scientific #10311725). The gel pieces were again centrifuged at 10,000×g for 5 min, the trifluoroacetic acid aspirated off and combined and mixed with the retained trypsinised peptide solution.

The extracted peptides were frozen at −80° C. until required for mass spectrometric analysis.

Mass Spectrometry Analysis

Tryptic peptide mixtures from the in-gel trypsin digestion were separated using nanoflow reversed phase liquid chromatography (RPLC) and analysed using a tandem mass spectrometer (nLC-MS/MS). Online chromatography was performed with the Thermo Easy nLC 1000 ultra-high pressure HPLC system (Thermo Fisher Scientific Ltd.) coupled to the Q Exactive mass spectrometer (Thermo Fisher Scientific Ltd.). The instrument was controlled by the Xcalibur software (Q Exactive Plus 2.3, ThermoFisher Scientific Ltd.).

For chromatographic separation, buffer A (0.1% (v/v) aqueous formic acid) and buffer B (0.1 (v/v) formic acid in acetonitrile) were used as mobile phases for gradient separation. Each sample (10 μl) was loaded onto a reversed phase Nano Trap Column (Acclaim PepMap 100, 100 μm i.d.×2 cm long, $C_{18}$, 5 μm, 100 Å) and further separated on an $C_{18}$ reversed-phase nanocolumn (Acclaim PepMap100, 75 μm i.d.×15 cm long, $C_{18}$, 3 μm, 100 Å; ThermoFisher Scientific Ltd.) with a linear gradient of 4-75% buffer B at a flow rate of 300 nl/min over 30 min, then to 95% B over 1 min and held at 95% B for 7 min (see Table 4). Due to loading, lead-in and washing steps, the total time for the nLC-MS/MS runs was 53 min.

TABLE 4

NanoLC parameters used to feed the electrospray ionisation (ESI) component of the tandem mass spectrometer. Buffer A (default) consisted of 0.1% (v/v) aqueous formic acid and buffer B of 0.1% (v/v) formic acid in acetonitrile.

| Time (min) | Duration (min) | Flow rate (nl/min) | % buffer B (in A) |
|---|---|---|---|
| 0.00 | 0.00 | 300 | 4 |
| 30.00 | 30.00 | 300 | 75 |
| 31.00 | 1.00 | 300 | 95 |
| 38.00 | 7.00 | 300 | 95 |

General mass spectrometric conditions were set as follows: spray voltage at 1.6 kV, capillary temperature at 260° C., S-lens RE level at 50. Nitrogen was used as collision gas, but no sheath or auxiliary gases were applied.

For data acquisition, the instrument was operated in positive ion mode and a data-dependent 'top 20' method was used. Full scans (300-2,000 amu) were acquired at a resolution of 70,000 at m/z=200 with maximum ion injection time (IIT) of 100 ms. MS/MS was performed by higher-energy collisional dissociation (HCD) fragmentation using collision-induced dissociation (CID). Resolution for HCD spectra was set to 17,500 at m/z=200 amu with maximum IIT of 50 ms. Normalized collision energy was set as 27%. The 'underfill ratio', specifying the minimum percentage of the target ion value likely to be reached at maximum fill time was defined as 1.0%. Default dynamic exclusion of 15.0 s was selected to prevent an ion from triggering a subsequent data-dependent scan after it has already triggered a data-dependent scan.

In Silico Analyses and Protein Identification

MS data were generated in the form of .RAW files (ThermoFinnigan file format), which contain all of the spectra detected from the LC-MS/MS analysis for each sample. Spectra acquired were searched against the non-redundant Uniprot protein database (http://www.uniprot.org—containing 8,955 C. burnetii protein sequences including randomly generated peptide decoys (TDA) to reduce the false discovery rate) using Proteome Discoverer™ (Version 1.4, Thermo Scientific). The search parameters used were: Enzyme: trypsin; Fixed (or static) Modifications: carbamidomethylation of cysteine; Variable Modifications: oxidation of methionine; Missed Cleavage Sites: 2; peptide mass tolerance±10 ppm. The search results were filtered using Scaffold (Version 4, Proteome Software, USA) to minimise the number of false positives, as indicated by a false discovery rate (FDR) of <2%. Protein identifications were accepted with at least two unique, exclusive identified peptides.

Organisation of Identified Proteins

The lists of identified proteins were compared to the five published reports of proteins discovered by 2D-PAGE followed by immunoblotting, spot-picking and mass spectrometry and the four reports of proteins discovered using microarray and ELISA/ELISPOT and in vitro translated open-reading frames of the C. burnetii genome. This comparison yielded three groups of identified proteins; those that were present in both 2D-PAGE picked spots and in the immunoprecipitated proteins, those that were present only in the immunoprecipitated proteins, and those present only in 2D-PAGE picked spots. These were further sub-divided into two groups each; those previously described in one or more of the seven published reports and those that were unique to this work.

Protein Functional Characterisation

Functional annotation of all identified proteins was based on the cellular process information from the COG database, the UniProt server, and the InterPro domains and functional sites database. The proteins were then assigned to 20 functional categories based on the criteria used in two published *C. burnetii* proteomics articles.

Newly-identified immune reactive proteins were further characterised using a range of tools to ascertain their size and isoelectric point using the "Compute pI/Mw tool" on the ExPASy server, their predicted subcellular localisation with PSORTb v3.0.2 and SOSUI$_{GramN}$, their predicted non-classical secretion probability with SecretomeP v2.0, the presence of predicted signal peptides using SignalP v4.1, the presence of predicted integral beta-barrels using BOMP, the presence of predicted lipoproteins using Lipo and LipoP v1.0, and the presence of predicted transmembrane regions using TMHMM v2.0. Table 5 shows the internet locations of these tools.

TABLE 5

Tools used to predict subcellular localisation and functionality of identified *C. burnetii* proteins.

| Tool name (and version where applicable) | Uniform resource locator (URL) of server hosting the tool |
|---|---|
| Compute pI/Mw tool | web.expasy.org/compute_pi/ |
| PSORTb v3.0.2 | www.psortb.org/psortb/ |

TABLE 5-continued

Tools used to predict subcellular localisation and functionality of identified *C. burnetii* proteins.

| Tool name (and version where applicable) | Uniform resource locator (URL) of server hosting the tool |
|---|---|
| SOSUI$_{GramN}$ | harrier.nagahama-i-bio.ac.jp/sosui/sosuigramn_submit.html |
| SecretomeP v2.0 | www.cbs.dtu.dk/services/SecretomeP/ |
| SignalP v4.1 | www.cbs.dtu.dk/services/SignalP/ |
| BOMP | services.cbu.uib.no/tools/bomp |
| Lipo | services.cbu.uib.no/tools/lipo |
| LipoP v1.0 | www.cbs.dtu.dk/services/LipoP/ |
| TMHMM v2.0 | www.cbs.dtu.dk/services/TMHMM/ |

Results—Protein Identification

Due to the fact that an immunoreactive spot picked from a 2D-PAGE gel can contain several proteins, proteins that were identified by spot picks alone have been excluded from the tables presented herein. Proteins identified in spot picks and captured by the guinea pig convalescent IgG during the immunoprecipitation (IP) experiments and proteins identified only by IP are presented.

Novel proteins that have not been described as immune-reactive in the literature previously as isolated by 2D-PAGE spot picks and validated by immunoprecipitation (IP) are presented (Table 6) as well as those isolated by IP only (Table 7).

TABLE 6

Novel proteins identified by 2D-PAGE spot picks and by immunoprecipitation methods that have not been previously reported as immunoreactive in the literature; the calculated molecular weight (MW) in Daltons (Da) and the estimated average isoelectric point (pI) are shown for each protein.

| SEQ ID NO: | Locus Tag | Functional Classification Protein Name | Spot locations | MW (Da) | pI |
|---|---|---|---|---|---|
| | | DNA metabolism - Replication, recombination and repair | | | |
| 1 | CBU_1337 | DNA polymerase III alpha subunit | L20 | 128,481 | 5.7 |
| | | Transcription | | | |
| 2 | CBU_0232 | DNA-directed RNA polymerase beta' chain | H2 | 157,104 | 7.6 |
| 3 | CBU_0852 | Polyribonucleotide nucleotidyltransferase/Polynucleotide adenylyltransferase | L6, L8, L9, L21, L22, H2, | 76,331 | 5.4 |
| | | Nucleotide and nucleoside biosynthesis and metabolism | | | |
| 4 | CBU_0326 | Phosphoribosylamine-glycine ligase | L11, L13, L19, H3, H4, H6, H7, C5 | 47,631 | 6.1 |
| 5 | CBU_0897 | Amidophosphoribosyltransferase | H3, H4 | 55,936 | 6.0 |
| 6 | CBU_1384 | Uridylate kinase | H1, C6 | 26,362 | 9.1 |
| | | Regulatory function | | | |
| 7 | CBU_1579 | Trp represser binding protein | H5, H6, H7 | 21,156 | 7.0 |
| | | Translation - Protein Biosynthesis | | | |
| 8 | CBU_1475 | Aspartyl/glutamyl-tRNA(Asn/Gln) amidotransferase subunit B | H2, L16, L17, L21, H3, H4, H7, C1, C2, C3 | 53,454 | 5.4 |

TABLE 6-continued

Novel proteins identified by 2D-PAGE spot picks and by immunoprecipitation methods that have not been previously reported as immunoreactive in the literature; the calculated molecular weight (MW) in Daltons (Da) and the estimated average isoelectric point (pI) are shown for each protein.

| SEQ ID NO: | Locus Tag | Functional Classification Protein Name | Spot locations | MW (Da) | pI |
|---|---|---|---|---|---|
| | | Amino acid biosynthesis and metabolism | | | |
| 9 | CBU_0517 | Aspartate aminotransferase/ Succinyldiaminopimelate aminotransferase | L12, L13, H3, H4, H6, H7, L19, C5 | 46,419 | 6.4 |
| | | Energy metabolism - electron transport | | | |
| 10 | CBU_0270 | Short-chain alcohol dehydrogenase | L10, L11, L13, L19, H7, C5 | 44,875 | 5.8 |
| 11 | CBU_0629 | Proline dehydrogenase/Delta-1-pyrroline-5-carboxylate dehydrogenase | H2 | 116,423 | 6.3 |
| 12 | CBU_0974 | Acetyl-CoA acetyltransferase | H6, H7 | 42,243 | 7.7 |
| 13 | CBU_1088 | Bifunctional NAD(P)H-hydrate repair enzyme Nnr | L16, L17, H7 | 51,699 | 5.7 |
| 14 | CBU_1116 | Alanine dehydrogenase | H6 | 39,472 | 6.1 |
| 15 | CBU_1193 | Thioredoxin reductase | H5, C2, C3, C4 | 34,620 | 5.9 |
| 16 | CBU_1296 | ATP-NAD kinase | L15, H5, C1, C2, C4 | 32,892 | 5.3 |
| 17 | CBU_1397 | Succinyl-CoA synthetase beta chain | L10, L11, L12, L13, L19, H3, H4, H6, H7 | 42,333 | 5.5 |
| 18 | CBU_1400 | Succinate dehydrogenase iron-sulfur protein | C6 | 27,792 | 8.2 |
| 19 | CBU_1401 | Succinate dehydrogenase flavoprotein subunit | H2, L21, L22, H3, H4 | 65,438 | 6.7 |
| 20 | CBU_1720 | Aconitate hydratase | H2, L22, H4 | 101,389 | 5.8 |
| | | Intermediary metabolism and other metabolic pathways | | | |
| 21 | CBU_0638 | Dihydrolipoamide acetyltransferase component of pyruvate dehydrogenase complex | L2, L10, L11, L12, L13, L19, H3, H4, H6, H7, C5 | 40,846 | 5.2 |
| 22 | CBU_0640 | Pyruvate dehydrogenase E1 component alpha subunit | L10, L11, L12, L13, L19, H3, H4, H6, H7, C1 | 41,138 | 5.3 |
| 23 | CBU_0962 | Short chain dehydrogenase | H1, H5, H6, H7 | 25,567 | 6.9 |
| | | Posttranslational modification, degradation, protein turnover, chaperones | | | |
| 24 | CBU_0073 | Xaa-Pro aminopeptidase | H2, L21 | 68,185 | 5.6 |
| 25 | CBU_0094 | ClpB protein | H2, L22 | 96,769 | 5.5 |
| 26 | CBU_0338 | Membrane alanine aminopeptidase | H2, L22, H4 | 103,023 | 6.1 |
| | | Cell division, chromosome partitioning | | | |
| 27 | CBU_1352 | Cell division protein ftsH | L15 | 71,610 | 6.2 |
| | | Protein and peptide secretion and trafficking | | | |
| 28 | CBU_1648 | DotA protein | H4, C8 | 86,867 | 5.4 |
| 29 | CBU_1652 | IcmX protein | H3, C3 | 41,352 | 6.0 |
| | | Adaptation to atypical conditions - response to starvation | | | |
| 30 | CBU_1275 | Starvation sensing protein rspA | L10, L19, H2, H3, H4, H6, H7, C5 | 45,431 | 5.7 |

TABLE 7

Novel proteins identified by immunoprecipitation method that have not been previously reported as immunoreactive in the literature; the calculated molecular weight (MW) in Daltons and the estimated average isoelectric point (pI) are shown for each.

| SEQ ID NO: | Locus Tag | Functional Classification Protein Name | MW (Da) | pI |
|---|---|---|---|---|
| | | DNA metabolism - Replication, recombination and repair | | |
| 31 | CBU_0297 | Exodeoxyribonuclease III | 30,453 | 9.2 |
| 32 | CBU_0916 | Endonuclease/Exonuclease/phosphatase family protein | 29,568 | 9.2 |
| 33 | CBU_1183 | Glycine-rich RNA-binding protein | 13,149 | 9.6 |
| 34 | CBU_1235 | Oligoribonuclease | 21,012 | 5.7 |
| | | DNA - medicated transformation (Competence) | | |
| 35 | CBU_0532 | COME operon protein 1 | 13,493 | 10.5 |
| 36 | CBU_0758 | Lipoprotein, ComL family | 30,899 | 9.6 |
| | | Transcription | | |
| 37 | CBU_2086 | Transcription termination factor rho | 46,814 | 6.3 |
| | | Nucleotide and nucleoside biosynthesis and metabolism | | |
| 38 | CBU_0043 | Xanthosine triphosphate pyrophosphatase | 21,777 | 4.7 |
| 39 | CBU_0296 | Orotate phosphoribosyltransferase | 24,190 | 6.4 |
| 40 | CBU_0531 | Orotidine 5'-phosphate decarboxylase | 25,849 | 7.6 |
| 41 | CBU_0631 | Phosphoribosylformylglycinamidine synthase | 146,552 | 6.3 |
| 42 | CBU_0796 | Adenosine 5'-monophosphoramidase/ Guanosine 5'-monophosphoramidase | 12,481 | 6.3 |
| 43 | CBU_1830 | Ribose-phosphate pyrophosphokinase | 35,221 | 5.8 |
| | | Translation - protein biosynthesis | | |
| 44 | CBU_0234 | SSU ribosomal protein S7P | 21,291 | 10.3 |
| 45 | CBU_0445 | SSU ribosomal protein S16P | 20,726 | 9.9 |
| 46 | CBU_0808 | Valyl-tRNA synthetase | 106,648 | 8.6 |
| 47 | CBU_0851 | SSU ribosomal protein S15P | 10,316 | 10.4 |
| 48 | CBU_1325 | Bacterial Protein Translation Initiation Factor 3 (IF-3) | 19,456 | 9.9 |
| 49 | CBU_1383 | Ribosome Recycling Factor (RRF) | 20,945 | 6.4 |
| 50 | CBU_1473 | Aspartyl/glutamyl-tRNA(Asn/Gln) amidotransferase subunit C | 11,102 | 4.7 |
| 51 | CBU_1594 | GatB/Yqey domain protein | 16,744 | 6.0 |
| 52 | CBU_1841 | Peptidyl-tRNA hydrolase | 20,771 | 9.0 |
| | | Amino acid biosynthesis and metabolism | | |
| 53 | CBU_1970 | Diaminopimelate epimerase | 30,071 | 6.1 |
| | | Energy metabolism - electron transport | | |
| 54 | CBU_0075 | 2-polyprenyl-6-methoxyphenol hydroxylase | 45,231 | 9.7 |
| 55 | CBU_2087 | Thioredoxin | 12,613 | 4.9 |
| | | Intermediary metabolism and other metabolic pathways | | |
| 56 | CBU_0502 | DNase, TatD family | 28,627 | 5.9 |
| 57 | CBU_0288 | Phosphopantetheine adenylyltransferase | 17,967 | 6.2 |
| 58 | CBU_0928 | Pyridoxamine 5'-phosphate oxidase | 23,636 | 6.3 |
| | | Posttranslational modification, degradation, protein turnover, chaperones | | |
| 59 | CBU_0738 | ATP-dependent endopeptidase clp proteolytic subunit clpP | 21,602 | 6.1 |
| 60 | CBU_2012 | ATP-dependent endopeptidase hsl ATP-binding subunit hslU | 52,123 | 5.5 |
| | | Lipopolysaccharide biosynthesis and metabolism | | |
| 61 | CBU_2092 | Phosphoenolpyruvate carboxykinase [ATP] | 56,809 | 5.8 |
| | | Protein and peptide secretion and trafficking | | |
| 62 | CBU_0091 | Peptidoglycan-associated lipoprotein OmpA-like | 21,357 | 9.5 |
| 63 | CBU_0155 | Type 4 pili biogenesis protein pilB (nuleotide-binding protein) | 57,831 | 8.6 |
| | | Pathogenicity and pathogenesis | | |
| 64 | CBU_1136 | Enhanced entry protein enhC, tetratricopeptide repeat family | 117,740 | 9.3 |
| | | Detoxication and Resistance | | |
| 65 | CBU_0943 | Rhodanese-related sulfurtransferases | 16,593 | 8.7 |
| 66 | CBU_1708 | Superoxide dismutase | 22,274 | 6.2 |

TABLE 7-continued

Novel proteins identified by immunoprecipitation method that have not been previously reported as immunoreactive in the literature; the calculated molecular weight (MW) in Daltons and the estimated average isoelectric point (pI) are shown for each.

| SEQ ID NO: | Locus Tag | Functional Classification Protein Name | MW (Da) | pI |
|---|---|---|---|---|
| | | Adaptation to atypical condition - response to starvation | | |
| 67 | CBU_1916 | Universal stress protein A | 15,779 | 6.6 |
| | | Poorly characterised | | |
| 68 | CBU_0114 | Protein yajQ | 18,184 | 7.9 |
| 69 | CBU_0510 | Hypothetical protein | 11,275 | 5.5 |
| 70 | CBU_0656 | Hypothetical transcriptional regulatory protein | 12,103 | 4.9 |
| 71 | CBU_2009 | Hypothetical protein | 50,169 | 9.1 |

The inventors also identified 36 immunoreactive *C. burnetii* proteins that have previously been described in the literature, thereby further validating the processes and methods used herein.

Further Characterisation of Unpublished Proteins

Of the 71 novel immune reactive proteins identified, 19 were identified as having particularly advantageous features and/or a predicted non-cytoplasmic location.

TABLE 8

Novel identified proteins (previously unpublished) that have predicted notable features and/or non-cytoplasmic locations. Predictions of transmembrane regions using TMHMM2.0, lipoproteins using Lipo and LipoP, secretion using SecretomeP2.0, signal peptides using SignalP4.1 and beta-barrel outer membrane regions using BOMP. Of particular interest for possible antibody-mediated vaccine targets are CBU_0091, CBU_1648, and CBU_1652 as inhibition of those features has been shown in the literature to inhibit bacteria replication. The two hypothetical proteins are also worthy of future study due to their, as yet, unknown functions.

| SEQ ID NO: | Locus Tag | Protein Name | Transmembrane | Lipoprotein | Secreted | Signal Peptide | BOMP | Predicted cellular location (program used) PSORTb | SoSui$_{GramN}$ |
|---|---|---|---|---|---|---|---|---|---|
| 54 | CBU_0075 | 2-polyprenyl-6-methoxyphenol hydroxylase | + | − | − | − | − | C | C |
| 62 | CBU_0091 | Peptidoglycan-associated lipoprotein OmpA-like | − | + | + | − | − | OM | OM |
| 25 | CBU_0094 | ClpB protein | − | − | + | − | − | C | C |
| 26 | CBU_0338 | Membrane alanine aminopeptidase | − | − | − | − | − | C | OM |
| 69 | CBU_0510 | Hypothetical protein | − | − | + | − | − | ukn | C |
| 35 | CBU_0532 | COME operon protein 1 | − | + | − | + | − | C | OM |
| 41 | CBU_0631 | Phosphoribosylformyl-glycinamidine synthase | − | − | − | − | − | IM | C |
| 36 | CBU_0758 | Lipoprotein, ComL family | − | + | − | − | − | OM | C |
| 23 | CBU_0962 | Short chain dehydrogenase | − | − | − | − | − | E | C |
| 64 | CBU_1136 | Enhanced entry protein enhC, tetratricopeptide repeat family | − | − | + | + | 1 | E | ukn |
| 15 | CBU_1193 | Thioredoxin reductase | − | − | − | − | − | C | P |
| 27 | CBU_1352 | Cell division protein ftsH | + | + | − | − | − | IM | IM |
| 18 | CBU_1400 | Succinate dehydrogenase iron-sulfur protein | − | − | − | − | − | IM | ukn |
| 19 | CBU_1401 | Succinate dehydrogenase flavoprotein subunit | − | − | − | − | − | IM | ukn |
| 7 | CBU_1579 | Trp repressor binding protein | − | − | + | − | − | ukn | C |
| 28 | CBU_1648 | DotA protein | + | + | − | + | 1 | IM | IM |
| 29 | CBU_1652 | IcmX protein | − | + | + | + | − | ukn | P |
| 66 | CBU_1708 | Superoxide dismutase | − | − | + | − | − | P | C |
| 71 | CBU_2009 | Hypothetical protein | + | − | + | − | − | ukn | IM |

Key:
C = Cytoplasmic;
IM = Inner/Cytoplasmic Membrane;
P = Periplasmic;
OM = Outer Membrane;
E = Extracellular;
ukn = unknown The inventors have identified five particularly preferred proteins. CBU0091 (SEQ ID NO: 62) is described as OmpA-like, is predicted to be situated on the outer membrane and be secreted. In addition, another OmpA molecule (CBU1260) has been reported as the first C. burnetii invasin, antibodies against which were demonstrated to inhibit bacterial internalization into cells. CBU1648 (DotA, SEQ ID NO: 28) and CBU1652 (IcmX, SEQ ID NO: 29) are both constituents of the type IV secretion system of C. burnetii and are essential for replication within cells. It is possible, therefore, that antibodies binding to these proteins could inhibit the organism. Finally, both CBU0510 (SEQ ID NO: 69) and CBU2009 (SEQ ID NO: 71) are hypothetical proteins with predicted secretory functions. Although the function of these proteins is unknown, the inventors believe that these proteins play a key role in protective ability.

Further Characterisation of Mechanisms of Immunity

Overlapping peptide pools representing the entire open reading frame (ORF) of four vaccine candidate proteins (CBU_0510, CBU_0091, CBU_2009 and CBU_1648) were synthesised. The peptides in each pool were 15 amino acids long and were overlapping such that each 15mer started at a five amino acid offset. These peptide pools (2 μg/peptide) were used to stimulate splenocytes harvested from acutely infected and recovered (convalescent) mice in an interferon-γ ELISpot re-stimulation assay. Peptide pools inducing an increase in spot count relative to unstimulated controls provide strong evidence that the protein that the pool represents induces protective cell-mediated immunity against part of Coxiella burnetii. Data are provided in Table 9, below:

TABLE 9

Further characterisation of mechanisms of immunity

| Peptide pool (Ag) | Mean increase (SFU*) | Statistically significant** |
|---|---|---|
| CBU_0510 | 0 | No - p = 0.7 |
| CBU_0091 | 29 | Yes - p = 0.0029 |
| CBU_2009 | 2 | No - p = 0.16 |
| CBU_1648 | 22.5 | Yes - p = 0.0029 |

*SFU—Spot Forming Units
**Analysis performed by Mann-Whitney test

The inventors found that peptide pools corresponding to CBU_0091 and CBU_1648 gave highly statistically significant interferon-γ responses in re-stimulated splenocytes. This is strong evidence that these vaccine antigens promote protective cell-mediated immunity to Coxiella burnetii, and (combined with their ability to elicit a humoral immune response, as demonstrated herein) renders these antigens highly desirable for use in immunisation. Peptide pools corresponding to CBU_0510 and CBU_2009 did not show a cell-mediated response, and so the inventors believe that these antigens contribute to immunity through antibody-mediated means.

Summary of Results

Despite previous efforts in the literature to identify immune reactive proteins of C. burnetii, the inventors have surprisingly identified 71 new immune reactive proteins.

The identified proteins fall into a diverse range of functional groups, only a small proportion of which are surface exposed. The inventors believe that the surface-located proteins are directly involved in the antibody-mediated humoral immune response, and propose that these surface-exposed proteins elicit antibodies that can neutralize or hinder bacterial attachment, entry into host cells and/or replication. Antibodies raised against these antigens are believed to provide neutralization of C. burnetii, and these antigens are highly desirable for use in immunogenic compositions, such as vaccines.

The inventors believe that immune recognition of proteins that are not surface exposed is also a phenomenon in C. burnetii infection. This belief is based the intracellular lifecycle of C. burnetii whereupon, during processing in the host's antigen-presenting cells, any of the organism's proteins, not just those located on the surface of the organism, could be presented to the CD4+ T-cells during immune recognition. The inventors therefore believe that the non-surface located proteins described herein are processed and presented by the host immune system, and are thus also highly desirable for use in immunogenic compositions, particularly vaccines. Such antigens are particularly useful for eliciting a cell-mediated immune response to C. burnetii in a patient.

SEQUENCES:

SEQ ID NO: 1
MTISFVHLKIHSEYSIVDSVVRIDQLLQRAVDLKMPAVALTDEVNLFALVKFYRQAINKGIKPIIGSELLLAEGDDVFRF
TALCQNQIGFRHLIQLLSRAYVEGRQRDHVLIQWEWLVQANEGLIILSGARRGNVGQALLQRRSPLAEERLTRWIN
HFPGRFYLELQRTRRDQEEEYIHSVIELALKHRVPVVATNEVCFLSQGDFEAHEARVCIHQGYLLQDVNRPREYSDQ
QYFKSAEEMTALFSDIPEALENTVEIAKRCSVPLSLDEVFLPKFPVPANLKVEDYFRAQAKQGLTRRLVGLEMKNNLT
HKDYEERLETEITVITKMGFASYFLIVADFIAWAKQHHIPVGPGRGSGAGSLVAYSLGITELDPLEHDLLFERFLNLER
VSMPDFDIDFCMEGRDRVIDYVAERYGQEAVAQIITYGTMAARAVLRDVGRVLGLPYGYVDKIAKLVPFELGVTLE
KALEQEEILAKRYAEDEEVKNLIDLAMKLEGLTRNAGKHAGGVVIAPTKLTDFVPLYSEPGSDHVVTQFDKDDVEAV
GLVKFDFLGLRTLTIINWAVQNINAKRKIQNETELDIGTIPLDDPKTYALLKSCATTAVFQLESRGMKELIRRLQPDNF
ADIMALVALFRPGPLQSGMVETFIACKHGEQSVHFLHPALEPILRTTYGVILYQEQVMQIAQVLAGYSLGAADVLR
HAMGKKKPEEMAKQRAVFLEGTKARGLKEALANQIFDLMEKFSGYGFNKSHSAAYALIAYQTAWLKAHYPAEFM
AAVLSSDMDNTDKVVGFINECRDMNLELLPPNINWSHYPFTVNTKGQIVYGLGAIKGVGEAAAMNIVAYREAEGE
FKGLFNFCSRVDLRKVNRRAVEPLIRSGAMDTFGVSRASLFESLTKAFQAAEQRNRDMILGQHDLFGEEVKGIDED
YTEVPEWNDSDRLRGEKETLGLYVSGHPLQACIKEMKAVGAVPINHLSLSEKNSVVVAGMMMGMRTITTRSGKR
MAILSLEDQTGKIDVTLFNDLYQQVAADLTDHAILVIRGTVGRDDYTGGQKMVADMLLTLDKVREQMVKRLLIRV
AGQDGVDQLLTELPPLIKPYVGGRCPVAIAYQSETAIAELLLGETWRVKLDDKLLSELSKLYGKDQVELEY

SEQ ID NO: 2
MRDLVKQLKSEKHTAEFDALRIKLASPEEVRSWSYGEVKKPETINYRTFKPEREGLFCAKIFGPIKDYECLCGKYKRLK
HRGVICEKCGVEVTLAKVRRERMGHIELASPVAHIWYLKSLPSRIGLLLDVTLRDIERILYFEAYVVVDPGMTDLEPR
QLLSEEAYLDALEEYGDDFTALMGAEAIQRLLRDIDVEAEVEALRTELQTTTSETKTKKLTKRLKVLSAFLESGNKPEW
MILTVLPVLPPDLRPLVPLDGGRFATSDLNDLYRRVINRNNRLKRLLDLNAPDIIVRNEKRMLQEAVDALLDNGRRG
RAILGSNRRQLKSLADMIKGKSGRFRQNLLGKRVDYSGRSVIVVGPTLKLHQAGLPKKMALELFKPFIFSKLQLRGLA
TTVKAAKKLVENEGPEVWDILEEVIREHPILLNRAPTLHRLGIQAFEPVLVEGKAIQLHPLVCTAYNADFDGDQMAV

SEQUENCES:

HVPLTLEAQLEARSLMMSTNNVLHPANGEPIIVPSQDVVLGLYYITRDRVNAKGEGMRFADAQEVVRAYENDQV
DLHARITVRIKEGILNEAGEIEESDRLVNTAAGRILLWQIVPKGLPFALVDQPMTKKAVTKLLDFCYRNLGLKTTVIFA
DKLMYMGFHYATHSGVSIGINDLVVPDQKEAIISRAEDEVREIEKQYASGLVTHGERRNKVIDIWSRTNDQVAKA
MMEKIAVEKVKDAEGKEVAQSSFNSIYMMSDSGARGSAAQTRQLAGMRGLMARPDGTIIETPITANFREGLNVL
QYFISTHGARKGLADTALKTANSGYLTRRLVDVAQDLVVTEHDCGTEASIEMMPHIEGGDVVEPLRERVLGRILAEP
VMDPKSRKELLAKDTFLDERRVDILEEHSIDRVRVRSAITCEARYGICSMCYGRDLARGHVVNVGEAIGVVAAQSIG
EPGTQLTMRTFHIGGAASRATAANNIGVKSTGKIKLRNLKIVEQAQGNLVAVSRSGELVVQDLQGSEREHYKVPY
GATISVRDGDSVKAGQIVAQWDPHTHPIITEVAGTLRFVDLVDGVTMNRQTDELTGLSSIVITSTKQRSASGKELRP
MVKLVDKNDDDLFLPGGKVPAHYFLPEGTFLTKEDGTTVNIGDVLARIPQETSKTRDITGGLPRVADLFEARRPKDA
AILAEISGVVSFGKDTKDKGRLIITAPDGTTHEELIPKWRHSVFEGETVEKGEVIADGPRDPHDILRLLGVNALANYI
VNEVQEVYRLQGVKINDKHIEVIVRQMLRKVKITQPGDTDLLQNEQVERTRVREENEKIIKKDGTVAKVEPILLGITK
ASLATESFISAASFQETTRVLTAASVAGKRDDLRGLKENVIVGRLIPAGTGFSYHQQRRAVAGKSVEEKEIEEKRVTA
SEAEQALSEALKSSAPQEAKAAQKDE

SEQ ID NO: 3
MNKIRKTFQYGKHEVTFETGEMARQATGAVVVRMGDTVLLVSVVAKKEAEEGRDFFPLTVNYQEKTYAAGKIPG
GYFKREGRPTEKETLTSRLIDRPLRPLFPKGFTNEVQVIATVLSVDSKVPTDIPAILGASAAIGLSGIPFNGSLGAARVG
YRGGEYLLNPSLDELKDSALDLVVAGTRDAVLMVESEAQELPESVMLGAVLHGHQAMQVAIQAIAEFIQEAGGAK
WEWEPPTVNTALEKWVVEKSEAPLKKAYQIQEKTARQAQIQAIRDQLLADRAAEREGEENAVNEHELAVIFHELE
RRIVREQILTGQPRIDGRDTKTVRPITVKVGVLPRSHGSALFTRGETQALVVTTLGTERDAQSIDDLDGDRQEEFIFH
YNFPPFCVGEVGFMSGPKRREIGHGRLAKRAVVPVVPTLDKFPYVIRVVSEILESNGSSSMASVCGSSLALMDAGV
PTKAPVAGIAMGLIKENDKYAVLSDILGDEDHLGDMDFKVAGTSNGVTALQMDIKIEGITKEIMEQALDQAKEGRL
HILSIMNKVLDKPRSQVSDLAPQYVTMKINPEKIRDVIGKGGVVIREITEATNCAIDISDDGTIKIAAHTTEEGEAAKR
RIEELTAEVELGKVYEGTVVKITDFGAFVQILPNTQGLVHISQIAQERVENVRDYLEEGQVIRVKVIEIDRQGRVRLS
MKQID

SEQ ID NO: 4
MLGVAEKCYDLTIMNILIIGNGGREHALAWKVAQSPRVEKIWVAPGNAGTARELKTQNVPIGVTDIKSLIAFAKKN
QINLTLVGPEIPLAAGIVDHFQQENLIVFGPTQAAAQLETSKSFCKTFMRRHGIPTARFEAFRNTSDAFSYLEQQSFPI
VIKASGLAAGKGVVIAQSLQEAKETVIAMMEEKQFGNAGAEIVIEEFLAGEELSFIAMVDGEHILPLAGSQDHKRRD
DGDRGPNTGGMGAYSPVPQLSDALQEKIMTTIMQPTVTALKSEGILYRGFLYAGIMITLNNEPKVLEFNVRLGDPE
TQPLMMRLRSDLIELILSALSGRLNQTQSAWDSRAALTVVLAAGGYPAHYQKGDIIQGLDQLSLPDVKVFHAGTQE
INHQVVTDGGRVLGVTALGKDLREAQQKAYQAAQLITWPNCYYRHDIGHRAIS

SEQ ID NO: 5
MCGIVG1 IANGIVVNQALYDALTILQHRGQDAAGIMTSDGERVFLRKSNGLVRDAIREPHMLHLVGNMGIGHVRYP
TAGSESPAESQPFYVNSPYGLSLVHNGNLVNVKELTNDLIRSDLRHLNTTSDSEILLNVVAHELQHYGGVQLSPKQL
FKAMTKVYERVEGAFAAVMIITGYGVIGFRDPHAIRPLVYGRRDNGNGPEYMLASESIALDALGFELIDDVGPGEVI
YFDREGSVHRERCAKQVSHSPCIFEYIYLARPDSIIDGVPVYQARSGMGESLAQKILRERPDHGIDVVIPIPDTSRNAA
QALARALDVPYSEGFVKNRYIGRTFIMPGQAKRRSSVRLKLNAIKAEFANKTVLLVDDSIVRGTTSKEIIQMARDVG
AKKVYFASAAPEVRYPNVYGIDMPTADELIAHNKSTEEVMHSIGADWLVYQNLEDVYQAINDAMGSRKPKIERFE
DSVFTGDYIAGNITKEYLAELAESRNDAAKMKKRALNEQEEANGLL

SEQ ID NO: 6
MTNGPQPLYRRVLLKMSGEALMGKGLHAIDPNVLDRMAKDVTQVYQLGVQIAIVIGGGNFFRGAALQAAGINRI
TGDYMGMLATLMNALALRDAFERSNLPVRILSAIPMTGVADAFHRRKAIHHLQQGRVVIFAAGTGNPLVTTDSAA
SLRGIEINADVVLKATNVDGVYSDDPAKNPQAKLYKHLSYQEALKKELAVMDLAAFCQCRDYNMPLRVFNINKPG
ALLSVIMNQEEGTLVDQGQ

SEQ ID NO: 7
MPFILVLYYSRYGATAEMAEQVARGVERVNKIEARIRTVPSVSPKTEATEPDVPKDGPPYVTHDDLKNCVGLALGSP
TRFGNMAAPLKYFLDTTSALWQSGSLIGKPAGFFTSTASLHGGQETTLLSMMMPLIHHGAIIVGVPYSETELFTTTA
GGTPYGPSHMAGADSNWPLTQTEKNLCQALGKRLAEISLKLKA

SEQ ID NO: 8
MEWEPVIGLEVHVQLRTQSKIFSGAATAYGAEPNTQACAIDLGLPGVLPVLNKEAVKLAVCFGLSVNASIPPYSIFA
RKNYFYPDLPKGYQISQYNFPIVQNGHLDIENEDGTTKRIGITRAHLEEDAGKSFHEGMQGYSGIDFNRAGTPLLEIV
SEPDIRSAQEAVAYLKALHSLVRYIGVSDANMQEGAFRCDVNISLRPKSEEKFGTRAEIKNVNSFRFVERAILFEINRQ
KEILENGGTIVQETRLYDAVQDETRSMRTKEEAHDYRYFPDPDLLPVEIGPEFIEAVKNQLPELPWEKRKRFAASYQL
SNYDVKLLTTQIEIANYFETVLKIDKTIPPKLAANWINGDLAAALNKNNLSITQSPINAEQLAGLLHRIADNTLSGSMG
KQVFETMWGGEGDADTIIERHGLKQITDTEALEKIIDEVIENNPTQVEQYRSGKDKLIAFFVGQVMKATKGKANPQ
QVNELFKKKL

SEQ ID NO: 9
MTFQKPCFPHCLPVYFPLLYHSNHKELRKMNDVLSVRAQQLEPSVTLAVSDLARELLNKGHDVISLSAGEPDFDTP
DFIKQSAIKAIQEGFTKYTNVDGTPALKAAIVHKLKRDNHLNYEPSEILVSGGAKQSIYNVLMGTLNAGDEAIIPAPY
WVSYPPMVQLAEEAKPIIISATIDQNFKLTPGQLSQAITPQSRLLILNSPNNPSGVAYTESELKALADVLMEHPQILILS
DEIYEYILWGQNRFVNILNVCPELRDRTIIINGASKAYAMTGWRIGYAAGPKSIIQAMKKIQSQSTSSPNSIAQVAAT
TALGAQRGDFAYMYEAYKTRHDLVLKALNQMKGVHCIPADGAFYLFPDVSAAIQQLGLEDDIKLGTYLLDKTKVAV
VPGSAFGSPGHVRLSCATSTEKLQEALERLASVLDY

SEQ ID NO: 10
MIVQPKVRGFICTTAHPEGCARHVGEWINYAKQEPSLTGGPQKVLIIGASTGFGLASRIVAAFGAGAKTIGVFFERP
ASGKRTASPGWYNTAAFEKTALAAGLYAKSINGDAFSDEIKQQTIDLIQKDWQGGVDLVIYSIASPRRVHPRTGEIF
NSVLKPIGQTYHNKTVDVMTGEVSPVSIEPATEKEIRDTEAVMGGDDWALWINALFKYNCLAEGVKTVAFTYIGPE
LTHAVYRNGTIGRAKLHLEKTARELDTQLESALSGQALISVNKALVTQASAAIPVVPLYISLLYKIMKEKNIHEGCIEQ

MWRLFKERLYSNQNIPTDSEGRIRIDDWEMREDVQAEIKRLWESINTGNVETVSDIAGYREDFYKLFGFGLNGIDY
ERGVEIEKAIPSITVTPENPE

SEQ ID NO: 11
MTDTHLLFFEKAIAQNAIRPSLNKTYRMDETTCVNHLLKTIAFTPRLEAAVSRLAKELVTAVREQESEKGGIEGFMM
QYDLSTEEGILLMCLAEALLRVPDKETENLLIRDKLTSAEWNKYVGASESSFVNFATWGLALSGKILKKEKDGQFKNV
WRNLVRRSGEPVIRKAVREAMKLMSEHFVLGRTIEEAVKRSQSAIKEGFRHSYDMLGEVARTQEDADRYYDSYHR
AISVLGKSHPTKSVHEAPGISVKLSALYPRYDFKKRELAVPFLIERVKELALHAKEQKIGMTIDAEEADRLDISLDIFEAL
FTDEAFENWQGLGLAVQAYQKRAFYLIDWLIDLAQRQKRRIPVRLVKGAYWDTEIKLAQMEGLSGYPVFTRKVNT
DISYIACAQKMLNAQDAIYPQFATHNAYSVAAILNLMDHHYDNYEFEFQQLQGMGKALHHYIVTKLKLPCRVYAP
VGYHEDLLPYLVRRLLENGANSSFVNRIADKTVPVDQLIESPVKKIEAFGDIPNPKIPLPKGIFKTRTNSSGIDLSNFAE
LMPLNEEIHHALEKEWEAAPFLQEIKNGKPVFDPTDNRRQIGVIELANESDVEKAIQAGHSAFPNWDQKGISARAT
ILRKMADLLEKHKAELMAVVVREGGRTLQNALSEVREATDFCRYYAEQAEQHLSDKALPGYTGESNTLRMNGRGII
LCISPWNFPIAIFTGQIAAALVTGNAVIAKPSGQTPLTGALVTRLFHEAGVPKEILQLMPGSGKTVGQALIEDTKISGV
IFTGSDATARHIQKTLAARPGPIVPFVAETSGINAMIADSTALPEQLVNDVIVSAFDSAGQRCSALRILYIQEDIADDV
IKMLKGAMAEIKMGDPLLLSTDVGPVIDANAQKTLQKHQALMQKEAKLIYKVDLPRETDFGTFVAPQAYELPNLGL
ITEEVFGPILHVIRYKRENLNKVIEEINGLGYGLTFGIQSRIDETVDYIQQRINAGNIYVNRNTVGAVVGVQPFGGSW
LSGTGPKAGGPHYLPRFCIESTLTINTTAAGGNASLMAMED

SEQ ID NO: 12
MENPIVIVSAARTPMGHYGGYFKEMPAPELGAAVIKAVVERAGLQPAEIDEVIMGCVLPAGQGQAPARQAALKA
GLPVSTPCTTINKMCGSGMKAIMLAHDEILADSYPHIIAGGMENMSRAPYLMMKARFGYRLGHDRIYDHMMLD
GLEDAYDKGKAMGVFAEKCVDKYQFTREALDKFAIESLLRAKKANENGSFAPEIVPITITHQRETLTVDHDENAMK
ANPEKIPQLKPVFKADGAVTAANSSSISDGAAAVTLMRLSEAKRLNIQPLAKIIGHFTYAEDPSWFTTAPIGAIRGLLK
KISWKKEAVDLFEINEAFAAVTMAAMKEIGLAHNKVNIHGGACALGHPIGASGARILVTLLYALQKNNLQRGIASLC
IGGGEATAIAIERGF

SEQ ID NO: 13
MTVLYQNRQIRELERLAVESGISEYELMCRAGEAAFKALLARWPEAQEITVCCGKGNNGGDLVLARLAYENGLKV
TVYLAGQRHQLKGAAAQAANACEASNLPILPFPEPLLFKGEVIVDALLGSGLSGEVKAPYDHLIAAINQAGQYVLAL
DVPSGINVDSGEVQGTAVKANLTVTFIAPKRGLYTDKAPAYCGELIVDRLGLSESFFRAVFTDTRLLEWKGVFPLLPK
RARDAHKGSYGHVLVIGGDYGMGGAVRMAAEAAARVGAGLVTVATRPEMCHQVAAADDLK
PLLTAATVVVIGPGLGKSDWAKSLLNKVLETDLPKVLDADSLNLLAESPSQREDWILTPHPGEASRLLGISCNEVQRD
RFQAINDLQEKYQGVLVLKGVGTLIKDESQAYYVCPAGNPGMATGGMGDILSGIIGGLVAQRLSLASAAQAGVFIH
SMAADRAAEEGGERGLLATDLFPHLRVLVNP

SEQ ID NO: 14
MLIGVPKEVKIEEYRVGLTPYSVRELVLHGHQVIMERDAGNAINFTDEAYLAAGAKIVDTPVEVYQAEMIVKVKEP
QSSEYALIREGQILFTYLHLAPDPQQAQALIKSGCIAIAYETVTDNEGGLPLLSPMSQVAGRLAIQAGAHCLEKPEGG
SGILLGGVPGVYAGKVTVIGGGVVGSNAVRMAMGKKAQVTVLDKSLRRLQELDFQFGGRLNTAYSTESSIEHYVID
ADLVVGAVLVPGHSAPKLVGQDVLKKMRPGSVMVDVAIDQGGCFETSKPTTHKKPTYVIDGIVHYCVANMPGAV
PRTSTLALNNATLPYVIALADKGYRQAFLDDPHFLNGLNVYCGQITHKGVAQGLQQEFNPPLALL

SEQ ID NO: 15
MNKPQHHSLIILGSGPAGYTAAIYAARANLKPIMITGMEQGGQLMTTTDVDNWPGEAPGLQGPQLMERMQKH
AERLDTQFIFDHINEADLNQRPFLLKGDNATYSCDALIIATGASARYLGLPSEKAYMGKGVSACATCDGFFYRGKKV
AVVGGGNTAVEEALYLSHIASHVTLIHRRDKLRAEKMLSAQLIKKVEEGKVAIVWSHVIEEVLGDDQGVTGVHLKH
VKEEKTQDLTIDGLFIAIGHDPNTKIFKEQLEMDEAGYLRAKSGLQGNATATNIPGVFAAGDVTDHVYRQAITAAG
MGCMAALDAERYLDSLNQA

SEQ ID NO: 16
MLKIVSKPSFNRIALMGREGVEGVPETLAALKDYLVSLNREVILEENAAHMIDGSRLLTVPANDLKKKADLLIVVGG
DGSLLNAAHIAVPQQLPVLGINRGRLGFLTDIPPNELTQISDILDGHYREEVRFLLEGTVEEGDEIVAQGIALNDIVLLP
GNAPKMIEFDIFINDEFVCNQRADGLIITTPTGSTAYALSGGGPILHPQLNAMALVPMFPHTLSSRPIVVDAESQIKI
TISPENDVSPYVSNDGQERVSIKPGGNVYTRKYHYPLHLIHPTDYNYYDTLRRKLDWEKRAAKV

SEQ ID NO: 17
MNLHEYQSKHLLKKYNIPVPASEVVFNPDAAVDAAAKIGGDRWVVKAQVHAGGRGKAGGVRLVKNKEELKSAVK
ALLGTRLVTYQTDERGQPVNQILVEQTSDIARELYLGAVIDRASQRIVFMASTEGGVEIEKVAEKSPEKILKVTIDPAI
GLQPFQCRQLFFGLGLQDLKQMRSFTDIVMGLYRLFTERDLSLLEINPLVITGSGELICLDAKINIDDSALYRQSELRE
MRDTTQEDEHETMAQQWELNYIKLDGNIGCMVNGAGLAMATMDLIKLSGGDPANFLDVGGSATKERVTEAFKI
IVSDKNVKGILVNIFGGIVRCDLIADGIISAVKEVGIDVPVVVRLEGNNAQLGAKKLADSGMNIIAAKGFADAAEQIV
KQVGVIA

SEQ ID NO: 18
MNSKKSRIMTFSIMRFNPETDKKPYMQDFELDVSAIQGKMLLNALEALREKHPDIGLRRSCAEGVCGSDGMNING
KNALACVTQLKDLPDRVVVRPLPGFPIIRDLIVDMEQFYAQYKKVKPYLLNDQEAPQKERLQSPEERAKLDGLYECIL
CACCSSSCPSYWWNPDKFIGPAGLLWSYRFIADSRDSKEKERLDAMKDPYSVFRCRTIMDCATVCPKNLNPAKAIR
KIRTEMLQETESGE

SEQ ID NO: 19
MSSIRVKQYDALIVGAGGAGLRAALEMAQSRQYKVAVVSKVFPTRSHTVSAQGGIAAALGNVVPDKPIWHMFDT
VKGSDYLGDQDAIQYMCEQAPPSVYELEHYGLPFSRLDDGRIYQRAFGGHTRDFGKEMARRTCACADRTGHAML
HTLYQKNVEAGTHFYYEWYGIDLVRGAQGGIAGMIAMNMETSELVFFKSRATIFATGGAGRIYETTSNAYTNTGD
GIGMVLRAGLPVQDMEFWQFHPTGIYGVGCLITEGARGEGGYLINKDGERFMERYSPHLKDLDCRDVVARSILQE
VMAGGGVGPKKDHVLLKLDHLGEKVLRERLPGIIELSEKFANVDITKEPIPILPTCHYMMGGIPTNIHGQALTVDEN
GKDQIIEGLFAAGECACVSVHGANRLGTNSLLDLVVFGRAIGLHLEEEALKTELKHRSENPDDIDAAIARLKRWEKPN

SEQUENCES:

NVENPALLRQEMRKAMSEDFGVFREEQKMKQGLERLQKLNERLQRAKLTDTSRTFNNARIEALELDNLMEVSYAT
AVSAQQRTESRGAHSRYDYKERDDANWLKHTVYFRDGHIAYRPVNMKPKGMDPFPPKSRD

SEQ ID NO: 20
MAGCGLTDFCRTFECVKLKRKIGCEVTMADSLKTRRELTAGGKTYHYHSLKAAEDAGLSNIHRLPYSLKILLENQLRH
EDGETVTQTHIEAFAHWLKDKHSDREIAYRPARVLMQDFTGVPAVVDLAAMRDAMARMKGDPTKINPHCPVDL
IIDHSVQVDEFGNEEAFRDNVRIEMERNHERYTFLKWGQQAFRHFQLVPPGTGICHQVNLEYLGRGVWSSQQDG
EWLAYPDTLVGTDSHTTMINGLGVLGWGVGGIEAEAAMLGQPISMLIPEVIGFYLSGQLCEGITATDLVLTVTQML
RQKGVVGKFVEFYGPGLAELPLADRATIGNMAPEYGATCGLFPIDAETIKYLELTGRDAEAIELVKAYSKAQGTWHD
ENTPEPIFSDTLSLDLSTVEPSLAGPKRPQDRVPLAKLKKTIEGVIATAERDQELDHSFQSTGDFDLHHGDVVIAAITS
CTNTSNPSVMLAAGLLAKNAVEKGLQRKPWVKSSLAPGSKVVTDYLHKTGLIDYLEKIGFYLVGYGCTTCIGNSGPL
PETVAKTVTENDLIVSSVLSGNRNFEGRIHPLVKTNWLASPPLVVAFALAGTTRIDLTKDPLGHNDRGEPIFLNDIWP
SNAEIAKTVMQVRNDMFRKEYADVFEGDEEWQRIHVSAGDTFSWQTNSTYVKNPPFFENMSAKPEPLKNIIDARI
LAILGDSVTTDHISPAGAIKADSPAGKYLIEHGIDIKDFNSYGSRRGNHEVLMRGTFANIRIRNEMLSKVEGGFTKHF
PDGEQLPIYDAAMKYHSENIPLVVIAGKEYGTGSSRDWAAKGPRLLGVKAVVAESFERIHRSNLVGMGVLPLEFKN
DDNRHSLKLEGNEVIDITGLENDLQPGGDVIMTVKRKDGTIEKIPLHCRIDTQNELAYYQHGGILQFVLRQMLRSS

SEQ ID NO: 21
MKVFKLPDLGEGLPDATIREWYIAVGDEVKIDQPLVAMETAKALVDVPSPLAGKIEKLFGEVGDVIETGSPLIGFEGE
AETEEPKDTGTVVGAIETSDIVLEESGAGIPVKKAAEKKNFKATPAVRMLAKQLGVDLTKITPKSSLISAEEVKQAAQ
ITKTGKTQKIEGELTPLSPVRRAMAQSMSQSHREVVPVSLMDDGDLSAWKGEQDITLRIIRAIEAACQAVPIMNAH
FDGETLGYKLNETINIGIAVDTPQGLYVPVLKDVSHQDDTALRNQINRFKELAQSRSFPPEDLRDATIMLSNFGAFA
GRYANPILLPPMVTIIGVGRTRDEIVPVDGKPAVHRILPLSVISDHRVITGGEIARFLKQLIDSLEKAS

SEQ ID NO: 22
MTPKTTTVANFTIRYLQFLDANSNPTQPFPDFADPDMLLYLYRRMALIRQLDNKAINLQRTGKMGTYPSSRGQEA
VGIGMGSAMQKEDIFCPYYRDQGALFEHGIKLSEILAYWGGDERGSRYANPDVKDDFPNCVPIAGQLLHAAGVAY
AVKYRKQARAVLTICGDGGTSKGDFYEAINLAGCWQLPLVFIINNNQWAISVARGEQTHCQTLAQKAIAGGFEGW
QVDGNDVIAVRYAVSKALEKARDGGGPTLIEALSYRLCDHTTADDATRYIPQEEWKVAWQKEPIARLGYYLESQGL
WSREKEAVLQKELAQEVDQVVEEFLTMPPPKATDMFDYLYAELPVSLEKQREELADNKPSHPSGREG

SEQ ID NO: 23
MKRILITGANRGIGLELVKQYLAAGWHVDGCYRDKKASNSLFELAAEKKQSLTLHELDVLDEKAIQALGEHLKNQPI
DILFNNAGVSAKNLREFGSIHDTENACEVFKINTIAPLLMVQALLESVEKSEKKLIINMSSEMGSIAQNVNGNYYVYR
ASKSALNAITKSLAIDLKRRGITVISMNPGWVRTDMGGEQAPLDVISSVRGMREVIERVDIKSTGGFLGYDGGEMPW

SEQ ID NO: 24
MRTLQLREGNMTNLIADRLAALRRLMHEIGVDYYYVPSSDPHKNEYVPSCWQRRAWISGFTGSAGDVVVGIDKA
FLWTDPRYFLQAEQQLDDSLYHLMKMGQGETPAIDQWLTQQRNGIVFAVDPRLINLQQSEKIQRALEKQNGKLL
ALDENLIDRVWKDQPPLPQSAIQLQPLQYAGLSAEDKLAALRQTLQKESADAIVLNTLDAIAWLFNIRGNDVAYNP
LVISYAVITQNEASLFVDPHKITEGDRSYFKKIPVHIEPYEGIGKLLESLSGSVWLDPGATNLWLRDQLKNTASLILKPS
PITLAKALKNPVEQKGAREAHIIDAIAMIQFLHWLENHWQSGVSEISAAEKLEFFRRGDSRCLDLSFPSISGFGPHGA
IVHYSATTDTDATINDSAPYLIDSGGQYHYGTTDITRTIHLGTPTEEEKRLYTLVLKGHLAIRQAVFPKGTCGEHLNAL
AHQFLWREALDYGHGTGHGVGSYLCVHEGPQAITSRYTGIPLQPGMIVSNEPGVYLTHKYGIRIENLCLVTEKFTVD
DSLTGDGPFYSFEDLTLVPYCRKLINPNLLTSEEIQQINDYHQRVDQTLRDLLPANELNDWLHEATAPL

SEQ ID NO: 25
MRIDKFTTAFQTALADAQSLAVGRDHQFIEPAHVMKVLLEQTQGTVAPLLEQSKVNLSRLIDGVNKAIDSYPQVEG
TGGEVHVSRELSKILTLMDKFAQQNRDQYISSEWFIPAALEAKGQLRDVLIEAGADKKAIEKNIMNLRKGERVTEQS
AEDQRQALAKYTIDLTEKAETGKLDPVIGRDEEIRRTVQVLQRRTKNNPVLIGEPGVGKTAIVEGLAQRIVNGEVPE
GLKQKRLLALDMGALIAGAKFRGEFEERLKAVLKDIAKEEGRVILFIDELHTMVGAGKAEGAMDAGNMLKPALAR
GELHCVGATTLDEYRKYIEKDAALERRFQKVLVEEPSTEDAIAILRGLKERYEVHHGVEITDPAIIAAATLSQRYITDRN
LPDKAIDLIDEAASQIRMEMDSKPVELDRLERRLIQLKIEREALKKETDEASKKRLSDLETEIKNVEKEYSDLEEVWKSE
KASLHGTQQIKEELEQARIELEAAGRAGDLARMSELQYGIIPELDKKLKAASQKEEQFHDHKLLRSRVTEEEVAEVVS
KWTHIPVSKMLEGEREKLLHMETELHKRVIGQDEAVNAVANAIRRSRAGLSDPNRPVGSFLFLGPTGVGKTELCKA
LAVFLFDTEDAMVRIDMSEFMEKHSVARLIGAPPGYVGYEEGGYLTEAIRRRPYSVILLDEIEKAHNDVFNVLLQVLD
DGRLTDGQGRTVDFRNTVIVMTSNLGSDLIREFSGENYDKMKDAVMEVVAQHFRPEFINRIDEAVVPHSLKKEQIR
NIAIIQIDRIKKRLKEKDYQLTISDDALDYLSELGYDPVYGARPLKRVLQQQLENPLSQKILEGKFVPGSLINIEKKGEQL
EFKEA

SEQ ID NO: 26
MGLEAFCLSSLQCQISFETAEPKMSNQKPRTVYLKDYRPSDFLVDTVHLYFDLHEEETHVKTILNLQRNPEGNATAP
LALTGEAMTLKKVALDGQTLASSDYTLDASSLTIANVPNEFTLETEVVIKPQENTQLMGLYKSRGNFCTQCESHGFR
RITYFLDRPDVMARYTTTITADKNKYPFLLSNGNLIETKILSDNRHWAHWEDPSKKPCYLFALVAGDFDLLEDTFVT
QSGREIALRLYLEKGFKDQGPFSLAALKKAMRWDEKRFGREYDLDIYMIVAVSDFNMGAMENKGLNIFNTKYILAN
PQSATDDNYVAIESVIGHEYPHNWSGNRVTCRDWFQITLKEGLTVFREGLTFEDTTSKGVARIGTVNILRNSQFPED
AGPMAHPIRPRSYIEVNNPFYTTTVYNKGSEVIRMVQTLLGEALFRKAMDLYFSRYDGQAVTTENFIQAMEDASGK
NLEQFKRWYDQAGTPVLDLNSEYNANDKTLTLTVKQSCPPTPGQSEKLPFHLPLTLGFVGPECQDMPTQLAGEKK
AIPGTRVLEIKDAETEFKFVNVNHKPTLSLLRGFSAPVRLNYPYSDEELVWLFQCDSDPFARYEAGQIFAQRLIFKLID
DSYQGKPLKIDERFIDAHRKIIAGPHRDHWYEAALLQLPSINYLMQLMKKMDVEALHTIRQFVKKALSNALVDDLKI
QYEHHQLPLYEYTPADIGKRKLKNICLAYLTESDDTQFRQVAYQQFKKSDNMTDTVGALSALLNHDCKERHQALDE
FYQQWKDQPLVVNKWLMLHASSTLPSTLEAVRKLTKHPAFDVKNPNNVYSLLGTFGANAVCFHEGSGEGYRLIAD
YVLAIDPANPQVAARVLQPLTRWQMMDKKRQELMKAELNRIAKAERLSSDVYEIVTKSLL

SEQ ID NO: 27
MNSMIKNLLLWLVIAVVLITVFSNFGSRQSDVQPYSYSQFVQAVNNDKVSSVVIQGHEIKGVTKDNKHFTTYLPME
DQALLNQLMAKGVSVKGEPPKQQSMFLHILISWLPFLILIFVWILFMRQMQGGGRGGGPMSFGRSKARLLSQDQ

SEQUENCES:

VKVTFDDVAGVDEAKEEVKELVEFLRDPGKFQRLGGKMPCGVLLVGPPGTGKTLLAKAVAGEAKVPFFTISGSDFV
EMFVGVGASRVRDMFDQAKKQAPCIIFIDEIDAVGRHRGAGLGGGHDEREQTLNQLLVEMDGFEGKEGIIVMAA
TNRPDVLDPALLRPGRFDRQVVVPLPDIKGREYILKVHMNKLPLAKDVKASVIARGTPGFSGADLANIVNEAALFAA
RENKKDVSMSEFERAKDKIMMGAERRSMVMSDDEKKLTAYHEAGHAIVGLHMLEHDPVYKVTIIPRGRALGVTM
FLPEHDRYSMTKRRLECQLAGLFGGRIAEEIIFGPDLVTTGASNDIEKATEIARNMVTKWGLSQKLGPLTYREEEGEV
FLGRSVTQRKDISDATNKEIDSEVRRIVDTAYTTAKQTLEEHIEQLHLMAKALIKYETIGEAQIKEILAGKEPSPPPDW
KEENGSASAHKENSEKELSEEKGEEKTVNPSRPRPAEDG

SEQ ID NO: 28
MKKLVSSLLASISLFLISAAAWADNLPTDFTDNTAMNTHHDLSVTYLSQVFGTVGNVLHGMSGQMLGHLFYRLNE
GIIVVAGMWLVYTVFTIVLRAAQDGSFMGPNKNVALVFLKIAFGFSLLVPNPATGYSLLQDVVMKVVVEGVGLAD
QTWEYGLTYINNGGSLWRRPETNGAGKDIISQSTVNSVLGGNSQNKEGPGQKIFASAVCMYSSDDNQSPLKSNN
NNIGPAVNGGPTVKYTYDVITDDSAHQFEFPGSGDTPPFKPGDDSCGAVTWDINNACTGAGSNSTKCTMAKEAV
SELVTSLLPAAKKYYCSQHSSSDLCLGVTHNDAFAENETSFFGALLNYVNTIVPLVQFNSGKSADEAKRFIDEAQNEG
WLSAGRYYWDLSQIQSHYDNVSNVDSYYPRTVDPTVNGNPEDDYQAALKQSLGYIYGVIDTANPHPIPVKGSVLY
QLAQYAQSQHSGDTGGGEENWGHGGLDAGIALIGGIFSETIYDIYKLIHTFTTGSDGAMGPDPILFLHKIGIRAISVA
ADIWFGFLGIMAIALFATGVCTATYNAQTPVQALLGWIKPLLMVVAVGLWGTGFVLAYYVPLYPYMLYTFGVIGW
IIVVIEAMVAAPLIAFGLTHPEGHDFLGEAKQGGMLLLGVFLRPVLMVVGLIAGMILSYVALRIVVYTFSGLAVDLFA
NTPSSGPASGSILHAATALMSNSMATAGSVTGAIVSLMVFPLVLIIFTILVYVVTTQSFSLIFALPDNVMRWIGIPGQ
RSEYDRMATQLESKVGGFASSTGRSGGLQASERIGKGAANANLGKQLHLGPSKK

SEQ ID NO: 29
MKNFRVLGIASFLALGVASTSALADIDPMSGVIKAIKEVGLEVQALAIASKKSVSNMKYQLDKNLDLALQADVEKNN
ALQTVKNNAGTNTQNQISGTLLQFPEQVINASQLNDAQMAATIKNRKNLIPNLTTAIPASDTLYLTDAEDPLANTY
GVAKPDSLYDNYFNFDSLFAPSAYNSDQQQAATTYLQYLTKPYQSLTDNIHFSELKDNLNKLSAEKRADKLKSFLNN
PAYQKFQLAVRSLIATKSLAIDNFNTLLNERVPVKGLGAKVGMPDDPHLPKGYASPLQVENYIANQRINSPDWFKQ
MKTASPAVVAREQVLILAEIESQLERNHLDNERLLATLSLMALQGTKNSEMELQTNTAADLNKLIDQIGK

SEQ ID NO: 30
MKITDAKVFVCSPGRNFVTVKIYTDEGIYGLGDGTLNGRELAVASYLEDHLLPCLIGKDPSQIEDIWQYFYKGAYWR
RGPVTMSAIGAIDMALWDIKGKALKTPVYNLLGGRSRKGVMVYGHANGKDVEETVDEVGKYIEKGYLAIRAQTGV
PGLPSTYGVSPDKLFYEPAEKGLPPENVWSTEKYLNHVPKLFKKLRDVYGDDPHLLHDCHHRLTPIEAGRLGKELEP
YHLFWLEDTVPAELQEGFRIIRNHTTTPLAVGEVFNVIYDCTTLITEQLIDYIRMSIVHGGGLTPMMKIASFADIYHVR
TGCHGPTDVSPVTMAAALHFETAINNFGIQEFMRHTPETDEVFPHHYYFENGYLNVKDEPGLGVDFDEKLAAKYP
YERAYLPINRKLDGTMYNW

SEQ ID NO: 31
MRIITLNLNGIRAAARRGFFDWLKRQKADIVCLQETKACLEITNGDQFHPKGYHCYYHDAEKSGYSGVGIYCREKPD
RVTTRLGWEHADKEGRYIQADFGSLSVASLYMPSGTTGEHRQKIKFDFMDRYMKRLKNIVHSKRSFIICGDWNIVH
KEIDIKNFKSNQKYSGCLPEERAWLDEVFTKVGLVDAFRVVNQKPDQYTWWSSRGRAWEKNVGWRIDYQVITSD
LKNSVKSERIYKDKRFSDHAPLIIDYEREISD

SEQ ID NO: 32
MESLTPKRDAFTVLSYNIHKGFSARYRRFVLPDIREALRAIDADIVLLQEVQGKHHKSRLKKFAHADLPQTEFIAESK
WPHYMYGKNAVYGSAHHGNALLSNFPFKMVENINVSLSQRASRSILHAIIDYEPTVELHVICIHLGLFRAERDYQLIT
LSKRIEAHVPSHAPLIIAGDFNDWRRGAFNYMEKELELKEVYKVLEGKHAKTYPASRPTLEVDRIYYRGLKLLSGEIFN
ESYWKKLSDHLPLHAKFAIE

SEQ ID NO: 33
MPKHFYFYFLRKMTMSQNKIYVGSLSYDVTADELQSFFGQYGEIEEAKLIMDRETGRSKGFAFITYGTQDAAQEAV
SKANGIDLQGRKIRVNIARENTGDRRRDGGSGGRGGRGGRF

SEQ ID NO: 34
MDFSDDNLIWLDLEMTGLDPERDRIIEIATIVTNSHLDILAEGPAFAIHQPDKLLTAMDNWNTSHHTASGLLERVK
NSSVDEVEAETLTLAFLEKYVSAGKSPLCGNSVCQDRRFLSRYMPRLNQFFHYRHLDVTTLKILAQRWAPQ1AAAH1
KESQHLALQDIRDSIEELRYYRAHLLNLSK

SEQ ID NO: 35
MMFELFKEIFMKKIIQLISAVLITSLVFSAQAKPASEVIKNKLHRHAAVSTQKTGPVDINTADATLLTTLKGIGVKKAK
AIIAYRKKEGNFKSIEALSSVPGISQKTVARLIRNNPHRLVVNP

SEQ ID NO: 36
MFYNGRICLALNPEEGPMKKILFLATLLLILSGCVRKDVDPYQAYRGKTSAELFTSGERALAKKDYSEAVKNFEALDAI
YPFGPHAEQAQLDIIYAYYKNNDTSSAIAAADRYIRLYPRGRNVDYAYYMRGVISFDLGLSWLQKLARVSPVSRDVS
TLQQSFTSFATLAEVFPHSRYTPDALTRMRYIRNLMAQREIMIAEFYMKRRAYVAAANRGSYVVQHFQGSPQVAK
ALAIMVQAYRALGLPKMADASNHLLQTNYPHTLEARKLRKA

SEQ ID NO: 37
MNLTDLKQKSVPELMQIAQEMNLEYVSRTRKQDIIFAVLKAHAKKGEDIFGDGVLEILQDGFGFLRSADSSYLAGPD
DIYVSPSQIRRFNLRTGDTVSGKIRPPKESERYFALLQVNEINLEKPEASKGKILFENLTPLFPNEQIRMETGNGSTEDI
TARIIDLISPIGKGQRGLIVSPPKAGKTMMLQNIAHSITTNHPECVLIVLLIDERPEEVTEMDRSVKGEVVASTFDEPA
SRHVQVAEMVIEKAKRLVEHKKDVVILLDSITRLARAYNTVIPASGKVLTGGVDANALQRPKRFFGAARNVEEGGSL
TIIATALVETGSKMDDVIYEEFKGTGNMEIHLDRRIAEKRTFPAININRSGTRREELMMPQDVLQKVWILRKILHPM
DELAASEFLIDRLKLTKTNNDFFDSMKG

SEQUENCES:

SEQ ID NO: 38
MLEIVLASQNSSKLAEMQELLRDLEIKFIPQTEFSVPDIEETGSTFVENAIIKARHAAKQTGLPALADDSGLTIAALNSA
PGVFSSRYAGKNATDAERIQKVLEALEAADDSDRSASFHCVIALMENENDPAPLICHGVWEGEIAREPRGKNGFGY
DPIFYVPSHQRTAAELDPQEKNAISHRGQALEQLSTVLTEAFLV

SEQ ID NO: 39
MCNNDFMNQATEIAKLLLNIKAVTLNLHEPYRYTSGILSPIYCDNRLIISYPEKRKMI1EAFLQLIEKNHLSFDIVAGTAT
AGIPHAAWIADRLDLPMIYVRAKAKTHGKQNQIEGRIRKGQRALIVEDLISTGKSALAAGLALREKGVTVTDCIAIFS
YQLPQAQQNFSDANINCHALSHFDTLIEMAVDEGYIDEIEKQKALAWNKDPEHWQP

SEQ ID NO: 40
MEKPDPKVIVAIDAGTVEQARAQINPLTPELCHLKIGSILFTRYGPAFVEELMQKGYRIFLDLKFYDIPQTVAGACRA
VAELGVWMMNIHISGGRTMMETVVNALQSITLKEKPLLIGVTILTSLDGSDLKTLGIQEKVPDIVCRMATLAKSAGL
DGVVCSAQEAALLRKQFDRNFLLVTPGIRLETDEKGDQKRVMTPRAAIQAGSDYLVIGRPITQSTDPLKALEAIDKDI
KTR

SEQ ID NO: 41
MYSIISCIPLRSIRATPILLKHDDLGSRMLFLQGSHVYTPFRHQQILFRLKQKQNTVRSVEAIYGYFVDGEKLLSRAEQE
RLERLLPKAYFSDYPKSAENFSVWVTPRLGTISPWSSKATDIAHNCEIPINRIERGIYFIIDGIAKRDKKAIEKVASELYD
PLTESLLFDAEDLAQLFQHPAPKTFNDIPVLGKGEAALKEADQNLGLALSDPDIHYLLRAFHQLNRNPTDIELMMFA
QVNSEHCRHKIFNAQWTIDGKEKKESLFDMIRYTYKTHPEKILVAYKDNAAVIEGFNCESFLINPSNHSYEKQKGRL
HTVLKVETHNHPTAIAPFAGAATGSGGEIRDEAATGRGAQSLAGLAGFSVSHLRIPDFLQPWEKAPSKKSLHSDSKP
KTLASALDIMLQGPIGAASFNNEFGRPTICGYFRTLEHLSSKTLWGYHKPIMIAGGIGHIRESQIEKQSFTEGALLVV
LGGPAMAIGLGGGSASSRTSGESTEALDFASVQRANPEMQRRAQEVINACLSLGDDNPILSLHDVGAGGLSNAFP
ELVHATECGGEFELRHIPNAEPGMSPLEIWCNEAQERFVLAIKPESLKVFSGIAERERCPFAVVGRAKEEKKLILNDA
HFHNRPIDLPLSFLFEDMPPMKREDKRVFSGETAWNISKINWADAVKRVLQYPCVADKSFLITIGDRTVGGMVAR
DQMVGPWQIPVADVAVTAHSFTGYEGQALAMGERSPIAIVHPAASARMAVGEAITNIAAAPIKAISDIVLSANW
MAAPDQPGEGAGLYEAVQTVAKELCPALGICIPVGKDSLSMQTSLEKEIVTAPLSLIITATAPVSDVRHALTPQLQTD
VGETRLLLIDLGQGANFLGGSCLAQTYNLLGKQPPDVDDPLLLRRFFEAIQSLNQKNLLLAYHDRSDGGLLATLCEM
AFTAHVGITIKLDSLGDDALASVFNEELGAVIQVKEKNIDIVFEILKSHKLQAHSHVIGELNQLDEIIFNFRGQTLYQET
RTTLQRWWSETSYRLQSLRDNPECAKQQYDGLLDKKDTGLFTKITFDNNEDIALPYINSGKRPRVAILREQGTNGH
REMAAAFHLAGFESVDVHMSDLLNERVNLMDPFKGAVAGGGFSYGDVLGAGRGWAQVILMHPKIRDKFSLFFES
KDRFALGVCNGCQLFSHLKSLIPGALHWPAFQRNVSEQFEARLSMVEIPQSPSLFFQGMAGSQLPVAVAHGEGRV
VFEKNTQEFENEKLIALRYVNYAGQPTENYPANPNGSPKGITGLTTPDGRITILMPHPERVFRTVQFSWHPKQWSE
MSPWMRIFKNARKWVG

SEQ ID NO: 42
MTACVFCKIAKGEIGELIYEDKQVVAFNDAAPQAPIHILVIPHRHIETINDVTPGDEDLLGHMVVVATRLAHDKNM
AADGYRLVMNCNRNGGQAVFHIHLHLLGGRQMHWPPG

SEQ ID NO: 43
MPNVDDIRIFHGSANPSLAENVAKELNTTIGNALISRFSDGEIRFEIEENVRGRDIYLIQSTGHPTNEHVMELILMGD
AFRRASAASITAVVPYFGYARQDRRVRSSRVPISAKVVADMMQKVGFSRLITVDLHADQIQGFFYMPVDNIYASIT
ALEEYRLLDKLETPMIVSPDVGGVVRARAIAKRLNDSDLAIIDKRRPAPNQAEVMNIGNVQNRHCVIVDDIVDTA
GTLCHAASALKEKGALTVSSYCTHPVLSGNAVKNIMDSDIDELIVTDTIPLHEEAAKCRKITQISLSRLIAETISRINQKE
SVSSMFLD

SEQ ID NO: 44
MARRKAAPKRETLPDPLFHSELLAKFINAVMRNGKKSVAEKIVYGALDVVAKRVQNKSGEQGDGDGESGGKAGGI
KKRSLGDIRTDENARALALETFKGALDKVMPNVEVKSRRVGGSTYQVPVEIRMARRQALARRWLVEYANKRNEKT
MVLRLAHEILDAVEGRGGAIKKREDVHRMAKANQAFAHYKW

SEQ ID NO: 45
MNDLNSDGLFLFHFQAHLRWTRLALACPHQFRIKYPTLTNTGTHMVVIRLARGGSKKNPFYHIVVADRRKPRDGR
FIERVGYYNPMARGQDIRLQLEKERISHWLNQGAQTSLRVKHLIKKLEKSPEEAQKGGMRKGEFKRLQAEQAAKA
QKKAVATEEPKAEEAKEAPPAESQAAEGKEE

SEQ ID NO: 46
MEKTYDPKAIEKKWADYWEKRQLSKPTAQGSPYCIMLPPPNVTGTLHMGHGFQQTLMDTLIRYHRMKGERTLW
QGGTDHAGIATQMVVEQQLAQEDLTREDLGRQAFIKRVWEWRERSGGKITHQMRRLGVSIDWSRERFSMDEG
LSRATTEAFIRLHHEGLIYRGKRLVNWDPKLNTAISDLEVVTEEVEGHLWHIRYPLAEGSGHLIIATTRPETLLGDVAI
AVHPQDERYQPFVGKKVRLPLTDRTIPVIADEAVDKEFGTGSLKITPGHDFNDYEIGQRHQLPLINILTSEGYLNENV
PEPYRGLERFEARKKIIADLQRENLLEKTEPYRVPVPRGERSGVIIEPLLTDGWLYKMEALAKPAMEAVESGELKFIPK
NWEKTYLQWLSNIQDWCISRQLWWGHRLPVWYDEEKNSYVGRSREEILKKYHLSPDVKLQQETDVLDTWFSASL
WPFATLGWPEKTESFKTFYPTQVLVTGFDIIFFWVARMVMMGLKLTHKIPFHSVYIHGLIRDSQGRKMSKSKGNVI
DPIDIIDGISLDALIEKRTHALLQPKMAKTIEKMTRKEFPNGIASFGTDALRFTFCALASRGRDINFDMGRIDGYRNFC
NKIWNAARFVTMNTQEKDLNPEKPLSYSAADEWIRTRLQQTIKNAEEALSQYRFDLLAQTLYEFTWNEYCDWYE
FAKCILYDKQAKPAQLRGTRVALLEVLEILLLRLLHPVMPFITEEIWQTVAPLAGKEGKSIMVEHWPQFNIHEMNYDA
KVEIEWVKNVITAIRTLRAEIGISPAKRIPVIFGKGDEKDKKRIAKMKSYIKTLGKVSQLRFAKHDDCFSATATGIVERL
EIHIPLAGVIDKQTEIARLKKEISKLQKEEEKSLKKLDNPNYLQRAPQEVVEKERLSLEKTQNALKKLQSQYASIESL

SEQ ID NO: 47
MSLASAETAKIVKEYQLGKDDTGSPEVQVAILTAKIIKLTDHMKAHKHDHHSRRGLLRMVSQRRKLLNFLKRNDLQ
RYLKLIERLGLRS

SEQUENCES:

```
SEQ ID NO: 48
MRLIDEKGEQVGVVRTDRALTMAEEAGLDLVEISPTAKPPVCRIMNFGKYQFEQSKRKAAQKKKQRLVHLKEVKF
RPGTDVGDYQVKLRKIATFLDRGDKVKVSLRFRGREMQHRELGLELLGRVKRDLGNIVVEQEPRLEGRQMTMVV
MKAKGEGNKTKREDHAEIKD

SEQ ID NO: 49
MINDIINDSKSRMEKSLGSLKTELAKLRTCRAHPSLLEHIKVDYYNVETPLSQVASIAIENPRTLSITPWEKNMVGPIE
KAIQKADLGLNPATVGMVIRVPLPPLTEERRKELARVVREEAEHARVAIRNIRREANNDLKELMKEKEISEDEERRA
QTAIQKLTDAQIAEVDKMASQKEADLMAV

SEQ ID NO: 50
MALLKSRDIDKIANLSKLIIPKNENDALLEALNKTFDLVIKMDKVDTSAVDPLAHPYNETQPLREDHVTESNQRDLFQ
KSAPQVEAGLYMVPVVIDNEG

SEQ ID NO: 51
MTESLKNRIQEDMKAAMRAQEKGRLGTIRLLLAAIKQREIDEQITLDDAGVMKVIEKMIKQRRDSITQYEAGNRPD
LAEKEKQEIDVLQAYLPEALSDAEIDIAVKQAIEETGATSMKDMGQLMGVLKGKLQGRVDMSMVSKKVKEHLS

SEQ ID NO: 52
MSGGVKLIAGLGNPGDQYARTRHNVGAWFLETLAQQRNQSLAKENKFHGFVAKCNDYWLLKPTTFMNESGQA
VAALAHFYKIKPSEILIAHDELDFPAGDIRLKEGGHGGHNGLRNIIQHLGSSDFYRLRIGINHPGHKDRVTPYVLSPP
SENDRIAILAAIEKGLRLIPELVQGDFQKVMRELHS

SEQ ID NO: 53
MKVNFTKMQGSGNDFVVIDATKTPFQLTTSQIQKMANRRFGVGFDQLLVIEPPKNNSVDFHFRIFNADGSEVGQ
CGNGARCIARFIRAHQLSDREELRVSTLNEVLELKIQPDGKVSVKMGVPRFEPTEIPFIASGVANFYDIAVDNQIVKL
GVVNIGNPHAIIPVERINAEEVGKLGARLSVHECFPEGANVGFMQVIDPQNIRLRVYERGTGETLACGSNACAAVA
VGRRCGLLQERVVVSQPGGSLTIDWQGPLTPVTMTGPATTVFCGEWLD

SEQ ID NO: 54
MNQTDIIIIGAGLVGTSVAVALQGHGIKIKILEHHLPSAAVTSSNDVRPLTLSFGSYQILKNLGVEADLANEACPISTV
HVSDQGALGALRFRASEFNVPALGYVVSFAKLQQSLYQRAALQKNAEIVPISTIDDIQCNTNHAQVTFSTINGQQQ
LQADLLIAADGTHSTARRLLKIPVEEENRNEVALIALLRLKQPHNHIAYERFTSQGTLALLPLFQANQCRLVWTLPKT
KADEIEQLSDDEFRAVLHRVFKPYIGAIQSVERGKRFPLQMLIAQEQVRPSFVMLGNASHTLYPIAAQGFNLGLRDA
AVLSEVLIDARRQLKPLGDIRFLQEYSRWRKTDQARITGLTRGLSQWFGVQLPLANQARGLGLLATGLLPPFKKRLA
KRLMGLSGRLPQLMRGLKLDDAI

SEQ ID NO: 55
MSEHVHTASDENFETEVLQADMPVLVDFWAEWCQPCKMISPVVEEIAKEYAGRVKVFKLNVDENAQTPTKYGV
RGIPSLLIFREGEVVDRKVGALNKSQLAAFLDESLHFSS

SEQ ID NO: 56
MFVDSHCHLNMLDLSPYEGDLGALIDKAKSMGVEHILCVGVDLTHAQTVIEIAARFENVSASVGLHPSEKVDHEPT
VQELVEVANHPKVVAIGETGLDYYYNHSELGKMRDRFRCHVQAALKLKKPLIIHSRSAQTDTIQIMQEENAQSVGG
VMHCFTESWEMAEQAMKLGFYISFSGIVTFKNAKNVAEVAKKVPLEKMLIETDAPYLAPVPYRGKKNEPQYIPYVA
ERIAELKNIPLNEVARKTTENYYHLFG

SEQ ID NO: 57
MKPIAIYPGTFDPLTNGHVDIIERALPLFNKIIVACAPTSRKDPHLKLEERVNLIADVLTDERVEVLPLTGLLVDFAKTH
QANFILRGLRAVSDFDYEFQLAHMNYQLSPEIETIFLPAREGYSYVSGTMVREIVTLGGDVSPFVPPLVARHLQKRRE
K

SEQ ID NO: 58
MFRLDLLSDPLEQFKLWYDEAIRHETLHPDAMVLATADSKGKPSARNVLYKGISKGGFLIFTNYHSRKAHELDENPQ
AAWVFYWPKTYKQVRGEGRVERLTQEESEAYFETRSYESQIAAWVSEQSQEIPDREYLITRYKKYREKFQDDVRCP
EFWGGFRLIPDRMEFWVGQEHRLHDRFCYLKENQEWKIIRLAP

SEQ ID NO: 59
MSVLVPMVVEQTSRGERAYDIYSRLLKDRVIFLVGQVEDHMANLAIAQMLFLESENPNKDINLYINSPGGAVTSA
MAIYDTMQFVKPDVRTLCIGQAASAGALLLAGGAKGKRHCLPHSSVMIHQVLGGYQGQGTDIQIHAKQTQRVSD
QLNQILAKHTGKDIERVEKDTNRDYFLTPEEAVEYGLIDSIFKERP

SEQ ID NO: 60
MADLNHSYLTENAPLAAQMTMTPREIVAELDKFIIGQNDAKRAVAIALRNRWRRMQLGEELRREIFPKNILMIGPT
GVGKTEIARRLSDLAGAPFLKIEATKFTEVGYVGRDVESIIRDLVDVKMTREKAIRQVKSLAEEAAEERVLDALIPP
ARGGFQGEPTAEEKPTEKKESATRQLFRKKLRNGELDDKEIEVEVSAHPSFEIMGPPGMEEMVSQLQGIMSSMSS
RRSKSRRLKVKDALRILGEEEAAKLVDEDQIKSTALASVEQNGIVFIDEIDKIVKREGAVGADVSREGVQRDLLPLVEG
STVFTKYGMVKTDHILFIASGAFHIAKPSDLVPELQGRFPIRVELKALTADDFVRILTEPKASLTEQYTELLKTENFGLSF
TKDGIKRLAEIAYQVNDRSENIGARRLHTIMERLLEEVSFEATDKQGESITIDADYVNKQLKKLAEDEDLSRYIL

SEQ ID NO: 61
MEQIAARVTYINLSPDELIQHAVKNGEGVLSSTGALAVTTGKRTGRSPKDRFIVKDEQTADQVAWGNINQPVEQR
TFDQLWERALRYLSERAVYISHLQVGADDNYFLPLKVVTEFAWHNLFACDLFIRPSGDHANGKPSWVILSAPGLKT
DPERDGVNSDGAVMINLSQRRVLLVGMPYAGEMKKAMFSVLNYLLPPHDVLPMHCAANAGQSGDVALFFGLS
GTGKTTLSADPHRFLIGDDEHGWSATSVFNFEGGCYAKCIDLSQEREPMIWNAIRHGAIMENVVLDENGVPDYAD
ARLTQNSRAAYPREYIPLRVENNRGRPPDAVLFLTCDLDGVLPPVALLTKEQAAYYFLSGYTALVGSTEVGSVKGVTS
```

| SEQUENCES: |
| --- |

TFSTCFGAPFFPRPPTVYAELLMKRIEATGCQVYLVNTGWTGGAYGEGGERFSIPTTRAIVNAVLSGKLKEGPTEVLS
GFNLTIPKSALGVDDHLLNPRKTWEDVSAYDARAQRLIQKFRENFEKFKVLAAIREAGPSDVH

SEQ ID NO: 62
MSRKFTD KIKGIVMNNLVKNSGLAVIALATLNLSGCKHHPAGANAATGLSDGTGAQAYALAEGKGYQGQLKKDSE
GRIINPLVAPANQTYYFDFDSTQLRSLDLGAIRVQANYLATHSTAKVRLEGNTDNRGSREYNIGLGWRRDQAVARIL
EQEGVAPKQIDMVSYGKERPAVMGNNENAWRLNRRVNLIYEAY

SEQ ID NO: 63
MQTKVEGLAHILLQTNALTNSQIARAIEQAAGAQSPLLHYLVTEKIVSSEKIAEACATYFGLEAINLQTQPLNPSLCHE
IPRKYLMRYAFIPLAVKSPTLAISDPLYFPLIEELQFQTNKQYKIVFAPYKSFAALINNFVSRQIYETVSQGEASIVELVN
QVLTDAIYREASDVHFEPMQQHYRIRMCIDGILHTTTLLPNTQSPAMSSRLKVLAELDISEKRLPQDGRFYFTTLTHL
KRDCRLSSCPTLFGEKIVIRLLNPVHHLLKFEELGLEEKPKQLIMKKIKQLQGLILVTGPTRSGKTVSLYAALNQINSTQ
KNISTVEDPIEIQLAGVTQVNIRPKAGLNFAAVLRVFLRQD DVIMVGEIRDFETASIAVRAAHTGHLVLSTLHTNSA
VECITRLIDMGIEPFNLASVLKLVVAQRLVRQLCAHCQATKISCPFCLNGYQGRTGIYEVLPITPSIIELILQKRSAQEIN
ACAIQEGMQTLWQAALNKAKTGITNLNEIYRVIQSENNYA

SEQ ID NO: 64
MKRIAVFILTLSFFSISYSDKNPVFQEYYEGNYRAAETGLKQLAEKNNGEATFYLATMYMNGFGVRRDFEKGFDYM
TRAAELKYLPAQLYLNGNYYFQQQKDLEKAVPWFKKAADAGDAGAQLFTGISYLNGYGVKKNIDIARKYFIRAAQNEI
PMGQYELAKIFLASRHAGDRRMGRIWLTKAADKYNYPDAQYLLGTMLYTGNEAEKDPVKGVEWLEKAAANGSK
EASKTLDKINRINTSDAKANSENRSEPTPWQIMVGLMQKAGVQLNNPITVTASINNFTKTPKSMALDKNSIIKLNLN
LVNSKDIPPEKILSYMTQLNYKEEKFDLTVPAYPFEMPPGANNYKEAFQSLSRVANYGYAQSLFRLGQMYENGLGV
QKDPETAFQLYMKAAEQNYLKAQYAIGTYYLQGKGVPQDYEKAISWFIRAALKGSLQAQFVLGNIYERGIKASNNK
ILFKNFDRAKAMYSLAVGGNLPIAAYRLAELYVSGFLNPDNNVSLETQNWKKAYALYQKAAKSGLEKADVALGYFY
LQQNQTTLAEKTFEIAQKAYQTNDPEAAMLLAILYDRGFGVNRNSRKSAEILEKLSKQNNAIAQFMLGNYYLKNKR
KENIAISLLEKSANQGNGYAKYNLAILAKQNKYTKPGENFLSLLIRAANHYDKIKEILADYYLLDTPVPGSEKKAVAIYQ
ELANKQDPAAELKLGFMNEHGLLFPKDYHKAEEWYQKSAEQGNPIAQYLLGNMYYLGRGVDRDVNKAIDWLKKS
AAQNYVPAKVGLGFIYEMSKHNYPEAKKWYTLASKFHNPQALYNLGLMYEYGKGVKSDPQKAFRLYKDAAQNGL
DLAAVQVAGMYLKGTGIGFDPNTALKMYSQAAQKNNSFATYQLGLMSESGVAQKIDLNKARLYYEKAAKEGSVE
AQLALARFYEFGISVPADISKSINFYQAAAAEGNEFAKQQLTRLSNQGKSSSNAMPFQCVNQVALEKVKNSFWKK
VTDWIAPVPNIDYMNAIDYLNSGKVEQATTALQKIIKVRPNFQPARETVSHYFCQKADRK

SEQ ID NO: 65
MLETEKCTKIFLSFSLNSRRIIMNLSLTQDPQKAKEFFEKKMAFTTGPVEVSGMLKKNAKIQVVDVRAAEDYKKGHV
PGAINLPSNEWEKAAEKLDKEKTNIIYCYSQVCHLAAKAAVKFAEQGFPVMEMEGGFKTWTEHKLETEK

SEQ ID NO: 66
MAFELPDLPYKLNALEPHISQETLEYHHGKHHRAYVNKLNKLIEGTPFEKEPLEEIIRKSDGGIFNNAAQHWNHTFY
WHCMSPDGGGDPSGELASAIDKTFGSLEKFKALFTDSANNHFGSGWAWLVKDNNGKLEVLSTVNARNPMTEGK
KPLMTCDVWEHAYYIDTRNDRPKYVNNFWQVVNWDFVMKNFKS

SEQ ID NO: 67
MDNYKKILVALALDPNSDRPLVEKAKELSANRDAQLYLIHAVEHLSSYGAAYGVAAGVDVEDMLLEEAKKRMNEIA
SQLNISSDHQIVKVGPAKFLILEQAKNWGVDLIIVGSHGRHGIQLLLGSTSNAVLHGAKCDVLAVRIKGS

SEQ ID NO: 68
MPSFDIQSELNKHEVSNAVDQANREVATRFDFKGSGATYKYEGNSITLQAETDFQLKQMIDILQNKFAKRQIDVAH
MKLEDPIIQHKSAQQTVMLLEGIDQTAAKKIIKLIKDQKLKVQAAIQGEKVRVTGKKRDDLQSVIGLLKEQEIGLPLQ
FDNFRD

SEQ ID NO: 69
MSNSGKKFDFQGVLNNIKSMISPESNTPSPDPSDAIGMKIAELSVLAQQLTKSHEEQAKELANVNRLLNDLFKDLEA
FRNPPENKTEEKQKDKKEETKKD

SEQ ID NO: 70
MIGGKFNLGSLMKNAKKIQEMMQKAQDELAKIRVTGESGAGMVKLTMTAQHEVVEMNLDDELLKESKEVIEDLI
KAALNDANQKILKITQEKMMSAGSLFGGNESDNEET

SEQ ID NO: 71
MIRSGKMRKLINSIIGVALIVVIVLLVLPLGMSFWLKNNYPSILTRLSQAHNVSLKLINFDRGWFASKAVIQVIIPNSED
KTTQPIKFTINQHIFNGPFIFSKNNHKVKLHCAKALVYTTSNDPNFTFHSSTLLRFNNSSKSSLYASNVNVANGQEQI
VLKDTNLEILYNPLTQRLVLNAVIKSALISEQQKTILIMDNITWRNDLHHATPLWEGKRSLSLNKFTYYLTPEQLIEVK
NFILENQQNAANDTTTFTFSSHADSIKDTSLNLAPLDIKFSLTQMNTAALVNLINTALNENHLKLNPQQLHQFHTPA
INLLAQGLEVSLAHLTFGTEEGQVSVQGQLHLPAQNQSPDLSQIMVNAKGNLQAKMPMAWLKKELSRIYEDKKV
ELDDQALTPEQIADQQIQYWINNKKLIPQNQDVELTINYDKGKLLVNNLPSHAPQQ

| SEQUENCE LISTING |
| --- |

<160> NUMBER OF SEQ ID NOS: 71

<210> SEQ ID NO 1
<211> LENGTH: 1143

<212> TYPE: PRT
<213> ORGANISM: Coxiella burnetii

<400> SEQUENCE: 1

Met Thr Ile Ser Phe Val His Leu Lys Ile His Ser Glu Tyr Ser Ile
1               5                   10                  15

Val Asp Ser Val Val Arg Ile Asp Gln Leu Leu Gln Arg Ala Val Asp
            20                  25                  30

Leu Lys Met Pro Ala Val Ala Leu Thr Asp Glu Val Asn Leu Phe Ala
        35                  40                  45

Leu Val Lys Phe Tyr Arg Gln Ala Ile Asn Lys Gly Ile Lys Pro Ile
    50                  55                  60

Ile Gly Ser Glu Leu Leu Leu Ala Glu Gly Asp Asp Val Phe Arg Phe
65                  70                  75                  80

Thr Ala Leu Cys Gln Asn Gln Ile Gly Phe Arg His Leu Ile Gln Leu
                85                  90                  95

Leu Ser Arg Ala Tyr Val Glu Gly Arg Gln Arg Asp His Val Leu Ile
            100                 105                 110

Gln Trp Glu Trp Leu Val Gln Ala Asn Glu Gly Leu Ile Ile Leu Ser
        115                 120                 125

Gly Ala Arg Arg Gly Asn Val Gly Gln Ala Leu Leu Gln Arg Arg Ser
    130                 135                 140

Pro Leu Ala Glu Glu Arg Leu Thr Arg Trp Ile Asn His Phe Pro Gly
145                 150                 155                 160

Arg Phe Tyr Leu Glu Leu Gln Arg Thr Arg Arg Asp Gln Glu Glu Glu
                165                 170                 175

Tyr Ile His Ser Val Ile Glu Leu Ala Leu Lys His Arg Val Pro Val
            180                 185                 190

Val Ala Thr Asn Glu Val Cys Phe Leu Ser Gln Gly Asp Phe Glu Ala
        195                 200                 205

His Glu Ala Arg Val Cys Ile His Gln Gly Tyr Leu Leu Gln Asp Val
    210                 215                 220

Asn Arg Pro Arg Glu Tyr Ser Asp Gln Gln Tyr Phe Lys Ser Ala Glu
225                 230                 235                 240

Glu Met Thr Ala Leu Phe Ser Asp Ile Pro Glu Ala Leu Glu Asn Thr
                245                 250                 255

Val Glu Ile Ala Lys Arg Cys Ser Val Pro Leu Ser Leu Asp Glu Val
            260                 265                 270

Phe Leu Pro Lys Phe Pro Val Pro Ala Asn Leu Lys Val Glu Asp Tyr
        275                 280                 285

Phe Arg Ala Gln Ala Lys Gln Gly Leu Thr Arg Arg Leu Val Gly Leu
    290                 295                 300

Glu Met Lys Asn Asn Leu Thr His Lys Asp Tyr Glu Glu Arg Leu Glu
305                 310                 315                 320

Thr Glu Ile Thr Val Ile Thr Lys Met Gly Phe Ala Ser Tyr Phe Leu
                325                 330                 335

Ile Val Ala Asp Phe Ile Ala Trp Ala Lys Gln His His Ile Pro Val
            340                 345                 350

Gly Pro Gly Arg Gly Ser Gly Ala Gly Ser Leu Val Ala Tyr Ser Leu
        355                 360                 365

Gly Ile Thr Glu Leu Asp Pro Leu Glu His Asp Leu Leu Phe Glu Arg
    370                 375                 380

Phe Leu Asn Leu Glu Arg Val Ser Met Pro Asp Phe Asp Ile Asp Phe
385                 390                 395                 400

```
Cys Met Glu Gly Arg Asp Arg Val Ile Asp Tyr Val Ala Glu Arg Tyr
            405                 410                 415
Gly Gln Glu Ala Val Ala Gln Ile Ile Thr Tyr Gly Thr Met Ala Ala
        420                 425                 430
Arg Ala Val Leu Arg Asp Val Gly Arg Val Leu Gly Leu Pro Tyr Gly
            435                 440                 445
Tyr Val Asp Lys Ile Ala Lys Leu Val Pro Phe Glu Leu Gly Val Thr
    450                 455                 460
Leu Glu Lys Ala Leu Glu Gln Glu Ile Leu Ala Lys Arg Tyr Ala
465                 470                 475                 480
Glu Asp Glu Glu Val Lys Asn Leu Ile Asp Leu Ala Met Lys Leu Glu
                485                 490                 495
Gly Leu Thr Arg Asn Ala Gly Lys His Ala Gly Gly Val Val Ile Ala
            500                 505                 510
Pro Thr Lys Leu Thr Asp Phe Val Pro Leu Tyr Ser Glu Pro Gly Ser
        515                 520                 525
Asp His Val Val Thr Gln Phe Asp Lys Asp Val Glu Ala Val Gly
            530                 535                 540
Leu Val Lys Phe Asp Phe Leu Gly Leu Arg Thr Leu Thr Ile Ile Asn
545                 550                 555                 560
Trp Ala Val Gln Asn Ile Asn Ala Lys Arg Lys Ile Gln Asn Glu Thr
                565                 570                 575
Glu Leu Asp Ile Gly Thr Ile Pro Leu Asp Asp Pro Lys Thr Tyr Ala
            580                 585                 590
Leu Leu Lys Ser Cys Ala Thr Thr Ala Val Phe Gln Leu Glu Ser Arg
            595                 600                 605
Gly Met Lys Glu Leu Ile Arg Arg Leu Gln Pro Asp Asn Phe Ala Asp
    610                 615                 620
Ile Met Ala Leu Val Ala Leu Phe Arg Pro Gly Pro Leu Gln Ser Gly
625                 630                 635                 640
Met Val Glu Thr Phe Ile Ala Cys Lys His Gly Glu Gln Ser Val His
                645                 650                 655
Phe Leu His Pro Ala Leu Glu Pro Ile Leu Arg Thr Thr Tyr Gly Val
            660                 665                 670
Ile Leu Tyr Gln Glu Gln Val Met Gln Ile Ala Gln Val Leu Ala Gly
        675                 680                 685
Tyr Ser Leu Gly Ala Ala Asp Val Leu Arg His Ala Met Gly Lys Lys
    690                 695                 700
Lys Pro Glu Glu Met Ala Lys Gln Arg Ala Val Phe Leu Glu Gly Thr
705                 710                 715                 720
Lys Ala Arg Gly Leu Lys Glu Ala Leu Ala Asn Gln Ile Phe Asp Leu
                725                 730                 735
Met Glu Lys Phe Ser Gly Tyr Gly Phe Asn Lys Ser His Ser Ala Ala
            740                 745                 750
Tyr Ala Leu Ile Ala Tyr Gln Thr Ala Trp Leu Lys Ala His Tyr Pro
        755                 760                 765
Ala Glu Phe Met Ala Ala Val Leu Ser Ser Asp Met Asp Asn Thr Asp
    770                 775                 780
Lys Val Val Gly Phe Ile Asn Glu Cys Arg Asp Met Asn Leu Glu Leu
785                 790                 795                 800
Leu Pro Pro Asn Ile Asn Trp Ser His Tyr Pro Phe Thr Val Asn Thr
                805                 810                 815
```

```
Lys Gly Gln Ile Val Tyr Gly Leu Gly Ala Ile Lys Gly Val Gly Glu
                820                 825                 830

Ala Ala Ala Met Asn Ile Val Ala Tyr Arg Glu Ala Glu Gly Glu Phe
            835                 840                 845

Lys Gly Leu Phe Asn Phe Cys Ser Arg Val Asp Leu Arg Lys Val Asn
        850                 855                 860

Arg Arg Ala Val Glu Pro Leu Ile Arg Ser Gly Ala Met Asp Thr Phe
865                 870                 875                 880

Gly Val Ser Arg Ala Ser Leu Phe Glu Ser Leu Thr Lys Ala Phe Gln
                885                 890                 895

Ala Ala Glu Gln Arg Asn Arg Asp Met Ile Leu Gly Gln His Asp Leu
            900                 905                 910

Phe Gly Glu Glu Val Lys Gly Ile Asp Glu Asp Tyr Thr Glu Val Pro
        915                 920                 925

Glu Trp Asn Asp Ser Asp Arg Leu Arg Gly Glu Lys Glu Thr Leu Gly
    930                 935                 940

Leu Tyr Val Ser Gly His Pro Leu Gln Ala Cys Ile Lys Glu Met Lys
945                 950                 955                 960

Ala Val Gly Ala Val Pro Ile Asn His Leu Ser Leu Ser Glu Lys Asn
                965                 970                 975

Ser Val Val Ala Gly Met Met Met Gly Met Arg Thr Ile Thr Thr
            980                 985                 990

Arg Ser Gly Lys Arg Met Ala Ile Leu Ser Leu Glu Asp Gln Thr Gly
        995                 1000                1005

Lys Ile Asp Val Thr Leu Phe Asn Asp Leu Tyr Gln Gln Val Ala
    1010                1015                1020

Ala Asp Leu Thr Asp His Ala Ile Leu Val Ile Arg Gly Thr Val
    1025                1030                1035

Gly Arg Asp Asp Tyr Thr Gly Gly Gln Lys Met Val Ala Asp Met
    1040                1045                1050

Leu Leu Thr Leu Asp Lys Val Arg Glu Gln Met Val Lys Arg Leu
    1055                1060                1065

Leu Ile Arg Val Ala Gly Gln Asp Gly Val Asp Gln Leu Leu Thr
    1070                1075                1080

Glu Leu Pro Pro Leu Ile Lys Pro Tyr Val Gly Gly Arg Cys Pro
    1085                1090                1095

Val Ala Ile Ala Tyr Gln Ser Glu Thr Ala Ile Ala Glu Leu Leu
    1100                1105                1110

Leu Gly Glu Thr Trp Arg Val Lys Leu Asp Asp Lys Leu Leu Ser
    1115                1120                1125

Glu Leu Ser Lys Leu Tyr Gly Lys Asp Gln Val Glu Leu Glu Tyr
    1130                1135                1140
```

<210> SEQ ID NO 2
<211> LENGTH: 1414
<212> TYPE: PRT
<213> ORGANISM: Coxiella burnetii

<400> SEQUENCE: 2

```
Met Arg Asp Leu Val Lys Gln Leu Lys Ser Glu Lys His Thr Ala Glu
1               5                   10                  15

Phe Asp Ala Leu Arg Ile Lys Leu Ala Ser Pro Glu Glu Val Arg Ser
            20                  25                  30

Trp Ser Tyr Gly Glu Val Lys Lys Pro Glu Thr Ile Asn Tyr Arg Thr
        35                  40                  45
```

```
Phe Lys Pro Glu Arg Glu Gly Leu Phe Cys Ala Lys Ile Phe Gly Pro
 50                  55                  60

Ile Lys Asp Tyr Glu Cys Leu Cys Gly Lys Tyr Lys Arg Leu Lys His
 65                  70                  75                  80

Arg Gly Val Ile Cys Glu Lys Cys Gly Val Glu Val Thr Leu Ala Lys
                 85                  90                  95

Val Arg Arg Glu Arg Met Gly His Ile Glu Leu Ala Ser Pro Val Ala
                100                 105                 110

His Ile Trp Tyr Leu Lys Ser Leu Pro Ser Arg Ile Gly Leu Leu Leu
            115                 120                 125

Asp Val Thr Leu Arg Asp Ile Glu Arg Ile Leu Tyr Phe Glu Ala Tyr
        130                 135                 140

Val Val Val Asp Pro Gly Met Thr Asp Leu Glu Pro Arg Gln Leu Leu
145                 150                 155                 160

Ser Glu Glu Ala Tyr Leu Asp Ala Leu Glu Glu Tyr Gly Asp Asp Phe
                165                 170                 175

Thr Ala Leu Met Gly Ala Glu Ala Ile Gln Arg Leu Leu Arg Asp Ile
            180                 185                 190

Asp Val Glu Ala Glu Val Glu Ala Leu Arg Thr Glu Leu Gln Thr Thr
        195                 200                 205

Thr Ser Glu Thr Lys Thr Lys Lys Leu Thr Lys Arg Leu Lys Val Leu
210                 215                 220

Ser Ala Phe Leu Glu Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
                260                 265                 270

Ile Asn Arg Asn Asn Arg Leu Lys Arg Leu Leu Asp Leu Asn Ala Pro
            275                 280                 285

Asp Ile Ile Val Arg Asn Glu Lys Arg Met Leu Gln Glu Ala Val Asp
        290                 295                 300

Ala Leu Leu Asp Asn Gly Arg Arg Gly Arg Ala Ile Leu Gly Ser Asn
305                 310                 315                 320

Arg Arg Gln Leu Lys Ser Leu Ala Asp Met Ile Lys Gly Lys Ser Gly
                325                 330                 335

Arg Phe Arg Gln Asn Leu Leu Gly Lys Arg Val Asp Tyr Ser Gly Arg
                340                 345                 350

Ser Val Ile Val Val Gly Pro Thr Leu Lys Leu His Gln Ala Gly Leu
            355                 360                 365

Pro Lys Lys Met Ala Leu Glu Leu Phe Lys Pro Phe Ile Phe Ser Lys
        370                 375                 380

Leu Gln Leu Arg Gly Leu Ala Thr Thr Val Lys Ala Ala Lys Lys Leu
385                 390                 395                 400

Val Glu Asn Glu Gly Pro Glu Val Trp Asp Ile Leu Glu Glu Val Ile
                405                 410                 415

Arg Glu His Pro Ile Leu Leu Asn Arg Ala Pro Thr Leu His Arg Leu
                420                 425                 430

Gly Ile Gln Ala Phe Glu Pro Val Leu Val Glu Gly Lys Ala Ile Gln
            435                 440                 445

Leu His Pro Leu Val Cys Thr Ala Tyr Asn Ala Asp Phe Asp Gly Asp
450                 455                 460
```

-continued

```
Gln Met Ala Val His Val Pro Leu Thr Leu Glu Ala Gln Leu Glu Ala
465                 470                 475                 480

Arg Ser Leu Met Met Ser Thr Asn Asn Val Leu His Pro Ala Asn Gly
                485                 490                 495

Glu Pro Ile Ile Val Pro Ser Gln Asp Val Val Leu Gly Leu Tyr Tyr
            500                 505                 510

Ile Thr Arg Asp Arg Val Asn Ala Lys Gly Glu Gly Met Arg Phe Ala
        515                 520                 525

Asp Ala Gln Glu Val Val Arg Ala Tyr Glu Asn Asp Gln Val Asp Leu
    530                 535                 540

His Ala Arg Ile Thr Val Arg Ile Lys Glu Gly Ile Leu Asn Glu Ala
545                 550                 555                 560

Gly Glu Ile Glu Glu Ser Asp Arg Leu Val Asn Thr Ala Ala Gly Arg
                565                 570                 575

Ile Leu Leu Trp Gln Ile Val Pro Lys Gly Leu Pro Phe Ala Leu Val
            580                 585                 590

Asp Gln Pro Met Thr Lys Lys Ala Val Thr Lys Leu Leu Asp Phe Cys
        595                 600                 605

Tyr Arg Asn Leu Gly Leu Lys Thr Thr Val Ile Phe Ala Asp Lys Leu
    610                 615                 620

Met Tyr Met Gly Phe His Tyr Ala Thr His Ser Gly Val Ser Ile Gly
625                 630                 635                 640

Ile Asn Asp Leu Val Val Pro Asp Gln Lys Glu Ala Ile Ile Ser Arg
                645                 650                 655

Ala Glu Asp Glu Val Arg Glu Ile Glu Lys Gln Tyr Ala Ser Gly Leu
            660                 665                 670

Val Thr His Gly Glu Arg Arg Asn Lys Val Ile Asp Ile Trp Ser Arg
        675                 680                 685

Thr Asn Asp Gln Val Ala Lys Ala Met Met Glu Lys Ile Ala Val Glu
    690                 695                 700

Lys Val Lys Asp Ala Glu Gly Lys Glu Val Ala Gln Ser Ser Phe Asn
705                 710                 715                 720

Ser Ile Tyr Met Met Ser Asp Ser Gly Ala Arg Gly Ser Ala Ala Gln
                725                 730                 735

Thr Arg Gln Leu Ala Gly Met Arg Gly Leu Met Ala Arg Pro Asp Gly
            740                 745                 750

Thr Ile Ile Glu Thr Pro Ile Thr Ala Asn Phe Arg Glu Gly Leu Asn
        755                 760                 765

Val Leu Gln Tyr Phe Ile Ser Thr His Gly Ala Arg Lys Gly Leu Ala
    770                 775                 780

Asp Thr Ala Leu Lys Thr Ala Asn Ser Gly Tyr Leu Thr Arg Arg Leu
785                 790                 795                 800

Val Asp Val Ala Gln Asp Leu Val Val Thr Glu His Asp Cys Gly Thr
                805                 810                 815

Glu Ala Ser Ile Glu Met Met Pro His Ile Gly Gly Asp Val Val
            820                 825                 830

Glu Pro Leu Arg Glu Arg Val Leu Gly Arg Ile Leu Ala Glu Pro Val
        835                 840                 845

Met Asp Pro Lys Ser Arg Lys Glu Leu Leu Ala Lys Asp Thr Phe Leu
    850                 855                 860

Asp Glu Arg Arg Val Asp Ile Leu Glu Glu His Ser Ile Asp Arg Val
865                 870                 875                 880

Arg Val Arg Ser Ala Ile Thr Cys Glu Ala Arg Tyr Gly Ile Cys Ser
```

```
                    885              890              895
Met Cys Tyr Gly Arg Asp Leu Ala Arg Gly His Val Val Asn Val Gly
                900              905              910

Glu Ala Ile Gly Val Val Ala Ala Gln Ser Ile Gly Glu Pro Gly Thr
                915              920              925

Gln Leu Thr Met Arg Thr Phe His Ile Gly Gly Ala Ala Ser Arg Ala
            930              935              940

Thr Ala Ala Asn Asn Ile Gly Val Lys Ser Thr Gly Lys Ile Lys Leu
945              950              955              960

Arg Asn Leu Lys Thr Val Glu Gln Ala Gln Gly Asn Leu Val Ala Val
                965              970              975

Ser Arg Ser Gly Glu Leu Val Val Gln Asp Leu Gln Gly Ser Glu Arg
                980              985              990

Glu His Tyr Lys Val Pro Tyr Gly Ala Thr Ile Ser Val Arg Asp Gly
            995              1000             1005

Asp Ser Val Lys Ala Gly Gln Ile Val Ala Gln Trp Asp Pro His
    1010             1015             1020

Thr His Pro Ile Ile Thr Glu Val Ala Gly Thr Leu Arg Phe Val
    1025             1030             1035

Asp Leu Val Asp Gly Val Thr Met Asn Arg Gln Thr Asp Glu Leu
    1040             1045             1050

Thr Gly Leu Ser Ser Ile Val Ile Thr Ser Thr Lys Gln Arg Ser
    1055             1060             1065

Ala Ser Gly Lys Glu Leu Arg Pro Met Val Lys Leu Val Asp Lys
    1070             1075             1080

Asn Asp Asp Asp Leu Phe Leu Pro Gly Gly Lys Val Pro Ala His
    1085             1090             1095

Tyr Phe Leu Pro Glu Gly Thr Phe Leu Thr Lys Glu Asp Gly Thr
    1100             1105             1110

Thr Val Asn Ile Gly Asp Val Leu Ala Arg Ile Pro Gln Glu Thr
    1115             1120             1125

Ser Lys Thr Arg Asp Ile Thr Gly Gly Leu Pro Arg Val Ala Asp
    1130             1135             1140

Leu Phe Glu Ala Arg Arg Pro Lys Asp Ala Ala Ile Leu Ala Glu
    1145             1150             1155

Ile Ser Gly Val Val Ser Phe Gly Lys Asp Thr Lys Asp Lys Gly
    1160             1165             1170

Arg Leu Ile Ile Thr Ala Pro Asp Gly Thr Thr His Glu Glu Leu
    1175             1180             1185

Ile Pro Lys Trp Arg His Val Ser Val Phe Glu Gly Glu Thr Val
    1190             1195             1200

Glu Lys Gly Glu Val Ile Ala Asp Gly Pro Arg Asp Pro His Asp
    1205             1210             1215

Ile Leu Arg Leu Leu Gly Val Asn Ala Leu Ala Asn Tyr Ile Val
    1220             1225             1230

Asn Glu Val Gln Glu Val Tyr Arg Leu Gln Gly Val Lys Ile Asn
    1235             1240             1245

Asp Lys His Ile Glu Val Ile Val Arg Gln Met Leu Arg Lys Val
    1250             1255             1260

Lys Ile Thr Gln Pro Gly Asp Thr Asp Leu Leu Gln Asn Glu Gln
    1265             1270             1275

Val Glu Arg Thr Arg Val Arg Glu Glu Asn Glu Lys Ile Ile Lys
    1280             1285             1290
```

```
Lys Asp Gly Thr Val Ala Lys Val Glu Pro Ile Leu Leu Gly Ile
    1295            1300                1305

Thr Lys Ala Ser Leu Ala Thr Glu Ser Phe Ile Ser Ala Ala Ser
    1310            1315                1320

Phe Gln Glu Thr Thr Arg Val Leu Thr Ala Ala Ser Val Ala Gly
    1325            1330                1335

Lys Arg Asp Asp Leu Arg Gly Leu Lys Glu Asn Val Ile Val Gly
    1340            1345                1350

Arg Leu Ile Pro Ala Gly Thr Gly Phe Ser Tyr His Gln Gln Arg
    1355            1360                1365

Arg Ala Val Ala Gly Lys Ser Val Glu Glu Lys Glu Ile Glu Glu
    1370            1375                1380

Lys Arg Val Thr Ala Ser Glu Ala Glu Gln Ala Leu Ser Glu Ala
    1385            1390                1395

Leu Lys Ser Ser Ala Pro Gln Glu Ala Lys Ala Ala Gln Lys Asp
    1400            1405                1410

Glu

<210> SEQ ID NO 3
<211> LENGTH: 696
<212> TYPE: PRT
<213> ORGANISM: Coxiella burnetii

<400> SEQUENCE: 3

Met Asn Lys Ile Arg Lys Thr Phe Gln Tyr Gly Lys His Glu Val Thr
1               5                   10                  15

Phe Glu Thr Gly Glu Met Ala Arg Gln Ala Thr Gly Ala Val Val Val
                20                  25                  30

Arg Met Gly Asp Thr Val Leu Leu Val Ser Val Val Ala Lys Lys Glu
            35                  40                  45

Ala Glu Glu Gly Arg Asp Phe Phe Pro Leu Thr Val Asn Tyr Gln Glu
        50                  55                  60

Lys Thr Tyr Ala Ala Gly Lys Ile Pro Gly Gly Tyr Phe Lys Arg Glu
65                  70                  75                  80

Gly Arg Pro Thr Glu Lys Glu Thr Leu Thr Ser Arg Leu Ile Asp Arg
                85                  90                  95

Pro Leu Arg Pro Leu Phe Pro Lys Gly Phe Thr Asn Glu Val Gln Val
                100                 105                 110

Ile Ala Thr Val Leu Ser Val Asp Ser Lys Val Pro Thr Asp Ile Pro
            115                 120                 125

Ala Ile Leu Gly Ala Ser Ala Ala Ile Gly Leu Ser Gly Ile Pro Phe
        130                 135                 140

Asn Gly Ser Leu Gly Ala Ala Arg Val Gly Tyr Arg Gly Gly Glu Tyr
145                 150                 155                 160

Leu Leu Asn Pro Ser Leu Asp Glu Leu Lys Asp Ser Ala Leu Asp Leu
                165                 170                 175

Val Val Ala Gly Thr Arg Asp Ala Val Leu Met Val Glu Ser Glu Ala
            180                 185                 190

Gln Glu Leu Pro Glu Ser Val Met Leu Gly Ala Val Leu His Gly His
        195                 200                 205

Gln Ala Met Gln Val Ala Ile Gln Ala Ile Ala Glu Phe Ile Gln Glu
    210                 215                 220

Ala Gly Gly Ala Lys Trp Glu Trp Glu Pro Pro Thr Val Asn Thr Ala
225                 230                 235                 240
```

```
Leu Glu Lys Trp Val Val Glu Lys Ser Glu Ala Pro Leu Lys Lys Ala
                245                 250                 255
Tyr Gln Ile Gln Glu Lys Thr Ala Arg Gln Ala Gln Ile Gln Ala Ile
            260                 265                 270
Arg Asp Gln Leu Leu Ala Asp Arg Ala Ala Glu Arg Glu Gly Glu Glu
        275                 280                 285
Asn Ala Val Asn Glu His Glu Leu Ala Val Ile Phe His Glu Leu Glu
    290                 295                 300
Arg Arg Ile Val Arg Glu Gln Ile Leu Thr Gly Gln Pro Arg Ile Asp
305                 310                 315                 320
Gly Arg Asp Thr Lys Thr Val Arg Pro Ile Thr Val Lys Val Gly Val
                325                 330                 335
Leu Pro Arg Ser His Gly Ser Ala Leu Phe Thr Arg Gly Glu Thr Gln
            340                 345                 350
Ala Leu Val Val Thr Thr Leu Gly Thr Glu Arg Asp Ala Gln Ser Ile
        355                 360                 365
Asp Asp Leu Asp Gly Asp Arg Gln Glu Glu Phe Ile Phe His Tyr Asn
    370                 375                 380
Phe Pro Pro Phe Cys Val Gly Glu Val Gly Phe Met Ser Gly Pro Lys
385                 390                 395                 400
Arg Arg Glu Ile Gly His Gly Arg Leu Ala Lys Arg Ala Val Val Pro
                405                 410                 415
Val Val Pro Thr Leu Asp Lys Phe Pro Tyr Val Ile Arg Val Val Ser
            420                 425                 430
Glu Ile Leu Glu Ser Asn Gly Ser Ser Met Ala Ser Val Cys Gly
        435                 440                 445
Ser Ser Leu Ala Leu Met Asp Ala Gly Val Pro Thr Lys Ala Pro Val
    450                 455                 460
Ala Gly Ile Ala Met Gly Leu Ile Lys Glu Asn Asp Lys Tyr Ala Val
465                 470                 475                 480
Leu Ser Asp Ile Leu Gly Asp Glu Asp His Leu Gly Asp Met Asp Phe
                485                 490                 495
Lys Val Ala Gly Thr Ser Asn Gly Val Thr Ala Leu Gln Met Asp Ile
            500                 505                 510
Lys Ile Glu Gly Ile Thr Lys Glu Ile Met Glu Gln Ala Leu Asp Gln
        515                 520                 525
Ala Lys Glu Gly Arg Leu His Ile Leu Ser Ile Met Asn Lys Val Leu
    530                 535                 540
Asp Lys Pro Arg Ser Gln Val Ser Asp Leu Ala Pro Gln Tyr Val Thr
545                 550                 555                 560
Met Lys Ile Asn Pro Glu Lys Ile Arg Asp Val Ile Gly Lys Gly Gly
                565                 570                 575
Val Val Ile Arg Glu Ile Thr Glu Ala Thr Asn Cys Ala Ile Asp Ile
            580                 585                 590
Ser Asp Asp Gly Thr Ile Lys Ile Ala Ala His Thr Thr Glu Glu Gly
        595                 600                 605
Glu Ala Ala Lys Arg Arg Ile Glu Glu Leu Thr Ala Glu Val Glu Leu
    610                 615                 620
Gly Lys Val Tyr Glu Gly Thr Val Val Lys Ile Thr Asp Phe Gly Ala
625                 630                 635                 640
Phe Val Gln Ile Leu Pro Asn Thr Gln Gly Leu Val His Ile Ser Gln
                645                 650                 655
```

Ile Ala Gln Glu Arg Val Glu Asn Val Arg Asp Tyr Leu Glu Gly
                660                 665                 670

Gln Val Ile Arg Val Lys Val Ile Glu Ile Asp Arg Gln Gly Arg Val
            675                 680                 685

Arg Leu Ser Met Lys Gln Ile Asp
    690                 695

<210> SEQ ID NO 4
<211> LENGTH: 437
<212> TYPE: PRT
<213> ORGANISM: Coxiella burnetii

<400> SEQUENCE: 4

Met Leu Gly Val Ala Glu Lys Cys Tyr Asp Leu Thr Ile Met Asn Ile
1               5                   10                  15

Leu Ile Ile Gly Asn Gly Gly Arg Glu His Ala Leu Ala Trp Lys Val
            20                  25                  30

Ala Gln Ser Pro Arg Val Glu Lys Ile Trp Val Ala Pro Gly Asn Ala
        35                  40                  45

Gly Thr Ala Arg Glu Leu Lys Thr Gln Asn Val Pro Ile Gly Val Thr
    50                  55                  60

Asp Ile Lys Ser Leu Ile Ala Phe Ala Lys Lys Asn Gln Ile Asn Leu
65                  70                  75                  80

Thr Leu Val Gly Pro Glu Ile Pro Leu Ala Ala Gly Ile Val Asp His
                85                  90                  95

Phe Gln Gln Glu Asn Leu Ile Val Phe Gly Pro Thr Gln Ala Ala Ala
            100                 105                 110

Gln Leu Glu Thr Ser Lys Ser Phe Cys Lys Thr Phe Met Arg Arg His
        115                 120                 125

Gly Ile Pro Thr Ala Arg Phe Glu Ala Phe Arg Asn Thr Ser Asp Ala
    130                 135                 140

Phe Ser Tyr Leu Glu Gln Gln Ser Phe Pro Ile Val Ile Lys Ala Ser
145                 150                 155                 160

Gly Leu Ala Ala Gly Lys Gly Val Val Ile Ala Gln Ser Leu Gln Glu
                165                 170                 175

Ala Lys Glu Thr Val Ile Ala Met Met Glu Glu Lys Gln Phe Gly Asn
            180                 185                 190

Ala Gly Ala Glu Ile Val Ile Glu Glu Phe Leu Ala Gly Glu Glu Leu
        195                 200                 205

Ser Phe Ile Ala Met Val Asp Gly Glu His Ile Leu Pro Leu Ala Gly
    210                 215                 220

Ser Gln Asp His Lys Arg Arg Asp Asp Gly Asp Arg Gly Pro Asn Thr
225                 230                 235                 240

Gly Gly Met Gly Ala Tyr Ser Pro Val Pro Gln Leu Ser Asp Ala Leu
                245                 250                 255

Gln Glu Lys Ile Met Thr Thr Ile Met Gln Pro Thr Val Thr Ala Leu
            260                 265                 270

Lys Ser Glu Gly Ile Leu Tyr Arg Gly Phe Leu Tyr Ala Gly Ile Met
        275                 280                 285

Ile Thr Leu Asn Asn Glu Pro Lys Val Leu Glu Phe Asn Val Arg Leu
    290                 295                 300

Gly Asp Pro Glu Thr Gln Pro Leu Met Met Arg Leu Arg Ser Asp Leu
305                 310                 315                 320

Ile Glu Leu Ile Leu Ser Ala Leu Ser Gly Arg Leu Asn Gln Thr Gln
                325                 330                 335

```
Ser Ala Trp Asp Ser Arg Ala Ala Leu Thr Val Val Leu Ala Ala Gly
                340                 345                 350

Gly Tyr Pro Ala His Tyr Gln Lys Gly Asp Ile Ile Gln Gly Leu Asp
            355                 360                 365

Gln Leu Ser Leu Pro Asp Val Lys Val Phe His Ala Gly Thr Gln Glu
370                 375                 380

Ile Asn His Gln Val Val Thr Asp Gly Gly Arg Val Leu Gly Val Thr
385                 390                 395                 400

Ala Leu Gly Lys Asp Leu Arg Glu Ala Gln Gln Lys Ala Tyr Gln Ala
                405                 410                 415

Ala Gln Leu Ile Thr Trp Pro Asn Cys Tyr Tyr Arg His Asp Ile Gly
            420                 425                 430

His Arg Ala Ile Ser
            435

<210> SEQ ID NO 5
<211> LENGTH: 506
<212> TYPE: PRT
<213> ORGANISM: Coxiella burnetii

<400> SEQUENCE: 5

Met Cys Gly Ile Val Gly Ile Ile Ala Asn Gly Ile Val Asn Gln Ala
1               5                   10                  15

Leu Tyr Asp Ala Leu Thr Ile Leu Gln His Arg Gly Gln Asp Ala Ala
                20                  25                  30

Gly Ile Met Thr Ser Asp Gly Glu Arg Val Phe Leu Arg Lys Ser Asn
            35                  40                  45

Gly Leu Val Arg Asp Ala Ile Arg Glu Pro His Met Leu His Leu Val
        50                  55                  60

Gly Asn Met Gly Ile Gly His Val Arg Tyr Pro Thr Ala Gly Ser Glu
65                  70                  75                  80

Ser Pro Ala Glu Ser Gln Pro Phe Tyr Val Asn Ser Pro Tyr Gly Leu
                85                  90                  95

Ser Leu Val His Asn Gly Asn Leu Val Asn Val Lys Glu Leu Thr Asn
                100                 105                 110

Asp Leu Ile Arg Ser Asp Leu Arg His Leu Asn Thr Thr Ser Asp Ser
            115                 120                 125

Glu Ile Leu Leu Asn Val Val Ala His Glu Leu Gln His Tyr Gly Gly
        130                 135                 140

Val Gln Leu Ser Pro Lys Gln Leu Phe Lys Ala Met Thr Lys Val Tyr
145                 150                 155                 160

Glu Arg Val Glu Gly Ala Phe Ala Ala Val Met Ile Ile Thr Gly Tyr
                165                 170                 175

Gly Val Ile Gly Phe Arg Asp Pro His Ala Ile Arg Pro Leu Val Tyr
            180                 185                 190

Gly Arg Arg Asp Asn Gly Asn Gly Pro Glu Tyr Met Leu Ala Ser Glu
        195                 200                 205

Ser Ile Ala Leu Asp Ala Leu Gly Phe Glu Leu Ile Asp Asp Val Gly
210                 215                 220

Pro Gly Glu Val Ile Tyr Phe Asp Arg Glu Gly Ser Val His Arg Glu
225                 230                 235                 240

Arg Cys Ala Lys Gln Val Ser His Ser Pro Cys Ile Phe Glu Tyr Ile
                245                 250                 255

Tyr Leu Ala Arg Pro Asp Ser Ile Ile Asp Gly Val Pro Val Tyr Gln
```

```
                    260                 265                 270
Ala Arg Ser Gly Met Gly Glu Ser Leu Ala Gln Lys Ile Leu Arg Glu
                275                 280                 285

Arg Pro Asp His Gly Ile Asp Val Val Ile Pro Ile Pro Asp Thr Ser
            290                 295                 300

Arg Asn Ala Ala Gln Ala Leu Ala Arg Ala Leu Asp Val Pro Tyr Ser
305                 310                 315                 320

Glu Gly Phe Val Lys Asn Arg Tyr Ile Gly Arg Thr Phe Ile Met Pro
                325                 330                 335

Gly Gln Ala Lys Arg Ser Ser Val Arg Leu Lys Leu Asn Ala Ile
            340                 345                 350

Lys Ala Glu Phe Ala Asn Lys Thr Val Leu Leu Val Asp Asp Ser Ile
            355                 360                 365

Val Arg Gly Thr Thr Ser Lys Glu Ile Ile Gln Met Ala Arg Asp Val
            370                 375                 380

Gly Ala Lys Lys Val Tyr Phe Ala Ser Ala Ala Pro Glu Val Arg Tyr
385                 390                 395                 400

Pro Asn Val Tyr Gly Ile Asp Met Pro Thr Ala Asp Glu Leu Ile Ala
                405                 410                 415

His Asn Lys Ser Thr Glu Glu Val Met His Ser Ile Gly Ala Asp Trp
                420                 425                 430

Leu Val Tyr Gln Asn Leu Glu Asp Val Tyr Gln Ala Ile Asn Asp Ala
            435                 440                 445

Met Gly Ser Arg Lys Pro Lys Ile Glu Arg Phe Glu Asp Ser Val Phe
        450                 455                 460

Thr Gly Asp Tyr Ile Ala Gly Asn Ile Thr Lys Glu Tyr Leu Ala Glu
465                 470                 475                 480

Leu Ala Glu Ser Arg Asn Asp Ala Ala Lys Met Lys Lys Arg Ala Leu
                485                 490                 495

Asn Glu Gln Glu Glu Ala Asn Gly Leu Leu
            500                 505

<210> SEQ ID NO 6
<211> LENGTH: 243
<212> TYPE: PRT
<213> ORGANISM: Coxiella burnetii

<400> SEQUENCE: 6

Met Thr Asn Gly Pro Gln Pro Leu Tyr Arg Arg Val Leu Leu Lys Met
1               5                   10                  15

Ser Gly Glu Ala Leu Met Gly Lys Gly Leu His Ala Ile Asp Pro Asn
            20                  25                  30

Val Leu Asp Arg Met Ala Lys Asp Val Thr Gln Val Tyr Gln Leu Gly
        35                  40                  45

Val Gln Ile Ala Ile Val Ile Gly Gly Gly Asn Phe Phe Arg Gly Ala
    50                  55                  60

Ala Leu Gln Ala Ala Gly Ile Asn Arg Ile Thr Gly Asp Tyr Met Gly
65                  70                  75                  80

Met Leu Ala Thr Leu Met Asn Ala Leu Ala Leu Arg Asp Ala Phe Glu
                85                  90                  95

Arg Ser Asn Leu Pro Val Arg Ile Leu Ser Ala Ile Pro Met Thr Gly
            100                 105                 110

Val Ala Asp Ala Phe His Arg Arg Lys Ala Ile His His Leu Gln Gln
        115                 120                 125
```

```
Gly Arg Val Val Ile Phe Ala Ala Gly Thr Gly Asn Pro Leu Val Thr
            130                 135                 140

Thr Asp Ser Ala Ala Ser Leu Arg Gly Ile Glu Ile Asn Ala Asp Val
145                 150                 155                 160

Val Leu Lys Ala Thr Asn Val Asp Gly Val Tyr Ser Asp Asp Pro Ala
                165                 170                 175

Lys Asn Pro Gln Ala Lys Leu Tyr Lys His Leu Ser Tyr Gln Glu Ala
            180                 185                 190

Leu Lys Lys Glu Leu Ala Val Met Asp Leu Ala Ala Phe Cys Gln Cys
        195                 200                 205

Arg Asp Tyr Asn Met Pro Leu Arg Val Phe Asn Ile Asn Lys Pro Gly
    210                 215                 220

Ala Leu Leu Ser Val Ile Met Asn Gln Glu Glu Gly Thr Leu Val Asp
225                 230                 235                 240

Gln Gly Gln
```

<210> SEQ ID NO 7
<211> LENGTH: 197
<212> TYPE: PRT
<213> ORGANISM: Coxiella burnetii

<400> SEQUENCE: 7

```
Met Pro Phe Ile Leu Val Leu Tyr Tyr Ser Arg Tyr Gly Ala Thr Ala
1               5                   10                  15

Glu Met Ala Glu Gln Val Ala Arg Gly Val Glu Arg Val Asn Lys Ile
            20                  25                  30

Glu Ala Arg Ile Arg Thr Val Pro Ser Val Ser Pro Lys Thr Glu Ala
        35                  40                  45

Thr Glu Pro Asp Val Pro Lys Asp Gly Pro Pro Tyr Val Thr His Asp
    50                  55                  60

Asp Leu Lys Asn Cys Val Gly Leu Ala Leu Gly Ser Pro Thr Arg Phe
65                  70                  75                  80

Gly Asn Met Ala Ala Pro Leu Lys Tyr Phe Leu Asp Thr Thr Ser Ala
                85                  90                  95

Leu Trp Gln Ser Gly Ser Leu Ile Gly Lys Pro Ala Gly Phe Phe Thr
            100                 105                 110

Ser Thr Ala Ser Leu His Gly Gly Gln Glu Thr Thr Leu Leu Ser Met
        115                 120                 125

Met Met Pro Leu Ile His His Gly Ala Ile Ile Val Gly Val Pro Tyr
    130                 135                 140

Ser Glu Thr Glu Leu Phe Thr Thr Thr Ala Gly Gly Thr Pro Tyr Gly
145                 150                 155                 160

Pro Ser His Met Ala Gly Ala Asp Ser Asn Trp Pro Leu Thr Gln Thr
                165                 170                 175

Glu Lys Asn Leu Cys Gln Ala Leu Gly Lys Arg Leu Ala Glu Ile Ser
            180                 185                 190

Leu Lys Leu Lys Ala
        195
```

<210> SEQ ID NO 8
<211> LENGTH: 477
<212> TYPE: PRT
<213> ORGANISM: Coxiella burnetii

<400> SEQUENCE: 8

Met Glu Trp Glu Pro Val Ile Gly Leu Glu Val His Val Gln Leu Arg

-continued

```
  1               5              10              15
Thr Gln Ser Lys Ile Phe Ser Gly Ala Ala Thr Ala Tyr Gly Ala Glu
             20              25              30

Pro Asn Thr Gln Ala Cys Ala Ile Asp Leu Gly Leu Pro Gly Val Leu
             35              40              45

Pro Val Leu Asn Lys Glu Ala Val Lys Leu Ala Val Cys Phe Gly Leu
 50              55              60

Ser Val Asn Ala Ser Ile Pro Pro Tyr Ser Ile Phe Ala Arg Lys Asn
 65              70              75              80

Tyr Phe Tyr Pro Asp Leu Pro Lys Gly Tyr Gln Ile Ser Gln Tyr Asn
             85              90              95

Phe Pro Ile Val Gln Asn Gly His Leu Asp Ile Glu Asn Glu Asp Gly
            100             105             110

Thr Thr Lys Arg Ile Gly Ile Thr Arg Ala His Leu Glu Glu Asp Ala
            115             120             125

Gly Lys Ser Phe His Glu Gly Met Gln Gly Tyr Ser Gly Ile Asp Phe
            130             135             140

Asn Arg Ala Gly Thr Pro Leu Leu Glu Ile Val Ser Glu Pro Asp Ile
145             150             155             160

Arg Ser Ala Gln Glu Ala Val Ala Tyr Leu Lys Ala Leu His Ser Leu
            165             170             175

Val Arg Tyr Ile Gly Val Ser Asp Ala Asn Met Gln Glu Gly Ala Phe
            180             185             190

Arg Cys Asp Val Asn Ile Ser Leu Arg Pro Lys Ser Glu Glu Lys Phe
            195             200             205

Gly Thr Arg Ala Glu Ile Lys Asn Val Asn Ser Phe Arg Phe Val Glu
210             215             220

Arg Ala Ile Leu Phe Glu Ile Asn Arg Gln Lys Glu Ile Leu Glu Asn
225             230             235             240

Gly Gly Thr Ile Val Gln Glu Thr Arg Leu Tyr Asp Ala Val Gln Asp
            245             250             255

Glu Thr Arg Ser Met Arg Thr Lys Glu Glu Ala His Asp Tyr Arg Tyr
            260             265             270

Phe Pro Asp Pro Asp Leu Leu Pro Val Glu Ile Gly Pro Glu Phe Ile
            275             280             285

Glu Ala Val Lys Asn Gln Leu Pro Glu Leu Pro Trp Glu Lys Arg Lys
            290             295             300

Arg Phe Ala Ala Ser Tyr Gln Leu Ser Asn Tyr Asp Val Lys Leu Leu
305             310             315             320

Thr Thr Gln Ile Glu Ile Ala Asn Tyr Phe Glu Thr Val Leu Lys Ile
            325             330             335

Asp Lys Thr Ile Pro Pro Lys Leu Ala Ala Asn Trp Ile Asn Gly Asp
            340             345             350

Leu Ala Ala Ala Leu Asn Lys Asn Asn Leu Ser Ile Thr Gln Ser Pro
            355             360             365

Ile Asn Ala Glu Gln Leu Ala Gly Leu Leu His Arg Ile Ala Asp Asn
            370             375             380

Thr Leu Ser Gly Ser Met Gly Lys Gln Val Phe Glu Thr Met Trp Gly
385             390             395             400

Gly Glu Gly Asp Ala Asp Thr Ile Ile Glu Arg His Gly Leu Lys Gln
            405             410             415

Ile Thr Asp Thr Glu Ala Leu Glu Lys Ile Ile Asp Glu Val Ile Glu
            420             425             430
```

Asn Asn Pro Thr Gln Val Glu Gln Tyr Arg Ser Gly Lys Asp Lys Leu
            435                 440                 445

Ile Ala Phe Phe Val Gly Gln Val Met Lys Ala Thr Lys Gly Lys Ala
450                 455                 460

Asn Pro Gln Gln Val Asn Glu Leu Phe Lys Lys Lys Leu
465                 470                 475

<210> SEQ ID NO 9
<211> LENGTH: 423
<212> TYPE: PRT
<213> ORGANISM: Coxiella burnetii

<400> SEQUENCE: 9

Met Thr Phe Gln Lys Pro Cys Phe Pro His Cys Leu Pro Val Tyr Phe
1               5                   10                  15

Pro Leu Leu Tyr His Ser Asn His Lys Glu Leu Arg Lys Met Asn Asp
            20                  25                  30

Val Leu Ser Val Arg Ala Gln Gln Leu Glu Pro Ser Val Thr Leu Ala
        35                  40                  45

Val Ser Asp Leu Ala Arg Glu Leu Leu Asn Lys Gly His Asp Val Ile
    50                  55                  60

Ser Leu Ser Ala Gly Glu Pro Asp Phe Asp Thr Pro Asp Phe Ile Lys
65                  70                  75                  80

Gln Ser Ala Ile Lys Ala Ile Gln Glu Gly Phe Thr Lys Tyr Thr Asn
                85                  90                  95

Val Asp Gly Thr Pro Ala Leu Lys Ala Ala Ile Val His Lys Leu Lys
            100                 105                 110

Arg Asp Asn His Leu Asn Tyr Glu Pro Ser Glu Ile Leu Val Ser Gly
        115                 120                 125

Gly Ala Lys Gln Ser Ile Tyr Asn Val Leu Met Gly Thr Leu Asn Ala
130                 135                 140

Gly Asp Glu Ala Ile Ile Pro Ala Pro Tyr Trp Val Ser Tyr Pro Pro
145                 150                 155                 160

Met Val Gln Leu Ala Glu Ala Lys Pro Ile Ile Ile Ser Ala Thr Ile
                165                 170                 175

Asp Gln Asn Phe Lys Leu Thr Pro Gly Gln Leu Ser Gln Ala Ile Thr
            180                 185                 190

Pro Gln Ser Arg Leu Leu Ile Leu Asn Ser Pro Asn Asn Pro Ser Gly
        195                 200                 205

Val Ala Tyr Thr Glu Ser Glu Leu Lys Ala Leu Ala Asp Val Leu Met
    210                 215                 220

Glu His Pro Gln Ile Leu Ile Leu Ser Asp Glu Ile Tyr Glu Tyr Ile
225                 230                 235                 240

Leu Trp Gly Gln Asn Arg Phe Val Asn Ile Leu Asn Val Cys Pro Glu
                245                 250                 255

Leu Arg Asp Arg Thr Ile Ile Ile Asn Gly Ala Ser Lys Ala Tyr Ala
            260                 265                 270

Met Thr Gly Trp Arg Ile Gly Tyr Ala Ala Gly Pro Lys Ser Ile Ile
        275                 280                 285

Gln Ala Met Lys Lys Ile Gln Ser Gln Ser Thr Ser Ser Pro Asn Ser
    290                 295                 300

Ile Ala Gln Val Ala Ala Thr Thr Ala Leu Gly Ala Gln Arg Gly Asp
305                 310                 315                 320

Phe Ala Tyr Met Tyr Glu Ala Tyr Lys Thr Arg His Asp Leu Val Leu

```
              325                 330                 335
Lys Ala Leu Asn Gln Met Lys Gly Val His Cys Ile Pro Ala Asp Gly
                340                 345                 350

Ala Phe Tyr Leu Phe Pro Asp Val Ser Ala Ala Ile Gln Gln Leu Gly
                355                 360                 365

Leu Glu Asp Asp Ile Lys Leu Gly Thr Tyr Leu Leu Asp Lys Thr Lys
                370                 375                 380

Val Ala Val Val Pro Gly Ser Ala Phe Gly Ser Pro Gly His Val Arg
385                 390                 395                 400

Leu Ser Cys Ala Thr Ser Thr Glu Lys Leu Gln Glu Ala Leu Glu Arg
                405                 410                 415

Leu Ala Ser Val Leu Asp Tyr
                420

<210> SEQ ID NO 10
<211> LENGTH: 406
<212> TYPE: PRT
<213> ORGANISM: Coxiella burnetii

<400> SEQUENCE: 10

Met Ile Val Gln Pro Lys Val Arg Gly Phe Ile Cys Thr Thr Ala His
1               5                   10                  15

Pro Glu Gly Cys Ala Arg His Val Gly Glu Trp Ile Asn Tyr Ala Lys
                20                  25                  30

Gln Glu Pro Ser Leu Thr Gly Gly Pro Gln Lys Val Leu Ile Ile Gly
                35                  40                  45

Ala Ser Thr Gly Phe Gly Leu Ala Ser Arg Ile Val Ala Ala Phe Gly
        50                  55                  60

Ala Gly Ala Lys Thr Ile Gly Val Phe Phe Glu Arg Pro Ala Ser Gly
65              70                  75                  80

Lys Arg Thr Ala Ser Pro Gly Trp Tyr Asn Thr Ala Ala Phe Glu Lys
                85                  90                  95

Thr Ala Leu Ala Ala Gly Leu Tyr Ala Lys Ser Ile Asn Gly Asp Ala
                100                 105                 110

Phe Ser Asp Glu Ile Lys Gln Gln Thr Ile Asp Leu Ile Gln Lys Asp
                115                 120                 125

Trp Gln Gly Gly Val Asp Leu Val Ile Tyr Ser Ile Ala Ser Pro Arg
                130                 135                 140

Arg Val His Pro Arg Thr Gly Glu Ile Phe Asn Ser Val Leu Lys Pro
145                 150                 155                 160

Ile Gly Gln Thr Tyr His Asn Lys Thr Val Asp Val Met Thr Gly Glu
                165                 170                 175

Val Ser Pro Val Ser Ile Glu Pro Ala Thr Glu Lys Glu Ile Arg Asp
                180                 185                 190

Thr Glu Ala Val Met Gly Gly Asp Asp Trp Ala Leu Trp Ile Asn Ala
                195                 200                 205

Leu Phe Lys Tyr Asn Cys Leu Ala Glu Gly Val Lys Thr Val Ala Phe
                210                 215                 220

Thr Tyr Ile Gly Pro Glu Leu Thr His Ala Val Tyr Arg Asn Gly Thr
225                 230                 235                 240

Ile Gly Arg Ala Lys Leu His Leu Glu Lys Thr Ala Arg Glu Leu Asp
                245                 250                 255

Thr Gln Leu Glu Ser Ala Leu Ser Gly Gln Ala Leu Ile Ser Val Asn
                260                 265                 270
```

```
Lys Ala Leu Val Thr Gln Ala Ser Ala Ala Ile Pro Val Pro Leu
            275                 280                 285
Tyr Ile Ser Leu Leu Tyr Lys Ile Met Lys Glu Lys Asn Ile His Glu
        290                 295                 300
Gly Cys Ile Glu Gln Met Trp Arg Leu Phe Lys Glu Arg Leu Tyr Ser
305                 310                 315                 320
Asn Gln Asn Ile Pro Thr Asp Ser Glu Gly Arg Ile Arg Ile Asp Asp
                325                 330                 335
Trp Glu Met Arg Glu Asp Val Gln Ala Glu Ile Lys Arg Leu Trp Glu
            340                 345                 350
Ser Ile Asn Thr Gly Asn Val Glu Thr Val Ser Asp Ile Ala Gly Tyr
        355                 360                 365
Arg Glu Asp Phe Tyr Lys Leu Phe Gly Phe Gly Leu Asn Gly Ile Asp
370                 375                 380
Tyr Glu Arg Gly Val Glu Ile Glu Lys Ala Ile Pro Ser Ile Thr Val
385                 390                 395                 400
Thr Pro Glu Asn Pro Glu
                405

<210> SEQ ID NO 11
<211> LENGTH: 1046
<212> TYPE: PRT
<213> ORGANISM: Coxiella burnetii

<400> SEQUENCE: 11

Met Thr Asp Thr His Leu Leu Phe Phe Glu Lys Ala Ile Ala Gln Asn
1               5                   10                  15
Ala Ile Arg Pro Ser Leu Asn Lys Thr Tyr Arg Met Asp Glu Thr Thr
            20                  25                  30
Cys Val Asn His Leu Leu Lys Thr Ile Ala Phe Thr Pro Arg Leu Glu
        35                  40                  45
Ala Ala Val Ser Arg Leu Ala Lys Glu Leu Val Thr Ala Val Arg Glu
    50                  55                  60
Gln Glu Ser Glu Lys Gly Gly Ile Gly Phe Met Met Gln Tyr Asp
65                  70                  75                  80
Leu Ser Thr Glu Glu Gly Ile Leu Leu Met Cys Leu Ala Glu Ala Leu
                85                  90                  95
Leu Arg Val Pro Asp Lys Glu Thr Glu Asn Leu Leu Ile Arg Asp Lys
            100                 105                 110
Leu Thr Ser Ala Glu Trp Asn Lys Tyr Val Gly Ala Ser Glu Ser Ser
        115                 120                 125
Phe Val Asn Phe Ala Thr Trp Gly Leu Ala Leu Ser Gly Lys Ile Leu
    130                 135                 140
Lys Lys Glu Lys Asp Gly Gln Phe Lys Asn Val Trp Arg Asn Leu Val
145                 150                 155                 160
Arg Arg Ser Gly Glu Pro Val Ile Arg Lys Ala Val Arg Glu Ala Met
                165                 170                 175
Lys Leu Met Ser Glu His Phe Val Leu Gly Arg Thr Ile Glu Glu Ala
            180                 185                 190
Val Lys Arg Ser Gln Ser Ala Ile Lys Glu Gly Phe Arg His Ser Tyr
        195                 200                 205
Asp Met Leu Gly Glu Val Ala Arg Thr Gln Glu Asp Ala Asp Arg Tyr
    210                 215                 220
Tyr Asp Ser Tyr His Arg Ala Ile Ser Val Leu Gly Lys Ser His Pro
225                 230                 235                 240
```

-continued

```
Thr Lys Ser Val His Glu Ala Pro Gly Ile Ser Val Lys Leu Ser Ala
            245                 250                 255

Leu Tyr Pro Arg Tyr Asp Phe Lys Lys Arg Glu Leu Ala Val Pro Phe
        260                 265                 270

Leu Ile Glu Arg Val Lys Glu Leu Ala Leu His Ala Lys Glu Gln Lys
    275                 280                 285

Ile Gly Met Thr Ile Asp Ala Glu Glu Ala Asp Arg Leu Asp Ile Ser
290                 295                 300

Leu Asp Ile Phe Glu Ala Leu Phe Thr Asp Glu Ala Phe Glu Asn Trp
305                 310                 315                 320

Gln Gly Leu Gly Leu Ala Val Gln Ala Tyr Gln Lys Arg Ala Phe Tyr
                325                 330                 335

Leu Ile Asp Trp Leu Ile Asp Leu Ala Gln Arg Gln Lys Arg Arg Ile
            340                 345                 350

Pro Val Arg Leu Val Lys Gly Ala Tyr Trp Asp Thr Glu Ile Lys Leu
        355                 360                 365

Ala Gln Met Glu Gly Leu Ser Gly Tyr Pro Val Phe Thr Arg Lys Val
    370                 375                 380

Asn Thr Asp Ile Ser Tyr Ile Ala Cys Ala Gln Lys Met Leu Asn Ala
385                 390                 395                 400

Gln Asp Ala Ile Tyr Pro Gln Phe Ala Thr His Asn Ala Tyr Ser Val
                405                 410                 415

Ala Ala Ile Leu Asn Leu Met Asp His His Tyr Asp Asn Tyr Glu Phe
            420                 425                 430

Glu Phe Gln Gln Leu Gln Gly Met Gly Lys Ala Leu His His Tyr Ile
        435                 440                 445

Val Thr Lys Leu Lys Leu Pro Cys Arg Val Tyr Ala Pro Val Gly Tyr
    450                 455                 460

His Glu Asp Leu Leu Pro Tyr Leu Val Arg Arg Leu Leu Glu Asn Gly
465                 470                 475                 480

Ala Asn Ser Ser Phe Val Asn Arg Ile Ala Asp Lys Thr Val Pro Val
                485                 490                 495

Asp Gln Leu Ile Glu Ser Pro Val Lys Lys Ile Glu Ala Phe Gly Asp
            500                 505                 510

Ile Pro Asn Pro Lys Ile Pro Leu Pro Lys Gly Ile Phe Lys Thr Arg
        515                 520                 525

Thr Asn Ser Ser Gly Ile Asp Leu Ser Asn Phe Ala Glu Leu Met Pro
    530                 535                 540

Leu Asn Glu Glu Ile His His Ala Leu Glu Lys Glu Trp Glu Ala Ala
545                 550                 555                 560

Pro Phe Leu Gln Glu Ile Lys Asn Gly Lys Pro Val Phe Asp Pro Thr
                565                 570                 575

Asp Asn Arg Arg Gln Ile Gly Val Ile Glu Leu Ala Asn Glu Ser Asp
            580                 585                 590

Val Glu Lys Ala Ile Gln Ala Gly His Ser Ala Phe Pro Asn Trp Asp
        595                 600                 605

Gln Lys Gly Ile Ser Ala Arg Ala Thr Ile Leu Arg Lys Met Ala Asp
    610                 615                 620

Leu Leu Glu Lys His Lys Ala Glu Leu Met Ala Val Val Arg Glu
625                 630                 635                 640

Gly Gly Arg Thr Leu Gln Asn Ala Leu Ser Glu Val Arg Glu Ala Thr
                645                 650                 655
```

Asp Phe Cys Arg Tyr Tyr Ala Glu Gln Ala Glu Gln His Leu Ser Asp
              660                 665                 670

Lys Ala Leu Pro Gly Tyr Thr Gly Glu Ser Asn Thr Leu Arg Met Asn
        675                 680                 685

Gly Arg Gly Ile Ile Leu Cys Ile Ser Pro Trp Asn Phe Pro Ile Ala
    690                 695                 700

Ile Phe Thr Gly Gln Ile Ala Ala Leu Val Thr Gly Asn Ala Val
705                 710                 715                 720

Ile Ala Lys Pro Ser Gly Gln Thr Pro Leu Thr Gly Ala Leu Val Thr
                725                 730                 735

Arg Leu Phe His Glu Ala Gly Val Pro Lys Glu Ile Leu Gln Leu Met
            740                 745                 750

Pro Gly Ser Gly Lys Thr Val Gly Gln Ala Leu Ile Glu Asp Thr Lys
        755                 760                 765

Ile Ser Gly Val Ile Phe Thr Gly Ser Asp Ala Thr Ala Arg His Ile
    770                 775                 780

Gln Lys Thr Leu Ala Ala Arg Pro Gly Pro Ile Val Pro Phe Val Ala
785                 790                 795                 800

Glu Thr Ser Gly Ile Asn Ala Met Ile Ala Asp Ser Thr Ala Leu Pro
                805                 810                 815

Glu Gln Leu Val Asn Asp Val Ile Val Ser Ala Phe Asp Ser Ala Gly
            820                 825                 830

Gln Arg Cys Ser Ala Leu Arg Ile Leu Tyr Ile Gln Glu Asp Ile Ala
        835                 840                 845

Asp Asp Val Ile Lys Met Leu Lys Gly Ala Met Ala Glu Ile Lys Met
850                 855                 860

Gly Asp Pro Leu Leu Leu Ser Thr Asp Val Gly Pro Val Ile Asp Ala
865                 870                 875                 880

Asn Ala Gln Lys Thr Leu Gln Lys His Gln Ala Leu Met Gln Lys Glu
                885                 890                 895

Ala Lys Leu Ile Tyr Lys Val Asp Leu Pro Arg Glu Thr Asp Phe Gly
            900                 905                 910

Thr Phe Val Ala Pro Gln Ala Tyr Glu Leu Pro Asn Leu Gly Leu Ile
        915                 920                 925

Thr Glu Glu Val Phe Gly Pro Ile Leu His Val Ile Arg Tyr Lys Arg
    930                 935                 940

Glu Asn Leu Asn Lys Val Ile Glu Glu Ile Asn Gly Leu Gly Tyr Gly
945                 950                 955                 960

Leu Thr Phe Gly Ile Gln Ser Arg Ile Asp Glu Thr Val Asp Tyr Ile
                965                 970                 975

Gln Gln Arg Ile Asn Ala Gly Asn Ile Tyr Val Asn Arg Asn Thr Val
            980                 985                 990

Gly Ala Val Val Gly Val Gln Pro Phe Gly Gly Ser Trp Leu Ser Gly
        995                 1000                1005

Thr Gly Pro Lys Ala Gly Gly Pro His Tyr Leu Pro Arg Phe Cys
    1010                1015                1020

Ile Glu Ser Thr Leu Thr Ile Asn Thr Thr Ala Ala Gly Gly Asn
    1025                1030                1035

Ala Ser Leu Met Ala Met Glu Asp
    1040                1045

<210> SEQ ID NO 12
<211> LENGTH: 394
<212> TYPE: PRT

<213> ORGANISM: Coxiella burnetii

<400> SEQUENCE: 12

Met Glu Asn Pro Ile Val Ile Val Ser Ala Ala Arg Thr Pro Met Gly
1               5                   10                  15

His Tyr Gly Gly Tyr Phe Lys Glu Met Pro Ala Pro Glu Leu Gly Ala
            20                  25                  30

Ala Val Ile Lys Ala Val Val Glu Arg Ala Gly Leu Gln Pro Ala Glu
        35                  40                  45

Ile Asp Glu Val Ile Met Gly Cys Val Leu Pro Ala Gly Gln Gly Gln
    50                  55                  60

Ala Pro Ala Arg Gln Ala Ala Leu Lys Ala Gly Leu Pro Val Ser Thr
65                  70                  75                  80

Pro Cys Thr Thr Ile Asn Lys Met Cys Gly Ser Gly Met Lys Ala Ile
                85                  90                  95

Met Leu Ala His Asp Glu Ile Leu Ala Asp Ser Tyr Pro His Ile Ile
            100                 105                 110

Ala Gly Gly Met Glu Asn Met Ser Arg Ala Pro Tyr Leu Met Met Lys
        115                 120                 125

Ala Arg Phe Gly Tyr Arg Leu Gly His Asp Arg Ile Tyr Asp His Met
    130                 135                 140

Met Leu Asp Gly Leu Glu Asp Ala Tyr Asp Lys Gly Lys Ala Met Gly
145                 150                 155                 160

Val Phe Ala Glu Lys Cys Val Asp Lys Tyr Gln Phe Thr Arg Glu Ala
                165                 170                 175

Leu Asp Lys Phe Ala Ile Glu Ser Leu Leu Arg Ala Lys Lys Ala Asn
            180                 185                 190

Glu Asn Gly Ser Phe Ala Pro Glu Ile Val Pro Ile Thr Ile Thr His
        195                 200                 205

Gln Arg Glu Thr Leu Thr Val Asp His Asp Glu Asn Ala Met Lys Ala
    210                 215                 220

Asn Pro Glu Lys Ile Pro Gln Leu Lys Pro Val Phe Lys Ala Asp Gly
225                 230                 235                 240

Ala Val Thr Ala Ala Asn Ser Ser Ser Ile Ser Asp Gly Ala Ala Ala
                245                 250                 255

Val Thr Leu Met Arg Leu Ser Glu Ala Lys Arg Leu Asn Ile Gln Pro
            260                 265                 270

Leu Ala Lys Ile Ile Gly His Phe Thr Tyr Ala Glu Asp Pro Ser Trp
        275                 280                 285

Phe Thr Thr Ala Pro Ile Gly Ala Ile Arg Gly Leu Leu Lys Lys Ile
    290                 295                 300

Ser Trp Lys Lys Glu Ala Val Asp Leu Phe Glu Ile Asn Glu Ala Phe
305                 310                 315                 320

Ala Ala Val Thr Met Ala Ala Met Lys Glu Ile Gly Leu Ala His Asn
                325                 330                 335

Lys Val Asn Ile His Gly Gly Ala Cys Ala Leu Gly His Pro Ile Gly
            340                 345                 350

Ala Ser Gly Ala Arg Ile Leu Val Thr Leu Leu Tyr Ala Leu Gln Lys
        355                 360                 365

Asn Asn Leu Gln Arg Gly Ile Ala Ser Leu Cys Ile Gly Gly Gly Glu
    370                 375                 380

Ala Thr Ala Ile Ala Ile Glu Arg Gly Phe
385                 390

<210> SEQ ID NO 13
<211> LENGTH: 488
<212> TYPE: PRT
<213> ORGANISM: Coxiella burnetii

<400> SEQUENCE: 13

```
Met Thr Val Leu Tyr Gln Asn Arg Gln Ile Arg Glu Leu Glu Arg Leu
1               5                   10                  15

Ala Val Glu Ser Gly Ile Ser Glu Tyr Glu Leu Met Cys Arg Ala Gly
            20                  25                  30

Glu Ala Ala Phe Lys Ala Leu Leu Ala Arg Trp Pro Glu Ala Gln Glu
        35                  40                  45

Ile Thr Val Cys Cys Gly Lys Gly Asn Asn Gly Gly Asp Gly Leu Val
    50                  55                  60

Leu Ala Arg Leu Ala Tyr Glu Asn Gly Leu Lys Val Thr Val Tyr Leu
65                  70                  75                  80

Ala Gly Gln Arg His Gln Leu Lys Gly Ala Ala Gln Ala Ala Asn
                85                  90                  95

Ala Cys Glu Ala Ser Asn Leu Pro Ile Leu Pro Phe Pro Glu Pro Leu
            100                 105                 110

Leu Phe Lys Gly Glu Val Ile Val Asp Ala Leu Leu Gly Ser Gly Leu
        115                 120                 125

Ser Gly Glu Val Lys Ala Pro Tyr Asp His Leu Ile Ala Ala Ile Asn
130                 135                 140

Gln Ala Gly Gln Tyr Val Leu Ala Leu Asp Val Pro Ser Gly Ile Asn
145                 150                 155                 160

Val Asp Ser Gly Glu Val Gln Gly Thr Ala Val Lys Ala Asn Leu Thr
                165                 170                 175

Val Thr Phe Ile Ala Pro Lys Arg Gly Leu Tyr Thr Asp Lys Ala Pro
            180                 185                 190

Ala Tyr Cys Gly Glu Leu Ile Val Asp Arg Leu Gly Leu Ser Glu Ser
        195                 200                 205

Phe Phe Arg Ala Val Phe Thr Asp Thr Arg Leu Leu Glu Trp Lys Gly
    210                 215                 220

Val Phe Pro Leu Leu Pro Lys Arg Ala Arg Asp Ala His Lys Gly Ser
225                 230                 235                 240

Tyr Gly His Val Leu Val Ile Gly Gly Asp Tyr Gly Met Gly Gly Ala
                245                 250                 255

Val Arg Met Ala Ala Glu Ala Ala Ala Arg Val Gly Ala Gly Leu Val
            260                 265                 270

Thr Val Ala Thr Arg Pro Glu His Val Pro Ile Val Ser Gly Pro Arg
        275                 280                 285

Pro Glu Leu Met Cys His Gln Val Ala Ala Ala Asp Asp Leu Lys Pro
    290                 295                 300

Leu Leu Thr Ala Ala Thr Val Val Val Ile Gly Pro Gly Leu Gly Lys
305                 310                 315                 320

Ser Asp Trp Ala Lys Ser Leu Leu Asn Lys Val Leu Glu Thr Asp Leu
                325                 330                 335

Pro Lys Val Leu Asp Ala Asp Ser Leu Asn Leu Ala Glu Ser Pro
            340                 345                 350

Ser Gln Arg Glu Asp Trp Ile Leu Thr Pro His Pro Gly Glu Ala Ser
        355                 360                 365

Arg Leu Leu Gly Ile Ser Cys Asn Glu Val Gln Arg Asp Arg Phe Gln
    370                 375                 380
```

```
Ala Ile Asn Asp Leu Gln Glu Lys Tyr Gln Gly Val Leu Val Leu Lys
385                 390                 395                 400

Gly Val Gly Thr Leu Ile Lys Asp Glu Ser Gln Ala Tyr Tyr Val Cys
                405                 410                 415

Pro Ala Gly Asn Pro Gly Met Ala Thr Gly Gly Met Gly Asp Ile Leu
            420                 425                 430

Ser Gly Ile Ile Gly Gly Leu Val Ala Gln Arg Leu Ser Leu Ala Ser
        435                 440                 445

Ala Ala Gln Ala Gly Val Phe Ile His Ser Met Ala Ala Asp Arg Ala
    450                 455                 460

Ala Glu Glu Gly Gly Glu Arg Gly Leu Leu Ala Thr Asp Leu Phe Pro
465                 470                 475                 480

His Leu Arg Val Leu Val Asn Pro
                485

<210> SEQ ID NO 14
<211> LENGTH: 369
<212> TYPE: PRT
<213> ORGANISM: Coxiella burnetii

<400> SEQUENCE: 14

Met Leu Ile Gly Val Pro Lys Glu Val Lys Ile Glu Glu Tyr Arg Val
1               5                   10                  15

Gly Leu Thr Pro Tyr Ser Val Arg Glu Leu Val Leu His Gly His Gln
            20                  25                  30

Val Ile Met Glu Arg Asp Ala Gly Asn Ala Ile Asn Phe Thr Asp Glu
        35                  40                  45

Ala Tyr Leu Ala Ala Gly Ala Lys Ile Val Asp Thr Pro Val Glu Val
    50                  55                  60

Tyr Gln Ala Glu Met Ile Val Lys Val Lys Glu Pro Gln Ser Ser Glu
65                  70                  75                  80

Tyr Ala Leu Ile Arg Glu Gly Gln Ile Leu Phe Thr Tyr Leu His Leu
                85                  90                  95

Ala Pro Asp Pro Gln Gln Ala Gln Ala Leu Ile Lys Ser Gly Cys Ile
            100                 105                 110

Ala Ile Ala Tyr Glu Thr Val Thr Asp Asn Glu Gly Gly Leu Pro Leu
        115                 120                 125

Leu Ser Pro Met Ser Gln Val Ala Gly Arg Leu Ala Ile Gln Ala Gly
    130                 135                 140

Ala His Cys Leu Glu Lys Pro Glu Gly Gly Ser Gly Ile Leu Leu Gly
145                 150                 155                 160

Gly Val Pro Gly Val Tyr Ala Gly Lys Val Thr Val Ile Gly Gly Gly
                165                 170                 175

Val Val Gly Ser Asn Ala Val Arg Met Ala Met Gly Lys Lys Ala Gln
            180                 185                 190

Val Thr Val Leu Asp Lys Ser Leu Arg Arg Leu Gln Glu Leu Asp Phe
        195                 200                 205

Gln Phe Gly Gly Arg Leu Asn Thr Ala Tyr Ser Thr Glu Ser Ser Ile
    210                 215                 220

Glu His Tyr Val Ile Asp Ala Asp Leu Val Gly Ala Val Leu Val
225                 230                 235                 240

Pro Gly His Ser Ala Pro Lys Leu Val Gly Gln Asp Val Leu Lys Lys
                245                 250                 255

Met Arg Pro Gly Ser Val Met Val Asp Val Ala Ile Asp Gln Gly Gly
```

```
              260                 265                 270
Cys Phe Glu Thr Ser Lys Pro Thr Thr His Lys Lys Pro Thr Tyr Val
            275                 280                 285
Ile Asp Gly Ile Val His Tyr Cys Val Ala Asn Met Pro Gly Ala Val
            290                 295                 300
Pro Arg Thr Ser Thr Leu Ala Leu Asn Asn Ala Thr Leu Pro Tyr Val
305                 310                 315                 320
Ile Ala Leu Ala Asp Lys Gly Tyr Arg Gln Ala Phe Leu Asp Asp Pro
                325                 330                 335
His Phe Leu Asn Gly Leu Asn Val Tyr Cys Gly Gln Ile Thr His Lys
                340                 345                 350
Gly Val Ala Gln Gly Leu Gln Gln Glu Phe Asn Pro Pro Leu Ala Leu
                355                 360                 365
Leu

<210> SEQ ID NO 15
<211> LENGTH: 320
<212> TYPE: PRT
<213> ORGANISM: Coxiella burnetii

<400> SEQUENCE: 15

Met Asn Lys Pro Gln His His Ser Leu Ile Ile Leu Gly Ser Gly Pro
1               5                   10                  15
Ala Gly Tyr Thr Ala Ala Ile Tyr Ala Ala Arg Ala Asn Leu Lys Pro
            20                  25                  30
Ile Met Ile Thr Gly Met Glu Gln Gly Gly Gln Leu Met Thr Thr Thr
        35                  40                  45
Asp Val Asp Asn Trp Pro Gly Glu Ala Pro Gly Leu Gln Gly Pro Gln
50                  55                  60
Leu Met Glu Arg Met Gln Lys His Ala Glu Arg Leu Asp Thr Gln Phe
65                  70                  75                  80
Ile Phe Asp His Ile Asn Glu Ala Asp Leu Asn Gln Arg Pro Phe Leu
                85                  90                  95
Leu Lys Gly Asp Asn Ala Thr Tyr Ser Cys Asp Ala Leu Ile Ile Ala
            100                 105                 110
Thr Gly Ala Ser Ala Arg Tyr Leu Gly Leu Pro Ser Glu Lys Ala Tyr
        115                 120                 125
Met Gly Lys Gly Val Ser Ala Cys Ala Thr Cys Asp Gly Phe Phe Tyr
    130                 135                 140
Arg Gly Lys Lys Val Ala Val Val Gly Gly Asn Thr Ala Val Glu
145                 150                 155                 160
Glu Ala Leu Tyr Leu Ser His Ile Ala Ser His Val Thr Leu Ile His
                165                 170                 175
Arg Arg Asp Lys Leu Arg Ala Glu Lys Met Leu Ser Ala Gln Leu Ile
                180                 185                 190
Lys Lys Val Glu Glu Gly Lys Val Ala Ile Val Trp Ser His Val Ile
            195                 200                 205
Glu Glu Val Leu Gly Asp Asp Gln Gly Val Thr Gly Val His Leu Lys
        210                 215                 220
His Val Lys Glu Glu Lys Thr Gln Asp Leu Thr Ile Asp Gly Leu Phe
225                 230                 235                 240
Ile Ala Ile Gly His Asp Pro Asn Thr Lys Ile Phe Lys Glu Gln Leu
                245                 250                 255
Glu Met Asp Glu Ala Gly Tyr Leu Arg Ala Lys Ser Gly Leu Gln Gly
```

```
            260                 265                 270
Asn Ala Thr Ala Thr Asn Ile Pro Gly Val Phe Ala Ala Gly Asp Val
            275                 280                 285

Thr Asp His Val Tyr Arg Gln Ala Ile Thr Ala Ala Gly Met Gly Cys
            290                 295                 300

Met Ala Ala Leu Asp Ala Glu Arg Tyr Leu Asp Ser Leu Asn Gln Ala
305                 310                 315                 320

<210> SEQ ID NO 16
<211> LENGTH: 299
<212> TYPE: PRT
<213> ORGANISM: Coxiella burnetii

<400> SEQUENCE: 16

Met Leu Lys Ile Val Ser Lys Pro Ser Phe Asn Arg Ile Ala Leu Met
1               5                   10                  15

Gly Arg Glu Gly Val Glu Gly Val Pro Glu Thr Leu Ala Ala Leu Lys
            20                  25                  30

Asp Tyr Leu Val Ser Leu Asn Arg Glu Val Ile Leu Glu Glu Asn Ala
            35                  40                  45

Ala His Met Ile Asp Gly Ser Arg Leu Leu Thr Val Pro Ala Asn Asp
        50                  55                  60

Leu Lys Lys Lys Ala Asp Leu Leu Ile Val Val Gly Gly Asp Gly Ser
65                  70                  75                  80

Leu Leu Asn Ala Ala His Ile Ala Val Pro Gln Gln Leu Pro Val Leu
                85                  90                  95

Gly Ile Asn Arg Gly Arg Leu Gly Phe Leu Thr Asp Ile Pro Pro Asn
            100                 105                 110

Glu Leu Thr Gln Ile Ser Asp Ile Leu Asp Gly His Tyr Arg Glu Glu
        115                 120                 125

Val Arg Phe Leu Leu Glu Gly Thr Val Glu Glu Gly Asp Glu Ile Val
    130                 135                 140

Ala Gln Gly Ile Ala Leu Asn Asp Ile Val Leu Leu Pro Gly Asn Ala
145                 150                 155                 160

Pro Lys Met Ile Glu Phe Asp Ile Phe Ile Asn Asp Glu Phe Val Cys
                165                 170                 175

Asn Gln Arg Ala Asp Gly Leu Ile Ile Thr Thr Pro Thr Gly Ser Thr
            180                 185                 190

Ala Tyr Ala Leu Ser Gly Gly Gly Pro Ile Leu His Pro Gln Leu Asn
        195                 200                 205

Ala Met Ala Leu Val Pro Met Phe Pro His Thr Leu Ser Ser Arg Pro
    210                 215                 220

Ile Val Val Asp Ala Glu Ser Gln Ile Lys Ile Thr Ile Ser Pro Glu
225                 230                 235                 240

Asn Asp Val Ser Pro Tyr Val Ser Asn Asp Gly Gln Glu Arg Val Ser
                245                 250                 255

Ile Lys Pro Gly Gly Asn Val Tyr Thr Arg Lys Tyr His Tyr Pro Leu
            260                 265                 270

His Leu Ile His Pro Thr Asp Tyr Asn Tyr Tyr Asp Thr Leu Arg Arg
        275                 280                 285

Lys Leu Asp Trp Glu Lys Arg Ala Ala Lys Val
    290                 295

<210> SEQ ID NO 17
<211> LENGTH: 390
```

<212> TYPE: PRT
<213> ORGANISM: Coxiella burnetii

<400> SEQUENCE: 17

Met Asn Leu His Glu Tyr Gln Ser Lys His Leu Leu Lys Lys Tyr Asn
1               5                   10                  15

Ile Pro Val Pro Ala Ser Glu Val Val Phe Asn Pro Asp Ala Ala Val
            20                  25                  30

Asp Ala Ala Lys Ile Gly Gly Asp Arg Trp Val Val Lys Ala Gln
        35                  40                  45

Val His Ala Gly Gly Arg Gly Lys Ala Gly Gly Val Arg Leu Val Lys
    50                  55                  60

Asn Lys Glu Glu Leu Lys Ser Ala Val Lys Ala Leu Leu Gly Thr Arg
65                  70                  75                  80

Leu Val Thr Tyr Gln Thr Asp Glu Arg Gly Gln Pro Val Asn Gln Ile
                85                  90                  95

Leu Val Glu Gln Thr Ser Asp Ile Ala Arg Glu Leu Tyr Leu Gly Ala
            100                 105                 110

Val Ile Asp Arg Ala Ser Gln Arg Ile Val Phe Met Ala Ser Thr Glu
        115                 120                 125

Gly Gly Val Glu Ile Glu Lys Val Ala Glu Lys Ser Pro Glu Lys Ile
    130                 135                 140

Leu Lys Val Thr Ile Asp Pro Ala Ile Gly Leu Gln Pro Phe Gln Cys
145                 150                 155                 160

Arg Gln Leu Phe Phe Gly Leu Gly Leu Gln Asp Leu Lys Gln Met Arg
                165                 170                 175

Ser Phe Thr Asp Ile Val Met Gly Leu Tyr Arg Leu Phe Thr Glu Arg
            180                 185                 190

Asp Leu Ser Leu Leu Glu Ile Asn Pro Leu Val Ile Thr Gly Ser Gly
        195                 200                 205

Glu Leu Ile Cys Leu Asp Ala Lys Ile Asn Ile Asp Asp Ser Ala Leu
210                 215                 220

Tyr Arg Gln Ser Glu Leu Arg Glu Met Arg Asp Thr Thr Gln Glu Asp
225                 230                 235                 240

Glu His Glu Thr Met Ala Gln Gln Trp Glu Leu Asn Tyr Ile Lys Leu
                245                 250                 255

Asp Gly Asn Ile Gly Cys Met Val Asn Gly Ala Gly Leu Ala Met Ala
            260                 265                 270

Thr Met Asp Leu Ile Lys Leu Ser Gly Gly Asp Pro Ala Asn Phe Leu
        275                 280                 285

Asp Val Gly Gly Ser Ala Thr Lys Glu Arg Val Thr Glu Ala Phe Lys
290                 295                 300

Ile Ile Val Ser Asp Lys Asn Val Lys Gly Ile Leu Val Asn Ile Phe
305                 310                 315                 320

Gly Gly Ile Val Arg Cys Asp Leu Ile Ala Asp Gly Ile Ile Ser Ala
                325                 330                 335

Val Lys Glu Val Gly Ile Asp Val Pro Val Val Arg Leu Glu Gly
            340                 345                 350

Asn Asn Ala Gln Leu Gly Ala Lys Lys Leu Ala Asp Ser Gly Met Asn
        355                 360                 365

Ile Ile Ala Ala Lys Gly Phe Ala Asp Ala Ala Glu Gln Ile Val Lys
    370                 375                 380

Gln Val Gly Val Ile Ala
385                 390

<210> SEQ ID NO 18
<211> LENGTH: 243
<212> TYPE: PRT
<213> ORGANISM: Coxiella burnetii

<400> SEQUENCE: 18

Met Asn Ser Lys Lys Ser Arg Ile Met Thr Phe Ser Ile Met Arg Phe
1               5                   10                  15

Asn Pro Glu Thr Asp Lys Lys Pro Tyr Met Gln Asp Phe Glu Leu Asp
            20                  25                  30

Val Ser Ala Ile Gln Gly Lys Met Leu Leu Asn Ala Leu Glu Ala Leu
        35                  40                  45

Arg Glu Lys His Pro Asp Ile Gly Leu Arg Arg Ser Cys Ala Glu Gly
    50                  55                  60

Val Cys Gly Ser Asp Gly Met Asn Ile Asn Gly Lys Asn Ala Leu Ala
65                  70                  75                  80

Cys Val Thr Gln Leu Lys Asp Leu Pro Asp Arg Val Val Arg Pro
                85                  90                  95

Leu Pro Gly Phe Pro Ile Ile Arg Asp Leu Ile Val Asp Met Glu Gln
            100                 105                 110

Phe Tyr Ala Gln Tyr Lys Lys Val Lys Pro Tyr Leu Leu Asn Asp Gln
        115                 120                 125

Glu Ala Pro Gln Lys Glu Arg Leu Gln Ser Pro Glu Arg Ala Lys
    130                 135                 140

Leu Asp Gly Leu Tyr Glu Cys Ile Leu Cys Ala Cys Cys Ser Ser Ser
145                 150                 155                 160

Cys Pro Ser Tyr Trp Trp Asn Pro Asp Lys Phe Ile Gly Pro Ala Gly
                165                 170                 175

Leu Leu Trp Ser Tyr Arg Phe Ile Ala Asp Ser Arg Asp Ser Lys Glu
            180                 185                 190

Lys Glu Arg Leu Asp Ala Met Lys Asp Pro Tyr Ser Val Phe Arg Cys
        195                 200                 205

Arg Thr Ile Met Asp Cys Ala Thr Val Cys Pro Lys Asn Leu Asn Pro
    210                 215                 220

Ala Lys Ala Ile Arg Lys Ile Arg Thr Glu Met Leu Gln Glu Thr Glu
225                 230                 235                 240

Ser Gly Glu

<210> SEQ ID NO 19
<211> LENGTH: 587
<212> TYPE: PRT
<213> ORGANISM: Coxiella burnetii

<400> SEQUENCE: 19

Met Ser Ser Ile Arg Val Lys Gln Tyr Asp Ala Leu Ile Val Gly Ala
1               5                   10                  15

Gly Gly Ala Gly Leu Arg Ala Ala Leu Glu Met Ala Gln Ser Arg Gln
            20                  25                  30

Tyr Lys Val Ala Val Val Ser Lys Val Phe Pro Thr Arg Ser His Thr
        35                  40                  45

Val Ser Ala Gln Gly Gly Ile Ala Ala Ala Leu Gly Asn Val Val Pro
    50                  55                  60

Asp Lys Pro Ile Trp His Met Phe Asp Thr Val Lys Gly Ser Asp Tyr
65                  70                  75                  80

```
Leu Gly Asp Gln Asp Ala Ile Gln Tyr Met Cys Glu Gln Ala Pro Pro
                85                  90                  95

Ser Val Tyr Glu Leu Glu His Tyr Gly Leu Pro Phe Ser Arg Leu Asp
            100                 105                 110

Asp Gly Arg Ile Tyr Gln Arg Ala Phe Gly Gly His Thr Arg Asp Phe
            115                 120                 125

Gly Lys Glu Met Ala Arg Arg Thr Cys Ala Cys Ala Asp Arg Thr Gly
            130                 135                 140

His Ala Met Leu His Thr Leu Tyr Gln Lys Asn Val Glu Ala Gly Thr
145                 150                 155                 160

His Phe Tyr Tyr Glu Trp Tyr Gly Ile Asp Leu Val Arg Gly Ala Gln
                165                 170                 175

Gly Gly Ile Ala Gly Met Ile Ala Met Asn Met Glu Thr Ser Glu Leu
            180                 185                 190

Val Phe Phe Lys Ser Arg Ala Thr Ile Phe Ala Thr Gly Gly Ala Gly
            195                 200                 205

Arg Ile Tyr Glu Thr Thr Ser Asn Ala Tyr Thr Asn Thr Gly Asp Gly
            210                 215                 220

Ile Gly Met Val Leu Arg Ala Gly Leu Pro Val Gln Asp Met Glu Phe
225                 230                 235                 240

Trp Gln Phe His Pro Thr Gly Ile Tyr Gly Val Gly Cys Leu Ile Thr
                245                 250                 255

Glu Gly Ala Arg Gly Glu Gly Gly Tyr Leu Ile Asn Lys Asp Gly Glu
            260                 265                 270

Arg Phe Met Glu Arg Tyr Ser Pro His Leu Lys Asp Leu Asp Cys Arg
            275                 280                 285

Asp Val Val Ala Arg Ser Ile Leu Gln Glu Val Met Ala Gly Gly Gly
            290                 295                 300

Val Gly Pro Lys Lys Asp His Val Leu Leu Lys Leu Asp His Leu Gly
305                 310                 315                 320

Glu Lys Val Leu Arg Glu Arg Leu Pro Gly Ile Glu Leu Ser Glu
            325                 330                 335

Lys Phe Ala Asn Val Asp Ile Thr Lys Glu Pro Ile Pro Ile Leu Pro
            340                 345                 350

Thr Cys His Tyr Met Met Gly Gly Ile Pro Thr Asn Ile His Gly Gln
            355                 360                 365

Ala Leu Thr Val Asp Glu Asn Gly Lys Asp Gln Ile Ile Glu Gly Leu
            370                 375                 380

Phe Ala Ala Gly Glu Cys Ala Cys Val Ser Val His Gly Ala Asn Arg
385                 390                 395                 400

Leu Gly Thr Asn Ser Leu Leu Asp Leu Val Val Phe Gly Arg Ala Ile
                405                 410                 415

Gly Leu His Leu Glu Glu Ala Leu Lys Thr Glu Leu Lys His Arg Ser
            420                 425                 430

Glu Asn Pro Asp Asp Ile Asp Ala Ala Ile Ala Arg Leu Lys Arg Trp
            435                 440                 445

Glu Lys Pro Asn Asn Val Glu Asn Pro Ala Leu Leu Arg Gln Glu Met
            450                 455                 460

Arg Lys Ala Met Ser Glu Asp Phe Gly Val Phe Arg Glu Glu Gln Lys
465                 470                 475                 480

Met Lys Gln Gly Leu Glu Arg Leu Gln Lys Leu Asn Glu Arg Leu Gln
                485                 490                 495

Arg Ala Lys Leu Thr Asp Thr Ser Arg Thr Phe Asn Asn Ala Arg Ile
```

```
                500                 505                 510
Glu Ala Leu Glu Leu Asp Asn Leu Met Glu Val Ser Tyr Ala Thr Ala
            515                 520                 525

Val Ser Ala Gln Gln Arg Thr Glu Ser Arg Gly Ala His Ser Arg Tyr
530                 535                 540

Asp Tyr Lys Glu Arg Asp Ala Asn Trp Leu Lys His Thr Val Tyr
545                 550                 555                 560

Phe Arg Asp Gly His Ile Ala Tyr Arg Pro Val Asn Met Lys Pro Lys
            565                 570                 575

Gly Met Asp Pro Phe Pro Pro Lys Ser Arg Asp
            580                 585

<210> SEQ ID NO 20
<211> LENGTH: 917
<212> TYPE: PRT
<213> ORGANISM: Coxiella burnetii

<400> SEQUENCE: 20

Met Ala Gly Cys Gly Leu Thr Asp Phe Cys Arg Thr Phe Glu Cys Val
1               5                   10                  15

Lys Leu Lys Arg Lys Ile Gly Cys Glu Val Thr Met Ala Asp Ser Leu
            20                  25                  30

Lys Thr Arg Arg Glu Leu Thr Ala Gly Gly Lys Thr Tyr His Tyr His
        35                  40                  45

Ser Leu Lys Ala Ala Glu Asp Ala Gly Leu Ser Asn Ile His Arg Leu
    50                  55                  60

Pro Tyr Ser Leu Lys Ile Leu Leu Glu Asn Gln Leu Arg His Glu Asp
65                  70                  75                  80

Gly Glu Thr Val Thr Gln Thr His Ile Glu Ala Phe Ala His Trp Leu
                85                  90                  95

Lys Asp Lys His Ser Asp Arg Glu Ile Ala Tyr Arg Pro Ala Arg Val
            100                 105                 110

Leu Met Gln Asp Phe Thr Gly Val Pro Ala Val Val Asp Leu Ala Ala
        115                 120                 125

Met Arg Asp Ala Met Ala Arg Met Lys Gly Asp Pro Thr Lys Ile Asn
130                 135                 140

Pro His Cys Pro Val Asp Leu Ile Ile Asp His Ser Val Gln Val Asp
145                 150                 155                 160

Glu Phe Gly Asn Glu Glu Ala Phe Arg Asp Asn Val Arg Ile Glu Met
                165                 170                 175

Glu Arg Asn His Glu Arg Tyr Thr Phe Leu Lys Trp Gly Gln Gln Ala
            180                 185                 190

Phe Arg His Phe Gln Leu Val Pro Pro Gly Thr Gly Ile Cys His Gln
        195                 200                 205

Val Asn Leu Glu Tyr Leu Gly Arg Gly Val Trp Ser Ser Gln Gln Asp
    210                 215                 220

Gly Glu Trp Leu Ala Tyr Pro Asp Thr Leu Val Gly Thr Asp Ser His
225                 230                 235                 240

Thr Thr Met Ile Asn Gly Leu Gly Val Leu Gly Trp Gly Val Gly Gly
                245                 250                 255

Ile Glu Ala Glu Ala Ala Met Leu Gly Gln Pro Ile Ser Met Leu Ile
            260                 265                 270

Pro Glu Val Ile Gly Phe Tyr Leu Ser Gly Gln Leu Cys Glu Gly Ile
        275                 280                 285
```

-continued

```
Thr Ala Thr Asp Leu Val Leu Thr Val Thr Gln Met Leu Arg Gln Lys
    290                 295                 300

Gly Val Val Gly Lys Phe Val Glu Phe Tyr Gly Pro Gly Leu Ala Glu
305                 310                 315                 320

Leu Pro Leu Ala Asp Arg Ala Thr Ile Gly Asn Met Ala Pro Glu Tyr
                325                 330                 335

Gly Ala Thr Cys Gly Leu Phe Pro Ile Asp Ala Glu Thr Ile Lys Tyr
                340                 345                 350

Leu Glu Leu Thr Gly Arg Asp Ala Glu Ala Ile Glu Leu Val Lys Ala
                355                 360                 365

Tyr Ser Lys Ala Gln Gly Thr Trp His Asp Glu Asn Thr Pro Glu Pro
370                 375                 380

Ile Phe Ser Asp Thr Leu Ser Leu Asp Leu Ser Thr Val Glu Pro Ser
385                 390                 395                 400

Leu Ala Gly Pro Lys Arg Pro Gln Asp Arg Val Pro Leu Ala Lys Leu
                405                 410                 415

Lys Lys Thr Ile Glu Gly Val Ile Ala Thr Ala Glu Arg Asp Gln Glu
                420                 425                 430

Leu Asp His Ser Phe Gln Ser Thr Gly Asp Phe Asp Leu His His Gly
                435                 440                 445

Asp Val Val Ile Ala Ala Ile Thr Ser Cys Thr Asn Thr Ser Asn Pro
450                 455                 460

Ser Val Met Leu Ala Ala Gly Leu Leu Ala Lys Asn Ala Val Glu Lys
465                 470                 475                 480

Gly Leu Gln Arg Lys Pro Trp Val Lys Ser Ser Leu Ala Pro Gly Ser
                485                 490                 495

Lys Val Val Thr Asp Tyr Leu His Lys Thr Gly Leu Ile Asp Tyr Leu
                500                 505                 510

Glu Lys Ile Gly Phe Tyr Leu Val Gly Tyr Gly Cys Thr Thr Cys Ile
                515                 520                 525

Gly Asn Ser Gly Pro Leu Pro Glu Thr Val Ala Lys Thr Val Thr Glu
530                 535                 540

Asn Asp Leu Ile Val Ser Ser Val Leu Ser Gly Asn Arg Asn Phe Glu
545                 550                 555                 560

Gly Arg Ile His Pro Leu Val Lys Thr Asn Trp Leu Ala Ser Pro Pro
                565                 570                 575

Leu Val Val Ala Phe Ala Leu Ala Gly Thr Thr Arg Ile Asp Leu Thr
                580                 585                 590

Lys Asp Pro Leu Gly His Asn Asp Arg Gly Glu Pro Ile Phe Leu Asn
                595                 600                 605

Asp Ile Trp Pro Ser Asn Ala Glu Ile Ala Lys Thr Val Met Gln Val
610                 615                 620

Arg Asn Asp Met Phe Arg Lys Glu Tyr Ala Asp Val Phe Glu Gly Asp
625                 630                 635                 640

Glu Glu Trp Gln Arg Ile His Val Ser Ala Gly Asp Thr Phe Ser Trp
                645                 650                 655

Gln Thr Asn Ser Thr Tyr Val Lys Asn Pro Pro Phe Phe Glu Asn Met
                660                 665                 670

Ser Ala Lys Pro Glu Pro Leu Lys Asn Ile Ile Asp Ala Arg Ile Leu
                675                 680                 685

Ala Ile Leu Gly Asp Ser Val Thr Thr Asp His Ile Ser Pro Ala Gly
690                 695                 700

Ala Ile Lys Ala Asp Ser Pro Ala Gly Lys Tyr Leu Ile Glu His Gly
```

-continued

```
                705                 710                 715                 720
Ile Asp Ile Lys Asp Phe Asn Ser Tyr Gly Ser Arg Arg Gly Asn His
                    725                 730                 735

Glu Val Leu Met Arg Gly Thr Phe Ala Asn Ile Arg Ile Arg Asn Glu
            740                 745                 750

Met Leu Ser Lys Val Glu Gly Gly Phe Thr Lys His Phe Pro Asp Gly
        755                 760                 765

Glu Gln Leu Pro Ile Tyr Asp Ala Ala Met Lys Tyr His Ser Glu Asn
    770                 775                 780

Ile Pro Leu Val Val Ile Ala Gly Lys Glu Tyr Gly Thr Gly Ser Ser
785                 790                 795                 800

Arg Asp Trp Ala Ala Lys Gly Pro Arg Leu Leu Gly Val Lys Ala Val
                805                 810                 815

Val Ala Glu Ser Phe Glu Arg Ile His Arg Ser Asn Leu Val Gly Met
            820                 825                 830

Gly Val Leu Pro Leu Glu Phe Lys Asn Asp Asp Asn Arg His Ser Leu
        835                 840                 845

Lys Leu Glu Gly Asn Glu Val Ile Asp Ile Thr Gly Leu Glu Asn Asp
    850                 855                 860

Leu Gln Pro Gly Gly Asp Val Ile Met Thr Val Lys Arg Lys Asp Gly
865                 870                 875                 880

Thr Ile Glu Lys Ile Pro Leu His Cys Arg Ile Asp Thr Gln Asn Glu
                885                 890                 895

Leu Ala Tyr Tyr Gln His Gly Gly Ile Leu Gln Phe Val Leu Arg Gln
            900                 905                 910

Met Leu Arg Ser Ser
        915

<210> SEQ ID NO 21
<211> LENGTH: 378
<212> TYPE: PRT
<213> ORGANISM: Coxiella burnetii

<400> SEQUENCE: 21

Met Lys Val Phe Lys Leu Pro Asp Leu Gly Glu Gly Leu Pro Asp Ala
1               5                   10                  15

Thr Ile Arg Glu Trp Tyr Ile Ala Val Gly Asp Glu Val Lys Ile Asp
            20                  25                  30

Gln Pro Leu Val Ala Met Glu Thr Ala Lys Ala Leu Val Asp Val Pro
        35                  40                  45

Ser Pro Leu Ala Gly Lys Ile Glu Lys Leu Phe Gly Glu Val Gly Asp
    50                  55                  60

Val Ile Glu Thr Gly Ser Pro Leu Ile Gly Phe Glu Gly Glu Ala Glu
65                  70                  75                  80

Thr Glu Glu Pro Lys Asp Thr Gly Thr Val Val Gly Ala Ile Glu Thr
                85                  90                  95

Ser Asp Thr Val Leu Glu Glu Ser Gly Ala Gly Ile Pro Val Lys Lys
            100                 105                 110

Ala Ala Glu Lys Lys Asn Phe Lys Ala Thr Pro Ala Val Arg Met Leu
        115                 120                 125

Ala Lys Gln Leu Gly Val Asp Leu Thr Lys Ile Thr Pro Lys Ser Ser
    130                 135                 140

Leu Ile Ser Ala Glu Glu Val Lys Gln Ala Ala Gln Ile Thr Lys Thr
145                 150                 155                 160
```

```
Gly Lys Thr Gln Lys Ile Glu Gly Glu Leu Thr Pro Leu Ser Pro Val
            165                 170                 175

Arg Arg Ala Met Ala Gln Ser Met Ser Gln Ser His Arg Glu Val Val
        180                 185                 190

Pro Val Ser Leu Met Asp Asp Gly Asp Leu Ser Ala Trp Lys Gly Glu
        195                 200                 205

Gln Asp Ile Thr Leu Arg Ile Ile Arg Ala Ile Glu Ala Ala Cys Gln
        210                 215                 220

Ala Val Pro Ile Met Asn Ala His Phe Asp Gly Glu Thr Leu Gly Tyr
225                 230                 235                 240

Lys Leu Asn Glu Thr Ile Asn Ile Gly Ile Ala Val Asp Thr Pro Gln
            245                 250                 255

Gly Leu Tyr Val Pro Val Leu Lys Asp Val Ser His Gln Asp Asp Thr
            260                 265                 270

Ala Leu Arg Asn Gln Ile Asn Arg Phe Lys Glu Leu Ala Gln Ser Arg
        275                 280                 285

Ser Phe Pro Pro Glu Asp Leu Arg Asp Ala Thr Ile Met Leu Ser Asn
        290                 295                 300

Phe Gly Ala Phe Ala Gly Arg Tyr Ala Asn Pro Ile Leu Leu Pro Pro
305                 310                 315                 320

Met Val Thr Ile Ile Gly Val Gly Arg Thr Arg Asp Glu Ile Val Pro
            325                 330                 335

Val Asp Gly Lys Pro Ala Val His Arg Ile Leu Pro Leu Ser Val Thr
            340                 345                 350

Ser Asp His Arg Val Ile Thr Gly Gly Glu Ile Ala Arg Phe Leu Lys
        355                 360                 365

Gln Leu Ile Asp Ser Leu Glu Lys Ala Ser
    370                 375

<210> SEQ ID NO 22
<211> LENGTH: 368
<212> TYPE: PRT
<213> ORGANISM: Coxiella burnetii

<400> SEQUENCE: 22

Met Thr Pro Lys Thr Thr Val Ala Asn Phe Thr Ile Arg Tyr Leu
1               5                   10                  15

Gln Phe Leu Asp Ala Asn Ser Asn Pro Thr Gln Pro Phe Pro Asp Phe
            20                  25                  30

Ala Asp Pro Asp Met Leu Leu Tyr Leu Tyr Arg Arg Met Ala Leu Ile
        35                  40                  45

Arg Gln Leu Asp Asn Lys Ala Ile Asn Leu Gln Arg Thr Gly Lys Met
    50                  55                  60

Gly Thr Tyr Pro Ser Ser Arg Gly Gln Glu Ala Val Gly Ile Gly Met
65                  70                  75                  80

Gly Ser Ala Met Gln Lys Glu Asp Ile Phe Cys Pro Tyr Tyr Arg Asp
                85                  90                  95

Gln Gly Ala Leu Phe Glu His Gly Ile Lys Leu Ser Glu Ile Leu Ala
            100                 105                 110

Tyr Trp Gly Gly Asp Glu Arg Gly Ser Arg Tyr Ala Asn Pro Asp Val
        115                 120                 125

Lys Asp Asp Phe Pro Asn Cys Val Pro Ile Ala Gly Gln Leu Leu His
    130                 135                 140

Ala Ala Gly Val Ala Tyr Ala Val Lys Tyr Arg Lys Gln Ala Arg Ala
145                 150                 155                 160
```

```
Val Leu Thr Ile Cys Gly Asp Gly Gly Thr Ser Lys Gly Asp Phe Tyr
                165                 170                 175

Glu Ala Ile Asn Leu Ala Gly Cys Trp Gln Leu Pro Leu Val Phe Ile
            180                 185                 190

Ile Asn Asn Asn Gln Trp Ala Ile Ser Val Ala Arg Gly Glu Gln Thr
                195                 200                 205

His Cys Gln Thr Leu Ala Gln Lys Ala Ile Ala Gly Gly Phe Glu Gly
            210                 215                 220

Trp Gln Val Asp Gly Asn Asp Val Ile Ala Val Arg Tyr Ala Val Ser
225                 230                 235                 240

Lys Ala Leu Glu Lys Ala Arg Asp Gly Gly Pro Thr Leu Ile Glu
                245                 250                 255

Ala Leu Ser Tyr Arg Leu Cys Asp His Thr Thr Ala Asp Asp Ala Thr
            260                 265                 270

Arg Tyr Ile Pro Gln Glu Glu Trp Lys Val Ala Trp Gln Lys Glu Pro
            275                 280                 285

Ile Ala Arg Leu Gly Tyr Tyr Leu Glu Ser Gln Gly Leu Trp Ser Arg
            290                 295                 300

Glu Lys Glu Ala Val Leu Gln Lys Glu Leu Ala Gln Glu Val Asp Gln
305                 310                 315                 320

Val Val Glu Glu Phe Leu Thr Met Pro Pro Lys Ala Thr Asp Met
                325                 330                 335

Phe Asp Tyr Leu Tyr Ala Glu Leu Pro Val Ser Leu Glu Lys Gln Arg
            340                 345                 350

Glu Glu Leu Ala Asp Asn Lys Pro Ser His Pro Ser Gly Arg Glu Gly
            355                 360                 365

<210> SEQ ID NO 23
<211> LENGTH: 232
<212> TYPE: PRT
<213> ORGANISM: Coxiella burnetii

<400> SEQUENCE: 23

Met Lys Arg Ile Leu Ile Thr Gly Ala Asn Arg Gly Ile Gly Leu Glu
1               5                   10                  15

Leu Val Lys Gln Tyr Leu Ala Ala Gly Trp His Val Asp Gly Cys Tyr
                20                  25                  30

Arg Asp Lys Lys Ala Ser Asn Ser Leu Phe Glu Leu Ala Ala Glu Lys
            35                  40                  45

Lys Gln Ser Leu Thr Leu His Glu Leu Asp Val Leu Asp Glu Lys Ala
50                  55                  60

Ile Gln Ala Leu Gly Glu His Leu Lys Asn Gln Pro Ile Asp Ile Leu
65                  70                  75                  80

Phe Asn Asn Ala Gly Val Ser Ala Lys Asn Leu Arg Glu Phe Gly Ser
                85                  90                  95

Ile His Asp Thr Glu Asn Ala Cys Glu Val Phe Lys Ile Asn Thr Ile
            100                 105                 110

Ala Pro Leu Leu Met Val Gln Ala Leu Leu Glu Ser Val Glu Lys Ser
            115                 120                 125

Glu Lys Lys Leu Ile Ile Asn Met Ser Ser Glu Met Gly Ser Ile Ala
            130                 135                 140

Gln Asn Val Asn Gly Asn Tyr Tyr Val Tyr Arg Ala Ser Lys Ser Ala
145                 150                 155                 160

Leu Asn Ala Ile Thr Lys Ser Leu Ala Ile Asp Leu Lys Arg Arg Gly
```

```
                165                 170                 175
Ile Thr Val Ile Ser Met Asn Pro Gly Trp Val Arg Thr Asp Met Gly
            180                 185                 190

Gly Glu Gln Ala Pro Leu Asp Val Ile Ser Ser Val Arg Gly Met Arg
        195                 200                 205

Glu Val Ile Glu Arg Val Asp Ile Lys Ser Thr Gly Gly Phe Leu Gly
210                 215                 220

Tyr Asp Gly Gly Glu Met Pro Trp
225                 230

<210> SEQ ID NO 24
<211> LENGTH: 607
<212> TYPE: PRT
<213> ORGANISM: Coxiella burnetii

<400> SEQUENCE: 24

Met Arg Thr Leu Gln Leu Arg Glu Gly Asn Met Thr Asn Leu Ile Ala
1               5                   10                  15

Asp Arg Leu Ala Ala Leu Arg Arg Leu Met His Glu Ile Gly Val Asp
            20                  25                  30

Tyr Tyr Tyr Val Pro Ser Ser Asp Pro His Lys Asn Glu Tyr Val Pro
        35                  40                  45

Ser Cys Trp Gln Arg Arg Ala Trp Ile Ser Gly Phe Thr Gly Ser Ala
    50                  55                  60

Gly Asp Val Val Gly Ile Asp Lys Ala Phe Leu Trp Thr Asp Pro
65                  70                  75                  80

Arg Tyr Phe Leu Gln Ala Glu Gln Leu Asp Asp Ser Leu Tyr His
                85                  90                  95

Leu Met Lys Met Gly Gln Gly Glu Thr Pro Ala Ile Asp Gln Trp Leu
            100                 105                 110

Thr Gln Gln Arg Asn Gly Ile Val Phe Ala Val Asp Pro Arg Leu Ile
        115                 120                 125

Asn Leu Gln Gln Ser Glu Lys Ile Gln Arg Ala Leu Glu Lys Gln Asn
130                 135                 140

Gly Lys Leu Leu Ala Leu Asp Glu Asn Leu Ile Asp Arg Val Trp Lys
145                 150                 155                 160

Asp Gln Pro Pro Leu Pro Gln Ser Ala Ile Gln Leu Gln Pro Leu Gln
                165                 170                 175

Tyr Ala Gly Leu Ser Ala Glu Asp Lys Leu Ala Ala Leu Arg Gln Thr
            180                 185                 190

Leu Gln Lys Glu Ser Ala Asp Ala Ile Val Leu Asn Thr Leu Asp Ala
        195                 200                 205

Ile Ala Trp Leu Phe Asn Ile Arg Gly Asn Asp Val Ala Tyr Asn Pro
    210                 215                 220

Leu Val Ile Ser Tyr Ala Val Ile Thr Gln Asn Glu Ala Ser Leu Phe
225                 230                 235                 240

Val Asp Pro His Lys Ile Thr Glu Gly Asp Arg Ser Tyr Phe Lys Lys
                245                 250                 255

Ile Pro Val His Ile Glu Pro Tyr Glu Gly Ile Gly Lys Leu Leu Glu
            260                 265                 270

Ser Leu Ser Gly Ser Val Trp Leu Asp Pro Gly Ala Thr Asn Leu Trp
        275                 280                 285

Leu Arg Asp Gln Leu Lys Asn Thr Ala Ser Leu Ile Leu Lys Pro Ser
    290                 295                 300
```

-continued

Pro Ile Thr Leu Ala Lys Ala Leu Lys Asn Pro Val Glu Gln Lys Gly
305                 310                 315                 320

Ala Arg Glu Ala His Ile Ile Asp Ala Ile Ala Met Ile Gln Phe Leu
            325                 330                 335

His Trp Leu Glu Asn His Trp Gln Ser Gly Val Ser Glu Ile Ser Ala
        340                 345                 350

Ala Glu Lys Leu Glu Phe Phe Arg Arg Gly Asp Ser Arg Cys Leu Asp
    355                 360                 365

Leu Ser Phe Pro Ser Ile Ser Gly Phe Gly Pro His Gly Ala Ile Val
370                 375                 380

His Tyr Ser Ala Thr Thr Asp Thr Asp Ala Thr Ile Asn Asp Ser Ala
385                 390                 395                 400

Pro Tyr Leu Ile Asp Ser Gly Gly Gln Tyr His Tyr Gly Thr Thr Asp
            405                 410                 415

Ile Thr Arg Thr Ile His Leu Gly Thr Pro Thr Glu Glu Lys Arg
        420                 425                 430

Leu Tyr Thr Leu Val Leu Lys Gly His Leu Ala Ile Arg Gln Ala Val
    435                 440                 445

Phe Pro Lys Gly Thr Cys Gly Glu His Leu Asn Ala Leu Ala His Gln
450                 455                 460

Phe Leu Trp Arg Glu Ala Leu Asp Tyr Gly His Gly Thr Gly His Gly
465                 470                 475                 480

Val Gly Ser Tyr Leu Cys Val His Glu Gly Pro Gln Ala Ile Thr Ser
            485                 490                 495

Arg Tyr Thr Gly Ile Pro Leu Gln Pro Gly Met Ile Val Ser Asn Glu
        500                 505                 510

Pro Gly Val Tyr Leu Thr His Lys Tyr Gly Ile Arg Ile Glu Asn Leu
    515                 520                 525

Cys Leu Val Thr Glu Lys Phe Thr Val Asp Asp Ser Leu Thr Gly Asp
530                 535                 540

Gly Pro Phe Tyr Ser Phe Glu Asp Leu Thr Leu Val Pro Tyr Cys Arg
545                 550                 555                 560

Lys Leu Ile Asn Pro Asn Leu Leu Thr Ser Glu Glu Ile Gln Gln Ile
            565                 570                 575

Asn Asp Tyr His Gln Arg Val Asp Gln Thr Leu Arg Asp Leu Leu Pro
        580                 585                 590

Ala Asn Glu Leu Asn Asp Trp Leu His Glu Ala Thr Ala Pro Leu
    595                 600                 605

<210> SEQ ID NO 25
<211> LENGTH: 859
<212> TYPE: PRT
<213> ORGANISM: Coxiella burnetii

<400> SEQUENCE: 25

Met Arg Ile Asp Lys Phe Thr Thr Ala Phe Gln Thr Ala Leu Ala Asp
1               5                   10                  15

Ala Gln Ser Leu Ala Val Gly Arg Asp His Gln Phe Ile Glu Pro Ala
            20                  25                  30

His Val Met Lys Val Leu Leu Glu Gln Thr Gln Gly Thr Val Ala Pro
        35                  40                  45

Leu Leu Glu Gln Ser Lys Val Asn Leu Ser Arg Leu Ile Asp Gly Val
    50                  55                  60

Asn Lys Ala Ile Asp Ser Tyr Pro Gln Val Glu Gly Thr Gly Gly Glu
65                  70                  75                  80

```
Val His Val Ser Arg Glu Leu Ser Lys Ile Leu Thr Leu Met Asp Lys
                85                  90                  95

Phe Ala Gln Gln Asn Lys Asp Gln Tyr Ile Ser Ser Glu Trp Phe Ile
            100                 105                 110

Pro Ala Ala Leu Glu Ala Lys Gly Gln Leu Arg Asp Val Leu Ile Glu
            115                 120                 125

Ala Gly Ala Asp Lys Lys Ala Ile Glu Lys Asn Ile Met Asn Leu Arg
130                 135                 140

Lys Gly Glu Arg Val Thr Glu Gln Ser Ala Glu Asp Gln Arg Gln Ala
145                 150                 155                 160

Leu Ala Lys Tyr Thr Ile Asp Leu Thr Glu Lys Ala Glu Thr Gly Lys
                165                 170                 175

Leu Asp Pro Val Ile Gly Arg Asp Glu Glu Ile Arg Arg Thr Val Gln
            180                 185                 190

Val Leu Gln Arg Arg Thr Lys Asn Asn Pro Val Leu Ile Gly Glu Pro
            195                 200                 205

Gly Val Gly Lys Thr Ala Ile Val Glu Gly Leu Ala Gln Arg Ile Val
210                 215                 220

Asn Gly Glu Val Pro Glu Gly Leu Lys Gln Lys Arg Leu Leu Ala Leu
225                 230                 235                 240

Asp Met Gly Ala Leu Ile Ala Gly Ala Lys Phe Arg Gly Glu Phe Glu
                245                 250                 255

Glu Arg Leu Lys Ala Val Leu Lys Asp Ile Ala Lys Glu Glu Gly Arg
            260                 265                 270

Val Ile Leu Phe Ile Asp Glu Leu His Thr Met Val Gly Ala Gly Lys
            275                 280                 285

Ala Glu Gly Ala Met Asp Ala Gly Asn Met Leu Lys Pro Ala Leu Ala
290                 295                 300

Arg Gly Glu Leu His Cys Val Gly Ala Thr Thr Leu Asp Glu Tyr Arg
305                 310                 315                 320

Lys Tyr Ile Glu Lys Asp Ala Ala Leu Glu Arg Arg Phe Gln Lys Val
                325                 330                 335

Leu Val Glu Glu Pro Ser Thr Glu Asp Ala Ile Ala Ile Leu Arg Gly
            340                 345                 350

Leu Lys Glu Arg Tyr Glu Val His His Gly Val Glu Ile Thr Asp Pro
            355                 360                 365

Ala Ile Ile Ala Ala Ala Thr Leu Ser Gln Arg Tyr Ile Thr Asp Arg
370                 375                 380

Asn Leu Pro Asp Lys Ala Ile Asp Leu Ile Asp Glu Ala Ala Ser Gln
385                 390                 395                 400

Ile Arg Met Glu Met Asp Ser Lys Pro Val Glu Leu Asp Arg Leu Glu
                405                 410                 415

Arg Arg Leu Ile Gln Leu Lys Ile Glu Arg Glu Ala Leu Lys Lys Glu
            420                 425                 430

Thr Asp Glu Ala Ser Lys Lys Arg Leu Ser Asp Leu Glu Thr Glu Ile
            435                 440                 445

Lys Asn Val Glu Lys Glu Tyr Ser Asp Leu Glu Glu Val Trp Lys Ser
450                 455                 460

Glu Lys Ala Ser Leu His Gly Thr Gln Gln Ile Lys Glu Glu Leu Glu
465                 470                 475                 480

Gln Ala Arg Ile Glu Leu Glu Ala Ala Gly Arg Ala Gly Asp Leu Ala
                485                 490                 495
```

Arg Met Ser Glu Leu Gln Tyr Gly Ile Ile Pro Glu Leu Asp Lys Lys
            500                 505                 510

Leu Lys Ala Ala Ser Gln Lys Glu Glu Gln Phe His Asp His Lys Leu
        515                 520                 525

Leu Arg Ser Arg Val Thr Glu Glu Val Ala Glu Val Ser Lys
    530                 535                 540

Trp Thr His Ile Pro Val Ser Lys Met Leu Glu Gly Glu Arg Glu Lys
545                 550                 555                 560

Leu Leu His Met Glu Thr Glu Leu His Lys Arg Val Ile Gly Gln Asp
                565                 570                 575

Glu Ala Val Asn Ala Val Ala Asn Ala Ile Arg Arg Ser Arg Ala Gly
            580                 585                 590

Leu Ser Asp Pro Asn Arg Pro Val Gly Ser Phe Leu Phe Leu Gly Pro
        595                 600                 605

Thr Gly Val Gly Lys Thr Glu Leu Cys Lys Ala Leu Ala Val Phe Leu
    610                 615                 620

Phe Asp Thr Glu Asp Ala Met Val Arg Ile Asp Met Ser Glu Phe Met
625                 630                 635                 640

Glu Lys His Ser Val Ala Arg Leu Ile Gly Ala Pro Pro Gly Tyr Val
                645                 650                 655

Gly Tyr Glu Glu Gly Gly Tyr Leu Thr Glu Ala Ile Arg Arg Arg Pro
            660                 665                 670

Tyr Ser Val Ile Leu Leu Asp Glu Ile Glu Lys Ala His Asn Asp Val
        675                 680                 685

Phe Asn Val Leu Leu Gln Val Leu Asp Asp Gly Arg Leu Thr Asp Gly
    690                 695                 700

Gln Gly Arg Thr Val Asp Phe Arg Asn Thr Val Ile Val Met Thr Ser
705                 710                 715                 720

Asn Leu Gly Ser Asp Leu Ile Arg Glu Phe Ser Gly Glu Asn Tyr Asp
                725                 730                 735

Lys Met Lys Asp Ala Val Met Glu Val Val Ala Gln His Phe Arg Pro
            740                 745                 750

Glu Phe Ile Asn Arg Ile Asp Glu Ala Val Val Phe His Ser Leu Lys
        755                 760                 765

Lys Glu Gln Ile Arg Asn Ile Ala Ile Ile Gln Ile Asp Arg Ile Lys
    770                 775                 780

Lys Arg Leu Lys Glu Lys Asp Tyr Gln Leu Thr Ile Ser Asp Asp Ala
785                 790                 795                 800

Leu Asp Tyr Leu Ser Glu Leu Gly Tyr Asp Pro Val Tyr Gly Ala Arg
                805                 810                 815

Pro Leu Lys Arg Val Leu Gln Gln Leu Glu Asn Pro Leu Ser Gln
            820                 825                 830

Lys Ile Leu Glu Gly Lys Phe Val Pro Gly Ser Leu Ile Asn Ile Glu
        835                 840                 845

Lys Lys Gly Glu Gln Leu Glu Phe Lys Glu Ala
    850                 855

<210> SEQ ID NO 26
<211> LENGTH: 901
<212> TYPE: PRT
<213> ORGANISM: Coxiella burnetii

<400> SEQUENCE: 26

Met Gly Leu Glu Ala Phe Cys Leu Ser Ser Leu Gln Cys Gln Ile Ser
1               5                   10                  15

-continued

Phe Glu Thr Ala Glu Pro Lys Met Ser Asn Gln Lys Pro Arg Thr Val
            20                  25                  30
Tyr Leu Lys Asp Tyr Arg Pro Ser Asp Phe Leu Val Asp Thr Val His
        35                  40                  45
Leu Tyr Phe Asp Leu His Glu Glu Thr His Val Lys Thr Ile Leu
50                  55                  60
Asn Leu Gln Arg Asn Pro Glu Gly Asn Ala Thr Ala Pro Leu Ala Leu
65                  70                  75                  80
Thr Gly Glu Ala Met Thr Leu Lys Lys Val Ala Leu Asp Gly Gln Thr
                85                  90                  95
Leu Ala Ser Ser Asp Tyr Thr Leu Asp Ala Ser Ser Leu Thr Ile Ala
            100                 105                 110
Asn Val Pro Asn Glu Phe Thr Leu Glu Thr Glu Val Val Ile Lys Pro
        115                 120                 125
Gln Glu Asn Thr Gln Leu Met Gly Leu Tyr Lys Ser Arg Gly Asn Phe
    130                 135                 140
Cys Thr Gln Cys Glu Ser His Gly Phe Arg Arg Ile Thr Tyr Phe Leu
145                 150                 155                 160
Asp Arg Pro Asp Val Met Ala Arg Tyr Thr Thr Thr Ile Thr Ala Asp
                165                 170                 175
Lys Asn Lys Tyr Pro Phe Leu Leu Ser Asn Gly Asn Leu Ile Glu Thr
            180                 185                 190
Lys Ile Leu Ser Asp Asn Arg His Trp Ala His Trp Glu Asp Pro Ser
        195                 200                 205
Lys Lys Pro Cys Tyr Leu Phe Ala Leu Val Ala Gly Asp Phe Asp Leu
    210                 215                 220
Leu Glu Asp Thr Phe Val Thr Gln Ser Gly Arg Glu Ile Ala Leu Arg
225                 230                 235                 240
Leu Tyr Leu Glu Lys Gly Phe Lys Asp Gln Gly Pro Phe Ser Leu Ala
                245                 250                 255
Ala Leu Lys Lys Ala Met Arg Trp Asp Glu Lys Arg Phe Gly Arg Glu
            260                 265                 270
Tyr Asp Leu Asp Ile Tyr Met Ile Val Ala Val Ser Asp Phe Asn Met
        275                 280                 285
Gly Ala Met Glu Asn Lys Gly Leu Asn Ile Phe Asn Thr Lys Tyr Ile
    290                 295                 300
Leu Ala Asn Pro Gln Ser Ala Thr Asp Asp Asn Tyr Val Ala Ile Glu
305                 310                 315                 320
Ser Val Ile Gly His Glu Tyr Phe His Asn Trp Ser Gly Asn Arg Val
                325                 330                 335
Thr Cys Arg Asp Trp Phe Gln Ile Thr Leu Lys Glu Gly Leu Thr Val
            340                 345                 350
Phe Arg Glu Gln Leu Phe Thr Glu Asp Thr Thr Ser Lys Gly Val Ala
        355                 360                 365
Arg Ile Gly Thr Val Asn Ile Leu Arg Asn Ser Gln Phe Pro Glu Asp
    370                 375                 380
Ala Gly Pro Met Ala His Pro Ile Arg Pro Arg Ser Tyr Ile Glu Val
385                 390                 395                 400
Asn Asn Phe Tyr Thr Thr Thr Val Tyr Asn Lys Gly Ser Glu Val Ile
                405                 410                 415
Arg Met Val Gln Thr Leu Leu Gly Glu Ala Leu Phe Arg Lys Ala Met
            420                 425                 430

-continued

```
Asp Leu Tyr Phe Ser Arg Tyr Asp Gly Gln Ala Val Thr Glu Asn
            435                 440                 445
Phe Ile Gln Ala Met Glu Asp Ala Ser Gly Lys Asn Leu Glu Gln Phe
450                 455                 460
Lys Arg Trp Tyr Asp Gln Ala Gly Thr Pro Val Leu Asp Leu Asn Ser
465                 470                 475                 480
Glu Tyr Asn Ala Asn Asp Lys Thr Leu Thr Leu Thr Val Lys Gln Ser
                485                 490                 495
Cys Pro Pro Thr Pro Gly Gln Ser Glu Lys Leu Pro Phe His Leu Pro
            500                 505                 510
Leu Thr Leu Gly Phe Val Gly Pro Glu Cys Gln Asp Met Pro Thr Gln
            515                 520                 525
Leu Ala Gly Glu Lys Lys Ala Ile Pro Gly Thr Arg Val Leu Glu Ile
            530                 535                 540
Lys Asp Ala Glu Thr Glu Phe Lys Phe Val Asn Val Asn His Lys Pro
545                 550                 555                 560
Thr Leu Ser Leu Leu Arg Gly Phe Ser Ala Pro Val Arg Leu Asn Tyr
                565                 570                 575
Pro Tyr Ser Asp Glu Glu Leu Val Trp Leu Phe Gln Cys Asp Ser Asp
            580                 585                 590
Pro Phe Ala Arg Tyr Glu Ala Gly Gln Ile Phe Ala Gln Arg Leu Ile
            595                 600                 605
Phe Lys Leu Ile Asp Asp Ser Tyr Gln Gly Lys Pro Leu Lys Ile Asp
            610                 615                 620
Glu Arg Phe Ile Asp Ala His Arg Lys Ile Ile Ala Gly Pro His Arg
625                 630                 635                 640
Asp His Trp Tyr Glu Ala Ala Leu Leu Gln Leu Pro Ser Ile Asn Tyr
                645                 650                 655
Leu Met Gln Leu Met Lys Lys Met Asp Val Glu Ala Leu His Thr Ile
            660                 665                 670
Arg Gln Phe Val Lys Lys Ala Leu Ser Asn Ala Leu Val Asp Asp Leu
            675                 680                 685
Lys Ile Gln Tyr Glu His His Gln Leu Pro Leu Tyr Glu Tyr Thr Pro
690                 695                 700
Ala Asp Ile Gly Lys Arg Lys Leu Lys Asn Ile Cys Leu Ala Tyr Leu
705                 710                 715                 720
Thr Glu Ser Asp Asp Thr Gln Phe Arg Gln Val Ala Tyr Gln Gln Phe
                725                 730                 735
Lys Lys Ser Asp Asn Met Thr Asp Thr Val Gly Ala Leu Ser Ala Leu
            740                 745                 750
Leu Asn His Asp Cys Lys Glu Arg His Gln Ala Leu Asp Glu Phe Tyr
            755                 760                 765
Gln Gln Trp Lys Asp Gln Pro Leu Val Val Asn Lys Trp Leu Met Leu
            770                 775                 780
His Ala Ser Ser Thr Leu Pro Ser Thr Leu Glu Ala Val Arg Lys Leu
785                 790                 795                 800
Thr Lys His Pro Ala Phe Asp Val Lys Asn Pro Asn Val Tyr Ser
                805                 810                 815
Leu Leu Gly Thr Phe Gly Ala Asn Ala Val Cys Phe His Glu Gly Ser
            820                 825                 830
Gly Glu Gly Tyr Arg Leu Ile Ala Asp Tyr Val Leu Ala Ile Asp Pro
            835                 840                 845
Ala Asn Pro Gln Val Ala Ala Arg Val Leu Gln Pro Leu Thr Arg Trp
```

```
                    850                 855                 860
Gln Met Met Asp Lys Lys Arg Gln Glu Leu Met Lys Ala Glu Leu Asn
865                 870                 875                 880

Arg Ile Ala Lys Ala Glu Arg Leu Ser Ser Asp Val Tyr Glu Ile Val
                    885                 890                 895

Thr Lys Ser Leu Leu
            900

<210> SEQ ID NO 27
<211> LENGTH: 647
<212> TYPE: PRT
<213> ORGANISM: Coxiella burnetii

<400> SEQUENCE: 27

Met Asn Ser Met Ile Lys Asn Leu Leu Leu Trp Leu Val Ile Ala Val
1               5                   10                  15

Val Leu Ile Thr Val Phe Ser Asn Phe Gly Ser Arg Gln Ser Asp Val
                20                  25                  30

Gln Pro Tyr Ser Tyr Ser Gln Phe Val Gln Ala Val Asn Asn Asp Lys
            35                  40                  45

Val Ser Ser Val Val Ile Gln Gly His Glu Ile Lys Gly Val Thr Lys
50                  55                  60

Asp Asn Lys His Phe Thr Thr Tyr Leu Pro Met Glu Asp Gln Ala Leu
65                  70                  75                  80

Leu Asn Gln Leu Met Ala Lys Gly Val Ser Val Lys Gly Glu Pro Pro
                85                  90                  95

Lys Gln Gln Ser Met Phe Leu His Ile Leu Ile Ser Trp Leu Pro Phe
            100                 105                 110

Leu Ile Leu Ile Phe Val Trp Ile Leu Phe Met Arg Gln Met Gln Gly
        115                 120                 125

Gly Gly Arg Gly Gly Gly Pro Met Ser Phe Gly Arg Ser Lys Ala Arg
130                 135                 140

Leu Leu Ser Gln Asp Gln Val Lys Val Thr Phe Asp Asp Val Ala Gly
145                 150                 155                 160

Val Asp Glu Ala Lys Glu Glu Val Lys Glu Leu Val Glu Phe Leu Arg
                165                 170                 175

Asp Pro Gly Lys Phe Gln Arg Leu Gly Gly Lys Met Pro Cys Gly Val
            180                 185                 190

Leu Leu Val Gly Pro Pro Gly Thr Gly Lys Thr Leu Leu Ala Lys Ala
        195                 200                 205

Val Ala Gly Glu Ala Lys Val Pro Phe Phe Thr Ile Ser Gly Ser Asp
210                 215                 220

Phe Val Glu Met Phe Val Gly Val Gly Ala Ser Arg Val Arg Asp Met
225                 230                 235                 240

Phe Asp Gln Ala Lys Lys Gln Ala Pro Cys Ile Ile Phe Ile Asp Glu
                245                 250                 255

Ile Asp Ala Val Gly Arg His Arg Gly Ala Gly Leu Gly Gly Gly His
            260                 265                 270

Asp Glu Arg Glu Gln Thr Leu Asn Gln Leu Leu Val Glu Met Asp Gly
        275                 280                 285

Phe Glu Gly Lys Glu Gly Ile Ile Val Met Ala Ala Thr Asn Arg Pro
290                 295                 300

Asp Val Leu Asp Pro Ala Leu Leu Arg Pro Gly Arg Phe Asp Arg Gln
305                 310                 315                 320
```

```
Val Val Val Pro Leu Pro Asp Ile Lys Gly Arg Glu Tyr Ile Leu Lys
            325                 330                 335

Val His Met Asn Lys Leu Pro Leu Ala Lys Asp Val Lys Ala Ser Val
            340                 345                 350

Ile Ala Arg Gly Thr Pro Gly Phe Ser Gly Ala Asp Leu Ala Asn Ile
            355                 360                 365

Val Asn Glu Ala Ala Leu Phe Ala Ala Arg Glu Asn Lys Lys Asp Val
        370                 375                 380

Ser Met Ser Glu Phe Glu Arg Ala Lys Asp Lys Ile Met Met Gly Ala
385                 390                 395                 400

Glu Arg Arg Ser Met Val Met Ser Asp Asp Glu Lys Lys Leu Thr Ala
                405                 410                 415

Tyr His Glu Ala Gly His Ala Ile Val Gly Leu His Met Leu Glu His
            420                 425                 430

Asp Pro Val Tyr Lys Val Thr Ile Ile Pro Arg Gly Arg Ala Leu Gly
            435                 440                 445

Val Thr Met Phe Leu Pro Glu His Asp Arg Tyr Ser Met Thr Lys Arg
        450                 455                 460

Arg Leu Glu Cys Gln Leu Ala Gly Leu Phe Gly Gly Arg Ile Ala Glu
465                 470                 475                 480

Glu Ile Ile Phe Gly Pro Asp Leu Val Thr Thr Gly Ala Ser Asn Asp
                485                 490                 495

Ile Glu Lys Ala Thr Glu Ile Ala Arg Asn Met Val Thr Lys Trp Gly
            500                 505                 510

Leu Ser Gln Lys Leu Gly Pro Leu Thr Tyr Arg Glu Glu Gly Glu
            515                 520                 525

Val Phe Leu Gly Arg Ser Val Thr Gln Arg Lys Asp Ile Ser Asp Ala
        530                 535                 540

Thr Asn Lys Glu Ile Asp Ser Glu Val Arg Arg Ile Val Asp Thr Ala
545                 550                 555                 560

Tyr Thr Thr Ala Lys Gln Thr Leu Glu Glu His Ile Glu Gln Leu His
                565                 570                 575

Leu Met Ala Lys Ala Leu Ile Lys Tyr Glu Thr Ile Gly Glu Ala Gln
            580                 585                 590

Ile Lys Glu Ile Leu Ala Gly Lys Glu Pro Ser Pro Pro Asp Trp
            595                 600                 605

Lys Glu Glu Asn Gly Ser Ala Ser Ala His Lys Glu Asn Ser Glu Lys
        610                 615                 620

Glu Leu Ser Glu Glu Lys Gly Glu Glu Lys Thr Val Asn Pro Ser Arg
625                 630                 635                 640

Pro Arg Pro Ala Glu Asp Gly
                645

<210> SEQ ID NO 28
<211> LENGTH: 814
<212> TYPE: PRT
<213> ORGANISM: Coxiella burnetii

<400> SEQUENCE: 28

Met Lys Lys Leu Val Ser Ser Leu Leu Ala Ser Ile Ser Leu Phe Leu
1               5                   10                  15

Ile Ser Ala Ala Ala Trp Ala Asp Asn Leu Pro Thr Asp Phe Thr Asp
            20                  25                  30

Asn Thr Ala Met Asn Thr His His Asp Leu Ser Val Thr Tyr Leu Ser
        35                  40                  45
```

-continued

```
Gln Val Phe Gly Thr Val Gly Asn Val Leu His Gly Met Ser Gly Gln
     50                  55                  60
Met Leu Gly His Leu Phe Tyr Arg Leu Asn Glu Gly Ile Ile Val Val
 65                  70                  75                  80
Ala Gly Met Trp Leu Val Tyr Thr Val Phe Thr Ile Val Leu Arg Ala
                     85                  90                  95
Ala Gln Asp Gly Ser Phe Met Gly Pro Asn Lys Asn Val Ala Leu Val
                    100                 105                 110
Phe Leu Lys Ile Ala Phe Gly Phe Ser Leu Leu Val Pro Asn Pro Ala
                115                 120                 125
Thr Gly Tyr Ser Leu Leu Gln Asp Val Val Met Lys Val Val Val Glu
    130                 135                 140
Gly Val Gly Leu Ala Asp Gln Thr Trp Glu Tyr Gly Leu Thr Tyr Ile
145                 150                 155                 160
Asn Asn Gly Gly Ser Leu Trp Arg Arg Pro Glu Thr Asn Gly Ala Gly
                165                 170                 175
Lys Asp Ile Ile Ser Gln Ser Thr Val Asn Ser Val Leu Gly Gly Asn
                180                 185                 190
Ser Gln Asn Lys Glu Gly Pro Gly Gln Lys Ile Phe Ala Ser Ala Val
    195                 200                 205
Cys Met Tyr Ser Ser Asp Asp Asn Gln Ser Pro Leu Lys Ser Asn Asn
210                 215                 220
Asn Asn Ile Gly Pro Ala Val Asn Gly Gly Pro Thr Val Lys Tyr Thr
225                 230                 235                 240
Tyr Asp Val Ile Thr Asp Ser Ala His Gln Phe Glu Phe Pro Gly
                245                 250                 255
Ser Gly Asp Thr Pro Pro Phe Lys Pro Gly Asp Asp Ser Cys Gly Ala
            260                 265                 270
Val Thr Trp Asp Ile Asn Asn Ala Cys Thr Gly Ala Gly Ser Asn Ser
            275                 280                 285
Thr Lys Cys Thr Met Ala Lys Glu Ala Val Ser Glu Leu Val Thr Ser
    290                 295                 300
Leu Leu Pro Ala Ala Lys Lys Tyr Tyr Cys Ser Gln His Ser Ser Ser
305                 310                 315                 320
Asp Leu Cys Leu Gly Val Thr His Asn Asp Ala Phe Ala Glu Asn Glu
                325                 330                 335
Thr Ser Phe Phe Gly Ala Leu Leu Asn Tyr Val Asn Thr Ile Val Pro
                340                 345                 350
Leu Val Gln Phe Asn Ser Gly Lys Ser Ala Asp Glu Ala Lys Arg Phe
                355                 360                 365
Ile Asp Glu Ala Gln Asn Glu Gly Trp Leu Ser Ala Gly Arg Tyr Tyr
    370                 375                 380
Trp Asp Leu Ser Gln Ile Gln Ser His Tyr Asp Asn Val Ser Asn Val
385                 390                 395                 400
Asp Ser Tyr Tyr Pro Arg Thr Val Asp Pro Thr Val Asn Gly Asn Pro
                405                 410                 415
Glu Asp Asp Tyr Gln Ala Ala Leu Lys Gln Ser Leu Gly Tyr Ile Tyr
                420                 425                 430
Gly Val Ile Asp Thr Ala Asn Pro His Pro Ile Pro Val Lys Gly Ser
            435                 440                 445
Val Leu Tyr Gln Leu Ala Gln Tyr Ala Gln Ser Gln His Ser Gly Asp
    450                 455                 460
```

Thr Gly Gly Gly Glu Glu Asn Trp Gly His Gly Gly Leu Asp Ala Gly
465                 470                 475                 480

Ile Ala Leu Ile Gly Gly Ile Phe Ser Glu Thr Ile Tyr Asp Ile Tyr
                485                 490                 495

Lys Leu Ile His Thr Phe Thr Thr Gly Ser Asp Gly Ala Met Gly Pro
            500                 505                 510

Asp Pro Ile Leu Phe Leu His Lys Ile Gly Ile Arg Ala Ile Ser Val
        515                 520                 525

Ala Ala Asp Ile Trp Phe Gly Phe Leu Gly Ile Met Ala Ile Ala Leu
    530                 535                 540

Phe Ala Thr Gly Val Cys Thr Ala Thr Tyr Asn Ala Gln Thr Pro Val
545                 550                 555                 560

Gln Ala Leu Leu Gly Trp Ile Lys Pro Leu Leu Met Val Val Ala Val
                565                 570                 575

Gly Leu Trp Gly Thr Gly Phe Val Leu Ala Tyr Tyr Val Pro Leu Tyr
            580                 585                 590

Pro Tyr Met Leu Tyr Thr Phe Gly Val Ile Gly Trp Ile Ile Val Val
        595                 600                 605

Ile Glu Ala Met Val Ala Ala Pro Leu Ile Ala Phe Gly Leu Thr His
    610                 615                 620

Pro Glu Gly His Asp Phe Leu Gly Glu Ala Lys Gln Gly Gly Met Leu
625                 630                 635                 640

Leu Leu Gly Val Phe Leu Arg Pro Val Leu Met Val Val Gly Leu Ile
                645                 650                 655

Ala Gly Met Ile Leu Ser Tyr Val Ala Leu Arg Ile Val Val Tyr Thr
            660                 665                 670

Phe Ser Gly Leu Ala Val Asp Leu Phe Ala Asn Thr Pro Ser Ser Gly
        675                 680                 685

Pro Ala Ser Gly Ser Ile Leu His Ala Ala Thr Ala Leu Met Ser Asn
    690                 695                 700

Ser Met Ala Thr Ala Gly Ser Val Thr Gly Ala Ile Val Ser Leu Met
705                 710                 715                 720

Val Phe Pro Leu Val Leu Ile Ile Phe Thr Ile Leu Val Tyr Val Val
                725                 730                 735

Thr Thr Gln Ser Phe Ser Leu Ile Phe Ala Leu Pro Asp Asn Val Met
            740                 745                 750

Arg Trp Ile Gly Ile Pro Gly Gln Arg Ser Glu Tyr Asp Arg Met Ala
        755                 760                 765

Thr Gln Leu Glu Ser Lys Val Gly Gly Phe Ala Ser Ser Thr Gly Arg
    770                 775                 780

Ser Gly Gly Leu Gln Ala Ser Glu Arg Ile Gly Lys Gly Ala Ala Asn
785                 790                 795                 800

Ala Asn Leu Gly Lys Gln Leu His Leu Gly Pro Ser Lys Lys
                805                 810

<210> SEQ ID NO 29
<211> LENGTH: 376
<212> TYPE: PRT
<213> ORGANISM: Coxiella burnetii

<400> SEQUENCE: 29

Met Lys Asn Phe Arg Val Leu Gly Ile Ala Ser Phe Leu Ala Leu Gly
1               5                   10                  15

Val Ala Ser Thr Ser Ala Leu Ala Asp Ile Asp Pro Met Ser Gly Val
            20                  25                  30

Ile Lys Ala Ile Lys Glu Val Gly Leu Glu Val Gln Ala Leu Ala Ile
             35                  40                  45

Ala Ser Lys Lys Ser Val Ser Asn Met Lys Tyr Gln Leu Asp Lys Asn
         50                  55                  60

Leu Asp Leu Ala Leu Gln Ala Asp Val Glu Lys Asn Asn Ala Leu Gln
 65                  70                  75                  80

Thr Val Lys Asn Asn Ala Gly Thr Asn Thr Gln Asn Gln Ile Ser Gly
                 85                  90                  95

Thr Leu Leu Gln Phe Pro Gln Val Ile Asn Ala Ser Gln Leu Asn
                100                 105                 110

Asp Ala Gln Met Ala Ala Thr Ile Lys Asn Arg Lys Asn Leu Ile Pro
                115                 120                 125

Asn Leu Thr Thr Ala Ile Pro Ala Ser Asp Thr Leu Tyr Leu Thr Asp
            130                 135                 140

Ala Glu Asp Pro Leu Ala Asn Thr Tyr Gly Val Ala Lys Pro Asp Ser
145                 150                 155                 160

Leu Tyr Asp Asn Tyr Phe Asn Phe Asp Ser Leu Phe Ala Pro Ser Ala
                165                 170                 175

Tyr Asn Ser Asp Gln Gln Gln Ala Ala Thr Thr Tyr Leu Gln Tyr Leu
            180                 185                 190

Thr Lys Pro Tyr Gln Ser Leu Thr Asp Asn Ile His Phe Ser Glu Leu
        195                 200                 205

Lys Asp Asn Leu Asn Lys Leu Ser Ala Glu Lys Arg Ala Asp Lys Leu
    210                 215                 220

Lys Ser Phe Leu Asn Asn Pro Ala Tyr Gln Lys Phe Gln Leu Ala Val
225                 230                 235                 240

Arg Ser Leu Ile Ala Thr Lys Ser Leu Ala Ile Asp Asn Phe Asn Thr
                245                 250                 255

Leu Leu Asn Glu Arg Val Pro Val Lys Gly Leu Gly Ala Lys Val Gly
            260                 265                 270

Met Pro Asp Asp Pro His Leu Pro Lys Gly Tyr Ala Ser Pro Leu Gln
        275                 280                 285

Val Glu Asn Tyr Ile Ala Asn Gln Arg Ile Asn Ser Pro Asp Trp Phe
    290                 295                 300

Lys Gln Met Lys Thr Ala Ser Pro Ala Val Val Ala Arg Glu Gln Val
305                 310                 315                 320

Leu Ile Leu Ala Glu Ile Glu Ser Gln Leu Glu Arg Asn His Leu Asp
                325                 330                 335

Asn Glu Arg Leu Leu Ala Thr Leu Ser Leu Met Ala Leu Gln Gly Thr
            340                 345                 350

Lys Asn Ser Glu Met Glu Leu Gln Thr Asn Thr Ala Ala Asp Leu Asn
        355                 360                 365

Lys Leu Ile Asp Gln Ile Gly Lys
    370                 375

<210> SEQ ID NO 30
<211> LENGTH: 402
<212> TYPE: PRT
<213> ORGANISM: Coxiella burnetii

<400> SEQUENCE: 30

Met Lys Ile Thr Asp Ala Lys Val Phe Val Cys Ser Pro Gly Arg Asn
1               5                   10                  15

Phe Val Thr Val Lys Ile Tyr Thr Asp Glu Gly Ile Tyr Gly Leu Gly

```
            20                  25                  30
Asp Gly Thr Leu Asn Gly Arg Glu Leu Ala Val Ala Ser Tyr Leu Glu
            35                  40                  45

Asp His Leu Leu Pro Cys Leu Ile Gly Lys Asp Pro Ser Gln Ile Glu
        50                  55                  60

Asp Ile Trp Gln Tyr Phe Tyr Lys Gly Ala Tyr Trp Arg Arg Gly Pro
65                  70                  75                  80

Val Thr Met Ser Ala Ile Gly Ala Ile Asp Met Ala Leu Trp Asp Ile
                85                  90                  95

Lys Gly Lys Ala Leu Lys Thr Pro Val Tyr Asn Leu Leu Gly Gly Arg
            100                 105                 110

Ser Arg Lys Gly Val Met Val Tyr Gly His Ala Asn Gly Lys Asp Val
            115                 120                 125

Glu Glu Thr Val Asp Glu Val Gly Lys Tyr Ile Glu Lys Gly Tyr Leu
            130                 135                 140

Ala Ile Arg Ala Gln Thr Gly Val Pro Gly Leu Pro Ser Thr Tyr Gly
145                 150                 155                 160

Val Ser Pro Asp Lys Leu Phe Tyr Glu Pro Ala Glu Lys Gly Leu Pro
                165                 170                 175

Pro Glu Asn Val Trp Ser Thr Glu Lys Tyr Leu Asn His Val Pro Lys
            180                 185                 190

Leu Phe Lys Lys Leu Arg Asp Val Tyr Gly Asp Pro His Leu Leu
            195                 200                 205

His Asp Cys His His Arg Leu Thr Pro Ile Glu Ala Gly Arg Leu Gly
        210                 215                 220

Lys Glu Leu Glu Pro Tyr His Leu Phe Trp Leu Glu Asp Thr Val Pro
225                 230                 235                 240

Ala Glu Leu Gln Glu Gly Phe Arg Ile Ile Arg Asn His Thr Thr Thr
                245                 250                 255

Pro Leu Ala Val Gly Glu Val Phe Asn Val Ile Tyr Asp Cys Thr Thr
            260                 265                 270

Leu Ile Thr Glu Gln Leu Ile Asp Tyr Ile Arg Met Ser Ile Val His
            275                 280                 285

Gly Gly Gly Leu Thr Pro Met Met Lys Ile Ala Ser Phe Ala Asp Ile
            290                 295                 300

Tyr His Val Arg Thr Gly Cys His Gly Pro Thr Asp Val Ser Pro Val
305                 310                 315                 320

Thr Met Ala Ala Ala Leu His Phe Glu Thr Ala Ile Asn Asn Phe Gly
                325                 330                 335

Ile Gln Glu Phe Met Arg His Thr Pro Glu Thr Asp Glu Val Phe Pro
            340                 345                 350

His His Tyr Tyr Phe Glu Asn Gly Tyr Leu Asn Val Lys Asp Glu Pro
            355                 360                 365

Gly Leu Gly Val Asp Phe Asp Glu Lys Leu Ala Ala Lys Tyr Pro Tyr
            370                 375                 380

Glu Arg Ala Tyr Leu Pro Ile Asn Arg Lys Leu Asp Gly Thr Met Tyr
385                 390                 395                 400

Asn Trp

<210> SEQ ID NO 31
<211> LENGTH: 259
<212> TYPE: PRT
<213> ORGANISM: Coxiella burnetii
```

<400> SEQUENCE: 31

```
Met Arg Ile Ile Thr Leu Asn Leu Asn Gly Ile Arg Ala Ala Ala Arg
1               5                   10                  15

Arg Gly Phe Phe Asp Trp Leu Lys Arg Gln Lys Ala Asp Ile Val Cys
            20                  25                  30

Leu Gln Glu Thr Lys Ala Cys Leu Glu Ile Thr Asn Gly Asp Gln Phe
        35                  40                  45

His Pro Lys Gly Tyr His Cys Tyr Tyr His Asp Ala Glu Lys Ser Gly
    50                  55                  60

Tyr Ser Gly Val Gly Ile Tyr Cys Arg Glu Lys Pro Asp Arg Val Thr
65                  70                  75                  80

Thr Arg Leu Gly Trp Glu His Ala Asp Lys Glu Gly Arg Tyr Ile Gln
                85                  90                  95

Ala Asp Phe Gly Ser Leu Ser Val Ala Ser Leu Tyr Met Pro Ser Gly
            100                 105                 110

Thr Thr Gly Glu His Arg Gln Lys Ile Lys Phe Asp Phe Met Asp Arg
        115                 120                 125

Tyr Met Lys Arg Leu Lys Asn Ile Val His Ser Lys Arg Ser Phe Ile
130                 135                 140

Ile Cys Gly Asp Trp Asn Ile Val His Lys Glu Ile Asp Ile Lys Asn
145                 150                 155                 160

Phe Lys Ser Asn Gln Lys Tyr Ser Gly Cys Leu Pro Glu Glu Arg Ala
                165                 170                 175

Trp Leu Asp Glu Val Phe Thr Lys Val Gly Leu Val Asp Ala Phe Arg
            180                 185                 190

Val Val Asn Gln Lys Pro Asp Gln Tyr Thr Trp Trp Ser Ser Arg Gly
        195                 200                 205

Arg Ala Trp Glu Lys Asn Val Gly Trp Arg Ile Asp Tyr Gln Val Ile
    210                 215                 220

Thr Ser Asp Leu Lys Asn Ser Val Lys Ser Glu Arg Ile Tyr Lys Asp
225                 230                 235                 240

Lys Arg Phe Ser Asp His Ala Pro Leu Ile Ile Asp Tyr Glu Arg Glu
                245                 250                 255

Ile Ser Asp
```

<210> SEQ ID NO 32
<211> LENGTH: 255
<212> TYPE: PRT
<213> ORGANISM: Coxiella burnetii

<400> SEQUENCE: 32

```
Met Glu Ser Leu Thr Pro Lys Arg Asp Ala Phe Thr Val Leu Ser Tyr
1               5                   10                  15

Asn Ile His Lys Gly Phe Ser Ala Arg Tyr Arg Arg Phe Val Leu Pro
            20                  25                  30

Asp Ile Arg Glu Ala Leu Arg Ala Ile Asp Ala Asp Ile Val Leu Leu
        35                  40                  45

Gln Glu Val Gln Gly Lys His His Lys Ser Arg Leu Lys Lys Phe Ala
    50                  55                  60

His Ala Asp Leu Pro Gln Thr Glu Phe Ile Ala Glu Ser Lys Trp Pro
65                  70                  75                  80

His Tyr Met Tyr Gly Lys Asn Ala Val Tyr Gly Ser Ala His His Gly
                85                  90                  95

Asn Ala Leu Leu Ser Asn Phe Pro Phe Lys Met Val Glu Asn Ile Asn
```

100                 105                 110
Val Ser Leu Ser Gln Arg Ala Ser Arg Ser Ile Leu His Ala Ile Ile
            115                 120                 125

Asp Tyr Glu Pro Thr Val Glu Leu His Val Ile Cys Ile His Leu Gly
        130                 135                 140

Leu Phe Arg Ala Glu Arg Asp Tyr Gln Leu Ile Thr Leu Ser Lys Arg
145                 150                 155                 160

Ile Glu Ala His Val Pro Ser His Ala Pro Leu Ile Ile Ala Gly Asp
                165                 170                 175

Phe Asn Asp Trp Arg Arg Gly Ala Phe Asn Tyr Met Glu Lys Glu Leu
            180                 185                 190

Glu Leu Lys Glu Val Tyr Lys Val Leu Glu Gly Lys His Ala Lys Thr
        195                 200                 205

Tyr Pro Ala Ser Arg Pro Thr Leu Glu Val Asp Arg Ile Tyr Tyr Arg
    210                 215                 220

Gly Leu Lys Leu Leu Ser Gly Glu Ile Phe Asn Glu Ser Tyr Trp Lys
225                 230                 235                 240

Lys Leu Ser Asp His Leu Pro Leu His Ala Lys Phe Ala Ile Glu
                245                 250                 255

<210> SEQ ID NO 33
<211> LENGTH: 117
<212> TYPE: PRT
<213> ORGANISM: Coxiella burnetii

<400> SEQUENCE: 33

Met Pro Lys His Phe Tyr Phe Tyr Phe Leu Arg Lys Met Thr Met Ser
1               5                   10                  15

Gln Asn Lys Ile Tyr Val Gly Ser Leu Ser Tyr Asp Val Thr Ala Asp
            20                  25                  30

Glu Leu Gln Ser Phe Phe Gly Gln Tyr Gly Glu Ile Glu Glu Ala Lys
        35                  40                  45

Leu Ile Met Asp Arg Glu Thr Gly Arg Ser Lys Gly Phe Ala Phe Ile
    50                  55                  60

Thr Tyr Gly Thr Gln Asp Ala Ala Gln Glu Ala Val Ser Lys Ala Asn
65                  70                  75                  80

Gly Ile Asp Leu Gln Gly Arg Lys Ile Arg Val Asn Ile Ala Arg Glu
                85                  90                  95

Asn Thr Gly Asp Arg Arg Arg Asp Gly Gly Ser Gly Gly Arg Gly Gly
            100                 105                 110

Arg Gly Gly Arg Phe
        115

<210> SEQ ID NO 34
<211> LENGTH: 183
<212> TYPE: PRT
<213> ORGANISM: Coxiella burnetii

<400> SEQUENCE: 34

Met Asp Phe Ser Asp Asp Asn Leu Ile Trp Leu Asp Leu Glu Met Thr
1               5                   10                  15

Gly Leu Asp Pro Glu Arg Asp Arg Ile Ile Glu Ile Ala Thr Ile Val
            20                  25                  30

Thr Asn Ser His Leu Asp Ile Leu Ala Glu Gly Pro Ala Phe Ala Ile
        35                  40                  45

His Gln Pro Asp Lys Leu Leu Thr Ala Met Asp Asn Trp Asn Thr Ser

```
            50                  55                  60
His His Thr Ala Ser Gly Leu Leu Glu Arg Val Lys Asn Ser Ser Val
 65                  70                  75                  80

Asp Glu Val Glu Ala Glu Thr Leu Thr Leu Ala Phe Leu Glu Lys Tyr
                85                  90                  95

Val Ser Ala Gly Lys Ser Pro Leu Cys Gly Asn Ser Val Cys Gln Asp
            100                 105                 110

Arg Arg Phe Leu Ser Arg Tyr Met Pro Arg Leu Asn Gln Phe Phe His
        115                 120                 125

Tyr Arg His Leu Asp Val Thr Thr Leu Lys Ile Leu Ala Gln Arg Trp
130                 135                 140

Ala Pro Gln Ile Ala Ala His Ile Lys Glu Ser Gln His Leu Ala
145                 150                 155                 160

Leu Gln Asp Ile Arg Asp Ser Ile Glu Glu Leu Arg Tyr Tyr Arg Ala
                165                 170                 175

His Leu Leu Asn Leu Ser Lys
            180
```

<210> SEQ ID NO 35
<211> LENGTH: 123
<212> TYPE: PRT
<213> ORGANISM: Coxiella burnetii

<400> SEQUENCE: 35

```
Met Met Phe Glu Leu Phe Lys Glu Ile Phe Met Lys Lys Ile Ile Gln
  1               5                  10                  15

Leu Ile Ser Ala Val Leu Ile Thr Ser Leu Val Phe Ser Ala Gln Ala
                20                  25                  30

Lys Pro Ala Ser Glu Val Ile Lys Asn Lys Leu His Arg His Ala Ala
            35                  40                  45

Val Ser Thr Gln Lys Thr Gly Pro Val Asp Ile Asn Thr Ala Asp Ala
         50                  55                  60

Thr Leu Leu Thr Thr Leu Lys Gly Ile Gly Val Lys Ala Lys Ala
 65                  70                  75                  80

Ile Ile Ala Tyr Arg Lys Lys Glu Gly Asn Phe Lys Ser Ile Glu Ala
                85                  90                  95

Leu Ser Ser Val Pro Gly Ile Ser Gln Lys Thr Val Ala Arg Leu Ile
            100                 105                 110

Arg Asn Asn Pro His Arg Leu Val Val Asn Pro
        115                 120
```

<210> SEQ ID NO 36
<211> LENGTH: 272
<212> TYPE: PRT
<213> ORGANISM: Coxiella burnetii

<400> SEQUENCE: 36

```
Met Phe Tyr Asn Gly Arg Ile Cys Leu Ala Leu Asn Pro Glu Glu Gly
  1               5                  10                  15

Pro Met Lys Lys Ile Leu Phe Leu Ala Thr Leu Leu Leu Ile Leu Ser
                20                  25                  30

Gly Cys Val Arg Lys Asp Val Asp Pro Tyr Gln Ala Tyr Arg Gly Lys
            35                  40                  45

Thr Ser Ala Glu Leu Phe Thr Ser Gly Glu Arg Ala Leu Ala Lys Lys
         50                  55                  60

Asp Tyr Ser Glu Ala Val Lys Asn Phe Glu Ala Leu Asp Ala Ile Tyr
```

```
            65                  70                  75                  80
        Pro Phe Gly Pro His Ala Glu Gln Ala Gln Leu Asp Ile Ile Tyr Ala
                            85                  90                  95

Tyr Tyr Lys Asn Asn Asp Thr Ser Ser Ala Ile Ala Ala Ala Asp Arg
                        100                 105                 110

Tyr Ile Arg Leu Tyr Pro Arg Gly Arg Asn Val Asp Tyr Ala Tyr Tyr
                        115                 120                 125

Met Arg Gly Val Ile Ser Phe Asp Leu Gly Leu Ser Trp Leu Gln Lys
                    130                 135                 140

Leu Ala Arg Val Ser Pro Val Ser Arg Asp Val Ser Thr Leu Gln Gln
        145                 150                 155                 160

Ser Phe Thr Ser Phe Ala Thr Leu Ala Glu Val Phe Pro His Ser Arg
                        165                 170                 175

Tyr Thr Pro Asp Ala Leu Thr Arg Met Arg Tyr Ile Arg Asn Leu Met
                    180                 185                 190

Ala Gln Arg Glu Ile Met Ile Ala Glu Phe Tyr Met Lys Arg Arg Ala
                    195                 200                 205

Tyr Val Ala Ala Ala Asn Arg Gly Ser Tyr Val Val Gln His Phe Gln
                    210                 215                 220

Gly Ser Pro Gln Val Ala Lys Ala Leu Ala Ile Met Val Gln Ala Tyr
        225                 230                 235                 240

Arg Ala Leu Gly Leu Pro Lys Met Ala Asp Ala Ser Asn His Leu Leu
                        245                 250                 255

Gln Thr Asn Tyr Pro His Thr Leu Glu Ala Arg Lys Leu Arg Lys Ala
                    260                 265                 270

<210> SEQ ID NO 37
<211> LENGTH: 418
<212> TYPE: PRT
<213> ORGANISM: Coxiella burnetii

<400> SEQUENCE: 37

Met Asn Leu Thr Asp Leu Lys Gln Lys Ser Val Pro Glu Leu Met Gln
1               5                   10                  15

Ile Ala Gln Glu Met Asn Leu Glu Tyr Val Ser Arg Thr Arg Lys Gln
                20                  25                  30

Asp Ile Ile Phe Ala Val Leu Lys Ala His Ala Lys Lys Gly Glu Asp
            35                  40                  45

Ile Phe Gly Asp Gly Val Leu Glu Ile Leu Gln Asp Gly Phe Gly Phe
        50                  55                  60

Leu Arg Ser Ala Asp Ser Ser Tyr Leu Ala Gly Pro Asp Asp Ile Tyr
65                  70                  75                  80

Val Ser Pro Ser Gln Ile Arg Arg Phe Asn Leu Arg Thr Gly Asp Thr
                85                  90                  95

Val Ser Gly Lys Ile Arg Pro Pro Lys Glu Ser Glu Arg Tyr Phe Ala
                100                 105                 110

Leu Leu Gln Val Asn Glu Ile Asn Leu Glu Lys Pro Glu Ala Ser Lys
            115                 120                 125

Gly Lys Ile Leu Phe Glu Asn Leu Thr Pro Leu Phe Pro Asn Glu Gln
        130                 135                 140

Ile Arg Met Glu Thr Gly Asn Gly Ser Thr Glu Asp Ile Thr Ala Arg
145                 150                 155                 160

Ile Ile Asp Leu Ile Ser Pro Ile Gly Lys Gly Gln Arg Gly Leu Ile
                165                 170                 175
```

Val Ser Pro Pro Lys Ala Gly Lys Thr Met Met Leu Gln Asn Ile Ala
            180                 185                 190

His Ser Ile Thr Thr Asn His Pro Glu Cys Val Leu Ile Val Leu Leu
        195                 200                 205

Ile Asp Glu Arg Pro Glu Val Thr Glu Met Asp Arg Ser Val Lys
210                 215                 220

Gly Glu Val Val Ala Ser Thr Phe Asp Glu Pro Ala Ser Arg His Val
225                 230                 235                 240

Gln Val Ala Glu Met Val Ile Glu Lys Ala Lys Arg Leu Val Glu His
            245                 250                 255

Lys Lys Asp Val Val Ile Leu Leu Asp Ser Ile Thr Arg Leu Ala Arg
            260                 265                 270

Ala Tyr Asn Thr Val Ile Pro Ala Ser Gly Lys Val Leu Thr Gly Gly
            275                 280                 285

Val Asp Ala Asn Ala Leu Gln Arg Pro Lys Arg Phe Phe Gly Ala Ala
            290                 295                 300

Arg Asn Val Glu Glu Gly Gly Ser Leu Thr Ile Ile Ala Thr Ala Leu
305                 310                 315                 320

Val Glu Thr Gly Ser Lys Met Asp Asp Val Ile Tyr Glu Glu Phe Lys
            325                 330                 335

Gly Thr Gly Asn Met Glu Ile His Leu Asp Arg Arg Ile Ala Glu Lys
            340                 345                 350

Arg Thr Phe Pro Ala Ile Asn Ile Asn Arg Ser Gly Thr Arg Arg Glu
            355                 360                 365

Glu Leu Met Met Pro Gln Asp Val Leu Gln Lys Val Trp Ile Leu Arg
            370                 375                 380

Lys Ile Leu His Pro Met Asp Glu Leu Ala Ala Ser Glu Phe Leu Ile
385                 390                 395                 400

Asp Arg Leu Lys Leu Thr Lys Thr Asn Asn Asp Phe Phe Asp Ser Met
                405                 410                 415

Lys Gly

<210> SEQ ID NO 38
<211> LENGTH: 200
<212> TYPE: PRT
<213> ORGANISM: Coxiella burnetii

<400> SEQUENCE: 38

Met Leu Glu Ile Val Leu Ala Ser Gln Asn Ser Ser Lys Leu Ala Glu
1               5                   10                  15

Met Gln Glu Leu Leu Arg Asp Leu Glu Ile Lys Phe Ile Pro Gln Thr
            20                  25                  30

Glu Phe Ser Val Pro Asp Ile Glu Glu Thr Gly Ser Thr Phe Val Glu
        35                  40                  45

Asn Ala Ile Ile Lys Ala Arg His Ala Ala Lys Gln Thr Gly Leu Pro
50                  55                  60

Ala Leu Ala Asp Asp Ser Gly Leu Thr Ile Ala Ala Leu Asn Ser Ala
65                  70                  75                  80

Pro Gly Val Phe Ser Ser Arg Tyr Ala Gly Lys Asn Ala Thr Asp Ala
            85                  90                  95

Glu Arg Ile Gln Lys Val Leu Glu Ala Leu Glu Ala Ala Asp Asp Ser
            100                 105                 110

Asp Arg Ser Ala Ser Phe His Cys Val Ile Ala Leu Met Glu Asn Glu
        115                 120                 125

```
Asn Asp Pro Ala Pro Leu Ile Cys His Gly Val Trp Glu Gly Glu Ile
    130                 135                 140
Ala Arg Glu Pro Arg Gly Lys Asn Gly Phe Gly Tyr Asp Pro Ile Phe
145                 150                 155                 160

Tyr Val Pro Ser His Gln Arg Thr Ala Ala Glu Leu Asp Pro Gln Glu
                165                 170                 175

Lys Asn Ala Ile Ser His Arg Gly Gln Ala Leu Glu Gln Leu Ser Thr
            180                 185                 190

Val Leu Thr Glu Ala Phe Leu Val
        195                 200
```

<210> SEQ ID NO 39
<211> LENGTH: 215
<212> TYPE: PRT
<213> ORGANISM: Coxiella burnetii

<400> SEQUENCE: 39

```
Met Cys Asn Asn Asp Phe Met Asn Gln Ala Thr Glu Ile Ala Lys Leu
1               5                   10                  15

Leu Leu Asn Ile Lys Ala Val Thr Leu Asn Leu His Glu Pro Tyr Arg
            20                  25                  30

Tyr Thr Ser Gly Ile Leu Ser Pro Ile Tyr Cys Asp Asn Arg Leu Ile
        35                  40                  45

Ile Ser Tyr Pro Glu Lys Arg Lys Met Ile Ile Glu Ala Phe Leu Gln
    50                  55                  60

Leu Ile Glu Lys Asn His Leu Ser Phe Asp Ile Val Ala Gly Thr Ala
65                  70                  75                  80

Thr Ala Gly Ile Pro His Ala Ala Trp Ile Ala Asp Arg Leu Asp Leu
                85                  90                  95

Pro Met Ile Tyr Val Arg Ala Lys Ala Lys Thr His Gly Lys Gln Asn
            100                 105                 110

Gln Ile Glu Gly Arg Ile Arg Lys Gly Gln Arg Ala Leu Ile Val Glu
        115                 120                 125

Asp Leu Ile Ser Thr Gly Lys Ser Ala Leu Ala Ala Gly Leu Ala Leu
    130                 135                 140

Arg Glu Lys Gly Val Thr Val Thr Asp Cys Ile Ala Ile Phe Ser Tyr
145                 150                 155                 160

Gln Leu Pro Gln Ala Gln Gln Asn Phe Ser Asp Ala Asn Ile Asn Cys
                165                 170                 175

His Ala Leu Ser His Phe Asp Thr Leu Ile Glu Met Ala Val Asp Glu
            180                 185                 190

Gly Tyr Ile Asp Glu Ile Glu Lys Gln Lys Ala Leu Ala Trp Asn Lys
        195                 200                 205

Asp Pro Glu His Trp Gln Pro
    210                 215
```

<210> SEQ ID NO 40
<211> LENGTH: 236
<212> TYPE: PRT
<213> ORGANISM: Coxiella burnetii

<400> SEQUENCE: 40

```
Met Glu Lys Pro Asp Pro Lys Val Ile Val Ala Ile Asp Ala Gly Thr
1               5                   10                  15

Val Glu Gln Ala Arg Ala Gln Ile Asn Pro Leu Thr Pro Glu Leu Cys
            20                  25                  30
```

His Leu Lys Ile Gly Ser Ile Leu Phe Thr Arg Tyr Gly Pro Ala Phe
                35                  40                  45

Val Glu Glu Leu Met Gln Lys Gly Tyr Arg Ile Phe Leu Asp Leu Lys
 50                  55                  60

Phe Tyr Asp Ile Pro Gln Thr Val Ala Gly Ala Cys Arg Ala Val Ala
 65                  70                  75                  80

Glu Leu Gly Val Trp Met Met Asn Ile His Ile Ser Gly Gly Arg Thr
                 85                  90                  95

Met Met Glu Thr Val Val Asn Ala Leu Gln Ser Ile Thr Leu Lys Glu
                100                 105                 110

Lys Pro Leu Leu Ile Gly Val Thr Ile Leu Thr Ser Leu Asp Gly Ser
                115                 120                 125

Asp Leu Lys Thr Leu Gly Ile Gln Glu Lys Val Pro Asp Ile Val Cys
130                 135                 140

Arg Met Ala Thr Leu Ala Lys Ser Ala Gly Leu Asp Gly Val Val Cys
145                 150                 155                 160

Ser Ala Gln Glu Ala Ala Leu Leu Arg Lys Gln Phe Asp Arg Asn Phe
                165                 170                 175

Leu Leu Val Thr Pro Gly Ile Arg Leu Glu Thr Asp Glu Lys Gly Asp
                180                 185                 190

Gln Lys Arg Val Met Thr Pro Arg Ala Ala Ile Gln Ala Gly Ser Asp
                195                 200                 205

Tyr Leu Val Ile Gly Arg Pro Ile Thr Gln Ser Thr Asp Pro Leu Lys
                210                 215                 220

Ala Leu Glu Ala Ile Asp Lys Asp Ile Lys Thr Arg
225                 230                 235

<210> SEQ ID NO 41
<211> LENGTH: 1324
<212> TYPE: PRT
<213> ORGANISM: Coxiella burnetii

<400> SEQUENCE: 41

Met Tyr Ser Ile Ile Ser Cys Ile Pro Leu Arg Ser Ile Arg Ala Thr
 1               5                  10                  15

Pro Ile Leu Leu Lys His Asp Asp Leu Gly Ser Arg Met Leu Phe Leu
                20                  25                  30

Gln Gly Ser His Val Tyr Thr Pro Phe Arg His Gln Gln Ile Leu Phe
                35                  40                  45

Arg Leu Lys Gln Lys Gln Asn Thr Val Arg Ser Val Glu Ala Ile Tyr
 50                  55                  60

Gly Tyr Phe Val Asp Gly Glu Lys Leu Leu Ser Arg Ala Glu Gln Glu
 65                  70                  75                  80

Arg Leu Glu Arg Leu Leu Pro Lys Ala Tyr Phe Ser Asp Tyr Pro Lys
                 85                  90                  95

Ser Ala Glu Asn Phe Ser Val Trp Val Thr Pro Arg Leu Gly Thr Ile
                100                 105                 110

Ser Pro Trp Ser Ser Lys Ala Thr Asp Ile Ala His Asn Cys Glu Ile
                115                 120                 125

Pro Ile Asn Arg Ile Glu Arg Gly Ile Tyr Phe Ile Ile Asp Gly Ile
                130                 135                 140

Ala Lys Arg Asp Lys Lys Ala Ile Glu Lys Val Ala Ser Glu Leu Tyr
145                 150                 155                 160

Asp Pro Leu Thr Glu Ser Leu Leu Phe Asp Ala Glu Asp Leu Ala Gln
                165                 170                 175

-continued

```
Leu Phe Gln His Pro Ala Pro Lys Thr Phe Asn Asp Ile Pro Val Leu
            180                 185                 190

Gly Lys Gly Glu Ala Ala Leu Lys Glu Ala Asp Gln Asn Leu Gly Leu
            195                 200                 205

Ala Leu Ser Asp Pro Asp Ile His Tyr Leu Leu Arg Ala Phe His Gln
210                 215                 220

Leu Asn Arg Asn Pro Thr Asp Ile Glu Leu Met Met Phe Ala Gln Val
225                 230                 235                 240

Asn Ser Glu His Cys Arg His Lys Ile Phe Asn Ala Gln Trp Thr Ile
            245                 250                 255

Asp Gly Lys Glu Lys Lys Glu Ser Leu Phe Asp Met Ile Arg Tyr Thr
            260                 265                 270

Tyr Lys Thr His Pro Glu Lys Ile Leu Val Ala Tyr Lys Asp Asn Ala
            275                 280                 285

Ala Val Ile Glu Gly Phe Asn Cys Glu Ser Phe Leu Ile Asn Pro Ser
            290                 295                 300

Asn His Ser Tyr Glu Lys Gln Lys Gly Arg Leu His Thr Val Leu Lys
305                 310                 315                 320

Val Glu Thr His Asn His Pro Thr Ala Ile Ala Pro Phe Ala Gly Ala
            325                 330                 335

Ala Thr Gly Ser Gly Gly Glu Ile Arg Asp Glu Ala Ala Thr Gly Arg
            340                 345                 350

Gly Ala Gln Ser Leu Ala Gly Leu Ala Gly Phe Ser Val Ser His Leu
            355                 360                 365

Arg Ile Pro Asp Phe Leu Gln Pro Trp Glu Lys Ala Pro Ser Lys Lys
            370                 375                 380

Ser Leu His Ser Asp Ser Lys Pro Lys Thr Leu Ala Ser Ala Leu Asp
385                 390                 395                 400

Ile Met Leu Gln Gly Pro Ile Gly Ala Ala Ser Phe Asn Asn Glu Phe
            405                 410                 415

Gly Arg Pro Thr Ile Cys Gly Tyr Phe Arg Thr Leu Glu His Leu Ser
            420                 425                 430

Ser Lys Thr Leu Lys Trp Gly Tyr His Lys Pro Ile Met Ile Ala Gly
            435                 440                 445

Gly Ile Gly His Ile Arg Glu Ser Gln Ile Glu Lys Gln Ser Phe Thr
            450                 455                 460

Glu Gly Ala Leu Leu Val Val Leu Gly Gly Pro Ala Met Ala Ile Gly
465                 470                 475                 480

Leu Gly Gly Gly Ser Ala Ser Ser Arg Thr Ser Gly Glu Ser Thr Glu
            485                 490                 495

Ala Leu Asp Phe Ala Ser Val Gln Arg Ala Asn Pro Glu Met Gln Arg
            500                 505                 510

Arg Ala Gln Glu Val Ile Asn Ala Cys Leu Ser Leu Gly Asp Asp Asn
            515                 520                 525

Pro Ile Leu Ser Leu His Asp Val Gly Ala Gly Leu Ser Asn Ala
            530                 535                 540

Phe Pro Glu Leu Val His Ala Thr Glu Cys Gly Gly Glu Phe Glu Leu
545                 550                 555                 560

Arg His Ile Pro Asn Ala Glu Pro Gly Met Ser Pro Leu Glu Ile Trp
            565                 570                 575

Cys Asn Glu Ala Gln Glu Arg Phe Val Leu Ala Ile Lys Pro Glu Ser
            580                 585                 590
```

-continued

```
Leu Lys Val Phe Ser Gly Ile Ala Glu Arg Glu Arg Cys Pro Phe Ala
        595                 600                 605
Val Val Gly Arg Ala Lys Glu Glu Lys Lys Leu Ile Leu Asn Asp Ala
610                 615                 620
His Phe His Asn Arg Pro Ile Asp Leu Pro Leu Ser Phe Leu Phe Glu
625                 630                 635                 640
Asp Met Pro Pro Met Lys Arg Glu Asp Lys Arg Val Phe Ser Gly Glu
                645                 650                 655
Thr Ala Trp Asn Ile Ser Lys Ile Asn Trp Ala Asp Ala Val Lys Arg
                660                 665                 670
Val Leu Gln Tyr Pro Cys Val Ala Asp Lys Ser Phe Leu Ile Thr Ile
        675                 680                 685
Gly Asp Arg Thr Val Gly Gly Met Val Ala Arg Asp Gln Met Val Gly
    690                 695                 700
Pro Trp Gln Ile Pro Val Ala Asp Val Ala Val Thr Ala His Ser Phe
705                 710                 715                 720
Thr Gly Tyr Glu Gly Gln Ala Leu Ala Met Gly Glu Arg Ser Pro Ile
                725                 730                 735
Ala Ile Val His Pro Ala Ala Ser Ala Arg Met Ala Val Gly Glu Ala
                740                 745                 750
Ile Thr Asn Ile Ala Ala Ala Pro Ile Lys Ala Ile Ser Asp Ile Val
        755                 760                 765
Leu Ser Ala Asn Trp Met Ala Ala Pro Asp Gln Pro Gly Glu Gly Ala
    770                 775                 780
Gly Leu Tyr Glu Ala Val Gln Thr Val Ala Lys Glu Leu Cys Pro Ala
785                 790                 795                 800
Leu Gly Ile Cys Ile Pro Val Gly Lys Asp Ser Leu Ser Met Gln Thr
                805                 810                 815
Ser Leu Glu Lys Glu Ile Val Thr Ala Pro Leu Ser Leu Ile Ile Thr
                820                 825                 830
Ala Thr Ala Pro Val Ser Asp Val Arg His Ala Leu Thr Pro Gln Leu
        835                 840                 845
Gln Thr Asp Val Gly Glu Thr Arg Leu Leu Leu Ile Asp Leu Gly Gln
    850                 855                 860
Gly Ala Asn Phe Leu Gly Gly Ser Cys Leu Ala Gln Thr Tyr Asn Leu
865                 870                 875                 880
Leu Gly Lys Gln Pro Pro Asp Val Asp Asp Pro Leu Leu Leu Arg Arg
                885                 890                 895
Phe Phe Glu Ala Ile Gln Ser Leu Asn Gln Lys Asn Leu Leu Leu Ala
                900                 905                 910
Tyr His Asp Arg Ser Asp Gly Leu Leu Ala Thr Leu Cys Glu Met
        915                 920                 925
Ala Phe Thr Ala His Val Gly Ile Thr Ile Lys Leu Asp Ser Leu Gly
    930                 935                 940
Asp Asp Ala Leu Ala Ser Val Phe Asn Glu Leu Gly Ala Val Ile
945                 950                 955                 960
Gln Val Lys Glu Lys Asn Ile Asp Ile Val Phe Glu Ile Leu Lys Ser
                965                 970                 975
His Lys Leu Gln Ala His Ser His Val Ile Gly Glu Leu Asn Gln Leu
                980                 985                 990
Asp Glu Ile Ile Phe Asn Phe Arg  Gly Gln Thr Leu Tyr  Gln Glu Thr
        995                 1000                1005
Arg Thr  Thr Leu Gln Arg Trp  Trp Ser Glu Thr Ser  Tyr Arg Leu
```

```
            1010                1015                1020

Gln Ser Leu Arg Asp Asn Pro Glu Cys Ala Lys Gln Gln Tyr Asp
        1025                1030                1035

Gly Leu Leu Asp Lys Lys Asp Thr Gly Leu Phe Thr Lys Ile Thr
        1040                1045                1050

Phe Asp Asn Asn Glu Asp Ile Ala Leu Pro Tyr Ile Asn Ser Gly
        1055                1060                1065

Lys Arg Pro Arg Val Ala Ile Leu Arg Glu Gln Gly Thr Asn Gly
        1070                1075                1080

His Arg Glu Met Ala Ala Ala Phe His Leu Ala Gly Phe Glu Ser
        1085                1090                1095

Val Asp Val His Met Ser Asp Leu Leu Asn Glu Arg Val Asn Leu
        1100                1105                1110

Met Asp Phe Lys Gly Ala Val Ala Gly Gly Gly Phe Ser Tyr Gly
        1115                1120                1125

Asp Val Leu Gly Ala Gly Arg Gly Trp Ala Gln Val Ile Leu Met
        1130                1135                1140

His Pro Lys Ile Arg Asp Lys Phe Ser Leu Phe Phe Glu Ser Lys
        1145                1150                1155

Asp Arg Phe Ala Leu Gly Val Cys Asn Gly Cys Gln Leu Phe Ser
        1160                1165                1170

His Leu Lys Ser Leu Ile Pro Gly Ala Leu His Trp Pro Ala Phe
        1175                1180                1185

Gln Arg Asn Val Ser Glu Gln Phe Glu Ala Arg Leu Ser Met Val
        1190                1195                1200

Glu Ile Pro Gln Ser Pro Ser Leu Phe Phe Gln Gly Met Ala Gly
        1205                1210                1215

Ser Gln Leu Pro Val Ala Val Ala His Gly Glu Gly Arg Val Val
        1220                1225                1230

Phe Glu Lys Asn Thr Gln Glu Phe Glu Asn Glu Lys Leu Ile Ala
        1235                1240                1245

Leu Arg Tyr Val Asn Tyr Ala Gly Gln Pro Thr Glu Asn Tyr Pro
        1250                1255                1260

Ala Asn Pro Asn Gly Ser Pro Lys Gly Ile Thr Gly Leu Thr Thr
        1265                1270                1275

Pro Asp Gly Arg Ile Thr Ile Leu Met Pro His Pro Glu Arg Val
        1280                1285                1290

Phe Arg Thr Val Gln Phe Ser Trp His Pro Lys Gln Trp Ser Glu
        1295                1300                1305

Met Ser Pro Trp Met Arg Ile Phe Lys Asn Ala Arg Lys Trp Val
        1310                1315                1320

Gly

<210> SEQ ID NO 42
<211> LENGTH: 113
<212> TYPE: PRT
<213> ORGANISM: Coxiella burnetii

<400> SEQUENCE: 42

Met Thr Ala Cys Val Phe Cys Lys Ile Ala Lys Gly Glu Ile Gly Glu
1               5                   10                  15

Leu Ile Tyr Glu Asp Lys Gln Val Val Ala Phe Asn Asp Ala Ala Pro
            20                  25                  30

Gln Ala Pro Ile His Ile Leu Val Ile Pro His Arg His Ile Glu Thr
```

```
            35                  40                  45
Ile Asn Asp Val Thr Pro Gly Asp Glu Asp Leu Leu Gly His Met Val
     50                  55                  60

Val Val Ala Thr Arg Leu Ala His Asp Lys Asn Met Ala Ala Asp Gly
 65                  70                  75                  80

Tyr Arg Leu Val Met Asn Cys Asn Arg Asn Gly Gly Gln Ala Val Phe
                 85                  90                  95

His Ile His Leu His Leu Leu Gly Gly Arg Gln Met His Trp Pro Pro
            100                 105                 110

Gly

<210> SEQ ID NO 43
<211> LENGTH: 319
<212> TYPE: PRT
<213> ORGANISM: Coxiella burnetii

<400> SEQUENCE: 43

Met Pro Asn Val Asp Asp Ile Arg Ile Phe His Gly Ser Ala Asn Pro
 1               5                  10                  15

Ser Leu Ala Glu Asn Val Ala Lys Glu Leu Asn Thr Thr Ile Gly Asn
             20                  25                  30

Ala Leu Ile Ser Arg Phe Ser Asp Gly Glu Ile Arg Phe Glu Ile Glu
         35                  40                  45

Glu Asn Val Arg Gly Arg Asp Ile Tyr Leu Ile Gln Ser Thr Gly His
     50                  55                  60

Pro Thr Asn Glu His Val Met Glu Leu Ile Leu Met Gly Asp Ala Phe
 65                  70                  75                  80

Arg Arg Ala Ser Ala Ala Ser Ile Thr Ala Val Val Pro Tyr Phe Gly
                 85                  90                  95

Tyr Ala Arg Gln Asp Arg Arg Val Arg Ser Ser Arg Val Pro Ile Ser
            100                 105                 110

Ala Lys Val Val Ala Asp Met Met Gln Lys Val Gly Phe Ser Arg Leu
        115                 120                 125

Ile Thr Val Asp Leu His Ala Asp Gln Ile Gln Gly Phe Phe Tyr Met
    130                 135                 140

Pro Val Asp Asn Ile Tyr Ala Ser Ile Thr Ala Leu Glu Glu Tyr Arg
145                 150                 155                 160

Leu Leu Asp Lys Leu Glu Thr Pro Met Ile Val Ser Pro Asp Val Gly
                165                 170                 175

Gly Val Val Arg Ala Arg Ala Ile Ala Lys Arg Leu Asn Asp Ser Asp
            180                 185                 190

Leu Ala Ile Ile Asp Lys Arg Arg Pro Ala Pro Asn Gln Ala Glu Val
        195                 200                 205

Met Asn Val Ile Gly Asn Val Gln Asn Arg His Cys Val Ile Val Asp
    210                 215                 220

Asp Ile Val Asp Thr Ala Gly Thr Leu Cys His Ala Ala Ser Ala Leu
225                 230                 235                 240

Lys Glu Lys Gly Ala Leu Thr Val Ser Ser Tyr Cys Thr His Pro Val
                245                 250                 255

Leu Ser Gly Asn Ala Val Lys Asn Ile Met Asp Ser Asp Ile Asp Glu
            260                 265                 270

Leu Ile Val Thr Asp Thr Ile Pro Leu His Glu Glu Ala Ala Lys Cys
        275                 280                 285

Arg Lys Ile Thr Gln Ile Ser Leu Ser Arg Leu Ile Ala Glu Thr Ile
```

```
            290                 295                 300
Ser Arg Ile Asn Gln Lys Glu Ser Val Ser Ser Met Phe Leu Asp
305                 310                 315
```

<210> SEQ ID NO 44
<211> LENGTH: 191
<212> TYPE: PRT
<213> ORGANISM: Coxiella burnetii

<400> SEQUENCE: 44

```
Met Ala Arg Arg Lys Ala Ala Pro Lys Arg Glu Thr Leu Pro Asp Pro
1               5                   10                  15

Leu Phe His Ser Glu Leu Leu Ala Lys Phe Ile Asn Ala Val Met Arg
                20                  25                  30

Asn Gly Lys Lys Ser Val Ala Glu Lys Ile Val Tyr Gly Ala Leu Asp
            35                  40                  45

Val Val Ala Lys Arg Val Gln Asn Lys Ser Gly Glu Gln Gly Asp Gly
        50                  55                  60

Asp Gly Glu Ser Gly Gly Lys Ala Gly Gly Ile Lys Lys Arg Ser Leu
65                  70                  75                  80

Gly Asp Ile Arg Thr Asp Glu Asn Ala Arg Ala Leu Ala Leu Glu Thr
                85                  90                  95

Phe Lys Gly Ala Leu Asp Lys Val Met Pro Asn Val Glu Val Lys Ser
            100                 105                 110

Arg Arg Val Gly Gly Ser Thr Tyr Gln Val Pro Val Glu Ile Arg Met
        115                 120                 125

Ala Arg Arg Gln Ala Leu Ala Arg Arg Trp Leu Val Glu Tyr Ala Asn
130                 135                 140

Lys Arg Asn Glu Lys Thr Met Val Leu Arg Leu Ala His Glu Ile Leu
145                 150                 155                 160

Asp Ala Val Glu Gly Arg Gly Gly Ala Ile Lys Lys Arg Glu Asp Val
                165                 170                 175

His Arg Met Ala Lys Ala Asn Gln Ala Phe Ala His Tyr Lys Trp
            180                 185                 190
```

<210> SEQ ID NO 45
<211> LENGTH: 181
<212> TYPE: PRT
<213> ORGANISM: Coxiella burnetii

<400> SEQUENCE: 45

```
Met Asn Asp Leu Asn Ser Asp Gly Leu Phe Leu Phe His Phe Gln Ala
1               5                   10                  15

His Leu Arg Trp Thr Arg Leu Ala Leu Ala Cys Pro His Gln Phe Arg
                20                  25                  30

Ile Lys Tyr Pro Thr Leu Thr Asn Thr Gly Thr His Met Val Val Ile
            35                  40                  45

Arg Leu Ala Arg Gly Gly Ser Lys Lys Asn Pro Phe Tyr His Ile Val
        50                  55                  60

Val Ala Asp Arg Lys Pro Arg Asp Gly Arg Phe Ile Glu Arg Val
65                  70                  75                  80

Gly Tyr Tyr Asn Pro Met Ala Arg Gly Gln Asp Ile Arg Leu Gln Leu
                85                  90                  95

Glu Lys Glu Arg Ile Ser His Trp Leu Asn Gln Gly Ala Gln Thr Ser
            100                 105                 110

Leu Arg Val Lys His Leu Ile Lys Lys Leu Glu Lys Ser Pro Glu Glu
```

```
            115                 120                 125
Ala Gln Lys Gly Gly Met Arg Lys Gly Glu Phe Lys Arg Leu Gln Ala
        130                 135                 140

Glu Gln Ala Ala Lys Ala Gln Lys Lys Ala Val Ala Thr Glu Glu Pro
145                 150                 155                 160

Lys Ala Glu Glu Ala Lys Glu Ala Pro Pro Ala Glu Ser Gln Ala Ala
                165                 170                 175

Glu Gly Lys Glu Glu
            180

<210> SEQ ID NO 46
<211> LENGTH: 920
<212> TYPE: PRT
<213> ORGANISM: Coxiella burnetii

<400> SEQUENCE: 46

Met Glu Lys Thr Tyr Asp Pro Lys Ala Ile Glu Lys Lys Trp Ala Asp
1               5                   10                  15

Tyr Trp Glu Lys Arg Gln Leu Ser Lys Pro Thr Ala Gln Gly Ser Pro
            20                  25                  30

Tyr Cys Ile Met Leu Pro Pro Asn Val Thr Gly Thr Leu His Met
        35                  40                  45

Gly His Gly Phe Gln Gln Thr Leu Met Asp Thr Leu Ile Arg Tyr His
    50                  55                  60

Arg Met Lys Gly Glu Arg Thr Leu Trp Gln Gly Thr Asp His Ala
65                  70                  75                  80

Gly Ile Ala Thr Gln Met Val Val Glu Gln Leu Ala Gln Glu Asp
                85                  90                  95

Leu Thr Arg Glu Asp Leu Gly Arg Gln Ala Phe Ile Lys Arg Val Trp
            100                 105                 110

Glu Trp Arg Glu Arg Ser Gly Gly Lys Ile Thr His Gln Met Arg Arg
        115                 120                 125

Leu Gly Val Ser Ile Asp Trp Ser Arg Glu Arg Phe Ser Met Asp Glu
    130                 135                 140

Gly Leu Ser Arg Ala Thr Thr Glu Ala Phe Ile Arg Leu His His Glu
145                 150                 155                 160

Gly Leu Ile Tyr Arg Gly Lys Arg Leu Val Asn Trp Asp Pro Lys Leu
                165                 170                 175

Asn Thr Ala Ile Ser Asp Leu Glu Val Val Thr Glu Glu Val Glu Gly
            180                 185                 190

His Leu Trp His Ile Arg Tyr Pro Leu Ala Glu Gly Ser Gly His Leu
        195                 200                 205

Ile Ile Ala Thr Thr Arg Pro Glu Thr Leu Leu Gly Asp Val Ala Ile
    210                 215                 220

Ala Val His Pro Gln Asp Glu Arg Tyr Gln Pro Phe Val Gly Lys Lys
225                 230                 235                 240

Val Arg Leu Pro Leu Thr Asp Arg Thr Ile Pro Val Ile Ala Asp Glu
                245                 250                 255

Ala Val Asp Lys Glu Phe Gly Thr Gly Ser Leu Lys Ile Thr Pro Gly
            260                 265                 270

His Asp Phe Asn Asp Tyr Glu Ile Gly Gln Arg His Gln Leu Pro Leu
        275                 280                 285

Ile Asn Ile Leu Thr Ser Glu Gly Tyr Leu Asn Glu Asn Val Pro Glu
    290                 295                 300
```

```
Pro Tyr Arg Gly Leu Glu Arg Phe Glu Ala Arg Lys Lys Ile Ile Ala
305                 310                 315                 320

Asp Leu Gln Arg Glu Asn Leu Leu Glu Lys Thr Glu Pro Tyr Arg Val
            325                 330                 335

Pro Val Pro Arg Gly Glu Arg Ser Gly Val Ile Ile Glu Pro Leu Leu
            340                 345                 350

Thr Asp Gln Trp Phe Ile Lys Met Glu Ala Leu Ala Lys Pro Ala Met
            355                 360                 365

Glu Ala Val Glu Ser Gly Leu Lys Phe Ile Pro Lys Asn Trp Glu
370                 375                 380

Lys Thr Tyr Leu Gln Trp Leu Ser Asn Ile Gln Asp Trp Cys Ile Ser
385                 390                 395                 400

Arg Gln Leu Trp Trp Gly His Arg Leu Pro Val Trp Tyr Asp Glu Glu
            405                 410                 415

Lys Asn Ser Tyr Val Gly Arg Ser Arg Glu Glu Ile Leu Lys Lys Tyr
            420                 425                 430

His Leu Ser Pro Asp Val Lys Leu Gln Gln Glu Thr Asp Val Leu Asp
            435                 440                 445

Thr Trp Phe Ser Ala Ser Leu Trp Pro Phe Ala Thr Leu Gly Trp Pro
450                 455                 460

Glu Lys Thr Glu Ser Phe Lys Thr Phe Tyr Pro Thr Gln Val Leu Val
465                 470                 475                 480

Thr Gly Phe Asp Ile Ile Phe Phe Trp Val Ala Arg Met Val Met Met
            485                 490                 495

Gly Leu Lys Leu Thr His Lys Ile Pro Phe His Ser Val Tyr Ile His
            500                 505                 510

Gly Leu Ile Arg Asp Ser Gln Gly Arg Lys Met Ser Lys Ser Lys Gly
            515                 520                 525

Asn Val Ile Asp Pro Ile Asp Ile Asp Gly Ile Ser Leu Asp Ala
            530                 535                 540

Leu Ile Glu Lys Arg Thr His Ala Leu Leu Gln Pro Lys Met Ala Lys
545                 550                 555                 560

Thr Ile Glu Lys Met Thr Arg Lys Glu Phe Pro Asn Gly Ile Ala Ser
            565                 570                 575

Phe Gly Thr Asp Ala Leu Arg Phe Thr Phe Cys Ala Leu Ala Ser Arg
            580                 585                 590

Gly Arg Asp Ile Asn Phe Asp Met Gly Arg Ile Asp Gly Tyr Arg Asn
            595                 600                 605

Phe Cys Asn Lys Ile Trp Asn Ala Ala Arg Phe Val Thr Met Asn Thr
            610                 615                 620

Gln Glu Lys Asp Leu Asn Pro Glu Lys Pro Leu Ser Tyr Ser Ala Ala
625                 630                 635                 640

Asp Glu Trp Ile Arg Thr Arg Leu Gln Gln Thr Ile Lys Asn Ala Glu
            645                 650                 655

Glu Ala Leu Ser Gln Tyr Arg Phe Asp Leu Leu Ala Gln Thr Leu Tyr
            660                 665                 670

Glu Phe Thr Trp Asn Glu Tyr Cys Asp Trp Tyr Val Glu Phe Ala Lys
            675                 680                 685

Cys Ile Leu Tyr Asp Lys Gln Ala Lys Pro Ala Gln Leu Arg Gly Thr
            690                 695                 700

Arg Val Ala Leu Leu Glu Val Leu Glu Ile Leu Leu Arg Leu Leu His
705                 710                 715                 720

Pro Val Met Pro Phe Ile Thr Glu Glu Ile Trp Gln Thr Val Ala Pro
```

```
                    725                 730                 735
Leu Ala Gly Lys Glu Gly Lys Ser Ile Met Val Glu His Trp Pro Gln
            740                 745                 750

Phe Asn Ile His Glu Met Asn Tyr Asp Ala Lys Val Glu Ile Glu Trp
            755                 760                 765

Val Lys Asn Val Ile Thr Ala Ile Arg Thr Leu Arg Ala Glu Ile Gly
            770                 775                 780

Ile Ser Pro Ala Lys Arg Ile Pro Val Ile Phe Gly Lys Gly Asp Glu
785                 790                 795                 800

Lys Asp Lys Lys Arg Ile Ala Lys Met Lys Ser Tyr Ile Lys Thr Leu
                805                 810                 815

Gly Lys Val Ser Gln Leu Arg Phe Ala Lys His Asp Asp Cys Phe Ser
            820                 825                 830

Ala Thr Ala Thr Gly Ile Val Glu Arg Leu Glu Ile His Ile Pro Leu
            835                 840                 845

Ala Gly Val Ile Asp Lys Gln Thr Glu Ile Ala Arg Leu Lys Lys Glu
            850                 855                 860

Ile Ser Lys Leu Gln Lys Glu Glu Lys Ser Leu Lys Lys Leu Asp
865                 870                 875                 880

Asn Pro Asn Tyr Leu Gln Arg Ala Pro Gln Glu Val Val Glu Lys Glu
                885                 890                 895

Arg Leu Ser Leu Glu Lys Thr Gln Asn Ala Leu Lys Lys Leu Gln Ser
            900                 905                 910

Gln Tyr Ala Ser Ile Glu Ser Leu
        915                 920

<210> SEQ ID NO 47
<211> LENGTH: 89
<212> TYPE: PRT
<213> ORGANISM: Coxiella burnetii

<400> SEQUENCE: 47

Met Ser Leu Ala Ser Ala Glu Thr Ala Lys Ile Val Lys Glu Tyr Gln
1               5                   10                  15

Leu Gly Lys Asp Asp Thr Gly Ser Pro Glu Val Gln Val Ala Ile Leu
            20                  25                  30

Thr Ala Lys Ile Ile Lys Leu Thr Asp His Met Lys Ala His Lys His
        35                  40                  45

Asp His His Ser Arg Arg Gly Leu Leu Arg Met Val Ser Gln Arg Arg
    50                  55                  60

Lys Leu Leu Asn Phe Leu Lys Arg Asn Asp Leu Gln Arg Tyr Leu Lys
65                  70                  75                  80

Leu Ile Glu Arg Leu Gly Leu Arg Ser
                85

<210> SEQ ID NO 48
<211> LENGTH: 169
<212> TYPE: PRT
<213> ORGANISM: Coxiella burnetii

<400> SEQUENCE: 48

Met Arg Leu Ile Asp Glu Lys Gly Glu Gln Val Gly Val Val Arg Thr
1               5                   10                  15

Asp Arg Ala Leu Thr Met Ala Glu Glu Ala Gly Leu Asp Leu Val Glu
            20                  25                  30

Ile Ser Pro Thr Ala Lys Pro Pro Val Cys Arg Ile Met Asn Phe Gly
```

```
                35                  40                  45
Lys Tyr Gln Phe Glu Gln Ser Lys Arg Lys Ala Ala Gln Lys Lys
 50                  55                  60

Gln Arg Leu Val His Leu Lys Glu Val Lys Phe Arg Pro Gly Thr Asp
 65                  70                  75                  80

Val Gly Asp Tyr Gln Val Lys Leu Arg Lys Ile Ala Thr Phe Leu Asp
                 85                  90                  95

Arg Gly Asp Lys Val Lys Val Ser Leu Arg Phe Arg Gly Arg Glu Met
                100                 105                 110

Gln His Arg Glu Leu Gly Leu Glu Leu Leu Gly Arg Val Lys Arg Asp
            115                 120                 125

Leu Gly Asn Ile Val Val Glu Gln Glu Pro Arg Leu Glu Gly Arg Gln
        130                 135                 140

Met Thr Met Val Val Met Lys Ala Lys Gly Gly Asn Lys Thr Lys
145                 150                 155                 160

Arg Glu Asp His Ala Glu Ile Lys Asp
                165

<210> SEQ ID NO 49
<211> LENGTH: 185
<212> TYPE: PRT
<213> ORGANISM: Coxiella burnetii

<400> SEQUENCE: 49

Met Ile Asn Asp Ile Ile Asn Asp Ser Lys Ser Arg Met Glu Lys Ser
 1               5                  10                  15

Leu Gly Ser Leu Lys Thr Glu Leu Ala Lys Leu Arg Thr Cys Arg Ala
                 20                  25                  30

His Pro Ser Leu Leu Glu His Ile Lys Val Asp Tyr Tyr Asn Val Glu
             35                  40                  45

Thr Pro Leu Ser Gln Val Ala Ser Ile Ala Ile Glu Asn Pro Arg Thr
         50                  55                  60

Leu Ser Ile Thr Pro Trp Glu Lys Asn Met Val Gly Pro Ile Glu Lys
 65                  70                  75                  80

Ala Ile Gln Lys Ala Asp Leu Gly Leu Asn Pro Ala Thr Val Gly Met
                 85                  90                  95

Val Ile Arg Val Pro Leu Pro Pro Leu Thr Glu Glu Arg Arg Lys Glu
                100                 105                 110

Leu Ala Arg Val Val Arg Glu Glu Ala Glu His Ala Arg Val Ala Ile
            115                 120                 125

Arg Asn Ile Arg Arg Glu Ala Asn Asn Asp Leu Lys Glu Leu Met Lys
        130                 135                 140

Glu Lys Glu Ile Ser Glu Asp Glu Glu Arg Arg Ala Gln Thr Ala Ile
145                 150                 155                 160

Gln Lys Leu Thr Asp Ala Gln Ile Ala Glu Val Asp Lys Met Ala Ser
                165                 170                 175

Gln Lys Glu Ala Asp Leu Met Ala Val
                180                 185

<210> SEQ ID NO 50
<211> LENGTH: 99
<212> TYPE: PRT
<213> ORGANISM: Coxiella burnetii

<400> SEQUENCE: 50

Met Ala Leu Leu Lys Ser Arg Asp Ile Asp Lys Ile Ala Asn Leu Ser
```

-continued

```
               1               5                  10                 15
Lys Leu Ile Ile Pro Lys Asn Glu Asn Asp Ala Leu Leu Glu Ala Leu
                    20                  25                  30

Asn Lys Thr Phe Asp Leu Val Ile Lys Met Asp Lys Val Asp Thr Ser
                35                  40                  45

Ala Val Asp Pro Leu Ala His Pro Tyr Asn Glu Thr Gln Pro Leu Arg
            50                  55                  60

Glu Asp His Val Thr Glu Ser Asn Gln Arg Asp Leu Phe Gln Lys Ser
65                  70                  75                  80

Ala Pro Gln Val Glu Ala Gly Leu Tyr Met Val Pro Val Val Ile Asp
                    85                  90                  95

Asn Glu Gly
```

<210> SEQ ID NO 51
<211> LENGTH: 149
<212> TYPE: PRT
<213> ORGANISM: Coxiella burnetii

<400> SEQUENCE: 51

```
Met Thr Glu Ser Leu Lys Asn Arg Ile Gln Glu Asp Met Lys Ala Ala
1               5                  10                  15

Met Arg Ala Gln Glu Lys Gly Arg Leu Gly Thr Ile Arg Leu Leu Leu
                20                  25                  30

Ala Ala Ile Lys Gln Arg Glu Ile Asp Glu Gln Ile Thr Leu Asp Asp
                35                  40                  45

Ala Gly Val Met Lys Val Ile Glu Lys Met Ile Lys Gln Arg Arg Asp
            50                  55                  60

Ser Ile Thr Gln Tyr Glu Ala Gly Asn Arg Pro Asp Leu Ala Glu Lys
65                  70                  75                  80

Glu Lys Gln Glu Ile Asp Val Leu Gln Ala Tyr Leu Pro Glu Ala Leu
                    85                  90                  95

Ser Asp Ala Glu Ile Asp Ile Ala Val Lys Gln Ala Ile Glu Glu Thr
                100                 105                 110

Gly Ala Thr Ser Met Lys Asp Met Gly Gln Leu Met Gly Val Leu Lys
                115                 120                 125

Gly Lys Leu Gln Gly Arg Val Asp Met Ser Met Val Ser Lys Lys Val
            130                 135                 140

Lys Glu His Leu Ser
145
```

<210> SEQ ID NO 52
<211> LENGTH: 187
<212> TYPE: PRT
<213> ORGANISM: Coxiella burnetii

<400> SEQUENCE: 52

```
Met Ser Gly Gly Val Lys Leu Ile Ala Gly Leu Gly Asn Pro Gly Asp
1               5                  10                  15

Gln Tyr Ala Arg Thr Arg His Asn Val Gly Ala Trp Phe Leu Glu Thr
                20                  25                  30

Leu Ala Gln Gln Arg Asn Gln Ser Leu Ala Lys Glu Asn Lys Phe His
                35                  40                  45

Gly Phe Val Ala Lys Cys Asn Asp Tyr Trp Leu Leu Lys Pro Thr Thr
            50                  55                  60

Phe Met Asn Glu Ser Gly Gln Ala Val Ala Ala Leu Ala His Phe Tyr
65                  70                  75                  80
```

```
Lys Ile Lys Pro Ser Glu Ile Leu Ile Ala His Asp Glu Leu Asp Phe
                85                  90                  95

Pro Ala Gly Asp Ile Arg Leu Lys Glu Gly Gly His Gly His
            100                 105                 110

Asn Gly Leu Arg Asn Ile Ile Gln His Leu Gly Ser Ser Asp Phe Tyr
            115                 120                 125

Arg Leu Arg Ile Gly Ile Asn His Pro Gly His Lys Asp Arg Val Thr
        130                 135                 140

Pro Tyr Val Leu Ser Pro Ser Glu Asn Asp Arg Ile Ala Ile Leu
145                 150                 155                 160

Ala Ala Ile Glu Lys Gly Leu Arg Leu Ile Pro Glu Leu Val Gln Gly
                165                 170                 175

Asp Phe Gln Lys Val Met Arg Glu Leu His Ser
            180                 185

<210> SEQ ID NO 53
<211> LENGTH: 276
<212> TYPE: PRT
<213> ORGANISM: Coxiella burnetii

<400> SEQUENCE: 53

Met Lys Val Asn Phe Thr Lys Met Gln Gly Ser Gly Asn Asp Phe Val
1               5                   10                  15

Val Ile Asp Ala Thr Lys Thr Pro Phe Gln Leu Thr Thr Ser Gln Ile
                20                  25                  30

Gln Lys Met Ala Asn Arg Arg Phe Gly Val Gly Phe Asp Gln Leu Leu
            35                  40                  45

Val Ile Glu Pro Pro Lys Asn Asn Ser Val Asp Phe His Phe Arg Ile
        50                  55                  60

Phe Asn Ala Asp Gly Ser Glu Val Gly Gln Cys Gly Asn Gly Ala Arg
65                  70                  75                  80

Cys Ile Ala Arg Phe Ile Arg Ala His Gln Leu Ser Asp Arg Glu Glu
                85                  90                  95

Leu Arg Val Ser Thr Leu Asn Glu Val Leu Glu Leu Lys Ile Gln Pro
            100                 105                 110

Asp Gly Lys Val Ser Val Lys Met Gly Val Pro Arg Phe Glu Pro Thr
        115                 120                 125

Glu Ile Pro Phe Ile Ala Ser Gly Val Ala Asn Phe Tyr Asp Ile Ala
130                 135                 140

Val Asp Asn Gln Ile Val Lys Leu Gly Val Val Asn Ile Gly Asn Pro
145                 150                 155                 160

His Ala Ile Ile Pro Val Glu Arg Ile Asn Ala Glu Glu Val Gly Lys
                165                 170                 175

Leu Gly Ala Arg Leu Ser Val His Glu Cys Phe Pro Glu Gly Ala Asn
            180                 185                 190

Val Gly Phe Met Gln Val Ile Asp Pro Gln Asn Ile Arg Leu Arg Val
        195                 200                 205

Tyr Glu Arg Gly Thr Gly Glu Thr Leu Ala Cys Gly Ser Asn Ala Cys
210                 215                 220

Ala Ala Val Ala Val Gly Arg Arg Cys Gly Leu Leu Gln Glu Arg Val
225                 230                 235                 240

Val Val Ser Gln Pro Gly Gly Ser Leu Thr Ile Asp Trp Gln Gly Pro
                245                 250                 255

Leu Thr Pro Val Thr Met Thr Gly Pro Ala Thr Thr Val Phe Cys Gly
```

260                 265                 270

Glu Trp Leu Asp
        275

<210> SEQ ID NO 54
<211> LENGTH: 410
<212> TYPE: PRT
<213> ORGANISM: Coxiella burnetii

<400> SEQUENCE: 54

Met Asn Gln Thr Asp Ile Ile Ile Gly Ala Gly Leu Val Gly Thr
1               5                   10                  15

Ser Val Ala Val Ala Leu Gln Gly His Gly Ile Lys Ile Lys Ile Leu
                20                  25                  30

Glu His His Leu Pro Ser Ala Ala Val Thr Ser Ser Asn Asp Val Arg
                35                  40                  45

Pro Leu Thr Leu Ser Phe Gly Ser Tyr Gln Ile Leu Lys Asn Leu Gly
            50                  55                  60

Val Glu Ala Asp Leu Ala Asn Glu Ala Cys Pro Ile Ser Thr Val His
65                  70                  75                  80

Val Ser Asp Gln Gly Ala Leu Gly Ala Leu Arg Phe Arg Ala Ser Glu
                85                  90                  95

Phe Asn Val Pro Ala Leu Gly Tyr Val Val Ser Phe Ala Lys Leu Gln
                100                 105                 110

Gln Ser Leu Tyr Gln Arg Ala Ala Leu Gln Lys Asn Ala Glu Ile Val
            115                 120                 125

Pro Ile Ser Thr Ile Asp Asp Ile Gln Cys Asn Thr Asn His Ala Gln
130                 135                 140

Val Thr Phe Ser Thr Ile Asn Gly Gln Gln Leu Gln Ala Asp Leu
145                 150                 155                 160

Leu Ile Ala Ala Asp Gly Thr His Ser Thr Ala Arg Arg Leu Leu Lys
                165                 170                 175

Ile Pro Val Glu Glu Asn Arg Asn Glu Val Ala Leu Ile Ala Leu
                180                 185                 190

Leu Arg Leu Lys Gln Pro His Asn His Ile Ala Tyr Glu Arg Phe Thr
            195                 200                 205

Ser Gln Gly Thr Leu Ala Leu Leu Pro Leu Phe Gln Ala Asn Gln Cys
210                 215                 220

Arg Leu Val Trp Thr Leu Pro Lys Thr Lys Ala Asp Glu Ile Glu Gln
225                 230                 235                 240

Leu Ser Asp Asp Glu Phe Arg Ala Val Leu His Arg Val Phe Lys Pro
                245                 250                 255

Tyr Ile Gly Ala Ile Gln Ser Val Glu Arg Gly Lys Arg Phe Pro Leu
                260                 265                 270

Gln Met Leu Ile Ala Gln Glu Gln Val Arg Pro Ser Phe Val Met Leu
            275                 280                 285

Gly Asn Ala Ser His Thr Leu Tyr Pro Ile Ala Ala Gln Gly Phe Asn
        290                 295                 300

Leu Gly Leu Arg Asp Ala Ala Val Leu Ser Glu Val Leu Ile Asp Ala
305                 310                 315                 320

Arg Arg Gln Leu Lys Pro Leu Gly Asp Ile Arg Phe Leu Gln Glu Tyr
                325                 330                 335

Ser Arg Trp Arg Lys Thr Asp Gln Ala Arg Ile Thr Gly Leu Thr Arg
            340                 345                 350

Gly Leu Ser Gln Trp Phe Gly Val Gln Leu Pro Leu Ala Asn Gln Ala
            355                 360                 365

Arg Gly Leu Gly Leu Leu Ala Thr Gly Leu Leu Pro Pro Phe Lys Lys
370                 375                 380

Arg Leu Ala Lys Arg Leu Met Gly Leu Ser Gly Arg Leu Pro Gln Leu
385                 390                 395                 400

Met Arg Gly Leu Lys Leu Asp Asp Ala Ile
            405                 410

<210> SEQ ID NO 55
<211> LENGTH: 112
<212> TYPE: PRT
<213> ORGANISM: Coxiella burnetii

<400> SEQUENCE: 55

Met Ser Glu His Val His Thr Ala Ser Asp Glu Asn Phe Glu Thr Glu
1               5                   10                  15

Val Leu Gln Ala Asp Met Pro Val Leu Val Asp Phe Trp Ala Glu Trp
            20                  25                  30

Cys Gln Pro Cys Lys Met Ile Ser Pro Val Val Glu Glu Ile Ala Lys
        35                  40                  45

Glu Tyr Ala Gly Arg Val Lys Val Phe Lys Leu Asn Val Asp Glu Asn
    50                  55                  60

Ala Gln Thr Pro Thr Lys Tyr Gly Val Arg Gly Ile Pro Ser Leu Leu
65                  70                  75                  80

Ile Phe Arg Glu Gly Glu Val Val Asp Arg Lys Val Gly Ala Leu Asn
                85                  90                  95

Lys Ser Gln Leu Ala Ala Phe Leu Asp Glu Ser Leu His Phe Ser Ser
            100                 105                 110

<210> SEQ ID NO 56
<211> LENGTH: 255
<212> TYPE: PRT
<213> ORGANISM: Coxiella burnetii

<400> SEQUENCE: 56

Met Phe Val Asp Ser His Cys His Leu Asn Met Leu Asp Leu Ser Pro
1               5                   10                  15

Tyr Glu Gly Asp Leu Gly Ala Leu Ile Asp Lys Ala Lys Ser Met Gly
            20                  25                  30

Val Glu His Ile Leu Cys Val Gly Val Asp Leu Thr His Ala Gln Thr
        35                  40                  45

Val Ile Glu Ile Ala Ala Arg Phe Glu Asn Val Ser Ala Ser Val Gly
    50                  55                  60

Leu His Pro Ser Glu Lys Val Asp His Glu Pro Thr Val Gln Glu Leu
65                  70                  75                  80

Val Glu Val Ala Asn His Pro Lys Val Ala Ile Gly Glu Thr Gly
                85                  90                  95

Leu Asp Tyr Tyr Tyr Asn His Ser Glu Leu Gly Lys Met Arg Asp Arg
            100                 105                 110

Phe Arg Cys His Val Gln Ala Ala Leu Lys Leu Lys Lys Pro Leu Ile
        115                 120                 125

Ile His Ser Arg Ser Ala Gln Thr Asp Thr Ile Gln Ile Met Gln Glu
    130                 135                 140

Glu Asn Ala Gln Ser Val Gly Gly Val Met His Cys Phe Thr Glu Ser
145                 150                 155                 160

-continued

```
Trp Glu Met Ala Glu Gln Ala Met Lys Leu Gly Phe Tyr Ile Ser Phe
                165                 170                 175

Ser Gly Ile Val Thr Phe Lys Asn Ala Lys Asn Val Ala Glu Val Ala
            180                 185                 190

Lys Lys Val Pro Leu Glu Lys Met Leu Ile Glu Thr Asp Ala Pro Tyr
        195                 200                 205

Leu Ala Pro Val Pro Tyr Arg Gly Lys Lys Asn Glu Pro Gln Tyr Ile
    210                 215                 220

Pro Tyr Val Ala Glu Arg Ile Ala Glu Leu Lys Asn Ile Pro Leu Asn
225                 230                 235                 240

Glu Val Ala Arg Lys Thr Thr Glu Asn Tyr Tyr His Leu Phe Gly
                245                 250                 255

<210> SEQ ID NO 57
<211> LENGTH: 159
<212> TYPE: PRT
<213> ORGANISM: Coxiella burnetii

<400> SEQUENCE: 57

Met Lys Pro Ile Ala Ile Tyr Pro Gly Thr Phe Asp Pro Leu Thr Asn
1               5                   10                  15

Gly His Val Asp Ile Ile Glu Arg Ala Leu Pro Leu Phe Asn Lys Ile
            20                  25                  30

Ile Val Ala Cys Ala Pro Thr Ser Arg Lys Asp Pro His Leu Lys Leu
        35                  40                  45

Glu Glu Arg Val Asn Leu Ile Ala Asp Val Leu Thr Asp Glu Arg Val
    50                  55                  60

Glu Val Leu Pro Leu Thr Gly Leu Leu Val Asp Phe Ala Lys Thr His
65                  70                  75                  80

Gln Ala Asn Phe Ile Leu Arg Gly Leu Arg Ala Val Ser Asp Phe Asp
                85                  90                  95

Tyr Glu Phe Gln Leu Ala His Met Asn Tyr Gln Leu Ser Pro Glu Ile
            100                 105                 110

Glu Thr Ile Phe Leu Pro Ala Arg Glu Gly Tyr Ser Tyr Val Ser Gly
        115                 120                 125

Thr Met Val Arg Glu Ile Val Thr Leu Gly Gly Asp Val Ser Pro Phe
    130                 135                 140

Val Pro Pro Leu Val Ala Arg His Leu Gln Lys Arg Arg Glu Lys
145                 150                 155

<210> SEQ ID NO 58
<211> LENGTH: 196
<212> TYPE: PRT
<213> ORGANISM: Coxiella burnetii

<400> SEQUENCE: 58

Met Phe Arg Leu Asp Leu Leu Ser Asp Pro Leu Glu Gln Phe Lys Leu
1               5                   10                  15

Trp Tyr Asp Glu Ala Ile Arg His Glu Thr Leu His Pro Asp Ala Met
            20                  25                  30

Val Leu Ala Thr Ala Asp Ser Lys Gly Lys Pro Ser Ala Arg Asn Val
        35                  40                  45

Leu Tyr Lys Gly Ile Ser Lys Gly Gly Phe Leu Ile Phe Thr Asn Tyr
    50                  55                  60

His Ser Arg Lys Ala His Glu Leu Asp Glu Asn Pro Gln Ala Ala Trp
65                  70                  75                  80
```

Val Phe Tyr Trp Pro Lys Thr Tyr Lys Gln Val Arg Gly Glu Gly Arg
                85                  90                  95

Val Glu Arg Leu Thr Gln Glu Glu Ser Glu Ala Tyr Phe Glu Thr Arg
            100                 105                 110

Ser Tyr Glu Ser Gln Ile Ala Ala Trp Val Ser Glu Gln Ser Gln Glu
            115                 120                 125

Ile Pro Asp Arg Glu Tyr Leu Ile Thr Arg Tyr Lys Lys Tyr Arg Glu
130                 135                 140

Lys Phe Gln Asp Asp Val Arg Cys Pro Glu Phe Trp Gly Gly Phe Arg
145                 150                 155                 160

Leu Ile Pro Asp Arg Met Glu Phe Trp Val Gly Gln Glu His Arg Leu
                165                 170                 175

His Asp Arg Phe Cys Tyr Leu Lys Glu Asn Gln Glu Trp Lys Ile Ile
            180                 185                 190

Arg Leu Ala Pro
        195

<210> SEQ ID NO 59
<211> LENGTH: 195
<212> TYPE: PRT
<213> ORGANISM: Coxiella burnetii

<400> SEQUENCE: 59

Met Ser Val Leu Val Pro Met Val Val Glu Gln Thr Ser Arg Gly Glu
1               5                   10                  15

Arg Ala Tyr Asp Ile Tyr Ser Arg Leu Leu Lys Asp Arg Val Ile Phe
            20                  25                  30

Leu Val Gly Gln Val Glu Asp His Met Ala Asn Leu Ala Ile Ala Gln
        35                  40                  45

Met Leu Phe Leu Glu Ser Glu Asn Pro Asn Lys Asp Ile Asn Leu Tyr
50                  55                  60

Ile Asn Ser Pro Gly Gly Ala Val Thr Ser Ala Met Ala Ile Tyr Asp
65                  70                  75                  80

Thr Met Gln Phe Val Lys Pro Asp Val Arg Thr Leu Cys Ile Gly Gln
                85                  90                  95

Ala Ala Ser Ala Gly Ala Leu Leu Leu Ala Gly Gly Ala Lys Gly Lys
            100                 105                 110

Arg His Cys Leu Pro His Ser Ser Val Met Ile His Gln Val Leu Gly
            115                 120                 125

Gly Tyr Gln Gly Gln Gly Thr Asp Ile Gln Ile His Ala Lys Gln Thr
130                 135                 140

Gln Arg Val Ser Asp Gln Leu Asn Gln Ile Leu Ala Lys His Thr Gly
145                 150                 155                 160

Lys Asp Ile Glu Arg Val Glu Lys Asp Thr Asn Arg Asp Tyr Phe Leu
                165                 170                 175

Thr Pro Glu Glu Ala Val Glu Tyr Gly Leu Ile Asp Ser Ile Phe Lys
            180                 185                 190

Glu Arg Pro
        195

<210> SEQ ID NO 60
<211> LENGTH: 465
<212> TYPE: PRT
<213> ORGANISM: Coxiella burnetii

<400> SEQUENCE: 60

```
Met Ala Asp Leu Asn His Ser Tyr Leu Thr Glu Asn Ala Pro Leu Ala
1               5                   10                  15

Ala Gln Met Thr Met Thr Pro Arg Glu Ile Val Ala Glu Leu Asp Lys
            20                  25                  30

Phe Ile Ile Gly Gln Asn Asp Ala Lys Arg Ala Val Ala Ile Ala Leu
        35                  40                  45

Arg Asn Arg Trp Arg Arg Met Gln Leu Gly Glu Leu Arg Arg Glu
    50                  55                  60

Ile Phe Pro Lys Asn Ile Leu Met Ile Gly Pro Thr Gly Val Gly Lys
65                  70                  75                  80

Thr Glu Ile Ala Arg Arg Leu Ser Asp Leu Ala Gly Ala Pro Phe Leu
                85                  90                  95

Lys Ile Glu Ala Thr Lys Phe Thr Glu Val Gly Tyr Val Gly Arg Asp
            100                 105                 110

Val Glu Ser Ile Ile Arg Asp Leu Val Asp Val Ala Val Lys Met Thr
            115                 120                 125

Arg Glu Lys Ala Ile Arg Gln Val Lys Ser Leu Ala Glu Glu Ala Ala
        130                 135                 140

Glu Glu Arg Val Leu Asp Ala Leu Ile Pro Pro Ala Arg Gly Gly Phe
145                 150                 155                 160

Gln Gly Glu Pro Thr Ala Glu Glu Lys Pro Thr Glu Lys Lys Glu Ser
                165                 170                 175

Ala Thr Arg Gln Leu Phe Arg Lys Lys Leu Arg Asn Gly Glu Leu Asp
            180                 185                 190

Asp Lys Glu Ile Glu Val Glu Val Ser Ala His Pro Ser Phe Glu Ile
        195                 200                 205

Met Gly Pro Pro Gly Met Glu Glu Met Val Ser Gln Leu Gln Gly Ile
210                 215                 220

Met Ser Ser Met Ser Ser Arg Arg Ser Lys Ser Arg Arg Leu Lys Val
225                 230                 235                 240

Lys Asp Ala Leu Arg Ile Leu Gly Glu Glu Ala Ala Lys Leu Val
            245                 250                 255

Asp Glu Asp Gln Ile Lys Ser Thr Ala Leu Ala Ser Val Glu Gln Asn
        260                 265                 270

Gly Ile Val Phe Ile Asp Glu Ile Asp Lys Ile Val Lys Arg Glu Gly
        275                 280                 285

Ala Val Gly Ala Asp Val Ser Arg Glu Gly Val Gln Arg Asp Leu Leu
        290                 295                 300

Pro Leu Val Glu Gly Ser Thr Val Phe Thr Lys Tyr Gly Met Val Lys
305                 310                 315                 320

Thr Asp His Ile Leu Phe Ile Ala Ser Gly Ala Phe His Ile Ala Lys
            325                 330                 335

Pro Ser Asp Leu Val Pro Glu Leu Gln Gly Arg Phe Pro Ile Arg Val
            340                 345                 350

Glu Leu Lys Ala Leu Thr Ala Asp Asp Phe Val Arg Ile Leu Thr Glu
        355                 360                 365

Pro Lys Ala Ser Leu Thr Glu Gln Tyr Thr Glu Leu Leu Lys Thr Glu
        370                 375                 380

Asn Phe Gly Leu Ser Phe Thr Lys Asp Gly Ile Lys Arg Leu Ala Glu
385                 390                 395                 400

Ile Ala Tyr Gln Val Asn Asp Arg Ser Glu Asn Ile Gly Ala Arg Arg
            405                 410                 415

Leu His Thr Ile Met Glu Arg Leu Leu Glu Glu Val Ser Phe Glu Ala
```

```
                420             425             430
Thr Asp Lys Gln Gly Glu Ser Ile Thr Ile Asp Ala Asp Tyr Val Asn
                435                 440                 445
Lys Gln Leu Lys Lys Leu Ala Glu Asp Glu Leu Ser Arg Tyr Ile
    450                 455                 460
Leu
465

<210> SEQ ID NO 61
<211> LENGTH: 517
<212> TYPE: PRT
<213> ORGANISM: Coxiella burnetii

<400> SEQUENCE: 61

Met Glu Gln Ile Ala Ala Arg Val Thr Tyr Ile Asn Leu Ser Pro Asp
 1               5                  10                  15
Glu Leu Ile Gln His Ala Val Lys Asn Gly Glu Gly Val Leu Ser Ser
                20                  25                  30
Thr Gly Ala Leu Ala Val Thr Thr Gly Lys Arg Thr Gly Arg Ser Pro
            35                  40                  45
Lys Asp Arg Phe Ile Val Lys Asp Glu Gln Thr Ala Asp Gln Val Ala
 50                  55                  60
Trp Gly Asn Ile Asn Gln Pro Val Gln Arg Thr Phe Asp Gln Leu
 65                  70                  75              80
Trp Glu Arg Ala Leu Arg Tyr Leu Ser Glu Arg Ala Val Tyr Ile Ser
                85                  90                  95
His Leu Gln Val Gly Ala Asp Asp Asn Tyr Phe Leu Pro Leu Lys Val
                100                 105                 110
Val Thr Glu Phe Ala Trp His Asn Leu Phe Ala Cys Asp Leu Phe Ile
            115                 120                 125
Arg Pro Ser Gly Asp His Ala Asn Gly Lys Pro Ser Trp Val Ile Leu
130                 135                 140
Ser Ala Pro Gly Leu Lys Thr Asp Pro Glu Arg Asp Gly Val Asn Ser
145                 150                 155                 160
Asp Gly Ala Val Met Ile Asn Leu Ser Gln Arg Arg Val Leu Leu Val
                165                 170                 175
Gly Met Pro Tyr Ala Gly Glu Met Lys Lys Ala Met Phe Ser Val Leu
            180                 185                 190
Asn Tyr Leu Leu Pro Pro His Asp Val Leu Pro Met His Cys Ala Ala
            195                 200                 205
Asn Ala Gly Gln Ser Gly Asp Val Ala Leu Phe Phe Gly Leu Ser Gly
        210                 215                 220
Thr Gly Lys Thr Thr Leu Ser Ala Asp Pro His Arg Phe Leu Ile Gly
225                 230                 235                 240
Asp Asp Glu His Gly Trp Ser Ala Thr Ser Val Phe Asn Phe Glu Gly
                245                 250                 255
Gly Cys Tyr Ala Lys Cys Ile Asp Leu Ser Gln Glu Arg Glu Pro Met
            260                 265                 270
Ile Trp Asn Ala Ile Arg His Gly Ala Ile Met Glu Asn Val Val Leu
        275                 280                 285
Asp Glu Asn Gly Val Pro Asp Tyr Ala Asp Ala Arg Leu Thr Gln Asn
        290                 295                 300
Ser Arg Ala Ala Tyr Pro Arg Glu Tyr Ile Pro Leu Arg Val Glu Asn
305                 310                 315                 320
```

Asn Arg Gly Arg Pro Pro Asp Ala Val Leu Phe Leu Thr Cys Asp Leu
            325                 330                 335

Asp Gly Val Leu Pro Pro Val Ala Leu Leu Thr Lys Glu Gln Ala Ala
        340                 345                 350

Tyr Tyr Phe Leu Ser Gly Tyr Thr Ala Leu Val Gly Ser Thr Glu Val
            355                 360                 365

Gly Ser Val Lys Gly Val Thr Ser Thr Phe Ser Thr Cys Phe Gly Ala
370                 375                 380

Pro Phe Phe Pro Arg Pro Thr Val Tyr Ala Glu Leu Leu Met Lys
385                 390                 395                 400

Arg Ile Glu Ala Thr Gly Cys Gln Val Tyr Leu Val Asn Thr Gly Trp
                405                 410                 415

Thr Gly Gly Ala Tyr Gly Glu Gly Gly Glu Arg Phe Ser Ile Pro Thr
            420                 425                 430

Thr Arg Ala Ile Val Asn Ala Val Leu Ser Gly Lys Leu Lys Glu Gly
        435                 440                 445

Pro Thr Glu Val Leu Ser Gly Phe Asn Leu Thr Ile Pro Lys Ser Ala
    450                 455                 460

Leu Gly Val Asp Asp His Leu Leu Asn Pro Arg Lys Thr Trp Glu Asp
465                 470                 475                 480

Val Ser Ala Tyr Asp Ala Arg Ala Gln Arg Leu Ile Gln Lys Phe Arg
                485                 490                 495

Glu Asn Phe Glu Lys Phe Lys Val Leu Ala Ala Ile Arg Glu Ala Gly
            500                 505                 510

Pro Ser Asp Val His
        515

<210> SEQ ID NO 62
<211> LENGTH: 195
<212> TYPE: PRT
<213> ORGANISM: Coxiella burnetii

<400> SEQUENCE: 62

Met Ser Arg Lys Phe Thr Asp Lys Ile Lys Gly Ile Val Met Asn Asn
1               5                   10                  15

Leu Val Lys Asn Ser Gly Leu Ala Val Ile Ala Leu Ala Thr Leu Asn
            20                  25                  30

Leu Ser Gly Cys Lys His His Pro Ala Gly Ala Asn Ala Ala Thr Gly
        35                  40                  45

Leu Ser Asp Gly Thr Gly Ala Gln Ala Tyr Ala Leu Ala Glu Gly Lys
    50                  55                  60

Gly Tyr Gln Gly Gln Leu Lys Lys Asp Ser Glu Gly Arg Ile Ile Asn
65                  70                  75                  80

Pro Leu Val Ala Pro Ala Asn Gln Thr Tyr Tyr Phe Asp Phe Asp Ser
                85                  90                  95

Thr Gln Leu Arg Ser Leu Asp Leu Gly Ala Ile Arg Val Gln Ala Asn
            100                 105                 110

Tyr Leu Ala Thr His Ser Thr Ala Lys Val Arg Leu Glu Gly Asn Thr
        115                 120                 125

Asp Asn Arg Gly Ser Arg Glu Tyr Asn Ile Gly Leu Gly Trp Arg Arg
    130                 135                 140

Asp Gln Ala Val Ala Arg Ile Leu Glu Gln Glu Gly Val Ala Pro Lys
145                 150                 155                 160

Gln Ile Asp Met Val Ser Tyr Gly Lys Glu Arg Pro Ala Val Met Gly
                165                 170                 175

```
Asn Asn Glu Asn Ala Trp Arg Leu Asn Arg Arg Val Asn Leu Ile Tyr
            180                 185                 190

Glu Ala Tyr
        195

<210> SEQ ID NO 63
<211> LENGTH: 517
<212> TYPE: PRT
<213> ORGANISM: Coxiella burnetii

<400> SEQUENCE: 63

Met Gln Thr Lys Val Glu Gly Leu Ala His Ile Leu Leu Gln Thr Asn
1               5                   10                  15

Ala Leu Thr Asn Ser Gln Ile Ala Arg Ala Ile Glu Gln Ala Ala Gly
            20                  25                  30

Ala Gln Ser Pro Leu Leu His Tyr Leu Val Thr Glu Lys Ile Val Ser
        35                  40                  45

Ser Glu Lys Ile Ala Glu Ala Cys Ala Thr Tyr Phe Gly Leu Glu Ala
    50                  55                  60

Ile Asn Leu Gln Thr Gln Pro Leu Asn Pro Ser Leu Cys His Glu Ile
65                  70                  75                  80

Pro Arg Lys Tyr Leu Met Arg Tyr Ala Phe Ile Pro Leu Ala Val Lys
                85                  90                  95

Ser Pro Thr Leu Ala Ile Ser Asp Pro Leu Tyr Phe Pro Leu Ile Glu
            100                 105                 110

Glu Leu Gln Phe Gln Thr Asn Lys Gln Tyr Lys Ile Val Phe Ala Pro
        115                 120                 125

Tyr Lys Ser Phe Ala Ala Leu Ile Asn Asn Phe Val Ser Arg Gln Ile
    130                 135                 140

Tyr Glu Thr Val Ser Gln Gly Glu Ala Ser Ile Val Glu Leu Val Asn
145                 150                 155                 160

Gln Val Leu Thr Asp Ala Ile Tyr Arg Glu Ala Ser Asp Val His Phe
                165                 170                 175

Glu Pro Met Gln Gln His Tyr Arg Ile Arg Met Cys Ile Asp Gly Ile
            180                 185                 190

Leu His Thr Thr Thr Leu Leu Pro Asn Thr Gln Ser Pro Ala Met Ser
        195                 200                 205

Ser Arg Leu Lys Val Leu Ala Glu Leu Asp Ile Ser Glu Lys Arg Leu
    210                 215                 220

Pro Gln Asp Gly Arg Phe Tyr Phe Thr Thr Leu Thr His Leu Lys Arg
225                 230                 235                 240

Asp Cys Arg Leu Ser Ser Cys Pro Thr Leu Phe Gly Glu Lys Ile Val
                245                 250                 255

Ile Arg Leu Leu Asn Pro Val His His Leu Leu Lys Phe Glu Glu Leu
            260                 265                 270

Gly Leu Glu Glu Lys Pro Lys Gln Leu Ile Met Lys Lys Ile Lys Gln
        275                 280                 285

Leu Gln Gly Leu Ile Leu Val Thr Gly Pro Thr Arg Ser Gly Lys Thr
    290                 295                 300

Val Ser Leu Tyr Ala Ala Leu Asn Gln Ile Asn Ser Thr Gln Lys Asn
305                 310                 315                 320

Ile Ser Thr Val Glu Asp Pro Ile Glu Ile Gln Leu Ala Gly Val Thr
                325                 330                 335

Gln Val Asn Ile Arg Pro Lys Ala Gly Leu Asn Phe Ala Ala Val Leu
```

-continued

```
                340                 345                 350
Arg Val Phe Leu Arg Gln Asp Pro Asp Val Ile Met Val Gly Glu Ile
            355                 360                 365
Arg Asp Phe Glu Thr Ala Ser Ile Ala Val Arg Ala Ala His Thr Gly
370                 375                 380
His Leu Val Leu Ser Thr Leu His Thr Asn Ser Ala Val Glu Cys Ile
385                 390                 395                 400
Thr Arg Leu Ile Asp Met Gly Ile Glu Pro Phe Asn Leu Ala Ser Val
                405                 410                 415
Leu Lys Leu Val Val Ala Gln Arg Leu Val Arg Gln Leu Cys Ala His
            420                 425                 430
Cys Gln Ala Thr Lys Ile Ser Cys Pro Phe Cys Leu Asn Gly Tyr Gln
        435                 440                 445
Gly Arg Thr Gly Ile Tyr Glu Val Leu Pro Ile Thr Pro Ser Ile Ile
    450                 455                 460
Glu Leu Ile Leu Gln Lys Arg Ser Ala Gln Glu Ile Asn Ala Cys Ala
465                 470                 475                 480
Ile Gln Glu Gly Met Gln Thr Leu Trp Gln Ala Leu Asn Lys Ala
                485                 490                 495
Lys Thr Gly Ile Thr Asn Leu Asn Glu Ile Tyr Arg Val Ile Gln Ser
            500                 505                 510
Glu Asn Asn Tyr Ala
        515

<210> SEQ ID NO 64
<211> LENGTH: 1044
<212> TYPE: PRT
<213> ORGANISM: Coxiella burnetii

<400> SEQUENCE: 64

Met Lys Arg Ile Ala Val Phe Ile Leu Thr Leu Ser Phe Phe Ser Ile
1               5                   10                  15
Ser Tyr Ser Asp Lys Asn Pro Val Phe Gln Glu Tyr Tyr Glu Gly Asn
            20                  25                  30
Tyr Arg Ala Ala Glu Thr Gly Leu Lys Gln Leu Ala Glu Lys Asn Asn
        35                  40                  45
Gly Glu Ala Thr Phe Tyr Leu Ala Thr Met Tyr Met Asn Gly Phe Gly
    50                  55                  60
Val Arg Arg Asp Phe Glu Lys Gly Phe Asp Tyr Met Thr Arg Ala Ala
65                  70                  75                  80
Glu Leu Lys Tyr Leu Pro Ala Gln Leu Tyr Leu Gly Asn Tyr Tyr Phe
                85                  90                  95
Gln Gln Gln Lys Asp Leu Glu Lys Ala Val Pro Trp Phe Lys Lys Ala
            100                 105                 110
Ala Asp Ala Gly Asp Ala Gly Ala Gln Leu Phe Thr Gly Ile Ser Tyr
        115                 120                 125
Leu Asn Gly Tyr Gly Val Lys Lys Asn Ile Asp Ile Ala Arg Lys Tyr
    130                 135                 140
Phe Ile Arg Ala Ala Gln Asn Glu Ile Pro Met Gly Gln Tyr Glu Leu
145                 150                 155                 160
Ala Lys Ile Phe Leu Ala Ser Arg His Ala Gly Asp Arg Arg Met Gly
                165                 170                 175
Arg Ile Trp Leu Thr Lys Ala Ala Asp Lys Tyr Asn Tyr Pro Asp Ala
            180                 185                 190
```

```
Gln Tyr Leu Leu Gly Thr Met Leu Tyr Thr Gly Asn Glu Ala Glu Lys
            195                 200                 205

Asp Pro Val Lys Gly Val Glu Trp Leu Glu Lys Ala Ala Asn Gly
210                 215                 220

Ser Lys Glu Ala Ser Lys Thr Leu Asp Lys Ile Asn Arg Ile Asn Thr
225                 230                 235                 240

Ser Asp Ala Lys Ala Asn Ser Glu Asn Arg Ser Glu Pro Thr Pro Trp
                245                 250                 255

Gln Ile Met Val Gly Leu Met Gln Lys Ala Gly Val Gln Leu Asn Asn
                260                 265                 270

Pro Ile Thr Val Thr Ala Ser Ile Asn Asn Phe Thr Lys Thr Pro Lys
                275                 280                 285

Ser Met Ala Leu Asp Lys Asn Ser Ile Ile Lys Leu Asn Leu Asn Leu
            290                 295                 300

Val Asn Ser Lys Asp Ile Pro Pro Glu Lys Ile Leu Ser Tyr Met Thr
305                 310                 315                 320

Gln Leu Asn Tyr Lys Glu Glu Lys Phe Asp Leu Thr Val Pro Ala Tyr
                325                 330                 335

Pro Phe Glu Met Pro Pro Gly Ala Asn Asn Tyr Lys Glu Ala Phe Gln
                340                 345                 350

Ser Leu Ser Arg Val Ala Asn Tyr Gly Tyr Ala Gln Ser Leu Phe Arg
            355                 360                 365

Leu Gly Gln Met Tyr Glu Asn Gly Leu Gly Val Gln Lys Asp Pro Glu
            370                 375                 380

Thr Ala Phe Gln Leu Tyr Met Lys Ala Ala Glu Gln Asn Tyr Leu Lys
385                 390                 395                 400

Ala Gln Tyr Ala Ile Gly Thr Tyr Tyr Leu Gln Gly Lys Gly Val Pro
                405                 410                 415

Gln Asp Tyr Glu Lys Ala Ile Ser Trp Phe Ile Arg Ala Ala Leu Lys
                420                 425                 430

Gly Ser Leu Gln Ala Gln Phe Val Leu Gly Asn Ile Tyr Glu Arg Gly
            435                 440                 445

Ile Lys Ala Ser Asn Asn Lys Ile Leu Phe Lys Asn Phe Asp Arg Ala
450                 455                 460

Lys Ala Met Tyr Ser Leu Ala Val Gly Gly Asn Leu Pro Ile Ala Ala
465                 470                 475                 480

Tyr Arg Leu Ala Glu Leu Tyr Val Ser Gly Phe Leu Asn Pro Asp Asn
                485                 490                 495

Asn Val Ser Leu Glu Thr Gln Asn Trp Lys Lys Ala Tyr Ala Leu Tyr
            500                 505                 510

Gln Lys Ala Ala Lys Ser Gly Leu Glu Lys Ala Asp Val Ala Leu Gly
            515                 520                 525

Tyr Phe Tyr Leu Gln Gln Asn Gln Thr Thr Leu Ala Glu Lys Thr Phe
530                 535                 540

Glu Ile Ala Gln Lys Ala Tyr Gln Thr Asn Asp Pro Glu Ala Ala Met
545                 550                 555                 560

Leu Leu Ala Ile Leu Tyr Asp Arg Gly Phe Gly Val Asn Arg Asn Ser
                565                 570                 575

Arg Lys Ser Ala Glu Ile Leu Glu Lys Leu Ser Lys Gln Asn Asn Ala
            580                 585                 590

Ile Ala Gln Phe Met Leu Gly Asn Tyr Tyr Leu Lys Asn Lys Arg Lys
            595                 600                 605

Glu Asn Ile Ala Ile Ser Leu Leu Glu Lys Ser Ala Asn Gln Gly Asn
```

-continued

```
            610                 615                 620
Gly Tyr Ala Lys Tyr Asn Leu Ala Ile Leu Ala Lys Gln Asn Lys Tyr
625                 630                 635                 640

Thr Lys Pro Gly Glu Asn Phe Leu Ser Leu Leu Ile Arg Ala Ala Asn
                645                 650                 655

His Tyr Asp Lys Ile Lys Glu Ile Leu Ala Asp Tyr Tyr Leu Leu Asp
                660                 665                 670

Thr Pro Val Pro Gly Ser Glu Lys Lys Ala Val Ala Ile Tyr Gln Glu
                675                 680                 685

Leu Ala Asn Lys Gln Asp Pro Ala Ala Glu Leu Lys Leu Gly Phe Met
690                 695                 700

Asn Glu His Gly Leu Leu Phe Pro Lys Asp Tyr His Lys Ala Glu Glu
705                 710                 715                 720

Trp Tyr Gln Lys Ser Ala Glu Gln Gly Asn Pro Ile Ala Gln Tyr Leu
                725                 730                 735

Leu Gly Asn Met Tyr Tyr Leu Gly Arg Gly Val Asp Arg Asp Val Asn
                740                 745                 750

Lys Ala Ile Asp Trp Leu Lys Lys Ser Ala Ala Gln Asn Tyr Val Pro
                755                 760                 765

Ala Lys Val Gly Leu Gly Phe Ile Tyr Glu Met Ser Lys His Asn Tyr
770                 775                 780

Pro Glu Ala Lys Lys Trp Tyr Thr Leu Ala Ser Lys Phe His Asn Pro
785                 790                 795                 800

Gln Ala Leu Tyr Asn Leu Gly Leu Met Tyr Glu Tyr Gly Lys Gly Val
                805                 810                 815

Lys Ser Asp Pro Gln Lys Ala Phe Arg Leu Tyr Lys Asp Ala Ala Gln
                820                 825                 830

Asn Gly Leu Asp Leu Ala Ala Val Gln Val Ala Gly Met Tyr Leu Lys
                835                 840                 845

Gly Thr Gly Ile Gly Phe Asp Pro Asn Thr Ala Leu Lys Met Tyr Ser
850                 855                 860

Gln Ala Ala Gln Lys Asn Asn Ser Phe Ala Thr Tyr Gln Leu Gly Leu
865                 870                 875                 880

Met Ser Glu Ser Gly Val Ala Gln Lys Ile Asp Leu Asn Lys Ala Arg
                885                 890                 895

Leu Tyr Tyr Glu Lys Ala Ala Lys Glu Gly Ser Val Glu Ala Gln Leu
                900                 905                 910

Ala Leu Ala Arg Phe Tyr Glu Phe Gly Ile Ser Val Pro Ala Asp Ile
                915                 920                 925

Ser Lys Ser Ile Asn Phe Tyr Gln Ala Ala Ala Glu Gly Asn Glu
930                 935                 940

Phe Ala Lys Gln Gln Leu Thr Arg Leu Ser Asn Gly Lys Ser Ser
945                 950                 955                 960

Ser Asn Ala Met Pro Phe Gln Cys Val Asn Gln Val Ala Leu Glu Lys
                965                 970                 975

Val Lys Asn Ser Phe Trp Lys Lys Val Thr Asp Trp Ile Ala Pro Val
                980                 985                 990

Pro Asn Ile Asp Tyr Met Asn Ala Ile Asp Tyr Leu Asn Ser Gly Lys
                995                 1000                1005

Val Glu Gln Ala Thr Thr Ala Leu Gln Lys Ile Ile Lys Val Arg
        1010                1015                1020

Pro Asn Phe Gln Pro Ala Arg Glu Thr Val Ser His Tyr Phe Cys
        1025                1030                1035
```

Gln Lys  Ala Asp Arg Lys
    1040

<210> SEQ ID NO 65
<211> LENGTH: 146
<212> TYPE: PRT
<213> ORGANISM: Coxiella burnetii

<400> SEQUENCE: 65

Met Leu Glu Thr Glu Lys Cys Thr Lys Ile Phe Leu Ser Phe Ser Leu
1               5                   10                  15

Asn Ser Arg Arg Ile Ile Met Asn Leu Ser Leu Thr Gln Asp Pro Gln
            20                  25                  30

Lys Ala Lys Glu Phe Phe Glu Lys Met Ala Phe Thr Thr Gly Pro
        35                  40                  45

Val Glu Val Ser Gly Met Leu Lys Lys Asn Ala Lys Ile Gln Val Val
    50                  55                  60

Asp Val Arg Ala Ala Glu Asp Tyr Lys Lys Gly His Val Pro Gly Ala
65                  70                  75                  80

Ile Asn Leu Pro Ser Asn Glu Trp Glu Lys Ala Ala Glu Lys Leu Asp
                85                  90                  95

Lys Glu Lys Thr Asn Ile Ile Tyr Cys Tyr Ser Gln Val Cys His Leu
            100                 105                 110

Ala Ala Lys Ala Ala Val Lys Phe Ala Glu Gln Gly Phe Pro Val Met
        115                 120                 125

Glu Met Glu Gly Gly Phe Lys Thr Trp Thr His Lys Leu Glu Thr
130                 135                 140

Glu Lys
145

<210> SEQ ID NO 66
<211> LENGTH: 193
<212> TYPE: PRT
<213> ORGANISM: Coxiella burnetii

<400> SEQUENCE: 66

Met Ala Phe Glu Leu Pro Asp Leu Pro Tyr Lys Leu Asn Ala Leu Glu
1               5                   10                  15

Pro His Ile Ser Gln Glu Thr Leu Glu Tyr His His Gly Lys His His
            20                  25                  30

Arg Ala Tyr Val Asn Lys Leu Asn Lys Leu Ile Glu Gly Thr Pro Phe
        35                  40                  45

Glu Lys Glu Pro Leu Glu Glu Ile Arg Lys Ser Asp Gly Gly Ile
    50                  55                  60

Phe Asn Asn Ala Ala Gln His Trp Asn His Thr Phe Tyr Trp His Cys
65                  70                  75                  80

Met Ser Pro Asp Gly Gly Asp Pro Ser Gly Glu Leu Ala Ser Ala
                85                  90                  95

Ile Asp Lys Thr Phe Gly Ser Leu Glu Lys Phe Lys Ala Leu Phe Thr
            100                 105                 110

Asp Ser Ala Asn Asn His Phe Gly Ser Gly Trp Ala Trp Leu Val Lys
        115                 120                 125

Asp Asn Asn Gly Lys Leu Glu Val Leu Ser Thr Val Asn Ala Arg Asn
    130                 135                 140

Pro Met Thr Glu Gly Lys Lys Pro Leu Met Thr Cys Asp Val Trp Glu
145                 150                 155                 160

His Ala Tyr Tyr Ile Asp Thr Arg Asn Asp Arg Pro Lys Tyr Val Asn
                165                 170                 175

Asn Phe Trp Gln Val Val Asn Trp Asp Phe Val Met Lys Asn Phe Lys
            180                 185                 190

Ser

<210> SEQ ID NO 67
<211> LENGTH: 146
<212> TYPE: PRT
<213> ORGANISM: Coxiella burnetii

<400> SEQUENCE: 67

Met Asp Asn Tyr Lys Lys Ile Leu Val Ala Leu Ala Leu Asp Pro Asn
1               5                   10                  15

Ser Asp Arg Pro Leu Val Glu Lys Ala Lys Glu Leu Ser Ala Asn Arg
            20                  25                  30

Asp Ala Gln Leu Tyr Leu Ile His Ala Val Glu His Leu Ser Ser Tyr
        35                  40                  45

Gly Ala Ala Tyr Gly Val Ala Ala Gly Val Asp Val Glu Asp Met Leu
    50                  55                  60

Leu Glu Glu Ala Lys Lys Arg Met Asn Glu Ile Ala Ser Gln Leu Asn
65                  70                  75                  80

Ile Ser Ser Asp His Gln Ile Val Lys Val Gly Pro Ala Lys Phe Leu
                85                  90                  95

Ile Leu Glu Gln Ala Lys Asn Trp Gly Val Asp Leu Ile Ile Val Gly
            100                 105                 110

Ser His Gly Arg His Gly Ile Gln Leu Leu Leu Gly Ser Thr Ser Asn
        115                 120                 125

Ala Val Leu His Gly Ala Lys Cys Asp Val Leu Ala Val Arg Ile Lys
    130                 135                 140

Gly Ser
145

<210> SEQ ID NO 68
<211> LENGTH: 160
<212> TYPE: PRT
<213> ORGANISM: Coxiella burnetii

<400> SEQUENCE: 68

Met Pro Ser Phe Asp Ile Gln Ser Glu Leu Asn Lys His Glu Val Ser
1               5                   10                  15

Asn Ala Val Asp Gln Ala Asn Arg Glu Val Ala Thr Arg Phe Asp Phe
            20                  25                  30

Lys Gly Ser Gly Ala Thr Tyr Lys Tyr Glu Gly Asn Ser Ile Thr Leu
        35                  40                  45

Gln Ala Glu Thr Asp Phe Gln Leu Lys Gln Met Ile Asp Ile Leu Gln
    50                  55                  60

Asn Lys Phe Ala Lys Arg Gln Ile Asp Val Ala His Met Lys Leu Glu
65                  70                  75                  80

Asp Pro Ile Ile Gln His Lys Ser Ala Gln Gln Thr Val Met Leu Leu
                85                  90                  95

Glu Gly Ile Asp Gln Thr Ala Ala Lys Lys Ile Ile Lys Leu Ile Lys
            100                 105                 110

Asp Gln Lys Leu Lys Val Gln Ala Ala Ile Gly Glu Lys Val Arg
        115                 120                 125

```
Val Thr Gly Lys Lys Arg Asp Asp Leu Gln Ser Val Ile Gly Leu Leu
    130                 135                 140

Lys Glu Gln Glu Ile Gly Leu Pro Leu Gln Phe Asp Asn Phe Arg Asp
145                 150                 155                 160
```

<210> SEQ ID NO 69
<211> LENGTH: 100
<212> TYPE: PRT
<213> ORGANISM: Coxiella burnetii

<400> SEQUENCE: 69

```
Met Ser Asn Ser Gly Lys Lys Phe Asp Phe Gln Gly Val Leu Asn Asn
1               5                   10                  15

Ile Lys Ser Met Ile Ser Pro Glu Ser Asn Thr Pro Ser Pro Asp Pro
                20                  25                  30

Ser Asp Ala Ile Gly Met Lys Ile Ala Glu Leu Ser Val Leu Ala Gln
            35                  40                  45

Gln Leu Thr Lys Ser His Glu Glu Gln Ala Lys Glu Leu Ala Asn Val
        50                  55                  60

Asn Arg Leu Leu Asn Asp Leu Phe Lys Asp Leu Glu Ala Phe Arg Asn
65                  70                  75                  80

Pro Pro Glu Asn Lys Thr Glu Leu Lys Gln Lys Asp Lys Lys Glu Glu
                85                  90                  95

Thr Lys Lys Asp
            100
```

<210> SEQ ID NO 70
<211> LENGTH: 110
<212> TYPE: PRT
<213> ORGANISM: Coxiella burnetii

<400> SEQUENCE: 70

```
Met Ile Gly Gly Lys Phe Asn Leu Gly Ser Leu Met Lys Asn Ala Lys
1               5                   10                  15

Lys Ile Gln Glu Met Met Gln Lys Ala Gln Asp Glu Leu Ala Lys Ile
                20                  25                  30

Arg Val Thr Gly Glu Ser Gly Ala Gly Met Val Lys Leu Thr Met Thr
            35                  40                  45

Ala Gln His Glu Val Val Glu Met Asn Leu Asp Asp Glu Leu Leu Lys
        50                  55                  60

Glu Ser Lys Glu Val Ile Glu Asp Leu Ile Lys Ala Ala Leu Asn Asp
65                  70                  75                  80

Ala Asn Gln Lys Ile Leu Lys Ile Thr Gln Lys Met Met Ser Ala
                85                  90                  95

Gly Ser Leu Phe Gly Gly Asn Glu Ser Asp Asn Glu Glu Thr
            100                 105                 110
```

<210> SEQ ID NO 71
<211> LENGTH: 444
<212> TYPE: PRT
<213> ORGANISM: Coxiella burnetii

<400> SEQUENCE: 71

```
Met Ile Arg Ser Gly Lys Met Arg Lys Leu Ile Asn Ser Ile Ile Gly
1               5                   10                  15

Val Ala Leu Ile Val Val Ile Val Leu Leu Val Leu Pro Leu Gly Met
                20                  25                  30

Ser Phe Trp Leu Lys Asn Asn Tyr Pro Ser Ile Leu Thr Arg Leu Ser
```

```
                35                  40                  45
Gln Ala His Asn Val Ser Leu Lys Leu Ile Asn Phe Asp Arg Gly Trp
 50                  55                  60
Phe Ala Ser Lys Ala Val Ile Gln Val Ile Ile Pro Asn Ser Glu Asp
 65                  70                  75                  80
Lys Thr Thr Gln Pro Ile Lys Phe Thr Ile Asn Gln His Ile Phe Asn
                 85                  90                  95
Gly Pro Phe Ile Phe Ser Lys Asn Asn His Lys Val Lys Leu His Cys
                100                 105                 110
Ala Lys Ala Leu Val Tyr Thr Thr Ser Asn Asp Pro Asn Phe Thr Phe
                115                 120                 125
His Ser Ser Thr Leu Leu Arg Phe Asn Asn Ser Ser Lys Ser Ser Leu
                130                 135                 140
Tyr Ala Ser Asn Val Asn Val Ala Asn Gly Gln Glu Gln Ile Val Leu
145                 150                 155                 160
Lys Asp Thr Asn Leu Glu Ile Leu Tyr Asn Pro Leu Thr Gln Arg Leu
                165                 170                 175
Val Leu Asn Ala Val Ile Lys Ser Ala Leu Ile Ser Glu Gln Gln Lys
                180                 185                 190
Thr Ile Leu Ile Met Asp Asn Ile Thr Trp Arg Asn Asp Leu His His
                195                 200                 205
Ala Thr Pro Leu Trp Glu Gly Lys Arg Ser Leu Ser Leu Asn Lys Phe
                210                 215                 220
Thr Tyr Tyr Leu Thr Pro Glu Gln Leu Ile Glu Val Lys Asn Phe Ile
225                 230                 235                 240
Leu Glu Asn Gln Gln Asn Ala Ala Asn Asp Thr Thr Thr Phe Thr Phe
                245                 250                 255
Ser Ser His Ala Asp Ser Ile Lys Asp Thr Ser Leu Asn Leu Ala Pro
                260                 265                 270
Leu Asp Ile Lys Phe Ser Leu Thr Gln Met Asn Thr Ala Ala Leu Val
                275                 280                 285
Asn Leu Ile Asn Thr Ala Leu Asn Glu Asn His Leu Lys Leu Asn Pro
                290                 295                 300
Gln Gln Leu His Gln Phe His Thr Pro Ala Ile Asn Leu Leu Ala Gln
305                 310                 315                 320
Gly Leu Glu Val Ser Leu Ala His Leu Thr Phe Gly Thr Glu Glu Gly
                325                 330                 335
Gln Val Ser Val Gln Gly Gln Leu His Leu Pro Ala Gln Asn Gln Ser
                340                 345                 350
Pro Asp Leu Ser Gln Ile Met Val Asn Ala Lys Gly Asn Leu Gln Ala
                355                 360                 365
Lys Met Pro Met Ala Trp Leu Lys Lys Glu Leu Ser Arg Ile Tyr Glu
                370                 375                 380
Asp Lys Lys Val Glu Leu Asp Asp Gln Ala Leu Thr Pro Glu Gln Ile
385                 390                 395                 400
Ala Asp Gln Gln Ile Gln Tyr Trp Ile Asn Asn Lys Lys Leu Ile Pro
                405                 410                 415
Gln Asn Gln Asp Val Glu Leu Thr Ile Asn Tyr Asp Lys Gly Lys Leu
                420                 425                 430
Leu Val Asn Asn Leu Pro Ser His Ala Pro Gln Gln
                435                 440
```

The invention claimed is:

1. An immunogenic composition comprising one or more isolated protein antigens selected from the group consisting of: (1) a CBU_0091 antigen; (2) a CBU_1648 antigen; (3) a CBU_0532 antigen; (4) a CBU_0758 antigen; (5) a CBU_1652 antigen; and (6) a CBU_2009 antigen; and further comprising an immune-effective amount of an adjuvant.

2. The immunogenic composition of claim 1 comprising a pharmaceutically acceptable carrier or excipient.

3. The immunogenic composition of claim 1 comprising one or more additional therapeutic agents.

4. The immunogenic composition of claim 3, wherein the one or more additional therapeutic agents comprises a bacteriostatic drug.

5. The immunogenic composition of claim 3, wherein the one or more additional therapeutic agents comprises a bactericidal agent.

* * * * *